(12) United States Patent
Lai et al.

(10) Patent No.: US 12,630,847 B2
(45) Date of Patent: May 19, 2026

(54) CRISPR-Cas SIGMA ENZYME AND SYSTEM

(71) Applicant: CHINA AGRICULTURAL UNIVERSITY, Beijing (CN)

(72) Inventors: Jinsheng Lai, Beijing (CN); Zhijia Yang, Beijing (CN); Meixia Yu, Beijing (CN); Jian Chen, Beijing (CN); Beibei Xin, Beijing (CN); Yunpeng Teng, Beijing (CN); Yueheng Zhou, Beijing (CN); Haiming Zhao, Beijing (CN); Weibin Song, Beijing (CN)

(73) Assignee: China Agricultural University, Beijing (CN)

( * ) Notice: Subject to any disclaimer, the term of this patent is extended or adjusted under 35 U.S.C. 154(b) by 0 days.

(21) Appl. No.: 19/011,407

(22) Filed: Jan. 6, 2025

(65) Prior Publication Data

US 2025/0179534 A1     Jun. 5, 2025

Related U.S. Application Data

(63) Continuation of application No. PCT/CN2024/116773, filed on Sep. 4, 2024.

(30) Foreign Application Priority Data

Sep. 4, 2023     (CN) .......................... 202311132967.0

(51) Int. Cl.
*C12N 15/90*     (2006.01)
*C12N 9/22*      (2006.01)
*C12N 15/11*     (2006.01)

(52) U.S. Cl.
CPC ............. *C12N 15/907* (2013.01); *C12N 9/22* (2013.01); *C12N 15/11* (2013.01); *C12N 15/902* (2013.01); *C12N 2310/20* (2017.05)

(58) Field of Classification Search
None
See application file for complete search history.

(56) References Cited

FOREIGN PATENT DOCUMENTS

| | | |
|---|---|---|
| CN | 113462672 A | 10/2021 |
| CN | 113930410 A | 1/2022 |
| CN | 114410609 A | 4/2022 |
| CN | 116334037 A | 6/2023 |
| CN | 117230042 A | * 12/2023 ............... C12N 9/22 |
| WO | 2019214604 A1 | 11/2019 |
| WO | WO 2020098772 A1 | 5/2020 |
| WO | WO-2021178933 A2 | * 9/2021 ........... C12N 15/102 |
| WO | 2022159741 A1 | 7/2022 |
| WO | 2023086938 A2 | 5/2023 |
| WO | WO-2024251229 A1 | * 12/2024 ............... C12N 9/22 |

OTHER PUBLICATIONS

Addgene ("Components of CRISPR/Cas9" Addgene commercial blog, published Mar. 26, 2020 (Year: 2020).*
Deng et al. Sensors and Actuators B: Chemical. vol. 373, Dec. 15, 22, 132767 (Year: 2022).*
Hu P et al. G3 Bethesda. Mar. 2, 2018;8(3):823-831 (Year: 2018).*
Yuan B et al. Molecules. Oct. 18, 2022;27(20):6999 (Year: 2022).*
Li SY et al. Cell Discov. Apr. 24, 2018;4:20 (Year: 2018).*
Li J et al. Diagnostics (Basel). Oct. 11, 2022;12(10):2455 (Year: 2022).*
International Search Report and Written Opinion in International Application No. PCT/CN2024/116773, dated Dec. 23, 2024, 11 pages. (English Translation).
Chinese Patent and Trademark Office, First Examination Opinion Notification for Chinese Application No. 202411237286.5, issued Mar. 28, 2025. English translation (16 pages).
Hillary, V Edwin, and S Antony Ceasar. "A Review on the Mechanism and Applications of CRISPR/Cas9/Cas12/Cas13/Cas14 Proteins Utilized for Genome Engineering." Molecular biotechnology vol. 65,3 (2023): 311-325. doi:10.1007/s12033-022-00567-0.
Tang, Lian Chao, and Feng Gu. "Next-generation CRISPR-Cas for genome editing: focusing on the Cas protein and PAM." Yi chuan = Hereditas vol. 42,3 (2020): 236-249. doi:10.16288/j.yczz.19-297.

* cited by examiner

*Primary Examiner* — Kimberly Chong
*Assistant Examiner* — Douglas Charles Ryan
(74) *Attorney, Agent, or Firm* — Morgan, Lewis & Bockius LLP

(57) ABSTRACT

The present invention relates to the field of nucleic acid editing, in particular to the field of clustered regularly interspaced short palindromic repeat (CRISPR) technology. Specifically, the present invention relates to Cas effector proteins, fusion proteins comprising such proteins, and nucleic acid molecules encoding them. The present invention also relates to complexes and compositions for nucleic acid editing (e.g., gene or genome editing), which comprise the proteins or fusion proteins of the present invention, or nucleic acid molecules encoding them. The present invention also relates to a method for nucleic acid editing (e.g., gene or genome editing), which uses the proteins or fusion proteins comprising the present invention.

22 Claims, 2 Drawing Sheets

Specification includes a Sequence Listing.

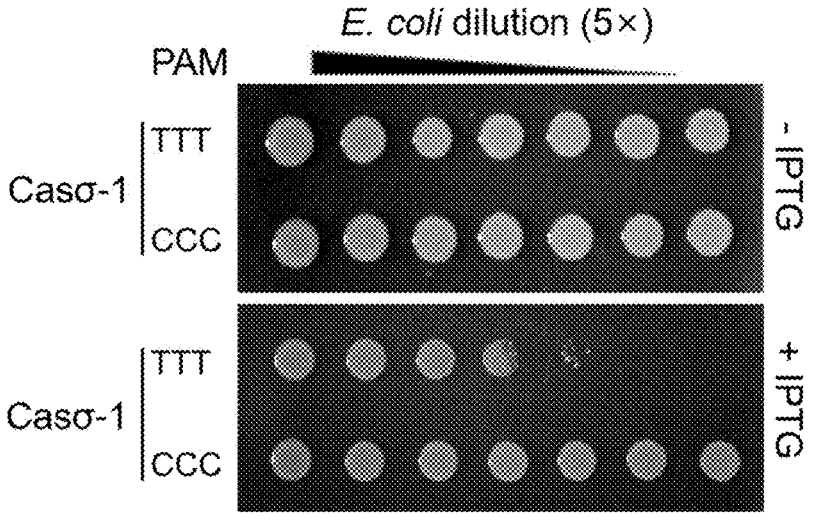

Fig. 3

SEQ ID NO: 84 TTTGCTTACGATGGAGCCAGAGAGGATCCTGGGAGGGAGAGCTTGGCAGGGG

SEQ ID NO: 85 AAACGAATGCTACCTCGGTCTCTCCTAGGACCCTCCCTCTCGAACCGTCCCC

Casσ-1 靶点

PAM

SEQ ID NO: 84 TTTGCTTACGATGGAGCCAGAGAGGATCCTGGGAGGGAGAGCTTGGCAGGGG

SEQ ID NO: 86 TTTGCTTACGATGGAGCCAGAGAG        CTTGGCAGGGG

SEQ ID NO: 86 TTTGCTTACGATGGAGCCAGAGAG        CTTGGCAGGGG

SEQ ID NO: 87 TTTGCTTACGATGGAGCCAGAGAGGATT        GCAGGGG

SEQ ID NO: 88 TTTGCTTACGATGGAGCCAGAGAGGATCC     AGAGCTTGGCAGGGG

SEQ ID NO: 88 TTTGCTTACGATGGAGCCAGAGAGGATCC     AGAGCTTGGCAGGGG

SEQ ID NO: 86 TTTGCTTACGATGGAGCCAGAGAG        CTTGGCAGGGG

Fig. 4

CRISPR-Cas SIGMA ENZYME AND SYSTEM

CROSS-REFERENCE-RELATED APPLICATIONS

The present application is a continuation application of International Application No. PCT/CN2024/116773 filed Sep. 4, 2024, which claims the priority of Chinese patent application No. 202311132967.0 filed on Sep. 4, 2023, and the entire contents of the patent applications are incorporated herein by reference in their entirety.

SEQUENCE LISTING

The instant application contains a Sequence Listing which has been submitted electronically in XML file format and is hereby incorporated by reference in its entirety. Said XML file, created on May 19, 2025, is named IEC240461PUS-OA1-seq.xml and is 172,567 bytes in size.

TECHNICAL FIELD

The present invention relates to nucleic acid editing, particularly the field of regularly clustered interspaced short palindromic repeats (CRISPR) technology. Specifically, the present invention relates to Cas effector proteins, fusion proteins comprising such proteins, and nucleic acid molecules encoding them. The present invention also relates to complexes and compositions for nucleic acid editing (e.g., gene or genome editing), which comprise proteins or fusion proteins of the present invention or nucleic acid molecules encoding them. The present invention also relates to methods for nucleic acid editing (e.g., gene or genome editing), which use proteins or fusion proteins comprising those of the present invention.

BACKGROUND

CRISPR/Cas technology is a widely used gene editing technique that utilizes biological non-homologous end joining or homologous recombination to perform site-directed gene editing by specifically binding to target sequences on the genome through RNA guidance and cutting the DNA to produce double-strand breaks.

CRISPR/Cas9 system is the most commonly used type II CRISPR system, which recognizes 3'-NGG PAM motifs and performs blunt-end cutting on the target sequences. CRISPR/Cas Type V system is a newly discovered CRISPR system in the last two years, which has a 5'-TTN motif and performs sticky-end cutting on the target sequence, and examples include Cpf1, C2c1, CasX, and CasY. However, different CRISPR/Cas currently have distinct advantages and disadvantages. For example, Cas9, C2c1, and CasX all require two RNAs for guide RNA, while Cpf1 requires only one guide RNA and can be used for multiple gene editing. CasX has a size of 980 amino acids, while the common Cas9, C2c1, CasY, and Cpf1 are usually around 1300 amino acids in size. In addition, the PAM sequences of Cas9, Cpf1, CasX, and CasY are relatively complex and diverse. At the same time, C2c1 recognizes a rigorous 5'-TTN, so its target site is easier to predict than other systems, thereby reducing potential off-target effects.

In summary, given that currently available CRISPR/Cas systems are limited by some shortcomings, developing a new CRISPR/Cas system that is more robust and has good performance in many aspects is of great significance to the development of biotechnology.

CONTENTS OF THE INVENTION

After extensive experiments and repeated explorations, the inventor of the present application unexpectedly discovered a new type of RNA-guided endonuclease. The inventors then developed a new CRISPR/Cas system and a gene editing method based on this system.

Cas Effector Protein

Therefore, in the first aspect, the present invention provides a protein having an amino acid sequence as set forth in any one of SEQ ID NOs: 1, 2, 3, 4, 5, 6, 7, 8, 9, 10, 11, 12 and 13, or ortholog, homolog, variant, functional fragment thereof; wherein the ortholog, homolog, variant or functional fragment substantially retain the biological function of the sequence from which it is derived.

In the present invention, the biological function of the above sequence includes but is not limited to, the activity of binding to a guide RNA, the activity of endonuclease, and the activity of binding to and cutting a specific site of a target sequence under the guidance of a guide RNA.

In certain embodiments, the ortholog, homolog, variant has a sequence identity of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% as compared to the sequence from which it is derived.

In certain embodiments, the ortholog, homolog, variant has a sequence identity of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% as compared to the sequence as set forth in any one of SEQ ID NO: 1, 2, 3, 4, 5, 6, 7, 8, 9, 10, 11, 12 and 13, and substantially retains the biological function of the sequence from which it is derived (e.g., the activity of binding to a guide RNA, the activity of endonuclease, the activity of binding to and cutting a specific site of a target sequence under the guidance of a guide RNA).

In certain embodiments, the protein is an effector protein in a CRISPR/Cas system.

In certain embodiments, the protein of the present invention comprises or consists of a sequence selected from the following:

(i) a sequence as set forth in any one of SEQ ID NOs: 1, 2, 3, 4, 5, 6, 7, 8, 9, 10, 11, 12 and 13;

(ii) a sequence having a substitution, deletion, or addition of one or more amino acids (e.g., a substitution, deletion, or addition of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40 amino acids) as compared to the sequence as set forth in any one of SEQ ID NOs: 1, 2, 3, 4, 5, 6, 7, 8, 9, 10, 11, 12 and 13; or (iii) a sequence having a sequence identity of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% as compared to the sequence as set forth in any one of SEQ ID NOs: 1 to 13.

Derivatized Protein

The protein of the present invention can be derivatized, for example, connected to another molecule (e.g., another polypeptide or protein). Generally, the derivatization (e.g., labeling) of a protein does not adversely affect the desired activity of the protein (e.g., the activity of binding to a guide RNA, the activity of endonuclease, the activity of binding to and cutting a specific site of a target sequence under the guidance of a guide RNA). Therefore, the protein of the present invention is also intended to include such derivatized forms. For example, the protein of the present invention can be functionally connected (by chemical coupling, gene fusion, non-covalent connection, or other means) to one or more different molecular groups, such as another protein or polypeptide, a detection agent, a pharmaceutical agent, etc.

In particular, the protein of the present invention can be linked to another functional unit. For example, it can be connected to a nuclear localization signal (NLS) sequence to improve the ability of the protein of the present invention to enter the cell nucleus. For example, it can be linked to a targeting moiety to endow the protein of the present invention with targeting ability. For instance, it can be connected to a detectable label to facilitate the detection of the protein of the present invention. For instance, it can be connected to an epitope tag to facilitate the expression, detection, tracing and/or purification of the protein of the present invention.

Conjugate

Therefore, in a second aspect, the present invention provides a conjugate that comprises the protein described above and a modified moiety.

In certain embodiments, the modified moiety is selected from the group consisting of an additional protein or polypeptide, a detectable label, and any combination thereof.

In certain embodiments, the additional protein or polypeptide is selected from the group consisting of an epitope tag, a reporter gene sequence, a nuclear localization signal (NLS) sequence, a targeting moiety, a transcriptional activation domain (e.g., VP64), a transcriptional repression domain (e.g., a KRAB domain or a SID domain), a nuclease domain (e.g., Fok1), a domain having an activity selected from the following: nucleotide deaminase, methylase activity, demethylase, transcriptional activation activity, transcriptional repression activity, transcriptional release factor activity, histone modification activity, nuclease activity, single-stranded RNA cleavage activity, double-stranded RNA cleavage activity, single-stranded DNA cleavage activity, double-stranded DNA cleavage activity and nucleic acid binding activity, and any combination thereof.

In certain embodiments, the conjugate of the present invention comprises one or more NLS sequences, such as a NLS of large T antigen of the SV40 virus. In certain exemplary embodiments, the NLS sequence is set forth in SEQ ID NO: 53. In certain embodiments, the NLS sequence is located at, near or close to the end (e.g., N-terminal or C-terminal) of the protein of the present invention. In certain exemplary embodiments, the NLS sequence is located at, near, or close to the C-terminal of the protein of the present invention.

In certain embodiments, the conjugate of the present invention comprises an epitope tag. Such epitope tags are well known to those skilled in the art, and examples thereof include but are not limited to, His, V5, FLAG, HA, Myc, VSV to G, Trx, etc., and those skilled in the art know how to select a suitable epitope tag according to the desired purpose (e.g., purification, detection or tracing).

In certain embodiments, the conjugate of the present invention comprises a reporter gene sequence. Such reporter genes are well known to those skilled in the art, and examples thereof include but are not limited to, GST, HRP, CAT, GFP, HcRed, DsRed, CFP, YFP, BFP, etc.

In certain embodiments, the conjugate of the present invention comprises a domain capable of binding to a DNA molecule or an intracellular molecule, such as a maltose binding protein (MBP), a DNA binding domain (DBD) of Lex A, a DBD of GAL4, etc.

In certain embodiments, the conjugate of the present invention comprises a detectable label, such as a fluorescent dye, such as FITC or DAPI.

In certain embodiments, the protein of the present invention is coupled, conjugated, or fused to the modification portion optionally via a linker.

In certain embodiments, the modification portion is directly connected to the N-terminal or C-terminal of the protein of the present invention.

In certain embodiments, the modification portion is connected to the N-terminal or C-terminal of the protein of the present invention via a linker. Such linkers are well known in the art, and examples thereof include but are not limited to, linkers comprising one or more (e.g., 1, 2, 3, 4 or 5) amino acids (e.g., Glu or Ser) or amino acid derivatives (e.g., Ahx, β-Ala, GABA or Ava), or PEG, etc.

Fusion Protein

In the third aspect, the present invention provides a fusion protein, which comprises the protein of the present invention and an additional protein or polypeptide.

In certain embodiments, the additional protein or polypeptide is selected from the group consisting of an epitope tag, a reporter gene sequence, a nuclear localization signal (NLS) sequence, a targeting moiety, a transcriptional activation domain (e.g., VP64), a transcriptional repression domain (e.g., a KRAB domain or a SID domain), a nuclease domain (e.g., Fok1), a domain having an activity selected from the following: nucleotide deaminase, methylase activity, demethylase, transcriptional activation activity, transcriptional repression activity, transcriptional release factor activity, histone modification activity, nuclease activity, single-stranded RNA cleavage activity, double-stranded RNA cleavage activity, single-stranded DNA cleavage activity, double-stranded DNA cleavage activity and nucleic acid binding activity, and any combination thereof.

In certain embodiments, the fusion protein of the present invention comprises one or more NLS sequences, such as a NLS of large T antigen of the SV40 virus. In certain embodiments, the NLS sequence is located at, near or close to the end (e.g., N-terminal or C-terminal) of the protein of the present invention. For example, the NLS has a sequence as shown in SEQ ID NO: 53. In certain exemplary embodiments, the NLS sequence is located at, near or close to the C-terminal of the protein of the present invention.

In certain embodiments, the fusion protein of the present invention comprises an epitope tag.

In certain embodiments, the fusion protein of the present invention comprises a reporter gene sequence.

In certain embodiments, the fusion protein of the present invention comprises a domain capable of binding to a DNA molecule or an intracellular molecule.

In certain embodiments, the protein of the present invention is fused to the additional protein or polypeptide optionally via a linker.

In certain embodiments, the additional protein or polypeptide is directly connected to the N-terminal or C-terminal of the protein of the present invention.

In certain embodiments, the additional protein or polypeptide is connected to the N-terminal or C-terminal of the protein of the present invention via a linker.

In certain exemplary embodiments, the fusion protein of the present invention has an amino acid sequence as set forth in any one of SEQ ID NOs: 54 to 66.

The protein of the present invention, the conjugate of the present invention or the fusion protein of the present invention is not limited by the production method thereof, for example, it can be produced by a genetic engineering method (recombinant technology) or by a chemical synthesis method.

Direct Repeat Sequence

In the fourth aspect, the present invention provides an isolated nucleic acid molecule, which comprises or consists of a sequence selected from the following sequences:

(i) a sequence as set forth in any one of SEQ ID NOs: 27 to 39;

(ii) a sequence having a substitution, deletion or addition of one or more bases (e.g., a substitution, deletion or addition of 1, 2, 3, 4, 5, 6, 7, 8, 9 or 10 bases) as compared to the sequence as set forth in any one of SEQ ID NOs: 27 to 39;

(iii) a sequence having a sequence identity of at least 20%, at least 30%, at least 40%, at least 50%, at least 60%, at least 70%, at least 80%, at least 90%, at least 95% as compared to the sequence as set forth in any one of SEQ ID NOs: 27 to 39;

(iv) a sequence capable of hybridizing with the sequence as described in any one of (i) to (iii) under a stringent condition; or (v) a complementary sequence of the sequence as described in any one of (i) to (iii);

and, the sequence as described in any one of (ii) to (v) substantially retains the biological function of the sequence from which it is derived, and the biological function of the sequence refers to the activity as a direct repeat sequence in the CRISPR-Cas system.

In certain embodiments, the isolated nucleic acid molecule is a direct repeat sequence in the CRISPR-Cas system.

In certain embodiments, the nucleic acid molecule comprises a sequence selected from the following, or consists of a sequence selected from the following:

(a) a nucleotide sequence as set forth in any one of SEQ ID NOs: 27 to 39;

(b) a sequence capable of hybridizing with the sequence as described in (a) under a stringent condition; or (c) a complementary sequence of the sequence as described in (a).

In certain embodiments, the isolated nucleic acid molecule is an RNA.

CRISPR/Cas Complex

In the fifth aspect, the present invention provides a complex, which comprises:

(i) a protein component, which is selected from the group consisting of the protein, conjugate or fusion protein of the present invention, and any combination thereof; and (ii) a nucleic acid component, which comprises, from the 5' to 3' direction, the isolated nucleic acid molecule as described above and a guide sequence capable of hybridizing with a target sequence, wherein the protein component and the nucleic acid component bind to each other to form a complex.

In some embodiments, the guide sequence is ligated to the 3' end of the nucleic acid molecule.

In some embodiments, the guide sequence comprises a complementary sequence to the target sequence.

In some embodiments, the nucleic acid component is a guide RNA in a CRISPR-Cas system.

In some embodiments, the nucleic acid molecule is an RNA.

In some embodiments, the complex does not comprise a trans-activating crRNA (tracrRNA).

In some embodiments, the guide sequence has a length of at least 5, at least 10, at least 15, at least 20, at least 25, or at least 30 nucleotides. In some embodiments, the guide sequence has a length of 10 to 30, or 15 to 25, or 15 to 22, or 19 to 25, or 19 to 22 nucleotides.

In some embodiments, the isolated nucleic acid molecule has a length of 55 to 70 nucleotides, such as 55 to 65 nucleotides, such as 60 to 65 nucleotides, such as 62 to 65 nucleotides, such as 63 to 64 nucleotides. In some embodiments, the isolated nucleic acid molecule has a length of 15 to 30 nucleotides, such as 15 to 25 nucleotides, such as 20 to 25 nucleotides, such as 22 to 24 nucleotides, such as 23 nucleotides.

Encoding Nucleic Acid, Vector, and Host Cell

In the sixth aspect, the present invention provides an isolated nucleic acid molecule, which comprises:

(i) a nucleotide sequence encoding the protein or fusion protein of the present invention;

(ii) a nucleotide sequence encoding the isolated nucleic acid molecule as described in the fourth aspect; or (iii) a nucleotide sequence comprising (i) and (ii).

In some embodiments, the nucleotide sequence as described in any one of (i) to (iii) is optimized with a codon for expression in prokaryotic cells. In some embodiments, the nucleotide sequence as described in any one of (i) to (iii) is optimized with a codon for expression in eukaryotic cells.

In the seventh aspect, the present invention also provides a vector, which comprises the isolated nucleic acid molecule as described in the sixth aspect. The vector of the present invention can be a cloning vector or an expression vector. In certain embodiments, the vector of the present invention is, for example, a plasmid, a cosmid, a phage, a Kos plasmid, and the like. In certain embodiments, the vector is capable of expressing the protein, fusion protein, isolated nucleic acid molecule as described in the fourth aspect, or the complex as described in the fifth aspect of the present invention in a subject (e.g., a mammal, such as a human).

In the eighth aspect, the present invention also provides a host cell comprising the isolated nucleic acid molecule or vector, as described above. Such host cells include but are not limited to, prokaryotic cells such as *Escherichia coli* cells, and eukaryotic cells such as yeast cells, insect cells, plant cells, and animal cells (e.g., mammalian cells, such as mouse cells, human cells, etc.).

The cell of the present invention can also be a cell line, such as a 293T cell.

Composition and Vector Composition

In the ninth aspect, the present invention also provides a composition, which comprises:

(i) a first component, which is selected from the group consisting of the protein, conjugate, fusion protein of the present invention, or a nucleotide sequence encoding the protein or fusion protein, and any combination thereof; and (ii) a second component, which is a nucleotide sequence comprising a guide RNA, or a nucleotide sequence encoding the nucleotide sequence comprising the guide RNA;

wherein, the guide RNA comprises a direct repeat sequence and a guide sequence from the 5' to 3' direction, and the guide sequence is capable of hybridizing with a target sequence;

the guide RNA is capable of forming a complex with the protein, conjugate or fusion protein as described in (i).

In certain embodiments, the direct repeat sequence is the isolated nucleic acid molecule as defined in the fourth aspect.

In certain embodiments, the guide sequence is ligated to the 3' end of the direct repeat sequence. In certain embodiments, the guide sequence comprises a complementary sequence of the target sequence.

In certain embodiments, the composition does not comprise a trans-activating crRNA (tracrRNA).

In certain embodiments, the composition is non-naturally occurring or modified. In certain embodiments, at least one component of the composition is non-naturally occurring or modified.

In certain embodiments, the first component is non-naturally occurring or modified; and/or, the second component is non-naturally occurring or modified.

In certain embodiments, when the target sequence is DNA, the target sequence is located at the 3' end of the protospacer adjacent motif (PAM), and the PAM has a sequence shown as 5'-NTN, wherein the N is each independently selected from A, G, T, or C; for example, the sequence of the PAM is ATG, ATG, GTG, ATA, ATA, GTA, GTA and/or GTG.

In certain embodiments, when the target sequence is RNA, the target sequence does not have a PAM domain restriction.

In certain embodiments, the target sequence is a DNA or RNA sequence from a prokaryotic cell or a eukaryotic cell. In certain embodiments, the target sequence is a non-naturally occurring DNA or RNA sequence.

In certain embodiments, the target sequence is present in a cell. In certain embodiments, the target sequence is present in the nucleus or the cytoplasm (e.g., an organelle). In certain embodiments, the cell is a eukaryotic cell. In certain embodiments, the cell is a prokaryotic cell.

In certain embodiments, the protein is linked to one or more NLS sequences. In certain embodiments, the conjugate or fusion protein comprises one or more NLS sequences. In certain embodiments, the NLS sequence is linked to the N-terminal or C-terminal of the protein. In certain embodiments, the NLS sequence is fused to the N-terminal or C-terminal of the protein.

In the tenth aspect, the present invention also provides a composition, which comprises one or more vectors, wherein the one or more vectors comprise:

(i) a first nucleic acid, which comprises a nucleotide sequence encoding the protein or fusion protein of the present invention; optionally, the first nucleic acid is operably linked to a first regulatory element; and (ii) a second nucleic acid, which comprises a nucleotide sequence encoding a guide RNA; optionally, the second nucleic acid is operably linked to a second regulatory element;

wherein:

the first nucleic acid and the second nucleic acid are present on the same vector or different vectors;

the guide RNA comprises a direct repeat sequence and a guide sequence from the 5' to 3' direction, and the guide sequence is capable of hybridizing with a target sequence;

the guide RNA is capable of forming a complex with the effector protein or fusion protein as described in (i).

In certain embodiments, the direct repeat sequence is an isolated nucleic acid molecule as defined in the fourth aspect.

In certain embodiments, the guide sequence is linked to the 3' end of the direct repeat sequence. In certain embodiments, the guide sequence comprises a complementary sequence of the target sequence.

In certain embodiments, the composition does not comprise a trans-activating crRNA (tracrRNA).

In certain embodiments, the composition is non-naturally occurring or modified. In some embodiments, at least one component of the composition is non-naturally occurring or modified.

In some embodiments, the first regulatory element is a promoter, such as an inducible promoter.

In some embodiments, the second regulatory element is a promoter, such as an inducible promoter.

In some embodiments, when the target sequence is DNA, the target sequence is located at the 3' end of the protospacer adjacent motif (PAM), and the PAM has a sequence shown as 5'-NTN, wherein the N is each independently selected from A, G, T, or C; for example, the PAM sequence is ATG, ATG, GTG, ATA, ATA, GTA, GTA and/or GTG.

In some embodiments, when the target sequence is RNA, and the target sequence does not have a PAM domain restriction.

In some embodiments, the target sequence is a DNA or RNA sequence from a prokaryotic cell or a eukaryotic cell. In some embodiments, the target sequence is a non-naturally occurring DNA or RNA sequence.

In some embodiments, the target sequence is present in a cell. In certain embodiments, the target sequence is present in the nucleus or the cytoplasm (e.g., an organelle). In certain embodiments, the cell is a eukaryotic cell. In certain embodiments, the cell is a prokaryotic cell.

In certain embodiments, the protein is linked to one or more NLS sequences. In certain embodiments, the conjugate or fusion protein comprises one or more NLS sequences. In certain embodiments, the NLS sequence is linked to the N-terminal or C-terminal of the protein. In certain embodiments, the NLS sequence is fused to the N-terminal or C-terminal of the protein.

In certain embodiments, one type of vector is a plasmid, which refers to a circular double-stranded DNA loop into which an additional DNA fragment can be inserted, for example, by standard molecular cloning techniques. Another type of vector is a viral vector, in which a virally derived DNA or RNA sequence is present in a vector for packaging a virus (e.g., a retrovirus, a replication-defective retrovirus, an adenovirus, a replication-defective adenovirus, and an adeno-associated virus). The viral vector further comprises a polynucleotide carried by a virus for transfection into a host cell. Certain vectors (e.g., bacterial vectors with bacterial replication origin, and episomal mammalian vectors) are capable of autonomous replication in host cells into which they are introduced. Other vectors (e.g., non-episomal mammalian vectors) are integrated into the genome of a host cell upon introduction into the host cell and are thereby replicated along with the host genome. Moreover, certain vectors are capable of directing the expression of genes to which they are operably linked. Such vectors are referred to herein as "expression vectors". Common expression vectors used in recombinant DNA technology are generally in the form of plasmids.

The recombinant expression vector may comprise the nucleic acid molecule of the present invention in a form suitable for nucleic acid expression in a host cell, meaning that such recombinant expression vector comprises one or more regulatory elements selected based on the host cell to be used for expression, and the regulatory elements are operably linked to the nucleic acid sequence to be expressed.

Delivery and Delivery Composition

The protein of the present invention, the conjugate of the present invention, the fusion protein of the present invention, the isolated nucleic acid molecule as described in the fourth aspect, the complex of the present invention, the isolated nucleic acid molecule as described in the sixth aspect, the vector as described in the seventh aspect, and the composition as described in the ninth and tenth aspects of the present invention may be delivered by any method known in the art. Such methods include but are not limited to, electroporation, lipofection, nucleofection, microinjection, sonoporation, gene gun, calcium phosphate-mediated transfection, cationic transfection, liposome transfection, dendritic transfection, heat shock transfection, nucleofection, magnetofection, lipofection, puncture transfection, optical transfection, agent-enhanced nucleic acid uptake, and delivery via liposome, immunoliposome, viral particle, artificial virion, etc.

Therefore, in another aspect, the present invention provides a delivery composition, which comprises a delivery vector, and one or more selected from the following: the protein of the present invention, the conjugate of the present invention, the fusion protein of the present invention, the isolated nucleic acid molecule as described in the fourth aspect, the complex of the present invention, the isolated nucleic acid molecule as described in the sixth aspect, the vector as described in the seventh aspect, and the composition as described in the ninth aspect and the tenth aspect.

In some embodiments, the delivery vector is a particle.

In some embodiments, the delivery vector is selected from the group consisting of lipid particle, sugar particle, metal particle, protein particle, liposome, exosome, microvesicle, gene gun, or viral vector (e.g., replication-defective retrovirus, lentivirus, adenovirus, or adeno-associated virus).

Kit

In another aspect, the present invention provides a kit, which comprises one or more of the components described above. In certain embodiments, the kit comprises one or more components selected from the following: the protein of the present invention, the conjugate of the present invention, the fusion protein of the present invention, the isolated nucleic acid molecule as described in the fourth aspect, the complex of the present invention, the isolated nucleic acid molecule as described in the sixth aspect, the vector as described in the seventh aspect, and the composition as described in the ninth and tenth aspects of the present invention.

In certain embodiments, the kit of the present invention comprises the composition as described in the ninth aspect. In certain embodiments, the kit further comprises instructions for using the composition.

In certain embodiments, the kit of the present invention comprises the composition as described in the tenth aspect. In certain embodiments, the kit further comprises instructions for using the composition.

In certain embodiments, the components contained in the kit of the present invention can be provided in any suitable container.

In certain embodiments, the kit further comprises one or more buffers. The buffers can be any buffer, including but not limited to sodium carbonate buffer, sodium bicarbonate buffer, borate buffer, Tris buffer, MOPS buffer, HEPES buffer, and combinations thereof. In certain embodiments, the buffer is alkaline. In certain embodiments, the buffer has a pH of about 7 to about 10.

In certain embodiments, the kit further comprises one or more oligonucleotides, and one or more oligonucleotides correspond to a guide sequence for insertion into a vector to effectively link the guide sequence and the regulatory element. In certain embodiments, the kit comprises a homologous recombination template polynucleotide.

Method and Use

In another aspect, the present invention provides a method to modify a target gene, which comprises: contacting the complex as described in the fifth aspect, the composition as described in the ninth aspect, or the composition as described in the tenth aspect with the target gene, or delivering it to a cell containing the target gene; the target sequence is present in the target gene.

In some embodiments, the method is used for modifying the target gene in vitro or ex vivo. In some embodiments, the method is not a method for treating a human or animal via therapy. In some embodiments, the method does not comprise a step of modifying a human germline genetic characteristic.

In some embodiments, the target gene is present in a cell. In some embodiments, the cell is a prokaryotic cell. In some embodiments, the cell is a eukaryotic cell. In some embodiments, the cell is a mammalian cell. In some embodiments, the cell is a human cell. In some embodiments, the cell is selected from the group consisting of non-human cells, primate cells, bovine cells, porcine cells or rodent cells. In some embodiments, the cell is a non-mammalian eukaryotic cell, such as a poultry or fish cell. In some embodiments, the cell is a plant cell, such as a cell of a cultivated plant (e.g., cassava, corn, sorghum, wheat, or rice), algae, tree, or vegetable.

In some embodiments, the target gene is present in a nucleic acid molecule (e.g., a plasmid) in vitro. In some embodiments, the target gene is present in a plasmid.

In some embodiments, the method results in a breakage in the target sequence (e.g., a double-strand breakage in DNA or a single-strand breakage in RNA). In some embodiments, the breakage results in a reduced transcription of the target gene.

In some embodiments, the method further comprises: contacting an editing template (e.g., an exogenous nucleic acid) with the target gene or delivering it to a cell comprising the target gene.

In such embodiments, the method repairs the broken target gene by homologous recombination with an editing template (e.g., an exogenous nucleic acid), wherein the repair results in a mutation comprising an insertion, deletion, or substitution of one or more nucleotides of the target gene. In some embodiments, the mutation results in one or more amino acid changes in a protein expressed from a gene comprising the target sequence.

Thus, in some embodiments, the modification further comprises inserting an editing template (e.g., an exogenous nucleic acid) into the breakage.

In certain embodiments, the protein, conjugate, fusion protein, isolated nucleic acid molecule, complex, vector or composition is contained in a delivery vehicle.

In certain embodiments, the delivery vehicle is selected from the group consisting of lipid particles, sugar particles, metal particles, protein particles, liposomes, exosomes, viral vectors (e.g., replication-defective retroviruses, lentiviruses, adenoviruses or adeno-associated viruses).

In certain embodiments, the method is used to modify a cell, cell line or organism by changing one or more target sequences in a target gene or a nucleic acid molecule encoding a target gene product.

In another aspect, the present invention provides a method for changing the expression of a gene product, which comprises: contacting the complex as described in the fifth aspect, the composition as described in the ninth aspect or the composition as described in the tenth aspect with a nucleic acid molecule encoding the gene product, or delivering it to a cell comprising the nucleic acid molecule; the target sequence is present in the nucleic acid molecule.

In certain embodiments, the method is used to change the expression of a gene product in vitro or ex vivo. In certain embodiments, the method is not a method for treating a human or animal by therapy. In certain embodiments, the method does not comprise a step of modifying a human germline genetic characteristic.

In certain embodiments, the nucleic acid molecule is present in a cell. In some embodiments, the cell is a prokaryotic cell. In some embodiments, the cell is a eukaryotic cell. In some embodiments, the cell is a mammalian cell. In some embodiments, the cell is a human cell. In some embodiments, the cell is selected from the group consisting of non-human primate cells, bovine cells, porcine cells or rodent cells. In some embodiments, the cell is a non-mammalian eukaryotic cell, such as a poultry or fish cell. In some embodiments, the cell is a plant cell, such as a cell of a cultivated plant (e.g., cassava, corn, sorghum, wheat, or rice), algae, tree, or vegetable.

In some embodiments, the nucleic acid molecule is present in a nucleic acid molecule (e.g., a plasmid) in vitro. In some embodiments, the nucleic acid molecule is present in a plasmid.

In some embodiments, the expression of the gene product is altered (e.g., enhanced or reduced). In some embodiments, the expression of the gene product is enhanced. In some embodiments, the expression of the gene product is reduced.

In some embodiments, the gene product is a protein.

In certain embodiments, the protein, conjugate, fusion protein, isolated nucleic acid molecule, complex, vector or composition is contained in a delivery vehicle.

In certain embodiments, the delivery vehicle is selected from the group consisting of lipid particles, sugar particles, metal particles, protein particles, liposomes, exosomes, viral vectors (e.g., replication-defective retroviruses, lentiviruses, adenoviruses or adeno-associated viruses).

In certain embodiments, the method is used to modify a cell, a cell line, or an organism by changing one or more target sequences in a target gene or a nucleic acid molecule encoding a target gene product.

In another aspect, the present invention relates to a use of the protein as described in the first aspect, the conjugate as described in the second aspect, the fusion protein as described in the third aspect, the isolated nucleic acid molecule as described in the fourth aspect, the complex as described in the fifth aspect, the isolated nucleic acid molecule as described in the sixth aspect, the vector as described in the seventh aspect, the composition as described in the ninth aspect, the composition as described in the tenth aspect, the kit of the present invention, in the manufacture of a preparation, in which the preparation is used for nucleic acid editing (e.g., in vitro or ex vivo nucleic acid editing).

In certain embodiments, the nucleic acid to be edited is present in a cell. In some embodiments, the cell is a prokaryotic cell or a eukaryotic cell. In some embodiments, the nucleic acid to be edited is present in a nucleic acid molecule (e.g., a plasmid) in vitro.

In some embodiments, the nucleic acid editing comprises gene or genome editing, such as modifying a gene, knocking out a gene, changing the expression of a gene product, repairing a mutation, and/or inserting a polynucleotide. In some embodiments, the gene or genome editing does not comprise a step of modifying a human germline's genetic characteristics. In some embodiments, the use is not a method of treating a human or animal by therapy.

In some embodiments, the use further comprises repairing the edited target sequence by homologous recombination with an exogenous template polynucleotide, wherein the repair can produce a mutation of the target sequence, which comprises an insertion, deletion, or substitution of one or more nucleotides.

In another aspect, the present invention relates to a use of the protein as described in the first aspect, the conjugate as described in the second aspect, the fusion protein as described in the third aspect, the isolated nucleic acid molecule as described in the fourth aspect, the complex as described in the fifth aspect, the isolated nucleic acid molecule as described in the sixth aspect, the vector as described in the seventh aspect, the composition as described in the ninth aspect, the composition as described in the tenth aspect, the kit of the present invention, in the manufacture of a preparation, in which the preparation is used for: (i) in vitro or ex vivo DNA detection; (ii) editing a target sequence in a target locus to modify an organism or a non-human organism (e.g., a prokaryotic organism).

In certain embodiments, the preparation is used for the detection of single-stranded DNA or double-stranded DNA (e.g., detection of single-stranded or double-stranded DNA in a prokaryotic cell).

In certain embodiments, the DNA detection is used to detect a tumor, a virus or a bacterium. Without being limited by theory, it is believed that due to the non-specific cleavage characteristics of Casσ on single-stranded DNA after target DNA recognition, when a target DNA (e.g., a tumor-specific label, virus or bacterium-specific label) is present, it is possible to achieve the detection of tumor, Ebola virus, avian influenza virus, African swine fever virus and other viruses or bacteria by adding a detectable single-stranded DNA and detecting the non-specific cleavage of the single-stranded DNA.

On the other hand, the present invention also provides a method for detecting whether a target nucleic acid is present in a sample, which comprises the following steps:

(1) contacting the sample with a labeled DNA probe and any of the following components: the complex of the present invention, the composition as described in the ninth aspect or the tenth aspect, or the kit of the present invention;

wherein, the guide sequence contained in the complex, composition or kit is capable of hybridizing with the target nucleic acid, and the DNA probe does not hybridize with the guide sequence;

in certain embodiments, the DNA probe emits a detectable signal after being cleaved;

(2) detecting the detectable signal generated by the cleavage of DNA probes by the protein contained in the complex, composition or kit cleaves the DNA probe, thereby determining whether the target nucleic acid is present in the sample.

In some embodiments, one end (e.g., 5' end) of the DNA probe is labeled with a fluorescent group, and the other end (e.g., 3' end) is labeled with a quenching group.

In some embodiments, the sequence of the target nucleic acid is a sequence obtained from a pathogen. In some embodiments, the pathogen is selected from the group consisting of a virus, a bacterium, a fungus, a protozoa, a parasite, or any combination thereof.

In some embodiments, the sequence of the target nucleic acid is obtained from the genome of a tumor cell.

The target nucleic acid detected in the present application can be a DNA or RNA. Therefore, in some embodiments, the method further comprises a step of contacting the sample with a reagent for reverse transcription. In some embodiments, the reagent for reverse transcription is selected from the group consisting of a reverse transcriptase, an oligonucleotide primer, a dNTP, or any combination thereof.

In some embodiments, the target nucleic acid is single-stranded or double-stranded. In some embodiments, the sequence of the target nucleic acid is a DNA or RNA sequence from a prokaryotic cell or a eukaryotic cell; or, the sequence of the target nucleic acid is a non-naturally occurring DNA or RNA sequence.

In some embodiments, the detectable signal is determined by one or more methods selected from the group consisting of imaging-based detection, sensor-based detection, color detection, gold nanoparticle-based detection, fluorescence polarization, colloidal phase transition/dispersion, electrochemical detection, and semiconductor-based sensing.

In some embodiments, the method further comprises a step of amplifying the target nucleic acid in the sample.

Cells and Cell Progeny

In some cases, the modification introduced into the cell by the method of the present invention may cause the cell and its progeny to be altered to improve the production of its biological product (e.g., antibody, starch, ethanol or other desired cell output). In some cases, the modification introduced into the cell by the method of the present invention may cause the cell and its progeny to comprise a change that causes a change in the produced biological product.

Therefore, in another aspect, the present invention also relates to a cell or progeny thereof obtained by the method as described above, wherein the cell comprises a modification that is not present in its wild type.

The present invention also relates to a cell product of the cell or progeny thereof as described above.

The present invention also relates to an in vitro, ex vivo or in vivo cell or cell line or progeny thereof, wherein the cell or cell line or progeny thereof comprises: the protein as described in the first aspect, the conjugate as described in the second aspect, the fusion protein as described in the third aspect, the isolated nucleic acid molecule as described in the fourth aspect, the complex as described in the fifth aspect, the isolated nucleic acid molecule as described in the sixth aspect, the vector as described in the seventh aspect, the composition as described in the ninth aspect, the composition as described in the tenth aspect, the kit or the delivery composition of the present invention.

In certain embodiments, the cell is a prokaryotic cell.

In certain embodiments, the cell is a eukaryotic cell. In certain embodiments, the cell is a mammalian cell. In certain embodiments, the cell is a human cell. In certain embodiments, the cell is a non-human mammalian cell, such as a cell of a non-human primate, cow, sheep, pig, dog, monkey, rabbit, or rodent (e.g., rat or mouse). In certain embodiments, the cell is a non-mammalian eukaryotic cell, such as a cell of a poultry bird (e.g., chicken), fish or crustacean (e.g., clam, shrimp). In some embodiments, the cell is a plant cell, such as a cell of a monocot or dicot plant a cell of a cultivated plant, or a cell of a food crop, such as cassava, corn, sorghum, soybean, wheat, oat or rice, such as algae, tree or production plant, fruit or vegetable (e.g., tree, such as citrus tree, nut tree; nightshade, cotton, tobacco, tomato, grape, coffee, cocoa, etc.).

In some embodiments, the cell is a stem cell or a stem cell line.

Definition of Terms

In the present invention, unless otherwise specified, the scientific and technical terms used herein have the meanings commonly understood by those skilled in the art. In addition, the molecular genetics, nucleic acid chemistry, chemistry, molecular biology, biochemistry, cell culture, microbiology, cell biology, genomics, and recombinant DNA operation steps used herein are all conventional steps widely used in the corresponding fields. At the same time, in order to better understand the present invention, the definitions and explanations of the relevant terms are provided below.

In the present invention, the expression "Casσ" refers to a Cas effector protein first discovered and identified by the inventors, which has an amino acid sequence selected from the following:

(i) a sequence as set forth in any one of SEQ ID NOs: 1 to 13;

(ii) a sequence having a substitution, deletion, or addition of one or more amino acids (e.g., a substitution, deletion, or addition of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids) as compared to the sequence as set forth in any one of SEQ ID NOs: 1 to 13; or (iii) a sequence having a sequence identity of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% as compared to the sequence as set forth in any one of SEQ ID NOs: 1 to 13.

The Casσ of the present invention is an endonuclease that binds to and cuts a specific site of a target sequence under the guidance of a guide RNA.

As used herein, the term "clustered regularly interspaced short palindromic repeats (CRISPR)-CRISPR-associated (Cas) (CRISPR-Cas) system" or "CRISPR system" is used interchangeably and has the meaning generally understood by those skilled in the art, which generally comprises a transcription product or other element related to the expression of a CRISPR-associated ("Cas") gene, or a transcription product or other element capable of directing the activity of the Cas gene. Such transcripts or other elements may comprise sequences encoding Cas effector proteins and guide RNAs comprising CRISPR RNA (crRNA), as well as trans-activating crRNA (tracrRNA) sequences contained in the CRISPR-Cas9 system, or other sequences or transcripts from CRISPR locus. In the Casσ-CRISPR system described in the present invention, the tracrRNA sequence is not required.

As used herein, the terms "Cas effector protein" and "Cas effector enzyme" are used interchangeably and refer to any protein greater than 800 amino acids in length presented in the CRISPR-Cas system. In some cases, such protein refers to a protein identified from the Cas locus.

As used herein, the terms "guide RNA" and "mature crRNA" are used interchangeably and have the meanings commonly understood by those skilled in the art. In general, the guide RNA may comprise a direct repeat sequence and a guide sequence or may consist essentially of or consist of a direct repeat sequence and a guide sequence (also referred to as a spacer in the context of an endogenous CRISPR system). In some cases, the guide sequence is any polynucleotide sequence that has sufficient complementarity with a target sequence to hybridize with the target sequence and guide the specific binding of the CRISPR/Cas complex to the target sequence. In certain embodiments, when optimally aligned, the degree of complementarity between the guide sequence and corresponding target sequence thereof is at least 50%, at least 60%, at least 70%, at least 80%, at least 90%, at least 95%, or at least 99%. Determining the optimal alignment is within the capabilities of a person of ordinary skill in the art. For example, there are publicly available and commercially available alignment algorithms and programs, such as, but not limited to, ClustalW, Smith-Waterman in Matlab, Bowtie, Geneious, Biopython, and SeqMan.

In some cases, the guide sequence has a length of at least 5, at least 10, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, or at least 50 nucleotides. In some cases, the guide sequence has a length of no more than 50, 45, 40, 35, 30, 25, 24, 23, 22, 21, 20, 15, 10 or fewer nucleotides. In certain embodiments, the guide sequence has a length of 10 to 30, or 15 to 25, or 15 to 22, or 19 to 25, or 19 to 22 nucleotides.

In some cases, the direct repeat sequence has a length of at least 10, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, at least 50, at least 55, at least 56, at least 57, at least 58, at least 59, at least 60, at least 61, at least 62, at least 63, at least 64, at least 65, or at least 70 nucleotides. In some cases, the direct repeat sequence has a length of no more than 70, 65, 64, 63, 62, 61, 60, 59, 58, 57, 56, 55, 50, 45, 40, 35, 30, 29, 28, 27, 26, 25, 24, 23, 22, 21, 20, 15, 10 or less nucleotides. In certain embodiments, the direct repeat sequence has a length of 55 to 70 nucleotides, such as 55 to 65 nucleotides, such as 60 to 65 nucleotides, such as 62 to 65 nucleotides, such as 63 to 64 nucleotides. In certain embodiments, the direct repeat sequence has a length of 15 to 30 nucleotides, such as 15 to 25 nucleotides, such as 20 to 25 nucleotides, such as 22 to 24 nucleotides, such as 23 nucleotides.

As used herein, the term "CRISPR/Cas complex" refers to a ribonucleoprotein complex formed by the binding of a guide RNA or mature crRNA to a Cas protein, which comprises a guide sequence that hybridizes to a target sequence and binds to the Cas protein. The ribonucleoprotein complex is capable of recognizing and cleaving a polynucleotide capable of hybridizing to the guide RNA or mature crRNA.

Therefore, in the case of forming a CRISPR/Cas complex, a "target sequence" refers to a polynucleotide targeted by a guide sequence designed to have targeting ability, such as a sequence complementary to the guide sequence, wherein the hybridization between the target sequence and the guide sequence will promote the formation of the CRISPR/Cas complex. Complete complementarity is not required, as long as there is sufficient complementarity to cause the hybridization and promote the formation of the CRISPR/Cas complex. The target sequence may comprise any polynucleotide, such as DNA or RNA. In some cases, the target sequence is located in the nucleus or cytoplasm of a cell. In some cases, the target sequence may be located in an organelle of a eukaryotic cell, such as a mitochondria or a chloroplast. A sequence or template that can be used for recombination into a target locus containing the target sequence is referred to as an "editing template", "editing polynucleotide", or "editing sequence". In certain embodiments, the editing template is an exogenous nucleic acid. In certain embodiments, the recombination is a homologous recombination.

In the present invention, the expression "target sequence" or "target polynucleotide" can be any polynucleotide that is endogenous or exogenous to a cell (e.g., a eukaryotic cell). For example, the target polynucleotide can be a polynucleotide present in the nucleus of a eukaryotic cell. The target polynucleotide can be a sequence encoding a gene product (e.g., a protein) or a non-coding sequence (e.g., a regulatory polynucleotide or a useless DNA). In some cases, it is believed that the target sequence should be associated with a protospacer adjacent motif (PAM). The exact sequence and length requirements for the PAM vary depending on the Cas effector enzyme used, but the PAM is typically a sequence of 2 to 5 base pairs adjacent to the protospacer sequence (i.e., the target sequence). Those skilled in the art are able to identify the PAM sequence for use together with a given Cas effector protein. Herein, "specific motif sequence recognized by Cas protein" or "motif sequence" refers to a PAM sequence.

In some cases, the target sequence or target polynucleotide may comprise multiple disease-related genes and polynucleotides and signal transduction biochemical pathway-related genes and polynucleotides. Non-limiting examples of such target sequences or target polynucleotides include those listed in U.S. provisional patent applications 61/736, 527 and 61/748,427 filed on Dec. 12, 2012 and Jan. 2, 2013, respectively, and international application PCT/US2013/074667 filed on Dec. 12, 2013, all of which are incorporated herein by reference.

In some cases, examples of target sequences or target polynucleotides include sequences related to signal transduction biochemical pathways, such as genes or polynucleotides related to signal transduction biochemical pathways. Examples of target polynucleotides include disease-related genes or polynucleotides. A "disease-associated" gene or polynucleotide refers to any gene or polynucleotide that produces a transcriptional or translational product at an abnormal level or in an abnormal form in cells derived from a disease-affected tissue compared to tissues or cells of a non-disease control. In cases where the altered expression is associated with the onset and/or progression of a disease, it may be a gene that is expressed at an abnormally high level; alternatively, it may be a gene that is expressed at an abnormally low level. A disease-associated gene also refers to a gene that has one or more mutations or genetic variations that are directly responsible for or in linkage disequilibrium with one or more genes responsible for the etiology of the disease. The transcribed or translated product may be known or unknown and may be at a normal level or abnormal level.

As used herein, the term "wild type" has the meaning commonly understood by those skilled in the art, which refers to a typical form of an organism, strain, gene, or a characteristic that distinguishes it from a mutant or variant form when it exists in nature, which can be isolated from a source in nature and has not been intentionally and artificially modified.

As used herein, the terms "non-naturally occurring" or "engineered" are used interchangeably and indicate artificial participation. When these terms are used to describe a nucleic acid molecule or polypeptide, it means that the nucleic acid molecule or polypeptide is at least substantially free from at least another component with which it is associated in nature or found in nature.

As used herein, the term "orthologue" or "ortholog" has the meaning commonly understood by those skilled in the art. As a further guide, an "ortholog" of protein, as described herein, refers to a protein belonging to a different species, and the protein performs the same or similar function as a protein that is its ortholog.

As used herein, the term "identity" is used to refer to the matching of sequences between two polypeptides or between two nucleic acids. When a position in both compared sequences is occupied by the same base or amino acid monomer subunit (e.g., a position in each of the two DNA molecules is occupied by adenine, or a position in each of the two polypeptides is occupied by lysine), then the molecules are identical at that position. The "percentage identity" between two sequences is a function of the number of matching positions shared by the two sequences divided by the number of positions compared×100. For example, if 6 out of 10 positions of the two sequences match, then the two sequences have an identity of 60%. For example, the DNA sequences CTGACT and CAGGTT have an identity of 50% (3 out of a total of 6 positions match). Typically, the two sequences are compared when they are aligned to produce maximum identity. Such an alignment can be achieved by using, for example, the method of Needleman et al. *J Mol. Biol.* 48: 443 to 453 (1970), which can be conveniently performed by a computer program such as the Align program (DNAstar, Inc.). The algorithm of E. Meyers and W. Miller (Comput. Appl Biosci., 4: 11 to 17 (1988)), which has been incorporated into the ALIGN program (version 2.0), can also be used to determine the percentage identity between two amino acid sequences using a PAM120 weight residue table, a gap length penalty of 12, and a gap penalty of 4. In addition, the percentage identity between two amino acid sequences can be determined using the algorithm of Needleman and Wunsch (J Mol Biol. 48:444 to 453 (1970)), which has been incorporated into the GAP program of the GCG software package (available at www.gcg.com), using a BLOSUM62 matrix or a PAM250 matrix as well as a gap weight of 16, 14, 12, 10, 8, 6 or 4 and a length weight of 1, 2, 3, 4, 5 or 6.

As used herein, the term "vector" refers to a nucleic acid delivery vehicle into which a polynucleotide can be inserted. When a vector is capable of expressing a protein encoded by the inserted polynucleotide, the vector is called an expression vector. The vector can be introduced into a host cell by transformation, transduction, or transfection so that the genetic material elements it carries are expressed in the host cell. Vectors are well known to those skilled in the art, including but not limited to: plasmid, phagemid, cosmid, artificial chromosome, such as yeast artificial chromosome (YAC), bacterial artificial chromosome (BAC) or P1-derived artificial chromosome (PAC); bacteriophage such as λ phage, or M13 phage and animal virus, etc. Animal viruses that can be used as vectors include but are not limited to retrovirus (including lentivirus), adenovirus, adeno-associated virus, herpes virus (e.g., herpes simplex virus), poxvirus, baculovirus, papillomavirus, papovavirus (e.g., SV40). A vector may contain a variety of elements for controlling expression, including but not limited to promoter sequence, transcription start sequence, enhancer sequence, selection element, and reporter gene. In addition, the vector may also comprise a replication origin.

As used herein, the term "host cell" refers to a cell that can be used to introduce a vector, including but not limited to prokaryotic cell such as *Escherichia coli* or *Bacillus subtilis*, fungal cell such as yeast cell or *Aspergillus*, insect cell such as S2 *Drosophila* cell or Sf9, or animal cell such as fibroblast, CHO cell, COS cell, NSO cell, HeLa cell, BHK cell, HEK 293 cell or human cell.

Those skilled in the art will understand that the design of an expression vector may depend on factors such as the choice of the host cell to be transformed, the desired expression level, etc. A vector can be introduced into a host cell to produce a transcript, protein, or peptide, including the protein, fusion protein, isolated nucleic acid molecule, etc., as described herein (e.g., CRISPR transcript, such as nucleic acid transcript, protein, or enzyme).

As used herein, the term "regulatory element" is intended to include a promoter, enhancer, internal ribosome entry site (IRES), and other expression control element (e.g., transcription termination signal, such as polyadenylation signal and poly-U sequence), which may be referred in details to Goeddel, GENE EXPRESSION TECHNOLOGY: METHODS IN ENZYMOLOGY 185, Academic Press, San Diego, California (1990). In some cases, regulatory elements include those sequences that direct the constitutive expression of a nucleotide sequence in many types of host cells and those sequences (e.g., tissue-specific regulatory sequences) that direct the nucleotide sequence to be expressed only in certain host cells. Tissue-specific promoters may primarily direct expression in the desired tissue of interest, such as muscle, neuron, bone, skin, blood, specific organ (e.g., liver, pancreas), or special cell type (e.g., lymphocyte). In some cases, regulatory elements may also direct expression in a timing-dependent manner (e.g., in a cell cycle-dependent or developmental stage-dependent manner), which may or may not be tissue or cell-type-specific. In some cases, the term "regulatory element" encompasses enhancer elements, such as WPRE; CMV enhancer; R-U5' fragment (Mol. Cell. Biol., Vol. 8(1), pp. 466 to 472, 1988); SV40 enhancer; and intron sequence between exons 2 and 3 of rabbit β-globin (Proc. Natl. Acad. Sci. USA., Vol. 78(3), pp. 1527 to 31, 1981).

As used herein, the term "promoter" has the meaning well known to those skilled in the art, which refers to a non-coding nucleotide sequence located upstream of a gene that can initiate the expression of a downstream gene. A constitutive promoter is a nucleotide sequence that, when operably linked to a polynucleotide encoding or defining a gene product, leads to the production of a gene product in a cell under most or all of the physiological conditions of the cell. An inducible promoter is a nucleotide sequence that, when operably linked to a polynucleotide encoding or defining a gene product, leads to the production of a gene product in a cell substantially only when an inducer corresponding to the promoter is present in the cell. A tissue-specific promoter is a nucleotide sequence that, when operably linked to a polynucleotide encoding or defining a gene product, leads to the production of a gene product in a cell substantially only when the cell is a cell of the tissue type corresponding to the promoter.

As used herein, the term "operably linked" is intended to mean that the nucleotide sequence of interest is linked to one or more regulatory elements in a manner that allows the expression of the nucleotide sequence (e.g., in an in vitro transcription/translation system or in a host cell when the vector is introduced into the host cell).

As used herein, the term "complementarity" refers to the ability of a nucleic acid to form one or more hydrogen bonds with another nucleic acid sequence by means of traditional Watson-Crick or other non-traditional types. The percentage of complementarity indicates the percentage of residues in a nucleic acid molecule that can form hydrogen bonds (e.g., Watson-Crick base pairing) with a second nucleic acid sequence (e.g., for 5, 6, 7, 8, 9, 10 out of 10, the complementarity is 50%, 60%, 70%, 80%, 90%, and 100%, respectively). "Complete complementarity" means that all consecutive residues of a nucleic acid sequence form hydrogen bonds with the same number of residues in a second nucleic acid sequence. As used herein, "substantially complementary" refers to a degree of complementarity of at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50 or more nucleotides, or refers to two nucleic acids that hybridize under stringent conditions.

As used herein, "stringent conditions" for hybridization refer to conditions in which a nucleic acid having complementarity to a target sequence predominantly hybridizes to the target sequence and does not substantially hybridize to non-target sequences. Stringent conditions are typically sequence-dependent and vary depending on many factors. In general, the longer the sequence, the higher the temperature at which the sequence specifically hybridizes to its target sequence. Non-limiting examples of stringent conditions are described in Tijssen, Laboratory Techniques In Biochemistry And Molecular Biology-Hybridization With Nucleic Acid Probes, Part I, Chapter 2, "Overview of principles of hybridization and the strategy of nucleic acid probe assay", (1993), Elsevier, New York.

As used herein, the term "hybridization" refers to a reaction in which one or more polynucleotides react to form a complex that is stabilized by hydrogen bonding of the bases between the nucleotide residues. Hydrogen bonding may occur by means of Watson-Crick base pairing, Hoogstein binding, or in any other sequence-specific manner. The complex may contain two strands forming a duplex, three or more strands forming a multi-stranded complex, a single self-hybridizing strand, or any combination thereof. A hybridization reaction may constitute a step in a broader process (e.g., initiation of PCR, or cleavage of polynucleotide by enzyme). A sequence capable of hybridizing to a given sequence is called the "complement" of the given sequence.

As used herein, the term "expression" refers to a process by which a polynucleotide is transcribed from a DNA template (e.g., transcribed into mRNA or other RNA transcript) and/or a process by which the transcribed mRNA is subsequently translated into a peptide, polypeptide or protein. The transcript and encoded polypeptide can be collectively referred to as "gene products". If the polynucleotide is derived from a genomic DNA, the expression may comprise splicing of mRNA in a eukaryotic cell.

As used herein, the term "linker" refers to a linear polypeptide formed by multiple amino acid residues connected by peptide bonds. The linker of the present invention can be an artificially synthesized amino acid sequence, or a naturally occurring polypeptide sequence, such as a polypeptide having a hinge region function. Such linker polypeptides are well known in the art (see, for example, Holliger, P. et al. (1993) Proc. Natl. Acad. Sci. USA 90: 6444 to 6448; Poljak, R. J. et al. (1994) Structure 2: 1121-1123).

As used herein, the term "treatment" refers to treating or curing a condition, delaying the onset of symptoms of a condition, and/or delaying the development of a condition.

As used herein, the term "subject" includes, but is not limited to, various animals, such as mammals, such as bovines, equines, ovines, porcines, canines, felines, lagomorphs, rodents (e.g., mice or rats), non-human primates (e.g., macaques or cynomolgus monkeys), or humans. In certain embodiments, the subject (e.g., a human) suffers from a condition (e.g., a condition caused by a disease-related gene defect).

Beneficial Effects of the Invention

Compared with the prior art, the Cas protein and system of the present invention have significant advantages. For example, the Cas effector protein of the present invention is smaller in molecular size than Cas9, C2c1, CasY and Cpf1 proteins, therefore has better transfection efficiency than Cas9, C2c1, CasY and Cpf1 proteins, and can improve the delivery efficiency in eukaryotic cells. For example, when using viral vectors (e.g., AAV vectors, etc.), it can be used for delivery to eukaryotic cells (e.g., mammalian cells, human cells, mouse cells, etc.), and can be used for research and/or clinical applications. Moreover, the Cas effector protein of the present invention can perform DNA cleavage in eukaryotic organisms. Compared with the reported FnCpf1 with 5'-TTN as PAM domain, the Cas protein of the present invention also has wider PAM recognition sites, which are 4 times larger than that of Cas9 or Cas12a.

The embodiments of the present invention will be described in detail below in conjunction with the accompanying drawings and examples, but those skilled in the art will understand that the following drawings and examples are only used to illustrate the present invention, rather than to limit the scope of the present invention. According to the following detailed description of the accompanying drawings and preferred embodiments, the various objects and advantages of the present invention will become apparent to those skilled in the art.

BRIEF DESCRIPTION OF THE DRAWINGS

FIG. 3 shows the verification results of the PAM domain in *Escherichia coli* in Example 3.

FIG. 4 shows the detection results of the editing activity in human cells in Example 4.

SEQUENCE INFORMATION

Figure 1:
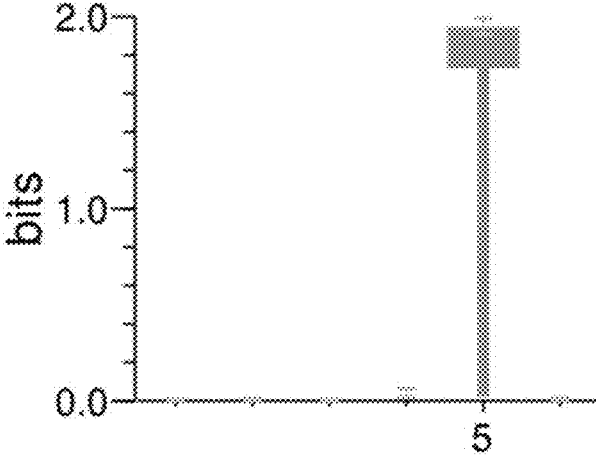
FIG. 1 shows the PAM structure and analysis results in Example 3.

The information of the partial sequences involved in the present invention is provided in Table 1 below.

TABLE 1

| Description of sequences | |
| --- | --- |
| SEQ ID NO: | Description |
| 1 | Amino acid sequence of Casσ-1 protein<br>MSNYKNIKFKLVPFSQKDLINMQLNVNLHQQCYREFVEQFCVLCNIPFPGLSKDQIE<br>QKRKQLNLSEDDEKDINYIKDLVKNKNNIGNSIYAFFTGTKKEMPSRKTDLTPLYRL<br>LKANILPFSLLKGRENYKKSIFQTVINQTLEKFKSYFKCNESVENNFKLSLNKDSNEE<br>QVLNESEMKDLQNLFENLSKNQSFSFFNFNKNWFSKDKIKTKLLNNETNKIKSLSSE<br>EIDLILSYKDKLYSNEFDLISMFVEFNLQKQKAESLKSQADLNLFKNNNYSFRIGSNY<br>ENFNLTQNNKDILLEINSSMGEKITFKIIPHKKTQIWNLEKNNVKITSGENLGNYKSV |

TABLE 1-continued

Description of sequences

SEQ
ID
NO:     Description

DVIKMKRPADIKAKLLKTSELNIEIKNNQIYCNFIYEYKCSDHGVYFFHCSGNKKPDE
        KNENILKERERTFSFIDLGLFPMYSISTFKYNNKSNDGEILVKSGSGNEKLDFGSAFKI
        HSIQIGKNSTNLNKIKQLLEKLKDLKTYLKFSKSISSFDENSYQRQLKTGVEISELNSL
        SFQKISEIKSINLGFNESFNKEYFLKLIENQTFTQKELLLLNCKIKDLFKILYKEYSNIK
        NSRIFKFNKEDDLICDGYYWLQVIDEIINIKKSLTYFNSKPSEKGNKSKFIFLKDFNYK
        NNFANNYAKIAASRLKKYCLEHKVDVCVFEKNLNNFLQSKDNDKKTNKTLINWAN
        RNLFEKIKLALEEHDICVSEVDGKHSSQLDPQTMNWGARDNLNGNGNKEKIFFERN
        GQIIQQNADLSASEVLAKRFFTRYEDIVHIYIDQKIKDDKTILKLVKGKVRVESYLKK
        TINSCYAIVDENGFLKPISKKDYNKFQELPSKPRTDIKSNEMYRHGSKWYHFQQHRE
        FQQDLLARGRELKKIA

2       Amino acid sequence of Casσ-2 protein
        MNKTDTQNNEQINKPTQLLNNKDIELTVKTVKSATVKVDNNSKKELFGLFNYFTSV
        ASGIKDKVYNLQSDEKTAPIFNDYVKQPQRGRSAATTLFTKLDAEKTYTSQHSFPGK
        WRDSGIFPLYNKESEKYDLSTHGYHYSANAEIHTQLDSHDECNKECEKEYAALRDE
        VNNYKYEFTLQFKAENAEKFYNFVEKLTLMGWRYDATFRSFFELHMHPKLKTGET
        TYRATYKLPSGKSKRYSFFRDDIADEIAKNPEFWPMLESSNAISWINSNNLLSRKKD
        KANYSSTSLIKSQIRLYLGNNGVPFTAREHDGRIYFSFRLPAINGEKGRMVEIPCSYK
        KVFNGKARKSCYLGGLTIEKTDAGKHIFKYSVNNKKPQVAELNECFLRLVVRNREY
        FNNVVAGKITDINTDHFDFYVDLPLNVKEDPIHDLSSTEVFGKNGLRSYYSSAYPEIK
        NLGSQIETGKNLTCPITKTHNIMGIDLGQRNPFAYCIKDNTGKLIAQGHMDGSKNET
        YKKYINFGKESTSVSHLIKETRSYLHGDPEAISKELYNEVAGFCNNPVSYEEYLKYL
        DSKKFLINKEDLSKNAMHLLRQKDHNWIGRDWLWYISKQYKKHNENRMQDADWR
        QTLYWIDSLYRYIDVMKSFHNFGSFYDKNLKKKVNGTVVGFCKTVHDQINNNNDD
        MFKKFTNELMSVIREHKVSVVALEKMDSMLGDKSRHTFENRNYNLWPVGQLKTF
        MEGKLESFNVALIEIDERNTSQVCKENWSYREADDLYYVTDGESHKVHADENAAN
        NIVDRCISRHTNMFSLHMVNPKDDYYVPTCIWDTTEESGKRVRGFLTKLYKNSDVV
        FTKKGDKLVKSKTSVKELKKLVGKTKEKRGQYWYRFEGKSWINEADRDTIILNAK
        KISRERDNGEQSTDTRSQNVTVSVLDVCETAEKKKLVLV 3       Amino acid sequence of Casσ-3 protein
        MKSIKSIKSIKTKVVKNNELKLIELSTWCSSICEQLERYIFILGKQIHDRDGVVVLDG
        AVERKIYCKKDKSLIAACEVVYKHFTDKSSKSRTFGSWFLGGKSEGDNTNKGRKST
        KEKTEKQIAKQIADKKELTDSLQLLWDKKLLPFPIDNKGYDFINTPRAKSYKWAITK
        TIHAKIKSYNEQCVETKKEYDALNAEINTYKTILFSGYSEKDIDDLQKFVDICEANNH
        RINYKFISFLKRKDLNFDEQTGKYRKEGKWIQHKNGKEVKSKYSMKDEIVEALYKY
        KSLTKNDVSVLCNEHQKEDEMGKVVHYNMKRYSDLLFRKKNKKEIPSYTKISLATS
        KIELGLNNVKYNVEQVEDKLIWTICDQTGKDIQFVTVYTRKKEDNRTNGKKGAGFY
        KGKHHQLEDLKIVPVGDIGTYDISFKVNGKRPFTGTLKEPNIICRGGKVFVQMPININ
        IDKTLNDARKKVLYAYRETYSGSVNGKKQKMIKIENSKIAESLKSLGRDAIVLGVDL
        GLRGLATAVVSHNGKNETVKSSQYIKGDIVEWEKYRVFNDNIREVKKYIFLTKKSY
        TATTEEYTEFYKECSKPEQDYLDSLKTYKDKNVKLNELKYTKNAWSVSKMFEDVS
        KMFETLKQDRLKYYDIFNMPYWAASLKNYMSLMKSYNYVGVDIKVSKEYMSKYQ
        SLYNNIKEDYAKKIGSYIVQLAVAKNCDIIVLEELKSNLGSVDRKSKRDNEMSLMW
        NCGRIKTHVENMAKDYGMFIDEVPEYGTSQVYHKTGNYGYRDEDNREIFWYEDNK
        DVAYIHADENAAINIAKRFLSQHTDNSSFSVILKGDAYYLNIASNSKRMRAAALKTF
        GDLNKPFKINANDKNGNLYKKTRIFKSDSRWIGVNDKDLYIEHIKSLRNLRVRQ 4       Amino acid sequence of Casσ-4 protein
        MPSFTKVDEDKIVLKLGNNYIPYGLSRISEDKMLWSFSSPQKKKLSIITNHRRVGKG
        KHFYLEGLEIADITKGDGDKTSPSGKYTISFSINGKQDVKGELKEPSFGLRNGNVYM
        FLPISIKQTDVFESRVEMRRLLSMAYQPTTVEDLILDDVETKQKTVKQGKKEVNTTN
        IAIQEAIKKHGRLLKVMGVDLGLRNFAFAIKNYDGHHDTLLRQLYSESDLNEKQRY
        TTLANDLSKVGNHIKFAAVFYGANDTEENTKMFDAECTDAESRTHLEWLRKAKKS
        GVLLKDLRKDKTWIVSIKYTELRNRLHALKFGRMKSYDYRNNLYWAATIKKFISLS
        ASFYGVGRPSRGKKDVRELKKKHTFFSTYQDLYNNVKEDYAKKVANLVVMTAKE
        NNVDIIVVENLTGHCGSKDYKTRAENEMSIMWNHGRIKTFIDCIANANGMLLAEVS
        EFETSQVYHETRNYGYRDKKMKEILWYMDSEGNVQYAHAEVNAAINIADRFLSQH
        TNLFSFPVCKSKKDENVYEIDIAEGKELEGQDEVKKAKKPKGGKRLNGAVVKTFGS
        TKIMFNGIVDKNKKGQIKTKTRVYNIDGEWGGKTQKDEYVDKIRKVVDAMSPEEK
        AKVKAALKKCFSS 5       Amino acid sequence of Casσ-5 protein
        MTKELSGVRVIELKTDLRKDQFWDRYERCFKTYHALYNEVPCWGLDWVEQKTQN
        QTSRELGCERVDLTAQRKALYERTDRTISYEQFSNCLKALWLGLLNCQQGNHMYT
        KLFEGAIQTDQMTAEDWAVLTEYVADPKSHNSQFLFRVSNTLKHIGFFSRPPFTATL
        FAPERKAITKDVMSDLKGWIEMKRMTEESYAAEEVQIQQMKAEVPVRIRQSLLRFF
        DTCIGLNLIGHEDERVHHYLRDCIIPALQQRTIPTEHFYLKSNRKDVGQKHIDFSLDIK
        FYELLAEMPELWNTLETSEDDLIPKPLILKHLHLLEAIMSHRAHRKTAAYAFVGEAD
        YHRFYYLLGGNYTKHLISATGSELPDRVIWDNDKDVLMRNGRKVERLYVKVGDRK
        ENFNFEVYTIAMNTKGLRGHRSTLKPTSYLQDLQIWSNPEGESTYLNFVRKGTERSA
        ICKEPVLVYRNGAFFLRLSMSVEGMRASEEHIALQYYLSAAATGSDLSKDTEKTVER
        FNLIQGKTYKVMSVDLGIRSPFAWAVTESTITGVANPSQILNSGEMEIADDPDYTELF
        YAYKNLGHLIGQVKSSSKGKGLKADSHLVDMIHTVQRFFADYKVAGQRRSQIFEQF TABLE 1-continued Description of sequences SEQ
ID
NO:     Description SKDPDPLYQMDQMMKRYENNLESVKKDFSFLINILFKYVTLQFGALRNRRRSYLSQ
NQMADQKFDQDFKWLNILEQRKRVTRSLSYLGTDNSRIPICLEQQKLDYNGCKDNF
LKQLASKIVRIAHQNDCCLIVLEDLEGYGKTLNQRDENFLTAFWSPKRVKDAIINAA
QWYGIGVVTVSEAQTSQVHHESGRIGYRKGRDLFFLTPDGQIESVPSDINAAKNIGH
RFFSRHTDLHQVYLKGSDEGAKRMKGCLLYQFGSLEAARTHLTGTGPTWYLDGVE
WIDKTERNLRRDLLKQRVEIEKMPF 6       Amino acid sequence of Casσ-6 protein
MKSIKSIKSIKTKVVKNNELKLIELSTWCSSICEQLERYIFILGGKQIHDRDGVVVLDG
AVERKIYCKKDKSLIAACEVVYKHFTDKSSKSRTFGSWFLGGKSEGDNTNKGRKST
KEKTEKQIAKQIADKKELTDSLQLLWDKKLLPFPIDNKGYDFINTPRAKSYKWAITK
TIHAKIKSYNEQCVETKKEYDALNAEINTYKTILFSGYSEKDIDDLQKFVDICEANNH
RINYKFISFLKRKDLNFDEQTGKYRKEGKWIQHKNGKEVKSKYSMKDEIVEALYKY
KSLTKNDVSVLCNEHQKEDEMGKVVHYNMKRYSDLLFRKKNKKEIPSYTKISLATS
KIELGLNNVKYNVEQVEDKLIWTICDQTGKDIQFVTVYTRKKEDNRTNGKKGAGFY
KGKHHQLEDLKIVPVGDIGTYDISFKVNGKRPFTGTLKEPNIICRGGKVFVQMPININ
IDKTLNDARKKVLYAYRETYSGSVNGKKQKMIKIENSKIAESLKSLGRDAIVLGVDL
GLRGLATAVVSHNGKNETVKSSQYIKGDIVEWEKYRVFNDNIREVKKYIFLTKKSY
TATTEEYTEFYKECSKPEQDYLDSLKTYKDKNVKLNELKYTKNAWSVSKMFEDVS
KMFETLKQDRLKYYDIFNMPYWAASLKNYMSLMKSYNYVGVDIKVSKEYMSKYQ
SLYNNIKEDYAKKIGSYIVQLAVAKNCDIIVLEELKSNLGSVDRKSKRDNEMSLMW
NCGRIKTHVENMAKDYGMFIDEVPEYGTSQVYHKTGNYGYRDEDNREIFWYEDNK
DVAYIHADENAAINIAKRFLSQHTDNSSFSVILKGDAYYLNIASNSKRMRAAALKTF
GDLNKPFKINANDKNGNLYKKTRIFKSDSRWIGVNDKDLYIEHIKSLRNLRVRQ 7       Amino acid sequence of Casσ-7 protein
MNKTDTQNNEQINKPTQLLNNKDIELTVKTVKSATVKVDNNSKKELFGLFNYFTSV
ASGIKDKVYNLQSDEKTAPIFNDYVKQPQRGRSAATTLFTKLDAEKTYTSQHSFPGK
WRDSGIFPLYNKESEKYDLSTHGYHYSANAEIHTQLDSHDECNKECEKEYAALRDE
VNNYKYEFTLQFKAENAEKFYNFVEKLTLMGWRYDATFRSFFELHMHPKLKTGET
TYRATYKLPSGKSKRYSFFRDDIADEIAKNPEFWPMLESSNAISWINSNNLLSRKKD
KANYSSTSLIKSQIRLYLGNNGVPFTAREHDGRIYFSFRLPAINGEKGRMVEIPCSYK
KVFNGKARKSCYLGGLTIEKTDAGKHIFKYSVNNKKPQVAELNECFLRLVVRNREY
FNNVVAGKITDINTDHFDFYVDLPLNVKEDPIHDLSSTEVFGKNGLRSYYSSAYPEIK
NLGSQIETGKNLTCPITKTHNIMGIDLGQRNPFAYCIKDNTGKLIAQGHMDGSKNET
YKKYINFGKESTSVSHLIKETRSYLHGDPEAISKELYNEVAGFCNNPVSYEEYLKYL
DSKKFLINKEDLSKNAMHLLRQKDHNWIGRDWLWYISKQYKKHNENRMQDADWR
QTLYWIDSLYRYIDVMKSFHNFGSFYDKNLKKKVNGTVVGFCKTVHDQINNNNDD
MFKKFTNELMSVIREHKVSVVALEKMDSMLGDKSRHTFENRNYNLWPVGQLKTF
MEGKLESFNVALIEIDERNTSQVCKENWSYREADDLYYVTDGESHKVHADENAAN
NIVDRCISRHTNMFSLHMVNPKDDYYVPTCIWDTTEESGKRVRGFLTKLYKNSDVV
FTKKGDKLVKSKTSVKELKKLVGKTKEKRGQYWYRFEGKSWINEADRDTIILNAK
KISRERDNGEQSTDTRSQNVTVSVLDVCETAEKKKLVLV 8       Amino acid sequence of Casσ-8 protein
MKKPKQNIEETDLKITTPKTATIKATNLDDKMRLFTFFNGFTTVCSKVKDDIYNFGQ
NEDTLPVYTDYIKASQRARMCATTLATKSECDFAKKYGEHFPLPHYNQEGMNYTT
HQHTYSVNSAVHTQLDSLNECDKLINGEYVKLKKTVDELEEKLTEEHGKEPLDFLV
KFVDEQILLGWRFDGKFRLFFEVAMLPELKNGNIIYKKAYKTSGGKGRRYSFYNPS
VADNISKNPTVWNLLSDVKAVDYISLSNSLLRKKPHAQYTNTTLNRAQVRPTFGNN
GVPFSISVSDDDYVYIRFRLPKKDGEEKGQEISVKCSYKTSYKGKRSKTLRKSCYLG
NLKIEENGKGKYICKYNINGRETTTAELNECFLRVRINNNRWFNKYLNGTLTKEDG
VLKSEYFDFYFDLCLNVHQKSIHGLTNSEIFGGKGKSIRSYYSTSYPEVKNLDGQKNI
KTDPGCYVDKPHNIMGIDLGQRNPFAWAVLDQNGNVKDVGHLDGAENDTYKDYL
TFSNRCKDVKNLILQSRDYLYGDDEAIDETLFDSVVQFVNSNITLNKYKSYLDEKKS
LINKESLEKNRLYELKKKDHGWFVRDCLWFLTKEYHRINSERKTHSDWRYTLYWV
DAIHRFIDVNKSFNSLGSYYDKKQSKSINGIQKDFCRSYWNQIDNLNEDTLKKFVFE
LLPVIKKNNVCLIAIEELKSMLGDDDKRAEDNRLYNLWPVGQLKTFLEGKLLPYNV
AVMEVSEQNTSQIVNGQWSYREGDDLYYVKNNDNNTMCKTHADENAAINIALRA
YSHHTNLYSIYMINPIDDYYVPSCIWNNKDEGSKRIRGFLTKTYGTSDVVFIKKNEKL
VKSDVSIKDVKRIVKNIGNEKNKKSEIWYRMNDIEWIDEGSRDIIINTIKSKVR 9       Amino acid sequence of Casσ-9 protein
MTDKSISFKQFSQILNVLYKCIVISGKGRGLTSIILGQPQCKDSLTSADWGNLETLSA
KDELTPAEVKDITKDLMYRASNTLVSIGFRNRSPFKLTLTSGERYAVVENVHRSLKS
WVEVDKITRENYLNEEIALSDAFNNIDETLLPTLKEFFDACMNENIIHHFDARVYAY
TRDCVIPALVAGLEIKDHFYIDGRDKAKRDYSLQGYAELLKGFPKLWQGVDPEILA
KLYILEAQMDHKKHRPCAAYAFIGEDSYSRVQYLLGNNYTSFSPYALGVDLDDVTC
GDDAEADTQFPKNKVIQFSQGKKVTKLSLTVSRGKEDTNKYSFDVFLADKYSNGSY
KPSPYFSDLSVWVSEIGMLMEFTRKGERVQAIVKEPSLIYRKGAFYVRLNMGVIQDT
SPEINDLYWYLSSGAPMSMTDRSKASETPKNTERLESIKGKSYRFLGIDLGLRSPFA
WAVGEASISGVINKPTIIATGDYTTARDTRYDTLFFALKNAGKVIGVTKSLANGKDA
SFNGLMGTITAAREYLAHYSGVATHKVAAIQAFCQDDNPLETLKGLLKSYNNDLVT
LKKDPRFIGGILLRYARLLKGELVTSRKMHLREHSVESKFGQEYMWLNILEREKRV TABLE 1-continued Description of sequences

| SEQ ID NO: | Description |
|---|---|

CRSLSYLGLGNDRDSVIMGNLTTPYNHCKENLLKQLAARIVSLAVENKCHVIVMES
LGGSNKSMNTRGQNFLEAFWSPQKIKDTIINAAAWHGIMVAEVSESQTSQVCFETG
TFGHRDRASLYFLDKNGDLQETHADMNAAKNLVERFTTRHTNLRQVNMDSLPKEG
PDKTPKKSPSKKKMEKAKMDNPEDQSKRLKGFLTVKFGNVKAAQEYFASRKPEQS
YSGKKDEAIYWYLDGDEWITKKEKESRVSVIEGLVGLKEVAV

10    Amino acid sequence of Casσ-10 protein
MAFQSKRRIVGNLVKEQCLKAVDGKVILTDQEKRELIKRYELHLEPYKWLLRLFLS
GYEGRDDGFYEELGNTNLDKEKFFEVTAGLRDALLRQSGSSRALKSSMLGKCPPSA
AVGKAAKHIQALRDAGILPFKTGLTSGEDYNVLQQAVQQLRSWVACDHRTREAYA
EQQEKTSQAEEAAKKAVNEVKPEDAKSLERHERALTKLRKQERRLERMRSHAQFSL
DEMDCTGYSLCMGANYLKDYCLEKEGRGLRLTLKNSTMAGSYYVSVGDGQHAGM
KNPGTPAGGSPEKGRRRNILFDFAVEKCGDNYLFRYDENGKRPRAGVVKEPRFCWR
RKGNSVELYLAMPINIENSMRNIFVGKQKSGKHSAFTRQWPKEVEGLDELRDAVVL
GVDIGINRAAFCAALKTSRFENGLPADVQVMDTTCDALTEKGQEYRQLRKDATCLA
WLIRTTRRFKADPGNKHNQIKEKDVERFDSADGAYRRYMDAIAEMPSDPLQVWEA
ARITGYGEWAKEIFARFNHYKHEHACCTVSLSLSDRLVWCRLIDRILSLKKCLHFGG
YESKHRKGFCKSLYRLRHNARNDVRKKLARFVVDAAVDAGASVIAMEKLPSSGGK
QSRDDNRIWDLMAPNTLATTVCLMAKVEGIGFVQVDPEFTSQWVFEQRVIGDREGR
IVSCLDAEGVRRDYDADENAAKNIAWLALTREAEPFCMAFEKRNGVVEPKGFRFDI
PEEPTREQDESNQDFKKRLEERDKLIERLQAKSDRMRAIVRRLFGDRRPWDAFADRI
PEGKSKRLFRHRDGLVLNKPFKGLCGSENSEQKASARNSR 11    Amino acid sequence of Casσ-11 protein
MDTDTELSDEVELSDEVELSDEVELSDEVELTVKKVKTTTVKVDNNFKKELFELFN
HFTSVASGIKDRLYDLQFDENTASIFKGYIKEAKRGHGAATTVFTKLNPKKIYSGKK
SFPRDYRDRGIFPFYNKESGKYDLSTCGYHYSANAEIHTQLNSHDECNKQCEKEYA
ALEKERNKYKHEFTRQFKAENVEKFSNFVEKLTLMGWRYDATFRNFFELHMHPKL
KTSETTYRATYKLPSGKSKRYSFSRDDIADEIAKNPEFWPMLESSNAVSWINSNNLL
SRKKEKANYSSTSLIKSQIRLYLGDNGVPFTAREHDGRIYFSFRLPSINGEKGRNVEIP
CSYKKVFNGKARKSCYLGGLTIENTGGSKHIFKYSVNNKKPQVAELNECFLRLVVR
NHGYFNKMVNGKLTDKDGKLHADYFDFCIDLPLNVKEDPIHDLTYQEINGVKANPE
KNIEKKVGLLGFYQSAYPEIKNLGSQIETGKNLTCPITKTHNIMGIDLGQRNPPAYCI
KDNNGKFIAKDHMDGSKNETYKKYINFGKESTSVSHLIKETRSYLHGDPEAISKELY
NEVSGLCNSPLSYEEYLKYLDSKKFLINKEDLNKNAMHLLRQKDHNWIGRDWLWY
ISKQYKKHNENRMQDADWRQTLYWIDSLYRYIDVMKSFHNFGSFYDKNLKKKVN
GTAVGFCKTIYDQINNNNKDMFKKFTNELIPIIRKHKVSVVALEKMESMLGDKSRNT
FENRNHNLWPVGQLKTFIENKLDGFNVIVVEVEDERNTSQMCDGNWSYREADDLYY
VKDGELREVHADENAANNIVDRCISRHTNIFSLYMTNPMDDYYVPACIWDRSENGK
RGRGFLTKMYKNSDVVFTKKDDKLVKSKMSVKELKKLVDKTKEKRGQYWYLFEG
KSWINAADRDTIISNAKKLFRERDGGEQSTDTRSQNVTVSVLDVCETVEKKKLVLV 12    Amino acid sequence of Casσ-12 protein
MSTEVDVKTINLKIAKKGGVYPILEQSIKENCKSNDLLEFFMVLNRLQTYYIESNEEI
LVDFPKKYDELFDIVKNNDSSVTREYFDSLCDKYITEVCANGFVNNVYIAHNKNQE
LNWAETSNDRKIKSNKTFMFGKIKGLIRDKFGREELSDKDATKQLCEDIFNLFILNN
ANIELDEKYNIIKDELIQIWNERNKEFIHIKDITLLFRQWGILPTYDNITHNCELKAIIA
EPVRRFKSWLECNSEANKNYDTEREKCTKYMDVMDSDLTVEFSKMVTELGNPFGA
NDKNIYKYFNQKFLLFFKQVVQPKFVNGEPLDESNGSYSGEIKINSAGKVENYSIAV
SVIDTIKKYPTIWSDRSWGESVISTVAKIDPQYGIDDITDDMQVSPFYLFYGYFTAYN
YIQQHKRNAKYTPISKDSLPSLYLGNNYIPFKIDCENVDDDRFYITIKNMNNLKLNVL
YRKPKLKFAKTKEKTKRNKCYFDNLKITNTNNNFKFEYNINGDPNRSVVAYLKEPV
IRYNNRKDYFYLSATISKDVETDSELTSACWSKISNDTARRVNAEQYFNDNGVNIVG
IDLGMNPIIAYSVLHYKNNEFIDLNITGKIADKDKHPNLNYKRMYEKRSEIKKLKTLI
KMIPDYVNSDSNIFEGDNNVFKQLDKKSKGRFRSSEYMGYYDKLNVDGKFISELEIV
KKVVNTKHYKNDTEKNNDIMRVYKGNKKNIIKKEIDTHRHQIHSIKDMNRRSDESN
LCYVYDMVSYIDDFKKLVTSYNKIGEDYNNPIKPLSDPMLFSKSKLYEYRQNIRDNF
LKDICYQMVKIAKQYNAVLVHEHFEQRKGGIDRVNNILMALFTPNDIIKKLKCVAK
REGVLVFNTNKNHTSQYVYNKNTVGYRDSNNKHNLYYIEDETTRKLGVVDSDINA
SKNIAARPFNKPLYAIKVKNYDDGLFLSDYNNKYVLYKKDGDKYVAIGDTYRIDKK
KIKQGSVTLYLHNGYYVDGEYKNNYIENIKKLVL 13    Amino acid sequence of Casσ-13 protein
MAFQSKRRIVGNFVKEQCLKAVDGKVILTDQEKRELIKRYELHLEPHKWLLRLFLS
GYEGRDDGFYEELGNTNLDKEKFFEVTAGLRDALLRQSGSSRALKSSMLGKCPPSA
AVGKAAKHIQTLRDAGILPFKTGLTSGEDYNVLQQAVQQLRSWVACDHRTREAYA
EQQEKTSQAEEAAKKAANEVKPEDAKSLERHERVLTKLRKQERRLERMKSHAQFS
LDEMDCTGYSLCMGANYLKDYCLEKEGRGLRLTLKNSTMAGSYYVSVGDGQHAG
MKNPGTPAGGSPEKGRRRNILFDFTVEKCGDNYLFRYDENGKRPRAGVVKEPRFC
WRRKGNSVELYLAMPINIENSMRNIFVGKQKSGKHSAFTRQWPKEVEGLDELRDAV
VLGVDIGINRAAFCAALKTSRFENGLPADVQVMDTTCDALTEKGQEYRQLRKDATC
LAWLIRTTRRFKADPGNKHNQIKEKDVERFDSADGAYRRYMDAIAEMPSDPLQVW
EAARITGYGEWAKEIFARFNHYKHEHACCAVSLSLSDRLVWCRLIDRILSLKKCLHF
GGYESKHRKGFCKSLYRLRHNARNDVRKKLARFIVDAAVDAGASVIAMEKLPSSG TABLE 1-continued Description of sequences

| SEQ ID NO: | Description |
|---|---|
| | GKQSKDDNRIWDLMAPNTLATTVCLMAKVEGIGFVQVDPEFTSQWVFEQRVIGDR |
| | EGRIVSCLDAEGVRRDYDADENAAKNIAWLALTREAEPFCMAFEKRNGVVEPKGL |
| | RFDIPEEPTREQDESDQDFKKRLEERDKLIERLQAKADRMQAIVQRLFGDRRPWDAF |
| | ADRIPEGKSKRLFRHRDGLVLNKPFKGLCGSENSGQKASARNSR |
| 14 | Encoding nucleotide sequence of Casσ-1 |
| | ATGAGCAACTACAAAAACATTAAGTTCAAGTTGGTTCCGTTCAGTCAAAAGGAT |
| | CTTATAAACATGCAGCTAAACGTGAATCTCCACCAGCAGTGTTATAGAGAGTTC |
| | GTGGAGCAGTTCTGCGTCCTCTGTAATATCCCCTTTCCTGGGCTTAGTAAAGATC |
| | AAATTGAGCAGAAGCGGAAACAATTAAATCTGTCTGAAGACGACGAGAAGGAC |
| | ATCAACTACATCAAGGACCTTGTAAAAAATAAGAATAACATCGGCAATTCAATC |
| | TATGCTTTTTTCACTGGTACAAAGAAGGAAATGCCAAGCAGAAAGACTGATTTA |
| | ACACCTCTTTACCGCCTCCTTAAGGCTAACATACTGCCCTTTAGCCTCCTCAAAG |
| | GGCGAGAGAACTATAAGAAAAGCATATTCCAAACTGTTATTAACCAGACACTGG |
| | AAAAGTTTAAGTCATATTTCAAGTGCAATGAATCAGTTGAAAACAACTTCAAAC |
| | TGTCTCTGAACAAGGACTCAAATGAGGAGCAAGTCCTGAATGAAAGCGAAATGA |
| | AAGACCTCCAAAACCTATTCGAGAATTTGTCTAAAAATCAGTCTTTTTCCTTCTT |
| | CAACTTCAATAAGAACTGGTTCTCCAAGGACAAGATCAAGACGAAACTCCTCAA |
| | TAACGAGACCAACAAAATTAAGTCGTTGTCATCTGAAGAGATCGACCTGATCCT |
| | TAGTTATAAGGATAAGTTGTACTCCAACGAATTTGATCTGATTTCCATGTTCGTG |
| | GAGTTCAACTTACAGAAACAGAAGGCGGAGTCCTTGAAATCACAGGCGGACTTG |
| | AACCTCTTCAAGAACAACAACTATTCTTTTCGGATTGGAAGCAACTATGAAAAC |
| | TTTAATCTAACTCAAAATAACAAGGACATCCTGCTGGAAATCAATTCTTCAATGG |
| | GTGAGAAGATTACCTTTAAGATCATTCCGCATAAGAAAACCCAGATCTGGAATT |
| | TAGAGAAGAATAATGTTAAGATAACTTCGGGCGAGAACCTGGGGAATTACAAAT |
| | CGGTGGACGTCATCAAGATGAAGCGGCCAGCAGACATTAAGGCAAAGCTGCTG |
| | AAGACGTCAGAGCTGAATATCGAGATCAAGAACAACCAAATCTATTGCAACTTC |
| | ATTTATGAGTACAAGTGCTCCGATCATGGCGTGTACTTCTTTCACTGCAGTGGCA |
| | ACAAGAAGCCAGATGAGAAGAATGAGAATATTCTAAAGGAGAGGGAGAGGACC |
| | TTTAGTTTCATTGATCTCGGTCTTTTTCCGATGTATTCCATCTCCACATTTAAGTA |
| | CAATAATAAGAGCAATGATGGTGAGATCCTAGTCAAGTCGGGATCTGGGAACGA |
| | GAAACTCGACTTCGGCTCTGCCTTCAAAATTCATTCAATCCAGATTGGAAAGAA |
| | CAGCACAAATCTCAACAAAATTAAGCAACTTCTTGAGAAGCTGAAAGACCTGAA |
| | GACCTACCTCAAATTCTCTAAGAGCATAAGCAGCTTCGACGAGAACAGCTACCA |
| | GCGCCAGCTTAAAACGGGAGTGGAGATCAGCGAGCTGAACAGCCTGTCGTTCCA |
| | AAAAATATCAGAAATTAAGTCCATTAATCTCGGCTTCAATGAATCCTTCAATAA |
| | AGAGTATTTTCTAAAGCTGATCGAAAACCAAACATTCACGCAGAAGGAGTTACT |
| | ACTGTTAAACTGCAAGATCAAAGACCTCTTCAAAATTCTCTACAAAGAATATTCT |
| | AACATCAAAAACAGTCGCATATTTAAATTCAATAAAGAAGATGATCTCATCTGT |
| | GACGGGTACTACTGGCTGCAGGTCATTGATGAAATAATCAATATTAAAAAGTCG |
| | CTTACTTACTTCAACAGCAAGCCGTCGGAGAAGGGGAACAAAGTAAGTTTATT |
| | TTCTTGAAGGATTTTAACTACAAAAATAATTTTGCAAACAACTACGCGAAAATC |
| | GCTGCGTCACGTCTCAAAAAATATTGTTTGGAGCACAAGGTTGACGTGTGTGTTT |
| | TTGAGAAGAACCTCAACAACTTTCTGCAAAGCAAGGACAACGATAAAAAGACA |
| | AATAAGACCTTGATTAATTGGGCGAACCGCAATCTTTTTGAGAAAATTAAATTG |
| | GCGCTGGAAGAGCATGACATCTGCGTGAGTGAGGTTGATGGTAAGCATTCGTCC |
| | CAGCTGGACCCGCAAACCATGAACTGGGCGCTAGAGATAATCTTAATGGAAAT |
| | GGTAACAAAGAAAAGATCTTTTTTGAAAGGAACGGGCAGATAATACAACAGAA |
| | CGCCGACCTCAGTGCTTCTGAAGTCCTCGCAAAACGATTCTTCACCAGGTACGA |
| | GGACATCGTGCACATCTACATTGACCAGAAAATAAAGGATGACAAAACGATCCT |
| | TAAGTTGGTGAAGGGTAAGGTGCGCGTAGAATCTTATCTGAAGAAGACTATAAA |
| | TTCCTGCTACGCCATAGTAGATGAAAATGGCTTCCTTAAACCTATATCTAAGAAA |
| | GACTACAACAAGTTCCAGGAGCTGCCGTCCAAGCCTCGCACAGATATTAAGTCG |
| | AATGAGATGTACAGACATGGCAGCAAGTGGTATCACTTCCAGCAACATAGGGAG |
| | TTTCAGCAGGACCTGTTGGCACGGGGCAGAGAGCTGAAGAAGATAGCCTGA |
| 15 | Encoding nucleotide sequence of Casσ-2 |
| | ATGAACAAGACGGACACCCAGAACAACGAGCAGATCAACAAGCCGACGCAGCT |
| | GCTCAACAACAAGGACATTGAGCTGACGGTGAAGACCGTGAAGTCCGCGACCGT |
| | GAAGGTGGACAACAACAGCAAGAAGGAGCTGTTCGGCCTGTTCAACTACTTCAC |
| | CAGCGTCGCCTCCGGCATCAAGGACAAGGTGTACAACCTGCAGTCCGATGAGAA |
| | GACCGCCCCGATCTTCAACGACTACGTGAAGCAGCCGCAGCGCGGCAGGTCTGC |
| | TGCTACTACTCTGTTCACCAAGCTGGACGCGGAGAAGACCTACACCTCTCAGCA |
| | CTCCTTCCCCGGCAAGTGGAGGGATTCCGGCATCTTCCCGCTGTACAACAAGGA |
| | GTCCGAGAAGTACGACCTGTCCACCCACGGCTACCACTACTCCGCTAACGCCGA |
| | GATCCACACCCAGCTGGACAGCCATGACGAGTGCAACAAGGAGTGCGAGAAGG |
| | AGTACGCCGCCCTTAGGGACGAGGTGAACAACTACAAGTACGAGTTCACGCTTC |
| | AGTTCAAGGCCGAGAACGCCGAGAAGTTCTACAACTTCGTGGAGAAGCTGACGC |
| | TGATGGGCTGGAGGTACGACGCTACGTTCAGGTCTTTCTTCGAGCTGCACATGCA |
| | CCCAAAGCTCAAGACCGGCGAGACAACGTACAGGGCCACCTACAAGCTGCCGTC |
| | CGGCAGTCTAAGAGGTACAGCTTCTTCAGGGACGACATCGCCGACGAGATTGC |
| | CAAGAACCCAGAGTTCTGGCCAATGCTGGAGTCCTCCAACGCCATCTCCTGGAT |
| | CAACTCCAACAACCTGCTCAGCAGGAAGAAGGACAAGGCCAACTACTCCTCAAC |
| | CTCCCTCATCAAGTCCCAGATTCGCCTGTACCTGGGCAACAACGGCGTGCCATTC |

TABLE 1-continued

Description of sequences

| SEQ ID NO: | Description |
|---|---|

ACCGCTAGGGAGCACGATGGCAGGATTTACTTCAGCTTCAGGCTCCCGGCCATC
AACGGCGAGAAGGGCAGGATGGTCGAGATCCCATGCAGCTACAAGAAGGTGTT
CAACGGCAAGGCCAGGAAGAGCTGCTACCTTGGCGGCCTTACCATCGAGAAGAC
CGACGCTGGCAAGCATATCTTCAAGTACTCCGTGAACAACAAGAAGCCGCAGGT
GGCCGAGCTGAACGAGTGCTTCCTGAGGCTGGTTGTGAGGAATAGGGAGTACTT
CAACAACGTGGTGGCCGGCAAGATCACCGACATCAACACCGATCACTTCGACTT
CTACGTCGATCTGCCGCTGAACGTGAAGGAGGACCCGATCCATGATCTGAGCAG
CACGGAGGTGTTCGGCAAGAATGGCCTGAGGTCCTACTACTCCTCCGCCTACCC
AGAGATTAAGAACCTGGGCTCCCAGATCGAGACGGGCAAGAACCTGACCTGCCC
GATCACCAAGACACACAACATCATGGGCATCGACCTTGGCCAGCGCAACCCATT
CGCCTACTGCATTAAGGACAACACCGGCAAGCTCATCGCCCAGGGCCATATGGA
CGGCTCTAAGAACGAGACGTACAAGAAGTACATCAATTTCGGCAAGGAGTCCAC
CTCCGTCTCCCACCTTATTAAGGAGACGAGGTCCTACCTGCACGGCGATCCAGA
GGCTATCTCCAAGGAGCTGTACAATGAGGTCGCCGGCTTCTGCAACAACCCGGT
TTCCTACGAGGAGTACCTTAAGTACCTGGACTCCAAGAAGTTCCTGATCAACAA
GGAGGACCTGTCCAAGAATGCCATGCACCTGCTGAGGCAGAAGGACCACAACTG
GATCGGCAGGGACTGGCTGTGGTACATCAGCAAGCAGTACAAGAAGCACAACG
AGAACAGGATGCAGGACGCCGACTGGAGGCAGACTCTGTACTGGATCGACAGC
CTGTACAGGTACATCGATGTGATGAAGTCCTTCCACAACTTCGGCAGCTTCTACG
ACAAGAACCTGAAGAAGAAGGTGAACGGCACCGTGGTGGGCTTCTGCAAGACG
GTTCACGACCAGATCAACAACAACAACGATGACATGTTCAAGAAGTTCACCAAC
GAGCTGATGAGCGTGATCAGGGAGCACAAGGTGAGCGTGGTGGCGCTTGAGAA
GATGGACAGCATGCTGGGCGACAAGTCAAGGCACACGTTCGAGAACAGGAACT
ACAACCTGTGGCCGGTGGGCCAGCTGAAGACATTCATGGAGGGCAAGCTGGAGT
CCTTCAACGTGGCCCTGATCGAGATCGATGAGAGGAACACCAGCCAGGTGTGCA
AGGAGAACTGGTCCTACAGGGAGGCGGATGACCTGTACTACGTGACGGACGGC
GAGTCCCACAAGGTGCATGCTGACGAGAACGCGGCCAACAACATCGTGGACAG
GTGCATTTCCAGGCACACCAACATGTTCAGCCTGCACATGGTGAACCCCAAAGGA
CGACTACTACGTGCCGACCTGCATTTGGGACACCACGGAGGAGTCCGGCAAGAG
GGTTAGGGGCTTCCTGACCAAGCTCTACAAGAACTCCGACGTGGTCTTCACCAA
GAAGGGCGACAAGCTGGTGAAGAGCAAGACCTCCGTGAAGGAGCTGAAGAAGC
TGGTGGGCAAGACCAAGGAGAAGAGGGGGCCAGTACTGGTACAGGTTCGAGGGC
AAGAGCTGGATCAACGAGGCCGACAGGGACACCATCATCCTGAACGCCAAGAA
GATCTCCAGGGAAAGGGACAACGGCGAGCAGTCCACGGATACCAGGAGCCAGA
ACGTGACCGTGTCCGTGCTGGACGTGTGCGAGACAGCTGAGAAGAAGAAGCTGG
TCCTTGTGTGA

16    Encoding nucleotide sequence of Casσ-3
ATGAAGAGCATAAAGAGCATAAAAAGCATCAAGACGAAGGTGGTGAAGAACAA
CGAGCTGAAGCTGATAGAGCTGAGTACGTGGTGCAGCAGCATATGCGAGCAGCT
GGAGAGGTACATATTCATCCTGGGGGGGGAAACAAATACACGACAGGGACGGCG
TGGTGGTGCTGGACGGCGCAGTGGAGAGGAAGATCTACTGTAAGAAAGACAAG
AGCTTGATCGCGGCCTGCGAGGTGGTGTACAAACACTTCACGGACAAGAGTTCC
AAGTCCAGGACGTTTGGGTCCTGGTTCCTGGGTGGGAAGTCCGAGGGCGACAAC
ACCAATAAGGGAAGGAAGAGTACCAAGGAGAAGACCGAGAAACAAATCGCAA
AGCAGATCGCCGACAAGAAGGAGCTGACGGACTCCCTGCAACTGCTGTGGGACA
AGAAGCTGCTGCCATTCCCGATAGCAACAAGGGCTACGACTTCATAAATACCC
CAAGGGCCAAATCCTACAAGTGGGCGATCACGAAAACCATCCACGCTAAAATCA
AATCCTACAACGAGCAATGCGTGGAGACCAAAAAAGAGTACGACGCCCTGAAC
GCCGAGATCAACACCTACAAGACCATCCTGTTCTCCGGCTACTCCGAAAAGGAC
ATCGACGACCTGCAGAAGTTCGTGGACATCTGCGAGGCAAACAACCACAGGATA
AACTACAAATTCATATCCTTTCTCAAGAGGAAAGACCTCAATTTCGACGAACAA
ACAGGGAAATACAGGAAGGAAGGCAAGTGGATTCAACACAAGAACGGAAAGG
AAGTCAAGAGCAAGTACAGCATGAAGGACGAGATAGTGGAGGCCCTGTACAAG
TACAAGTCCCTGACAAAGAACGACGTGAGCGTGCTGTGCAACGAGCACCAAAA
AGAGGACGAAATGGGCAAGGTGGTGCATTACAACATGAAGAGGTACTCTGATCT
GCTGTTCAGAAAGAAGAACAAAAAGGAAATCCCGAGTTACACGAAAATCAGCC
TGGCCACCAGCAAGATTGAGTTGGGGGTTGAACAATGTGAAGTACAACGTGGAGC
AGGTGGAGGACAAACTGATATGGACCATATGCGACCAGACCGGCAAGGACATC
CAGTTCGTGACCGTGTACACCAGGAAGAAGGAGGATAACAGGACCAATGGCAA
GAAAGGGGCGGGGTTCTACAAGGGCAAACACCACCAGCTGGAGGACCTGAAAA
TAGTGCCGGTGGGCGACATAGGGACCTACGACATCAGCTTCAAGGTGAACGGGA
AGAGGCCGTTCACAGGGACCCTGAAGGAACCGAACATCATATGCAGGGGCGGG
AAGGTGTTCGTCCAGATGCCGATCAACATCAACATCGACAAAACCCTGAACGAC
GCGAGGAAGAAGGTGCTGTACGCATACGGGGACGTACTCCGGCTCCGTGAAC
GGCAAGAAGCAGAAGATGATAAAGATCGAAAACTCCAAAATCGCCGAGTCCCT
GAAATCCCTGGGGGGGGACGCGATAGTCCTGGGCGTGGATCTGGGGCTGAGGGG
GCTGGCTACAGCGGTGGTGAGCCACAACGGGAAAAACGAGACAGTGAAGAGCA
GCCAATACATTAAGGGCGACATTGTGGAGTGGGAGAAGTACAGGGTGTTTAACG
ACAACATCAGGGAGGTGAAGAAGTACATATTCCTGACCAAGAAGTCCTATACCG
CCACGACGGAGGAATACACCGAGTTTTACAAGGAGTGCTCGAAGCCGGAGCAG
GACTATCTGGACTCCCTCAAGACCTATAAAGACAAGAACGTGAAACTCAACGAG
CTGAAATACACGAAGAACGCGTGGTCCGTGAGCAAGATGTTCGAAGACGTCTCC
AAAATGTTCGAAACCCTCAAGCAGGACAGGCTGAAGTACTACGACATCTTCAAC TABLE 1-continued Description of sequences

| SEQ ID NO: | Description |
|---|---|
| | ATGCCATACTGGGCCGCCTCCCTGAAGAACTACATGAGCCTGATGAAGTCCTAC<br>AACTACGTCGGCGTGGACATAAAGGTGTCCAAAGAATACATGAGCAAGTACCAG<br>TCCCTGTACAACAACATCAAGGAAGATTACGCCAAAAAAATCGGCTCCTACATC<br>GTGCAGCTCGCCGTGGCCAAGAATTGCGACATCATTGTCCTGGAGGAGCTGAAA<br>TCCAACCTCGGCTCCGTGGACAGGAAGAGCAAGAGAGACAACGAGATGTCCCTG<br>ATGTGGAACTGCGGCCGCATCAAGACCCACGTCGAGAACATGGCAAAGGACTAT<br>GGGATGTTCATTGACGAAGTCCCGGAGTATGGCACGTCCCAGGTGTATCACAAG<br>ACCGGCAACTACGGCTACAGGGATGAAGACAACAGGGAGATATTTTGGTACGA<br>GGACAACAAGGACGTGGCCTACATACACGCCGACGAGAACGCGGCAATCAACA<br>TAGCCAAAAGATTCCTGTCCCAACATACCGACAACTCCAGCTTCAGCGTTATCCT<br>GAAGGGCGACGCCTACTACCTGAACATCGCCTCCAACTCCAAACGCATGAGGGC<br>CGCCGCACTGAAAACCTTCGGCGACCTCAACAAACCGTTCAAAATCAACGCCAA<br>CGACAAAAACGGAAACCTGTACAAGAAGACCAGGATCTTCAAGTCCGACTCCAG<br>ATGGATAGGCGTCAACGACAAAGACCTCTACATAGAACACATCAAATCCCTCCG<br>CAACCTCCGCGTGCGCCAGTGA |
| 17 | Encoding nucleotide sequence of Casσ-4<br>ATGCCGAGCTTCACGAAGGTGGACGAGGACAAAATAGTGCTGAAGCTGGGGAA<br>CAACTACATCCCGTATGGGCTGAGCAGGATTTCCGAGGACAAGATGCTGTGGAG<br>CTTTTCCTCCCCGCAAAAAAAGAAGCTGTCTATAATAACGAACCACAGGCGCGT<br>CGGCAAGGGCAAACACTTTTACCTGGAAGGCTTGGAGATCGCCGACATTACCAA<br>GGGCGACGGCGACAAGACGTCCCCAAGCGGCAAATATACCATCTCCTTCAGCAT<br>CAACGGCAAGCAGGACGTGAAGGGCGAGCTGAAGGAGCCGAGCTTCGGCCTGA<br>GGAACGGCAACGTGTACATGTTTCTGCCAATCTCCATAAAGCAGACCGACGTGT<br>TCGAGTCCAGGGTGGAGATGAGGAGGTTGCTGTCTATGGCCTACCAGCCAACCA<br>CCGTGGAGGATCTGATCCTGGATGACGTGGAGACCAAGCAGAAGACCGTGAAG<br>CAGGGGAAGAAGGAGGTGAACACCACGAACATAGCGATTCAAGAGGCGATCAA<br>GAAGCACGGCCGCCTGCTGAAGGTGATGGGCGTGGACCTGGGGCTGAGGAACTT<br>CGCGTTTGCCATCAAGAACTACGACGGCCACCACGACACCCTGTTGCGGCAGTT<br>GTACTCCGAGTCCGACCTGAACGAGAAACAGAGGTACACTACCCTGGCCAATGA<br>CTTGTCCAAGGTGGGCAACCACATCAAGTTCGCCGCGGTCTTCTACGGCGCCAA<br>CGACACCGAGGAGAACACCAAGATGTTCGACGCCGAGTGCACGGACGCCGAGT<br>CCAGGACCCACCTGGAGTGGCTGAGGGAAAGCCAAGAAGTCCGGTGTGCTGCTCA<br>AGGACCTGAGGAAGGACAAGACGTGGATCGTGTCGATCAAGTATACCGAGTTGA<br>GGAATAGGCTGCACGCACTGAAATTCGGCAGGATGAAGAGCTACGACTACAGG<br>AATAACCTCTACTGGGCCGCGACCATTAAGAAGTTCATCTCGCTCTCCGCCAGCT<br>TCTACGGCGTGGGGAGGCCTAGCCGCGGCAAGAAGGACGTGAGGGAGTTGAAG<br>AAAAAGCACACCTTCTTCTCCACGTATCAGGACCTGTACAACAACGTGAAGGAA<br>GATTACGCGAAGAAGGTGGCGAATCTGGTGGTGATGACGGCCAAAGAGAATAA<br>CGTGGACATCATCGTGGTGGAGAACCTGACCGGGCACTGCGGGTCCAAGGACTA<br>CAAGACCAGGGCCGAGAACGAGATGAGTATAATGTGGAATCATGGCAGGATCA<br>AGACGTTCATCGATTGCATCGCCAATGCCAACGGCATGTTGTTGGCCGAGGTGT<br>CCGAGTTCGAGACGTCCCAGGTGTACCACGAGACGAGGAACTACGGGTACAGG<br>GACAAGAAGATGAAAGAGATCCTGTGGTACATGGACTCCGAGGGGAACGTGCA<br>GTATGCCCACGCCGAGGTGAACGCCGCCATCAATATCGCCGACAGGTTCCTGTC<br>CCAGCACACCAACCTGTTCTCCTTCCCAGTGTGCAAGTCCAAGAAAGACGAGAA<br>TGTGTACGAGATCGACATCGCCGAGGGGAAAGAACTTGAGGGCCAGGATGAAG<br>TGAAGAAGGCCAAGAAACCGAAAGGCGGGAAGAGGCTGAACGGGGCGGTGGTG<br>AAGACGTTTGGGAGTACCAAGATCATGTTCAACGGGATAGTGGACAAAAACAA<br>GAAGGGGCAGATAAAGACGAAGACGAGGGTGTACAACATAGACGGGGAGTGGG<br>GGGGGAAGACCCAGAAAGACGAGTACGTGGACAAAATCAGGAAGGTGGTGGAC<br>GCGATGAGCCCGGAGGAGAAAGCGAAGGTGAAGGCGGCGCTGAAGAAGTGCTT<br>CAGCAGCTGA |
| 18 | Encoding nucleotide sequence of Casσ-5<br>ATGACGAAGGAGCTGAGCGGGGTGAGGGTGATAGAGCTGAAGACCGACCTGAG<br>GAAGGACCAGTTCTGGGACAGGTACGAGAGGTGCTTCAAAACGTACCACGCCCT<br>GTACAACGAGGTGCCATGCTGGGGCCTGGACTGGGTGGAGCAGAAAACACAAA<br>ACCAAACCTCCAGGGAACTCGGCTGCGAGAGAGTGGATCTGACCGCCCAACGCA<br>AGGCACTGTATGAGAGGACGGACCGCACCATCTCTTACGAGCAGTTTAGCAACT<br>GCCTCAAAGCCCTCTGGCTGGGGCTGCTGAACTGTCAGCAGGGGAACCACATGT<br>ACACCAAACTGTTTGAAGGCGCGATACAAACCGACCAGATGACCGCGGAGGACT<br>GGGCCGTGCTGACCGAATACGTCGCGGACCCGAAGAGCCACAACTCCCAGTTCC<br>TGTTCAGGGTGTCCAACACCCTGAAGCACATCGGCTTCTTCTCCAGGCCGCCATT<br>TACCGCCACCCTGTTTGCCCCAGAGAGGAAGGCTATTACCAAGGACGTCATGTC<br>CGACCTGAAAGGATGGATTGAGATGAAGAGGATGACCGAGGAGTCTTACGCCG<br>CGGAGGAGGTGCAAATTCAACAAATGAAGGCCGAGGTGCCGGTGCGCATCAGG<br>CAGAGCCTGCTGAGGTTTTTCGACACCTGCATAGGCCTGAACCTCATCGGACACT<br>TCGACGAAAGGGTGCACCCACTACCTGAGGGACTGCATAATACCGGCGCTGCAGC<br>AAAGGACGATACCGACCGAACACTTCTACCTGAAATCCAACCGCAAAGACGTGG<br>GCCAGAAACACATAGACTTCAGCCTCGACATCAAATTCTACGAGCTGCTGGCTG<br>AAATGCCAGAGCTGTGGAACACCCTGGAGACCTCCGAGGACGACCTCATCCCCA<br>AACCGCTGATCCTCAAACACCTGCACCTGCTGGAAGCCATCATGTCCCACAGGG<br>CCCACAGGAAGACCGCCGCCTACGCCTTCGTGGGCGAAGCCGACTACCACAGGT |

TABLE 1-continued

Description of sequences

SEQ
ID
NO:     Description

```
        TCTACTACCTGCTCGGCGGCAACTACACAAAACACCTCATCAGCGCCACCGGCT
        CCGAACTGCCGGACAGGGTGATCTGGGACAACGACAAGGACGTTCTGATGAGG
        AACGGCAGGAAGGTGGAGAGGCTGTACGTGAAAGTGGGCGACAGGAAAGAGAA
        CTTCAACTTCGAGGTGTACACGATAGCGATGAACACGAAGGGCCTGAGGGGGCA
        CAGGAGCACGCTGAAGCCGACGAGTTACTTGCAAGACCTGCAGATTTGGAGCAA
        CCCGGAGGGCGAGAGCACCTATCTGAACTTCGTGAGGAAGGGCACAGAGAGGA
        GCGCGATTTGCAAAGAGCCAGTGCTGGTGTACAGGAACCGGCGCCTTTTTTCTTA
        GGCTGAGCATGAGCGTGGAAGGGATGCGGGCCTCCGAGGAGCATATCGCGCTGC
        AGTACTACCTTTCTGCCGCGGCCACGGGCTCTGACTTGTCTAAGGACACGGAGA
        AGACCGTGGAGAGGTTCAACTTGATCCAGGGGAAGACATACAAGGTGATGTCCG
        TGGATCTCGGCATCCGCTCCCCCTTCGCCTGGGCTGTGACCGAGTCGACCATCAC
        GGGCGTGGCCAACCCGAGCCAGATCCTGAACAGCGGCGAGATGGAAATCGCGG
        ACGACCCGGACTATACCGAGCTGTTCTACGCTTACAAAAACCTGGGGCACCTGA
        TCGGCCAGGTCAAGAGCAGCAGCAAGGGGAAAGGCCTCAAAGCGGACAGCCAC
        CTGGTGGATATGATTCATACGGTGCAAAGGTTCTTCGCCGACTACAAAGTGGCC
        GGGCAGAGGAGGAGTCAAATATTCGAGCAGTTCAGCAAGGACCCGGACCCGTT
        GTACCAGATGGACCAGATGATGAAGAGGTACGAGAACAACCTGGAGAGTGTGA
        AGAAGGATTTTAGTTTCCTGATAAACATCCTGTTCAAGTACGTGACCCTGCAGTT
        CGGAGCCCTGAGGAACCGGAGAAGGAGCTACCTGTCACAAAACCAGATGGCCG
        ACCAGAAGTTCGACCAAGACTTCAAGTGGCTGAACATCCTCGAGCAGAGGAAGC
        GCGTGACCAGGAGCCTGAGCTACCTGGGCACAGACAACAGCAGGATTCCTATCT
        GCCTGGAACAGCAGAAGCTGGACTACAACGGCTGCAAGGACAACTTCCTGAAGC
        AGCTGGCCTCCAAGATCGTGAGGATCGCCCACCAAAACGACTGCTGCCTGATTG
        TGCTGGAGGACCTTGAGGGGTACGGGAAAACGCTCAACCAGAGGGACGAGAAC
        TTCCTCACGGCCTTCTGGTCTCCGAAGAGGGTGAAGGATGCCATCATCAACGCC
        GCCCAATGGTACGGCATTGGGGTGGTGACGGTGAGCGAGGCCCAGACGTCCCAG
        GTGCACCACGAGTCCGGCAGGATCGGCTATAGAAAGGGGAGGGACCTGTTTTTC
        CTGACCCCAGACGGCCAGATCGAGTCCGTGCCGAGCGACATTAACGCCGCCAAG
        AACATTGGCCATAGGTTCTTTTCCAGGCACACCGACCTGCACCAGGTGTACCTGA
        AGGGTTCCGACGAGGGCGCCAAGAGGATGAAAGGCTGCCTTCTGTATCAGTTCG
        GGAGTCTGGAGGCGGCCCGCACGCACCTTACCGGAACAGGACCGACCTGGTACT
        TGGACGGCGTGGAGTGGATAGACAAGACGGAGAGGAACCTGAGGAGGGACCTG
        CTGAAGCAGAGGGTGGAAATCGAGAAAATGCCATTCTGA
```

19      Encoding nucleotide sequence of Casσ-6
```
        ATGAAGAGCATCAAGTCGATCAAGAGCATTAAGACTAAAGTTGTCAAGAACAAC
        GAGCTGAAGCTCATCGAGCTGTCTACCTGGTGTAGCTCGATCTGCGAGCAGCTC
        GAGAGGTACATCTTCATACTGGGCGGCAAGCAGATTCACGATCGCGATGGCGTC
        GTTGTTCTCGATGGCGCCGTTGAGCGGAAGATCTACTGCAAGAAAGACAAGAGC
        CTGATCGCCGCCTGCGAGGTTGTCTATAAGCACTTTACCGACAAATCGTCCAAGT
        CTCGCACCTTTGGCAGCTGGTTCTTGGGCGGCAAGAGCGAGGGCGATAACACAA
        ACAAGGGCAGAAAGTCCACCAAAGAGAAGACTGAGAAGCAGATCGCTAAGCAG
        ATCGCCGACAAGAAGGAGCTGACCGATTCTCTGCAGCTCTTGTGGGATAAGAAA
        CTGCTGCCATTTCCGATTGATAACAAGGGTTACGACTTCATCAACACACACCACGCG
        CCAAGAGCTACAAGTGGGCTATCACCAAGACCATTCACGCGAAGATCAAGAGCT
        ACAACGAGCAGTGTGTCGAGACGAAGAAAGAGTACGACGCGCTGAACGCCGAG
        ATTAATACATACAAGACTATTCTGTTCAGCGGTTACTCCGAGAAAGACATTGAC
        GACCTCCAGAAGTTCGTCGATATATGTGAGGCCAACAACCACAGGATCAACTAC
        AAGTTTATCAGCTTCTTGAAGCGCAAAGATTTGAATTTCGACGAGCAGACAGGC
        AAGTACCGCAAGGAGGGCAAGTGGATTCAGCACAAGAACGGCAAAGAAGTTAA
        GTCCAAGTACAGCATGAAAGATGAGATCGTCGAGGCGCTGTACAAGTACAAGA
        GCCTGACTAAGAACGACGTGAGCGTGCTCTGCAACGAGCATCAGAAGGAGGAC
        GAGATGGGTAAGGTGGTCCACTACAACATGAAGCGCTATTCCGACCTGCTGTTC
        CGCAAGAAGAACAAGAAGGAAATACCAAGCTACACAAAGATCTCACTTGCCAC
        GTCCAAGATCGAGCTGGGCCTCAACAACGTCAAGTACAACGTTGAGCAGGTTGA
        GGACAAGCTCATCTGGACAATCTGCGATCAAACAGGCAAAGACATCCAGTTCGT
        GACTGTCTATACAAGAAAGAAAGAAGATAACAGGACCAATGGCAAGAAGGGAG
        CGGGCTTCTATAAGGGCAAGCATCACCAGCTCGAAGACCTGAAGATCGTGCCTG
        TGGGAGACATTGGCACTTACGACATCAGCTTCAAGGTCAACGGCAAGCGTCCGT
        TTACTGGCACTCTGAAAGAGCCGAACATCATTTGCCGCGGAGGCAAAGTGTTCG
        TGCAGATGCCAATTAATATCAATATCGATAAGACTCTCAACGACGCTCGGAAGA
        AGGTTCTGTACGCCTACAGGGAGACGTACAGCGGCTCCGTCAACGGTAAGAAAC
        AGAAGATGATCAAGATCGAGAACAGCAAGATCGCCGAGTCACTCAAGTCTTTGG
        GCAGAGACGCCATTGTGCTTGGCGTGGATTTGGGCTTGCGCGGACTTGCTACCG
        CCGTTGTGAGCCACAACGGAAAGAACGAGACTGTTAAGAGCAGCCAGTACATCA
        AGGGCGATATTGTGGAGTGGGAGAAGTACAGGGTGTTCAATGATAATATCAGGG
        AGGTCAAGAAGTACATCTTCTTGACCAAGAAAAGCTACACCGCCACAACGGAAG
        AATACACAGAATTTTACAAGGAGTGCAGCAAGCCTGAGCAAGACTATCTTGATA
        GCCTCAAGACGTACAAGGACAAGAACGTTAAACTGAACGAACTGAAGTACACC
        AAGAACGCCTGGAGCGTCTCGAAGATGTTTGAAGACGTTTCCAAGATGTTCGAG
        ACACTCAAGCAAGACAGGCTCAAGTACTACGACATCTTCAATATGCCGTATTGG
        GCGGCCTCACTGAAGAACTATATGTCGTTGATGAAGTCGTACAATTATGTTGGC
        GTGGACATCAAGGTCAGCAAAGAGTACATGTCCAAGTACCAATCCCTGTATAAC
        AACATCAAGGAGGACTACGCCAAGAAGATCGGCAGCTACATTGTCCAGCTGGCT
```

TABLE 1-continued

Description of sequences

| SEQ ID NO: | Description |
| --- | --- |

GTGGCAAAGAACTGCGACATCATCGTGCTTGAAGAGCTGAAGTCGAACCTGGGC
AGCGTTGATCGCAAGTCCAAGCGCGATAACGAAATGAGCCTCATGTGGAACTGC
GGCAGAATCAAGACTCATGTCGAGAACATGGCCAAAGATTACGGCATGTTTATC
GATGAGGTGCCTGAGTATGGTACTTCGCAGGTGTACCATAAGACCGGTAACTAC
GGCTATAGAGATGAAGCAACAGGGAAATCTTCTGGTACGAGGATAACAAAGA
CGTCGCCTACATCCATGCAGACGAGAATGCTGCCATCAACATCGCGAAGCGCTT
TCTGTCACAGCATACCGACAACAGCTCATTCTCCGTGATTCTCAAGGGCGACGCT
TACTACCTGAACATCGCTTCCAACTCCAAGAGAATGCGCGCCGCCGCTCTCAAG
ACCTTTGGAGATCTCAACAAGCCTTTCAAGATTAATGCCAACGATAAGAACGGC
AACCTCTACAAGAAGACAAGAATCTTCAAGTCAGACTCTCGCTGGATCGGCGTG
AACGACAAGGACCTCTACATCGAGCACATCAAGAGCCTGAGAAATCTCAGGGTG
AGGCAGTGA

20   Encoding nucleotide sequence of Casσ-7
ATGAACAAGACGGACACCCAGAACAACGAGCAGATCAACAAGCCGACGCAGCT
GCTCAACAACAAGGACATTGAGCTGACGGTGAAGACCGTGAAGTCCGCGACCGT
GAAGGTGGACAACAACAGCAAGAAGGAGCTGTTCGGCCTGTTCAACTACTTCAC
CAGCGTCGCCTCCGGCATCAAGGACAAGGTGTACAACCTGCAGTCCGATGAGAA
GACCGCCCCGATCTTCAACGACTACGTGAAGCAGCCGCAGCGCGGCAGGTCTGC
TGCTACTACTCTGTTCACCAAGCTGGACGCGGAGAAGACCTACACCTCTCAGCA
CTCCTTCCCCGGCAAGTGGAGGGATTCCGGCATCTTCCCGCTGTACAACAAGGA
GTCCGAGAAGTACGACCTGTCCACCCACGGCTACCACTACTCCGCTAACGCCGA
GATCCACACCCAGCTGGACAGCCATGACGAGTGCAACAAGGAGTGCGAGAAGG
AGTACGCCGCCCTTAGGGACGAGGTGAACAACTACAAGTACGAGTTCACGCTTC
AGTTCAAGGCCGAGAACGCCGAGAAGTTCTACAACTTCGTGGAGAAGCTGACGC
TGATGGGCTGGAGGTACGACGCTACGTTCAGGTCTTTCTTCGAGCTGCACATGCA
CCCAAAGCTCAAGACCGGCGAGACAACGTACAGGGCCACCTACAAGCTGCCGTC
CGGCAAGTCTAAGAGGTACAGCTTCTTCAGGGACGACATCGCCGACGAGATTGC
CAAGAACCCAGAGTTCTGGCCAATGCTGGAGTCCTCCAACGCCATCTCCTGGAT
CAACTCCAACAACCTGCTCAGCAGGAAGAAGGACAAGGCCAACTACTCCTCAAC
CTCCCTCATCAAGTCCCAGATTCGCCTGTACCTGGGCAACAACGGCGTGCCATTC
ACCGCTAGGGAGCACGATGGCAGGATTTACTTCAGGCTTCAGGCTCCCGGCCATC
AACGGCGAGAAGGGCAGGATGGTCGAGATCCCATGCAGCTACAAGAAGGTGTT
CAACGGCAAGGCCAGGAAGAGCTGCTACCTTGGCGGCCTTACCATCGAGAAGAC
CGACGCTGGCAAGCATATCTTCAAGTACTCCGTGAACAACAAGAAGCCGCAGGT
GGCCGAGCTGAACGAGTGCTTCCTGAGGCTGGTTGTGAGGAATAGGGAGTACTT
CAACAACGTGGTGGCCGGCAAGATCACCGACATCAACACCGATCACTTCGACTT
CTACGTCGATCTGCCGCTGAACGTGAAGGAGGACCCGATCCATGATCTGAGCAG
CACGGAGGTGTTCGGCAAGAATGGCCTGAGGTCCTACTACTCCTCCGCCTACCC
AGAGATTAAGAACCTGGGCTCCCAGATCGAGACCGGCAAGAACCTCACCTGCCC
GATCACCAAGACACACAACATCATGGGCATCGACCTTGGCCAGCGCAACCCATT
CGCCTACTGCATTAAGGACAACACCGGCAAGCTCATCGCCCAGGGCCATATGGA
CGGCTCTAAGAACGAGACCTACAAGAAGTACATCAATTTCGGCAAGGAGAGCAC
CTCAGTCTCCCACCTCATCAAGGAGACCAGGAGCTACCTGCACGGCGATCCAGA
GGCTATCAGCAAGGAGCTGTACAACGAGGTGGCCGGCTTCTGCAACAACCCGGT
TTCCTACGAGGAGTACCTCAAGTACCTGGACAGCAAGAAGTTCCTGATCAACAA
GGAGGACCTGTCCAAGAACGCGATGCATCTCCTGAGGCAGAAGGATCACAACTG
GATCGGCAGGGACTGGCTGTGGTACATCAGCAAGCAGTACAAGAAGCACAACG
AGAACAGGATGCAGGACGCCGACTGGAGGCAGACTCTTTACTGGATCGACAGCC
TGTACCGCTACATCGACGTGATGAAGTCCTTCCACAACTTCGGCTCCTTCTACGA
CAAGAACCTGAAGAAGAAGGTGAACGGCACGGTGGTGGGCTTCTGCAAGACGG
TTCACGACCAGATCAATAACAACAACGACGACATGTTCAAGAAGTTCACGAATG
AGCTGATGAGCGTGATCAGGGAGCACAAGGTGAGCGTGGTCGCCCTTGAGAAG
ATGGACTCCATGCTCGGCGACAAGTCCAGGCACACCTTCGAGAACAGGAACTAC
AACCTGTGGCCGGTTGGCCAGCTGAAGACGTTCATGGAGGGCAAGCTGGAGTCC
TTCAACGTGGCGCTTATCGAGATCGACGAGAGGAACACCTCCCAGGTTTGCAAG
GAGAACTGGAGCTACAGGGAGGCGGACGACCTGTACTACGTGACGGACGGCGA
GTCCCACAAGGTGCATGCTGACGAGAACGCCGCGAACAACATCGTCGACAGGTG
CATCAGCAGGCACACCAACATGTTCAGCCTGCACATGGTGAACCCGAAGGACGA
CTACTACGTGCCGACCTGCATCTGGGACACCACCGAGGAGAGCGGCAAGAGGGT
TAGGGGCTTCCTCACGAAGCTCTACAAGAACTCCGACGTTGCTTCACCAAGAA
GGGCGACAAGCTGGTGAAGTCCAAGACCAGCGTGAAGGAGCTGAAGAAGCTGG
TTGGCAAGACCAAGGAGAAGAGGGGCCAGTACTGGTACAGGTTCGAGGGCAAG
AGCTGGATCAACGAGGCCGACAGGGACACGATCATCCTGAACGCGAAGAAGAT
CAGCAGGGAGAGGGACAACGGCGAGCAGTCAACGGATACCCGGAGCCAGAACG
TGACGGTGAGCGTTCTGGACGTGTGCGAGACCGCTGAGAAGAAGAAGCTGGTGC
TGGTGTGA 21   Encoding nucleotide sequence of Casσ-8
ATGAAGAAGCCGAAGCAGAACATCGAGGAGACGGACCTGAAGATCACCACCCC
AAAGACCGCGACCATCAAGGCCACCAACCTGGACGACAAGATGAGGCTCTTCAC
CTTCTTCAACGGCTTCACCACCGTGTGCTCCAAGGTGAAGGACGACATCTACAA
CTTCGGCCAGAACGAGGACACACTGCCGGTGTACACCGACTACATTAAGGCCTC
CCAGAGGGCCAGGATGTGCGCTACTACCCTCGCTACCAAGAGCGAGTGCGACTT TABLE 1-continued Description of sequences

| SEQ ID NO: | Description |
|---|---|

CGCCAAGAAGTACGGCGAGCACTTCCCGCTCCCCCATTACAACCAGGAGGGCAT
GAACTACACCACCCACCAGCACACCTACTCAGTGAACTCCGCCGTGCACACACA
GCTCGACTCCCTTAACGAGTGCGACAAGCTCACCAACGGCGAGTACGTCAAGCT
CAAGAAGACCGTCGACGAGCTGGAGGAGAAGCTGACCGAGGAGCACGGCAAGG
AGCCACTTGATTTCCTGGTGAAGTTCGTGGACGAGCAGATCCTCCTGGGCTGGA
GGTTCGACGGCAAGTTCAGGCTGTTCTTCGAGGTGGCGATGCTGCCAGAGCTTA
AGAACGGCAACATCATCTACAAGAAGGCGTACAAGACCTCCGGCGGCAAGGGC
AGGAGGTACTCTTTCTACAACCCGTCCGTGGCCGATAACATTTCTAAGAACCCCA
CCGTGTGGAACCTGCTGAGCGACGTTAAGGCGGTGGACTACATCTCCCTGTCTA
ATTCCCTGCTGAGGAAGAAGCCGCACGCCCAGTACACCAACACAACCCTGAACA
GGGCCCAGGTGAGGCCTACATTCGGCAACAACGGCGTGCCATTCTCCATCTCCG
TCTCCGACGACGACTACGTGTACATCCGCTTCAGGCTGCCCAAGAAGGACGGCG
AGGAGAAGGGCCAGGAGATCTCAGTCAAGTGCAGCTACAAGACTTCATACAAG
GGCAAGCGCAGCAAGACGCTGAGGAAGAGCTGCTACCTGGGCAACCTGAAGAT
CGAGGAGAATGGCAAGGGCAAGTACATTTGCAAGTACAACATCAACGGCAGGG
AGACGACCACCGCGGAGCTTAATGAGTGCTTCCTGAGGGTGAGGATCAACAACA
ACCGCTGGTTCAACAAGTACCTGAACGGCACGCTGACCAAGGAGGACGGCGTTC
TTAAGAGCGAGTACTTCGACTTCTACTTCGACCTGTGCCTGAATGTGCATCAGAA
GTCCATCCACGGCCTGACCAACTCCGAGATTTTCGGCGGCAAGGGCAAGAGCAT
CAGGAGCTACTACTCCACCTCCTACCCGGAGGTGAAGAACCTGGACGGCCAGAA
GAACATCAAGACCGACTTCGGCTGCTACGTGGACAAGCCGCACAACATCATGGG
CATCGACCTGGGCCAGAGGAACCCATTCGCCTGGGCTGTTCTGGACCAGAACGG
CAATGTGAAGGACGTGGGCCACCTGGACGGCGCTGAGAACGATACATACAAGG
ACTACCTGACGTTCTCCAACAGGTGCAAGGACGTTAAGAATCTGATCCTGCAGT
CCAGGGACTACCTGTACGGCGACGATGAGGCCATTGACGAGACCCTGTTCGACT
CCGTGGTGCAGTTCGTGAACAGCAACATCACGCTGAACAAGTACAAGTCCTACC
TGGACGAGAAGAAGAGCCTGATCAACAAGGAGTCCCTGGAGAAGAACCGCCTG
TACGAGCTGAAGAAGAAGGACCACGGCTGGTTCGTGAGGGACTGCCTTTGGTTC
CTGACCAAGGAGTACCACAGGATCAACTCCGAGCGCAAGACGCACTCCGACTGG
AGGTACACCCTGTACTGGGTGGACGCCATTCACCGGTTCATTGACGTGAACAAG
TCCTTCAACTCCCTCGGCAGCTACTACGACAAGAAGCAGTCCAAGTCCATCAAC
GGCATCCAGAAGGACTTCTGCAGGAGCTACTGGAACCAGATCGACAACCTGAAC
GAGGACACCCTCAAGAAGTTCGTGTTCGAGCTGCTGCCAGTGATCAAGAAGAAC
AACGTGTGCCTGATCGCCATCGAGGAGCTGAAGTCCATGCTGGGCGACGACGAC
AAGAGGGCTGAGGATAACAGGCTGTACAACCTGTGGCCGGTGGGCCAGCTTAAG
ACGTTCCTGGAGGGCAAGCTGCTGCCGTACAACGTGGCTGTGATGGAGGTGAGC
GAGCAGAACACGAGCCAGATCGTGAACGGCCAGTGGTCCTACAGGGAGGGCGA
TGATCTCTACTACGTGAAGAACAACGACAACAACACCATGTGCAAGACCCACGC
GGACGAGAACGCGGCTATCAACATCGCCCTGAGGGCCTACTCCCACCACACTAA
CCTGTACTCCATCTACATGATCAATCCGATCGACGACTACTACGTCCCGAGCTGC
ATCTGGAACAACAAGGACGAGGGCTCCAAGAGGATTAGGGGCTTCCTGACCAA
GACCTACGGCACCTCCGACGTGGTGTTCATCAAGAAGAATGAGAAGCTGGTGAA
GTCCGACGTGAGCATCAAGGACGTGAAGAGGATCGTGAAGAACATCGGCAATG
AGAAGAACAAGAAGAGCGAGATCTGGTACAGGATGAACGACACATCGAGTGGATC
GACGAGGGCAGCAGGGACATCATCATCAACACAATCAAGAGCAAGGTGAGGTG
A

| 22 | Encoding nucleotide sequence of Casσ-9 |
|---|---|

ATGACGGACAAGAGCATCAGCTTCAAGCAGTTCAGCCAGATCCTCAATGTGCTG
TACAAGTGCATCGTGATTTCCGGCAAGGGCCGCGGCCTTACTTCCATTATCCTGG
GCCAGCCGCAGTGCAAGGACTCACTTACCTCCGCCGACTGGGGCAACCTGGAGA
CTCTTTCCGCCAAGGACGAGCTGACCCCTGCTGAGGTTAAGGATATTACCAAGG
ACCTGATGTACAGGGCCAGCAACACCCTGGTCTCCATCGGCTTCAGGAACAGGT
CCCCTTTCAAGCTGACCCTGACCTCCGGCGAGAGGTACGCTGTTGTGGAGAACG
TGCACCGCTCCCTCAAGTCCTGGGTGGAGGTTGACAAGATTACCAGGGAGAACT
ACCTCAACGAGGAGATCGCCCTGAGCGATGCCTTCAATAACATCGACGAGACGC
TGCTGCCAACCCTTAAGGAGTTCTTCGACGCGTGCATGAATGAGAACATCATCC
ACCACTTCGACGCCAGGGTGTACGCCTACACGAGGGATTGCGTCATCCCAGCCC
TGGTGGCTGGCCTTGAGATCAAGGACCACTTCTACATCGACGGCCGCGACAAGG
CCAAGAGGGATTACAGCCTGCAAGGTTACGCCGAGCTTCTGAAGGGCTTCCCGA
AGCTCTGGCAGGGCGTTGATCCGGAGATCCTGGCTAAGCTGTACATCCTGGAGG
CCCAGATGGACCACAAGAAGCACAGGCCATGCGCCGCTTACGCGTTCATCGGCG
AGGATTCCTACAGCAGGGTGCAGTACCTTCTGGGCAACAACTACACCTCCTTCA
GCCCCTACGCCCTCGGCGTTGATCTGGATGACGTGACCTGCGGCGATGACGCTG
AGGCTGATACACAGTTCCCCAAGAACAAGGTGATCCAGTTCAGCCAGGGCAAGA
AGGTGACCAAGCTGTCCCTGACCGTGAGCAGGGGCAAGGAGGATACCAACAAG
TACTCCTTCGATGTGTTCCTGGCCGACAAGTACAGCAACGGCTCCTACAAGCCA
AGCCCGTACTTCTCTGACCTGTCCGTTTGGGTGAGCGAGATCGGCATGCTGATGG
AGTTCACCCGCAAGGGCGAGAGGGTGCAGGCTATTGTGAAGGAGCCATCCCTGA
TTTACCGCAAGGGCGCCTTCTACGTGAGGCTTAATATGGGCGTGATTCAGGACA
CCTCCCCCGGAGATCAACGACCTGTACTGGTACTTGTCCTCCGGCGCCCCAATGTC
CATGACCGATAGGTCCAAGGCTTCCGAGACCCCCGAAGAACACCGAGAGGCTGG
AGTCAATTAAGGGCAAGAGCTACCGCTTCCTGGGCATCGACCTGGGCCTTAGGT
CCCCCATTCGCCTGGGCTGTTGGCGAGGCTTCTATCTCCGGCGTCATCAACAAGCC

TABLE 1-continued

Description of sequences

SEQ
ID
NO:    Description

GACGATCATTGCCACCGGCGACTACACCACCGCCAGGGATACTAGGTACGACAC
GCTCTTCTTCGCCCTCAAGAATGCGGGCAAGGTGATTGGCGTGACCAAGTCCCTC
GCCAACGGCAAGGACGCTTCTTTCAATGGCCTGATGGGCACCATCACCGCCGCT
AGGGAGTACCTTGCGCACTACTCCGGCGTCGCTACCCATAAGGTGGCCGCTATC
CAGGCCTTCTGCCAGGATGACAACCCGCTGGAGACCCTTAAGGGCCTGCTCAAG
TCCTACAACAACGACCTCGTCACCCTCAAGAAGGACCCTAGGTTCATCGGCGGC
ATCCTGCTCAGGTACGCCAGGCTTCTGAAGGGCGAGCTTGTGACCTCCAGGAAG
ATGCACCTGCGGGAGCACTCCGTGGAGTCTAAGTTCGGCCAGGAGTACATGTGG
CTGAATATTCTGGAGAGGGAGAAGAGGGTGTGCAGGAGCCTGTCCTACCTGGGC
CTTGGCAACGACAGGGACAGCGTTATCATGGGCAACCTGACCACGCCGTACAAC
CACTGCAAGGAGAACCTGCTTAAGCAGCTGGCCGCGAGGATTGTGTCACTGGCT
GTGGAGAATAAGTGCCACGTTATCGTGATGGAGTCCCTGGGCGGCTCCAACAAG
TCCATGAATACCAGGGGCCAGAACTTCCTCGAGGCCTTCTGGTCCCCACAGAAG
ATCAAGGACACCATCATCAACGCCGCCGCCTGGCATGGCATCATGGTTGCTGAG
GTGAGCGAGAGCCAGACCTCCCAGGTTTGCTTCGAGACCGGCACCTTCGGCCAC
AGGGATAGGGCTTCTCTGTACTTCCTGGACAAGAACGGCGACCTCCAGGAGACG
CATGCCGATATGAACGCCGCCAAGAACCTCGTGGAGAGGTTCACCACCAGGCAC
ACCAACCTGAGGCAGGTGAATATGGACTCCCTCCCCAAGGAGGGCCCGGATAAG
ACACCAAAGAAGTCCCCGTCCAAGAAGAAGATGGAGAAGGCGAAGATGGACAA
CCCAGAGGACCAGTCCAAGAGGCTCAAGGGCTTCCTGACCGTGAAGTTCGGCAA
TGTGAAGGCCGCCCAGGAGTACTTCGCCTCTAGGAAGCCGGAGCAGAGCTACAG
CGGCAAGAAGGACGAGGCCATCTACTGGTACTTGGACGGCGACGAGTGGATCAC
CAAGAAGGAGAAGGAGTCCAGGGTCAGCGTGATTGAGGGCCTGGTGGGCCTTA
AGGAGGTGGCTGTTTGA

23    Encoding nucleotide sequence of Casσ-10
ATGGCGTTCCAGAGCAAGAGGAGGATTGTGGGCAACCTGGTGAAGGAGCAGTG
CCTCAAGGCCGTGGATGGCAAGGTGATCCTGACCGACCAGGAGAAGAGGGAGC
TGATCAAGAGGTACGAGCTGCACCTGGAGCCGTACAAGTGGCTGCTGAGGCTGT
TCCTGTCCGGCTACGAGGGCAGGGATGACGGCTTCTACGAGGAGCTGGGCAACA
CGAACCTGGACAAGGAGAAGTTCTTCGAGGTCACCGCGGGCCTCAGGGATGCTC
TTCTTAGGCAGTCTGGCTCCTCCAGGGCGCTTAAGTCCTCCATGCTGGGCAAGTG
CCCGCCATCAGCTGCTGTTGGCAAGGCTGCTAAGCACATCCAGGCTCTGCGCGA
CGCTGGCATTCTTCCATTCAAGACGGGCCTCACCTCCGGCGAGGATTACAACGT
GCTTCAGCAGGCCGTCCAGCAGCTGAGGTCATGGGTTGCTTGCGATCACAGGAC
CAGGGAGGCGTACGCTGAGCAGCAGGAGAAGACATCCCAGGCCGAGGAGGCTG
CTAAGAAGGCTGTGAACGAGGTGAAGCCAGAGGACGCCAAGAGCCTGGAGAGG
CATGAGAGGGCTCTGACGAAGCTGAGGAAGCAGGAGAGGAGGCTGGAGAGGAT
GAGGAGCCACGCTCAGTTCAGCCTGGACGAGATGGACTGCACGGGCTACAGCCT
GTGCATGGGCGCTAACTACCTGAAGGACTACTGCCTGGAGAAGGAGGGCCAGGG
GCCTTAGGCTTACCCTGAAGAATAGCACTATGGCCGGCAGCTACTACGTTTCCGT
GGGCGATGGCCAGCACGCTGGCATGAAGAACCCAGGTACTCCGGCGGGCGGCTC
TCCAGAGAAGGGCAGGAGGAGGAACATCCTGTTCGACTTCGCGGTTGAGAAGTG
CGGCGACAACTACCTTTTCAGGTACGACGAGAACGGCAAGCGCCCGAGGGCTGG
CGTTGTTAAGGAGCCAAGGTTCTGCTGGAGGCGGAAGGGCAACTCCGTGGAGCT
TTACCTGGCCATGCCGATCAACATCGAGAACAGCATGAGGAACATCTTCGTCGG
CAAGCAGAAGAGCGGCAAGCACTCCGCTTTCACCCGGCAGTGGCCAAAGGAGG
TGGAGGGCCTTGACGAGCTGAGGGATGCTGTGGTGCTGGGCGTTGACATCGGCA
TCAACAGGGCGGCTTTCTGCGCGGCTCTGAAGACTTCCCGCTTCGAGAACGGCC
TGCCGGCTGATGTTCAGGTTATGGATACCACCTGCGATGCTCTGACCGAGAAGG
GCCAGGAGTACAGGCAGCTGAGGAAGGACGCCCACCTGCCTTGCTTGGCTGATCA
GGACAACCAGGAGGTTCAAGGCCGACCCAGGTAACAAGCACAACCAGATCAAG
GAGAAGGACGTGGAGAGGTTCGACAGCGCCGACGGCGCTTACAGGAGGTACAT
GGACGCCATCGCGGAGATGCCGTCCGATCCACTTCAGGTGTGGGAGGCTGCCAG
GATCACCGGCTACGGCGAGTGGGCTAAGGAGATTTTCGCCAGGTTCAATCACTA
CAAGCACGAGCATGCCTGCTGCACCGTCTCCCTTTCCCTGTCTGACCGCCTGGTG
TGGTGCAGGCTTATCGATAGGATCTTGTCTCTCAAGAAGTGCCTTCACTTCGGCG
GCTACGAGTCCAAGCACAGGAAGGGCTTCTGCAAGTCCCTCTACAGGCTTAGGC
ACAATGCCAGGAACGACGTCAGGAAGAAGCTGCCAGGTTCGTGGTGGACGCC
GCTGTTGATGCGGGCGCTTCTGTTATCGCGATGGAAAAGCTCCCGTCCTCCGGCG
GCAAGCAGTCTAGGGATGACAACCGGATCTGGGACCTGATGGCCCCAAACACCC
TGGCTACCACCGTGTGCCTCATGGCTAAGGTTGAGGGCATCGGCTTCGTGCAGG
TGGACCCAGAGTTCACCTCCCAGTGGGTGTTCGAGCAGAGGGTGATTGGCGATA
GGGAGGGCAGGATTGTGTCCTGCCTGGACGCTGAGGGCGTGAGGAGGGATTACG
ACGCTGACGAGAACGCCGCGAAGAACATCGCCTGGCTGGCTCTTACTAGGGAGG
CGGAGCCATTCTGCATGGCCTTCGAGAAGCGGAATGGCGTGGTGGAGCCGAAGG
GCTTCAGGTTCGACATTCCGGAGGAGCCGACCAGGGAGCAGGATGAGTCAAACC
AGGACTTCAAGAAGAGGCTGGAGGAGAGGGACAAGCTGATCGAGAGGCTGCAG
GCGAAGAGCGATAGGATGAGGGCGATCGTGAGGAGGCTCTTCGGCGATAGGAG
GCCGTGGGATGCTTTCGCTGACAGGATTCCTGAGGGCAAGTCCAAGAGGCTGTT
CCGGCACAGGGATGGCCTGGTTCTGAACAAGCCGTTCAAGGGCCTGTGCGGCTC
CGAGAATAGCGAGCAGAAGGCCTCCGCCAGGAACTCTAGGTGA TABLE 1-continued Description of sequences SEQ
ID
NO:    Description 24     Encoding nucleotide sequence of Casσ-11
ATGGACACGGACACGGAGCTGAGCGACGAGGTTGAGCTGAGCGATGAGGTGGA
GCTGAGCGACGAGGTGGAGCTTTCCGACGAGGTGGAGCTGACGGTGAAGAAGG
TGAAGACGACGACGGTGAAGGTGGACAACAATTTCAAGAAGGAGCTGTTCGAG
CTGTTCAATCACTTCACCAGCGTGGCGAGCGGCATCAAGGACAGGCTTTACGAC
CTGCAGTTCGATGAGAACACTGCCTCCATCTTCAAGGGCTACATCAAGGAGGCC
AAGAGGGGCCACGGCGCTGCTACTACTGTGTTCACTAAGCTGAACCCGAAGAAG
ATCTACTCCGGCAAGAAGTCCTTCCCAAGGGATTACAGGGACCGGGGCATCTTC
CCGTTCTACAACAAGGAGTCTGGCAAGTACGACCTGTCCACCTGCGGCTACCAC
TACAGCGCTAACGCCGAGATTCACACCCAGCTCAACAGCCACGACGAGTGCAAC
AAGCAGTGCGAGAAGGAGTACGCGGCGCTGGAGAAGGAGAGGAACAAGTACAA
GCATGAGTTCACGAGGCAGTTCAAGGCCGAGAACGTGGAGAAGTTCAGCAACTT
CGTGGAGAAGCTGACACTGATGGGCTGGAGGTACGATGCGACCTTCAGGAACTT
CTTCGAGCTGCACATGCACCCAAAGCTCAAGACGTCCGAGACCACCTACAGGGC
CACCTACAAGCTGCCGTCCGGCAAGTCTAAGCGGTACTCCTTCTCCAGGGACGA
TATTGCCGACGAGATCGCCAAGAACCCCGAGTTCTGGCCAATGCTGGAGTCCTC
CAACGCCGTTTCCTGGATCAACTCCAACAATCTGCTCTCCAGGAAGAAGGAGAA
GGCCAATTACTCCAGCACCAGCCTGATCAAGTCCCAGATTAGGCTGTACCTGGG
CGACAACGGCGTGCCATTCACCGCTAGGGAGCACGATGGCAGGATCTACTTCAG
CTTCAGGCTCCCGTCCATCAACGGCGAGAAGGGCAGGAACGTCGAGATCCCATG
CTCCTACAAGAAGGTCTTCAATGGCAAGGCCAGGAAGTCCTGCTACCTGGGCGG
CCTTACCATCGAGAACACCGGCGGCTCAAAGCACATTTTCAAGTACTCCGTGAA
CAACAAGAAGCCGCAGGTGGCGGGAGCTGAACGAGTGCTTCCTGAGGCTGGTCGT
GAGGAATCATGGCTACTTCAACAAGATGGTGAACGGCAAGCTCACGGATAAGG
ACGGCAAGCTGCACGCCGACTACTTCGATTTCTGCATCGACCTGCCGCTTAACGT
GAAGGAGGACCCGATCCACGACCTGACCTACCAGGAGATTAACGGCGTGAAGG
CCAACCCGGAGAAGAACATCGAGAAGAAGGTGGGCCTGCTGGGCTTCTACCAGT
CCGCTTACCCAGAGATCAAGAACCTCGGCTCCCAGATCGAGACCGGCAAGAACC
TGACCTGCCCGATCACCAAGACCCACAACATCATGGGCATCGACCTCGGCCAGC
GCAACCCATTCGCTTACTGCATCAAGGACAACAACGGCAAGTTCATCGCGAAGG
ACCACATGGACGGCTCCAAGAACGAGACATACAAGAAGTACATCAATTTCGGCA
AGGAGAGCACCTCAGTCTCCCACCTGATCAAGGAGACCAGGTCCTACCTGCATG
GCGATCCGGAGGCTATCTCCAAGGAGCTGTACAACGAGGTCAGCGGCCTGTGCA
ACTCTCCGCTTAGCTACGAGGAGTACCTTAAGTACCTGGACAGCAAGAAGTTCC
TGATCAACAAGGAGGACCTGAACAAGAACGCCATGCACCTGCTGAGGCAGAAG
GACCACAACTGGATCGGCAGGGACTGGCTGTGGTACATCAGCAAGCAGTACAAG
AAGCACAACGAGAACAGGATGCAGGACGCCGACTGGAGGCAGACTCTGTACTG
GATCGACAGCCTGTACAGGTACATCGATGTGATGAAGTCCTTCCACAACTTCGG
CAGCTTCTACGACAAGAACCTGAAGAAGAAGGTGAACGGCACCGCCGCCGCTGGGCTT
CTGCAAGACTATCTACGACCAGATCAACAACAACAACAAGGACATGTTCAAGAA
GTTCACCAATGAGCTGATCCCGATCATCCGCAAGCACAAGGTGTCCGTGGTGGC
CCTTGAGAAGATGGAGTCCATGCTGGGCGACAAGTCCAGGAACACATTCGAGAA
CAGGAACCACAACCTGTGGCCAGTCGGCCAGCTGAAGACCTTCATCGAGAACAA
GCTGGATGGCTTCAACGTGATCGTGGTGGAGGTGGACGAGAGGAACACGAGCC
AGATGTGCGACGGCAACTGGTCCTACAGGGAGGCTGACGACCTCTACTACGTCA
AGGACGGCGAGCTGAGGGAGGTTCACGCTGATGAGAATGCGGCCAACAACATC
GTCGACAGGTGCATCTCCAGGCATACCAACATCTTCAGCCTGTACATGACCAAC
CCGATGGACGACTACTACGTGCCGGCGTGCATCTGGGACAGGTCAGAGAATGGC
AAGAGGGGCCAGGGGCTTCCTGACCAAGATGTACAAGAACAGCGACGTGGTGTTC
ACCAAGAAGGACGACAAGCTGGTGAAGTCCAAGATGTCCGTGAAGGAGCTGAA
GAAGCTGGTGGACAAGACCAAGGAGAAGAGGGGCCAGTACTGGTACTTGTTCG
AGGGCAAGAGCTGGATCAACGCCGCCGATAGGGATACCATTATCTCCAACGCGA
AGAAGCTCTTCAGGGAGAGGGATGGCGGCGAGCAGTCAACTGATACCCGCTCTC
AGAACGTGACGGTGTCCGTGCTGGACGTGTGCGAGACTGTGGAGAAGAAGAAG
CTGGTCCTGGTGTGA 25     Encoding nucleotide sequence of Casσ-12
ATGAGCACGGAGGTGGACGTGAAGACGATCAACCTGAAGATCGCGAAGAAGGG
CGGCGTGTACCCGATTCTGGAGCAGTCAATTAAGGAGAACTGCAAGAGCAACGA
CCTGCTGGAGTTCTTCATGGTGCTGAACAGGCTGCAGACCTACTACATCGAGAG
CAACGAGGAGATTCTGGTGGACTTCCCCAAGAAGTACGACGAGCTGTTCGACAT
CGTGAAGAACAACGACTCCTCCGTGACCAGGGAATACTTCGACTCCCTCTGCGA
CAAGTACATCACAGAGGTGTGCGCCAATGGCTTCGTCAACAACGTGTACATTGC
CCACAACAAGAACCAGGAGCTGAACTGGGCTGAGACGAGCAACGACCGCAAGA
TCAAGAGCAACAAGACCTTCATGTTCGGCAAGATCAAGGGCCTGATCCGCGACA
AGTTCGGCAGGGAGGAGCTGTCAGACAAGGACGCTACGAAGCAGCTGTGCGAG
GACATCTTCAACCTCTTCATCCTGAACAACGCCAACATCGAGCTGGACGAGAAG
TACAACATCATCAAGGACGAGCTGATCCAGATCTGGAACGAGAGAGGAACAAGGA
GTTCATCCACATCAAGGACATCACCCTGCTGTTCAGGCAGTGGGGCATCCTGCCT
ACCTACGACAACATCACCCACAACTGCGAGCTGAAGGCCATCATCGCCGAGCCA
GTGAGGAGGTTCAAGTCCTGGCTGGAGTGCAACTCTGAGGCGAACAAGAACTAC
GACACCGAGAGGGAGAAGTGCACCAAGTACATGGACGTGATGGACTCCGACCT
GACCGTGGAGTTCAGCAAGATGGTGACGGAGCTGGGCAACCCATTCGGCGCTAA TABLE 1-continued Description of sequences

| SEQ ID NO: | Description |
|---|---|

CGACAAGAACATCTACAAGTACTTCAACCAGAAGTTCCTCCTGTTCTTCAAGCA
GGTTGTGCAGCCCAAGTTCGTTAACGGCGAGCCGCTGGACGAGTCTAATGGCTC
TTACTCCGGCGAGATCAAGATCAACTCCGCGGGCAAGGTGGAGAACTACTCCAT
CGCCGTGTCCGTGATTGACACCATCAAGAAGTACCCGACGATCTGGTCCGACCG
CTCCTGGGGCGAGTCTGTTATCTCCACCGTGGCCAAGATTGATCCGCAGTACGGC
ATCGACGACATCACCGACGATATGCAGGTGTCCCCGTTCTACCTCTTCTACGGCT
ACTTCACCGCCTACAACTACATCCAGCAGCACAAGAGGAACGCCAAGTACACCC
CGATCTCCAAGGACTCCCTGCCATCCCTGTACCTCGGCAACAACTACATCCCATT
CAAGATCGACTGCGAGAACGTCGACGACGACCGGTTCTACATCACCATCAAGAA
CATGAACAACCTGAAGCTGAACGTCCTCTACCGCAAGCCCAAGCTGAAGTTCGC
CAAGACCAAGGAGAAGACCAAGAGGAACAAGTGCTACTTCGACAACCTCAAGA
TCACCAACACCAACAACAACTTCAAGTTCGAGTACAACATCAACGGCGACCCAA
ACAGGTCCGTGGTGGCTTACCTGAAGGAGCCAGTGATCCGCTACAACAACAGGA
AGGACTACTTCTACCTGAGCGCCACAATCAGCAAGGACGTGGAGACCGACTCCG
AGCTGACCTCTGCTTGCTGGTCGAAGATCTCCAACGACCACCGCCCCGCAGGGTCA
ACGCTGAGCAGTACTTCAACGACAACGGCGTGAACATCGTGGGCATTGACCTGG
GCATGAACCCGATCATCGCCTACTCTGTTCTGCACTACAAGAACAACGAGTTCAT
TGACCTGAACATTACCGGCAAGATCGCCGACAAGGATAAGCACCCCAATCTGAA
CTACAAGAGGATGTACGAGAAGAGGTCCGAGATCAAGAAGCTCAAGACCCTGA
TCAAGATGATCCCCGGACTACGTGAACAGCGACAGCAACATCTTCGAGGGCGACA
ATAACGTGTTCAAGCAGCTGGACAAGAAGAGCAAGGGCAGGTTCAGGTCCTCCG
AGTACATGGGCTACTACGACAAGCTGAACGTGGACGGCAAGTTCATCTCCGAGC
TGGAGATCGTGAAGAAGGTGGTGAACACAAAGCACTACAAGAATGACACCGAG
AAGAACAACGATATTATGAGGGTGTACAAGGGCAATAAGAAGAACATCATCAA
GAAGGAGATCGACACCCACAGGCACCAGATCCACTCCATCAAGGACATGAACA
GGAGGTCCGACGAGAGCAACCTGTGCTACGTGTACGACATGGTGAGCTACATCG
ACGACTTCAAGAAGCTGGTGACCTCCTACAACAAGATCGGCGAGGACTACAACA
ACCCGATCAAGCCGCTGAGCGACCCGATGCTTTTCTCCAAGTCCAAGCTGTACG
AGTACAGGCAGAACATCAGGGACAATTTCCTGAAGGACATCTGCTACCAGATGG
TGAAGATCGCCAAGCAGTACAATGCCGTGCTGGTGCACGAGCACTTCGAGCAGA
GGAAGGGCGGCATTGACAGGGTGAACAACATCCTGATGGCCCTGTTCACGCCGA
ACGACATCATCAAGAAGCTGAAGTGCGTGGCCAAGAGGGAGGGGCGTTCTGGTTT
TCAACACCAACAAGAACCATACCTCCCAGTACGTGTACAACAAGAACACCGTCG
GCTACCGCGACAGCAACAACAAGCACAACCTGTACTACATCGAGGACGAGACC
ACCAGGAAGCTCGGCGTTGTGGACTCCGACATCAACGCCTCCAAGAACATCGCC
GCCCGCCCATTCAACAAGCCACTCTACGCCATCAAGGTGAAGAACTACGATGAC
GGCCTGTTCCTGTCAGACTACAACAATAAGTACGTTCTGTACAAGAAGGACGGC
GACAAGTACGTGGCCATCGGCGATACATACAGGATCGACAAGAAGAAGATCAA
GCAGGGCTCCGTGACCCTGTACCTGCATAACGGCTACTACGTGGATGGCGAGTA
CAAGAACAATTACATCGAGAATATCAAGAAGCTGGTCCTGTGA

| | |
|---|---|
| 26 | Encoding nucleotide sequence of Casσ-13 |

ATGGCGTTCCAGAGCAAGAGGAGGATTGTGGGCAACTTCGTGAAGGAGCAGTGC
CTGAAGGCCGTGGATGGCAAGGTGATCCTGACGGACCAGGAGAAGAGGGAGCT
GATTAAGAGGTACGAGCTGCACCTGGAGCCGCATAAGTGGCTGCTGAGGCTGTT
CCTGTCCGGCTACGAGGGCAGGGATGACGGCTTCTACGAGGAGCTGGGCAACAC
GAACCTGGACAAGGAGAAGTTCTTCGAGGTCACCGCGGGCCTGAGGGATGCTCT
TCTTAGGCAGTCTGGCAGCAGCAGGGCGCTTAAGTCCTCCATGCTGGGCAAGTG
CCCGCCATCAGCTGCTGTTGGCAAGGCTGCTAAGCACATCCAGACCCTGAGGGA
CGCCGGCATTCTCCCATTCAAGACGGGCCTGACCTCCGGCGAGGATTACAACGT
GCTGCAGCAGGCCGTGCAGCAGCTTAGGTCATGGGTGGCTTGCGACCACAGGAC
GAGGGAGGCTTACGCTGAGCAGCAGGAGAAGACAAGCCAGGCCGAGGAGGCTG
CTAAGAAGGCTGCTAACGAGGTGAAGCCGGAGGATGCGAAGTCTCTGGAGAGG
CACGAGAGGGTGCTGACGAAGCTGAGGAAGCAGGAGAGGAGGCTGGAGAGGAT
GAAGAGCCACGCGCAGTTCAGCCTGGACGAGATGGACTGCACGGGCTACTCCCT
GTGCATGGGCGCTAATTACCTGAAGGACTACTGCCTGGAGAAGGAGGGCAGGG
GCCTTAGGCTTACCCTGAAGAATAGCACGATGGCTGGCAGCTACTACGTTTCCGT
GGGCGACGGCCAGCACGCTGGCATGAAGAATCCGGGCACCCCAGCTGGCGGCTC
TCCAGAGAAGGGCAGGAGGAGGAATATCCTGTTCGACTTCACCGTGGAGAAGTG
CGGCGACAATTACCTGTTCAGGTACGACGAGAACGGCAAGAGGCCGAGGGCTG
GCGTTGTTAAGGAGCCAAGGTTCTGCTGGAGGCGGAAGGGCAACAGCGTGGAG
CTTTACCTGGCGATGCCGATCAACATCGAGAACAGCATGAGGAACATCTTCGTG
GGCAAGCAGAAGTCCGGCAAGCACTCCGCTTTCACCCGGCAGTGGCCAAAGGAG
GTCGAGGGCCTTGACGAGCTTAGGGACGCTGTGGTGCTGGGCGTTGACATCGGC
ATCAACAGGGCGGCTTTCTGCGCCGCTCTGAAGACTTCCAGGTTCGAGAATGGC
CTGCCGGCCGATGTGCAGGTTATGGATACCACCTGCGATGCGCTGACCGAGAAG
GGCCAGGAGTACAGGCAGCTGAGGAAGGACGCCCACCTGCCTTGCTTGGCTGATC
AGGACGACCAGGAGGTTCAAGGCTGACCCAGGTAACAAGCACAACCAGATCAA
GGAGAAGGACGTGGAGAGGTTCGACAGCGCCGACGGCGCTTACAGGAGGGTACA
TGGACGCCATCGCGGAGATGCCGAGCGATCCACTTCAGGTCTGGGAGGCTGCCA
GGATCACCGGCTACGGCGAGTGGGCTAAGGAGATTTTCGCCAGGTTCAACCACT
ACAAGCATGAGCACGCCTGCTGCGCCGTGTCTCTTTCTCTTTCCGACAGGCTGGT
GTGGTGCAGGCTCATCGACAGGATCTTGTCTCTGAAGAAGTGCCTCCACTTCGGC
GGCTACGAGTCCAAGCACAGGAAGGGCTTCTGCAAGTCCCTGTACAGGCTGAGG

TABLE 1-continued

Description of sequences

SEQ
ID
NO:    Description

CACAACGCCAGGAACGACGTGAGGAAGAAGCTGGCCAGGTTCATCGTGGATGC
      CGCCGTTGACGCGGGCGCTTCTGTTATTGCGATGGAGAAGCTGCCGTCCTCTGGC
      GGCAAGCAGTCAAAGGACGACAACAGGATCTGGGACCTGATGGCCCCGAACAC
      CCTGGCTACTACTGTGTGCCTGATGGCCAAGGTGGAGGGCATCGGCTTCGTCCA
      GGTCGATCCAGAGTTCACCTCCCAGTGGGTGTTCGAGCAGAGGGTGATTGGCGA
      TAGGGAGGGCAGGATCGTGAGCTGCCTGGATGCTGAGGGCGTGAGGAGGGATT
      ACGACGCTGACGAGAACGCCGCGAAGAACATCGCCTGGCTGGCTCTTACCAGGG
      AGGCTGAGCCATTCTGCATGGCGTTCGAGAAGAGGAACGGCGTGGTGGAGCCGA
      AGGGCCTTAGGTTCGACATCCCGGAGGAGCCTACCAGGGAGCAGGATGAGTCGG
      ACCAGGACTTCAAGAAGAGGCTGGAGGAGAGGGACAAGCTGATCGAGAGGCTG
      CAGGCGAAGGCGGATAGGATGCAGGCTATCGTTCAGAGGCTTTTCGGCGACAGG
      AGGCCGTGGGATGCTTTCGCTGACAGGATTCCTGAGGGCAAGAGCAAGAGGCTG
      TTCAGGCACAGGGACGGCCTGGTTCTGAACAAGCCGTTCAAGGGCCTGTGCGGC
      TCCGAGAATAGCGGCCAGAAGGCTTCTGCTAGGAACAGCCGCTGA

27    Direct repeat sequence of Casσ-1
      AGUGCAAUAGUUACAGAAUAGUAAUUAUAUUCGCAC 28    Direct repeat sequence of Casσ-2
      UGUUGGUAUCUAGUAAAAUCUAGAGCCGUUGACA 29    Direct repeat sequence of Casσ-3
      GUGUCAACGCAUCCUCUAUAGUUGAGGAAG 30    Direct repeat sequence of Casσ-4
      GUGUUGUCCUCAUUAUAAUAUGAUGGACAGAGACAC 31    Direct repeat sequence of Casσ-5
      CUAACUGUGUGAGCUUCUAACCGAAGCUAAUGACAC 32    Direct repeat sequence of Casσ-6
      GUGUCAACGCAUCCUCUAUAGUUGAGGAAGCAACAC 33    Direct repeat sequence of Casσ-7
      GUGUCAACGGCUCUAGAUUUUACUAGAUACCAACACA 34    Direct repeat sequence of Casσ-8
      GUGUUAGUAUCUUGUAGAAUCAGGAGCUAUUGACAC 35    Direct repeat sequence of Casσ-9
      GUGUCAAUGAUCCAUUUUAUGGAUCCACACUGAGAU 36    Direct repeat sequence of Casσ-10
      GUGUCAUUAGCCACCCCAUUCAGAGGAGGCCUACAC 37    Direct repeat sequence of Casσ-11
      GUGUUGGUAUCUAGUAAAAUCUAGAGCCGUUGACAC 38    Direct repeat sequence of Casσ-12
      AUAGUCGAGGGUGUAAUAAUAUGCACCUAAUGCGAC 39    Direct repeat sequence of Casσ-13
      GUGUAGGCCUCCUCUGAAUGGGGUGGCUAAUGACAC 40    Encoding nucleic acid sequence of direct repeat sequence of Casσ-1
      AGTGCAATAGTTACAGAATAGTAATTATATTCGCAC 41    Encoding nucleic acid sequence of direct repeat sequence of Casσ-2
      TGTTGGTATCTAGTAAAATCTAGAGCCGTTGACA 42    Encoding nucleic acid sequence of direct repeat sequence of Casσ-3
      GTGTCAACGCATCCTCTATAGTTGAGGAAG 43    Encoding nucleic acid sequence of direct repeat sequence of Casσ-4
      GTGTTGTCCTCATTATAATATGATGGACAGAGACAC 44    Encoding nucleic acid sequence of direct repeat sequence of Casσ-5
      CTAACTGTGTGAGCTTCTAACCGAAGCTAATGACAC 45    Encoding nucleic acid sequence of direct repeat sequence of Casσ-6
      GTGTCAACGCATCCTCTATAGTTGAGGAAGCAACAC 46    Encoding nucleic acid sequence of direct repeat sequence of Casσ-7
      GTGTCAACGGCTCTAGATTTTACTAGATACCAACACA TABLE 1-continued Description of sequences

| SEQ ID NO: | Description |
|---|---|

47    Encoding nucleic acid sequence of direct repeat sequence of Casσ-8
      GTGTTAGTATCTTGTAGAATCAGGAGCTATTGACAC 48    Encoding nucleic acid sequence of direct repeat sequence of Casσ-9
      GTGTCAATGATCCATTTTATGGATCCACACTGAGAT 49    Encoding nucleic acid sequence of direct repeat sequence of Casσ-10
      GTGTCATTAGCCACCCCATTCAGAGGAGGCCTACAC 50    Encoding nucleic acid sequence of direct repeat sequence of Casσ-11
      GTGTTGGTATCTAGTAAAATCTAGAGCCGTTGACAC 51    Encoding nucleic acid sequence of direct repeat sequence of Casσ-12
      ATAGTCGAGGGTGTAATAATATGCACCTAATGCGAC 52    Encoding nucleic acid sequence of direct repeat sequence of Casσ-13
      GTGTAGGCCTCCTCTGAATGGGGTGGCTAATGACAC 53    NLS sequence
      SRADPKKKRKV 54    Amino acid sequence of Casσ-1-NLS fusion protein
      MGPKKKRKVMDYKDHDGDYKDHDIDYKDDDDKMSNYKNIKFKLVPFSQKDLINM
      QLNVNLHQQCYREFVEQFCVLCNIPFPGLSKDQIEQKRKQLNLSEDDEKDINYIKDL
      VKNKNNIGNSIYAFFTGTKKEMPSRKTDLTPLYRLLKANILPFSLLKGRENYKKSIFQ
      TVINQTLEKFKSYPKCNESVENNFKLSLNKDSNEEQVLNESEMKDLQNLFENLSKN
      QSFSFFNFNKNWFSKDKIKTKLLNNETNKIKSLSSEEIDLILSYKDKLYSNEFDLISMF
      VEFNLQKQKAESLKSQADLNLFKNNNYSFRIGSNYENFNLTQNNKDILLEINSSMGE
      KITFKIIPHKKTQIWNLEKNNVKITSGENLGNYKSVDVIKMKRPADIKAKLLKTSELN
      IEIKNNQIYCNFIYEYKCSDHGVYFFHCSGNKKPDEKNENILKERERTFSFIDLGLFPM
      YSISTFKYNNKSNDGEILVKSGSGNEKLDFGSAFKIHSIQIGKNSTNLNKIKQLLEKLK
      DLKTYLKFSKSISSFDENSYQRQLKTGVEISELNSLSFQKISEIKSINLGFNESFNKEYF
      LKLIENQTFTQKELLLLNCKIKDLFKILYKEYSNIKNSRIFKFNKEDDLICDGYYWLQ
      VIDEIINIKKSLTYFNSKPSEKGNKSKFIFLKDFNYKNNFANNYAKIAASRLKKYCLE
      HKVDVCVFEKNLNNFLQSKDNDKKTNKTLINWANRNLFEKIKLALEEHDICVSEVD
      GKHSSQLDPQTMNWGARDNLNGNGNKEKIFFERNGQIIQQNADLSASEVLAKRFFT
      RYEDIVHIYIDQKIKDDKTILKLVKGKVRVESYLKKTINSCYAIVDENGFLKPISKKD
      YNKFQELPSKPRTDIKSNEMYRHGSKWYHFQQHREFQQDLLARGRELKKIASRADP
      KKKRKV 55    Amino acid sequence of Casσ-2-NLS fusion protein
      MGPKKKRKVMDYKDHDGDYKDHDIDYKDDDDKMNKTDTQNNEQINKPTQLLNN
      KDIELTVKTVKSATVKVDNNSKKELFGLFNYFTSVASGIKDKVYNLQSDEKTAPIFN
      DYVKQPQRGRSAATTLFTKLDAEKTYTSQHSFPGKWRDSGIFPLYNKESEKYDLST
      HGYHYSANAEIHTQLDSHDECNKECEKEYAALRDEVNNYKYEFTLQFKAENAEKF
      YNFVEKLTLMGWRYDATFRSFFELHMHPKLKTGETTYRATYKLPSGKSKRYSFFRD
      DIADEIAKNPEFWPMLESSNAISWINSNNLLSRKKDKANYSSTSLIKSQIRLYLGNNG
      VPFTAREHDGRIYFSFRLPAINGEKGRMVEIPCSYKKVFNGKARKSCYLGGLTIEKT
      DAGKHIFKYSVNNKKPQVAELNECFLRLVVRNREYFNNVVAGKITDINTDHFDFYV
      DLPLNVKEDPIHDLSSTEVFGKNGLRSYYSSAYPEIKNLGSQIETGKNLTCPITKTHNI
      MGIDLGQRNPFAYCIKDNTGKLIAQGHMDGSKNETYKKYINFGKESTSVSHLIKETR
      SYLHGDPEAISKELYNEVAGFCNNPVSYEEYLKYLDSKKFLINKEDLSKNAMHLLR
      QKDHNWIGRDWLWYISKQYKKHNENRMQDADWRQTLYWIDSLYRYIDVMKSFH
      NFGSFYDKNLKKKVNGTVVGFCKTVHDQINNNNDDMFKKFTNELMSVIREHKVSV
      VALEKMDSMLGDKSRHTFENRNYNLWPVGQLKTFMEGKLESFNVALIEIDERNTSQ
      VCKENWSYREADDLYYVTDGESHKVHADENAANNIVDRCISRHTNMFSLHMVNPK
      DDYYVPTCIWDTTEESGKRVRGFLTKLYKNSDVVFTKKGDKLVKSKTSVKELKKL
      VGKTKEKRGQYWYRFEGKSWINEADRDTIILNAKKISRERDNGEQSTDTRSQNVTV
      SVLDVCETAEKKKLVLVSRADPKKKRKV 56    Amino acid sequence of Casσ-3-NLS fusion protein
      MGPKKKRKVMDYKDHDGDYKDHDIDYKDDDDKMKSIKSIKSIKTKVVKNNELKLI
      ELSTWCSSICEQLERYIFILGGKQIHDRDGVVVLDGAVERKIYCKKDKSLIAACEVV
      YKHFTDKSSKSRTFGSWFLGGKSEGDNTNKGRKSTKEKTEKQIAKQIADKKELTDS
      LQLLWDKKLLPFPIDNKGYDFINTPRAKSYKWAITKTIHAKIKSYNEQCVETKKEYD
      ALNAEINTYKTILFSGYSEKDIDDLQKFVDICEANNHRINYKFISFLKRKDLNFDEQT
      GKYRKEGKWIQHKNGKEVKSKYSMKDEIVEALYKYKSLTKNDVSVLCNEHQKEDE
      MGKVVHYNMKRYSDLLFRKKNKKEIPSYTKISLATSKIELGLNNVKYNVEQVEDKL
      IWTICDQTGKDIQFVTVYTRKKEDNRTNGKKGAGFYKGKHHQLEDLKIVPVGDIGT
      YDISFKVNGKRPFTGTLKEPNIICRGGKVFVQMPININIDKTLNDARKKVLYAYRETY
      SGSVNGKKQKMIKIENSKIAESLKSLGRDAIVLGVDLGLRGLATAVVSHNGKNETV
      KSSQYIKGDIVEWEKYRVFNDNIREVKKYIFLTKKSYTATTEEYTEFYKECSKPEQD
      YLDSLKTYKDKNVKLNELKYTKNAWSVSKMFEDVSKMFETLKQDRLKYYDIFNMP

50

TABLE 1-continued

Description of sequences

| SEQ ID NO: | Description |
|---|---|

YWAASLKNYMSLMKSYNYVGVDIKVSKEYMSKYQSLYNNIKEDYAKKIGSYIVQL
AVAKNCDIIVLEELKSNLGSVDRKSKRDNEMSLMWNCGRIKTHVENMAKDYGMFI
DEVPEYGTSQVYHKTGNYGYRDEDNREIFWYEDNKDVAYIHADENAAINIAKRFLS
QHTDNSSFSVILKGDAYYLNIASNSKRMRAAALKTFGDLNKPFKINANDKNGNLYK
KTRIFKSDSRWIGVNDKDLYIEHIKSLRNLRVRQSRADPKKKRKV

57    Amino acid sequence of Casσ-4-NLS fusion protein
MGPKKKRKVMDYKDHDGDYKDHDIDYKDDDDKMPSFTKVDEDKIVLKLGNNYIP
YGLSRISEDKMLWSFSSPQKKKLSIITNHRRVGKGKHFYLEGLEIADITKGDGDKTSP
SGKYTISFSINGKQDVKGELKEPSFGLRNGNVYMFLPISIKQTDVFESRVEMRRLLSM
AYQPTTVEDLILDDVETKQTVKQGKKEVNTTNIAIQEAIKKHGRLLKVMGVDLGL
RNFAFAIKNYDGHHDTLLRQLYSESDLNEKQRYTTLANDLSKVGNHIKFAAVFYGA
NDTEENTKMFDAECTDAESRTHLEWLRKAKKSGVLLKDLRKDKTWIVSIKYTELRN
RLHALKFGRMKSYDYRNNLYWAATIKKFISLSASFYGVGRPSRGKKDVRELKKKHT
FFSTYQDLYNNVKEDYAKKVANLVVMTAKENNVDIIVVENLIGHCGSKDYKTRAE
NEMSIMWNHGRIKTFIDCIANANGMLLAEVSEFETSQVYHETRNYGYRDKKMKEIL
WYMDSEGNVQYAHAEVNAAINIADRFLSQHTNLFSFPVCKSKKDENVYEIDIAEGK
ELEGQDEVKKAKKPKGGKRLNGAVVKTFGSTKIMFNGIVDKNKKGQIKTKTRVYNI
DGEWGGKTQKDEYVDKIRKVVDAMSPEEKAKVKAALKKCFSSSRADPKKKRKV 58    Amino acid sequence of Casσ-5-NLS fusion protein
MGPKKKRKVMDYKDHDGDYKDHDIDYKDDDDKMTKELSGVRVIELKTDLRKDQF
WDRYERCFKTYHALYNEVPCWGLDWVEQKTQNQTSRELGCERVDLTAQRKALYE
RTDRTISYEQFSNCLKALWLGLLNCQQGNHMYTKLFEGAIQTDQMTAEDWAVLTE
YVADPKSHNSQFLFRVSNTLKHIGFFSRPPFTATLFAPERKAITKDVMSDLKGWIEM
KRMTEESYAAEEVQIQQMKAEVPVRIRQSLLRFFDTCIGLNLIGHEDERVHHYLRDC
IIPALQQRTIPTEHFYLKSNRKDVGQKHIDFSLDIKFYELLAEMPELWNTLETSEDDLI
PKPLILKHLHLLEAIMSHRAHRKTAAYAFVGEADYHRFYYLLGGNYTKHLISATGSE
LPDRVIWDNDKDVLMRNGRKVERLYVKVGDRKENFNFEVYTIAMNTKGLRGHRST
LKPTSYLQDLQIWSNPEGESTYLNFVRKGTERSAICKEPVLVYRNGAFFLRLSMSVE
GMRASEEHIALQYYLSAAATGSDLSKDTEKTVERFNLIQGKTYKVMSVDLGIRSPFA
WAVTESTITGVANPSQILNSGEMEIADDPDYTELFYAYKNLGHLIGQVKSSSKGKGL
KADSHLVDMIHTVQRFFADYKVAGQRRSQIFEQFSKDPDPLYQMDQMMKRYENNL
ESVKKDFSFLINILFKYVTLQFGALRNRRRSYLSQNQMADQKFDQDFKWLNILEQR
KRVTRSLSYLGTDNSRIPICLEQQKLDYNGCKDNFLKQLASKIVRIAHQNDCCLIVLE
DLEGYGKTLNQRDENFLTAFWSPKRVKDAIINAAQWYGIGVVTVSEAQTSQVHHES
GRIGYRKGRDLFFLTPDGQIESVPSDINAAKNIGHRFFSRHTDLHQVYLKGSDEGAK
RMKGCLLYQFGSLEAARTHLTGTGPTWYLDGVEWIDKTERNLRRDLLKQRVEIEK
MPFSRADPKKKRKV 59    Amino acid sequence of Casσ-6-NLS fusion protein
MGPKKKRKVMDYKDHDGDYKDHDIDYKDDDDKMKSIKSIKSIKTKVVKNNELKLI
ELSTWCSSICEQLERYIFILGGKQIHDRDGVVVLDGAVERKIYCKKDKSLIAACEVV
YKHFTDKSSKSRTFGSWFLGGKSEGDNTNKGRKSTKEKTEKQIAKQIADKKELTDS
LQLLWDKKLLPFPIDNKGYDFINTPRAKSYKWAITKTIHAKIKSYNEQCVETKKEYD
ALNAEINTYKTILFSGYSEKDIDDLQKFVDICEANNHRINYKFISFLKRKDLNFDEQT
GKYRKEGKWIQHKNGKEVKSKYSMKDEIVEALYKYKSLTKNDVSVLCNEHQKEDE
MGKVVHYNMKRYSDLLFRKKNKKEIPSYTKISLATSKIELGLNNVKYNVEQVEDKL
IWTICDQTGKDIQFVTVYTRKKEDNRTNGKKGAGFYKGKHHQLEDLKIVPVGDIGT
YDISFKVNGKRPFTGTLKEPNIICRGGKVFVQMPININIDKTLNDARKKVLYAYRETY
SGSVNGKKQKMIKIENSKIAESLKSLGRDAIVLGVDLGLRGLATAVVSHNGKNETV
KSSQYIKGDIVEWEKYRVFNDNIREVKKYIFLTKKSYTATTEEYTEFYKECSKPEQD
YLDSLKTYKDKNVKLNELKYTKNAWSVSKMFEDVSKMFETLKQDRLKYYDIFNMP
YWAASLKNYMSLMKSYNYVGVDIKVSKEYMSKYQSLYNNIKEDYAKKIGSYIVQL
AVAKNCDIIVLEELKSNLGSVDRKSKRDNEMSLMWNCGRIKTHVENMAKDYGMFI
DEVPEYGTSQVYHKTGNYGYRDEDNREIFWYEDNKDVAYIHADENAAINIAKRFLS
QHTDNSSFSVILKGDAYYLNIASNSKRMRAAALKTFGDLNKPFKINANDKNGNLYK
KTRIFKSDSRWIGVNDKDLYIEHIKSLRNLRVRQSRADPKKKRKV 60    Amino acid sequence of Casσ-7-NLS fusion protein
MGPKKKRKVMDYKDHDGDYKDHDIDYKDDDDKMNKTDTQNNEQINKPTQLLNN
KDIELTVKTVKSATVKVDNNSKKELFGLFNYFTSVASGIKDKVYNLQSDEKTAPIFN
DYVKQPQRGRSAATTLFTKLDAEKTYTSQHSFPGKWRDSGIFPLYNKESEKYDLST
HGYHYSANAEIHTQLDSHDECNKECEKEYAALRDEVNNYKYEFTLQFKAENAEKF
YNFVEKLTLMGWRYDATFRSFFELHMHPKLKTGETTYRATYKLPSGKSKRYSFFRD
DIADEIAKNPEFWPMLESSNAISWINSNNLLSRKKDKANYSSTSLIKSQIRLYLGNNG
VPPFTAREHDGRIYFSFRLPAINGEKGRMVEIPCSYKKVFNGKARKSCYLGGLTIEKT
DAGKHIFKYSVNNKKPQVAELNECFLRLVVRNREYFNNVVAGKITDINTDHFDFYV
DLPLNVKEDPIHDLSSTEVFGKNGLRSYYSSAYPEIKNLGSQIETGKNLTCPITKTHNI
MGIDLGQRNPFAYCIKDNTGKLIAQGHMDGSKNETYKKYINFGKESTSVSHLIKETR
SYLHGDPEAISKELYNEVAGFCNNPVSYEEYLKYLDSKKFLINKEDLSKNAMHLLR
QKDHNWIGRDWLWYISKQYKKHNENRMQDADWRQTLYWIDSLYRYIDVMKSFH
NFGSFYDKNLKKKVNGTVVGFCKTVHDQINNNNDDMFKKFTNELMSVIREHKVSV
VALEKMDSMLGDKSRHTFENRNYNLWPVGQLKTFMEGKLESFNVALIEIDERNTSQ TABLE 1-continued Description of sequences SEQ
ID
NO:    Description VCKENWSYREADDLYYVTDGESHKVHADENAANNIVDRCISRHTNMFSLHMVNPK
       DDYYVPTCIWDTTEESGKRVRGFLTKLYKNSDVVFTKKGDKLVKSKTSVKELKKL
       VGKTKEKRGQYWYRFEGKSWINEADRDTIILNAKKISRERDNGEQSTDTRSQNVTV
       SVLDVCETAEKKKLVLVSRADPKKKRKV 61     Amino acid sequence of Casσ-8-NLS fusion protein
       MGPKKKRKVMDYKDHDGDYKDHDIDYKDDDDKMKKPKQNIEETDLKITTPKTATI
       KATNLDDKMRLFTFFNGFTTVCSKVKDDIYNFGQNEDTLPVYTDYIKASQRARMCA
       TTLATKSECDFAKKYGEHFPLPHYNQEGMNYTTHQHTYSVNSAVHTQLDSLNECD
       KLTNGEYVKLKKTVDELEEKLTEEHGKEPLDFLVKFVDEQILLGWRFDGKFRLFFE
       VAMLPELKNGNIIYKKAYKTSGGKGRRYSFYNPSVADNISKNPTVWNLLSDVKAVD
       YISLSNSLLRKKPHAQYTNTTLNRAQVRPTFGNNGVPFSISVSDDDYVYIRFRLPKKD
       GEEKGQEISVKCSYKTSYKGKRSKTLRKSCYLGNLKIEENGKGKYICKYNINGRETT
       TAELNECFLRVRINNNRWFNKYLNGTLTKEDGVLKSEYFDFYFDLCLNVHQKSIHG
       LTNSEIFGGKGKSIRSYYSTSYPEVKNLDGQKNIKTDFGCYVDKPHNIMGIDLGQRN
       PFAWAVLDQNGNVKDVGHLDGAENDTYKDYLTFSNRCKDVKNLILQSRDYLYGD
       DEAIDETLFDSVVQFVNSNITLNKYKSYLDEKKSLINKESLEKNRLYELKKKDHGWF
       VRDCLWFLTKEYHRINSERKTHSDWRYTLYWVDAIHRFIDVNKSFNSLGSYYDKKQ
       SKSINGIQKDFCRSYWNQIDNLNEDTLKKFVFELLPVIKKNNVCLIAIEELKSMLGDD
       DKRAEDNRLYNLWPVGQLKTFLEGKLLPYNVAVMEVSEQNTSQIVNGQWSYREGD
       DLYYVKNNDNNTMCKTHADENAAINIALRAYSHHTNLYSIYMINPIDDYYVPSCIW
       NNKDEGSKRIRGFLTKTYGTSDVVFIKKNEKLVKSDVSIKDVKRIVKNIGNEKNKKS
       EIWYRMNDIEWIDEGSRDIIINTIKSKVRSRADPKKKRKV 62     Amino acid sequence of Casσ-9-NLS fusion protein
       MGPKKKRKVMDYKDHDGDYKDHDIDYKDDDDKMTDKSISFKQFSQILNVLYKCIV
       ISGKGRGLTSIILGQPQCKDSLTSADWGNLETLSAKDELTPAEVKDITKDLMYRASN
       TLVSIGFRNRSPFKLTLTSGERYAVVENVHRSLKSWVEVDKITRENYLNEEIALSDAF
       NNIDETLLPTLKEFFDACMNENIIHHFDARVYAYTRDCVIPALVAGLEIKDHFYIDGR
       DKAKRDYSLQGYAELLKGFPKLWQGVDPEILAKLYILEAQMDHKKHRPCAAYAFI
       GEDSYSRVQYLLGNNYTSFSPYALGVDLDDVTCGDDAEADTQFPKNKVIQFSQGKK
       VTKLSLTVSRGKEDTNKYSFDVFLADKYSNGSYKPSPYFSDLSVWVSEIGMLMEFT
       RKGERVQAIVKEPSLIYRKGAFYVRLNMGVIQDTSPEINDLYWYLSSGAPMSMTDR
       SKASETPKNTERLESIKGKSYRFLGIDLGLRSPFAWAVGEASISGVINKPTIIATGDYT
       TARDTRYDTLFFALKNAGKVIGVTKSLANGKDASFNGLMGTITAAREYLAHYSGVA
       THKVAAIQAFCQDDNPLETLKGLLKSYNNDLVTLKKDPRFIGGILLRYARLLKGELV
       TSRKMHLREHSVESKFGQEYMWLNILEREKRVCRSLSYLGLGNDRDSVIMGNLTTP
       YNHCKENLLKQLAARIVSLAVENKCHVIVMESLGGSNKSMNTRGQNFLEAFWSPQ
       KIKDTIINAAAWHGIMVAEVSESQTSQVCFETGTFGHRDRASLYFLDKNGDLQETH
       ADMNAAKNLVERFTTRHTNLRQVNMDSLPKEGPDKTPKKSPSKKKMEKAKMDNP
       EDQSKRLKGFLTVKFGNVKAAQEYFASRKPEQSYSGKKDEAIYWYLDGDEWITKK
       EKESRVSVIEGLVGLKEVAVSRADPKKKRKV 63     Amino acid sequence of Casσ-10-NLS fusion protein
       MGPKKKRKVMDYKDHDGDYKDHDIDYKDDDDKMAFQSKRRIVGNLVKEQCLKA
       VDGKVILTDQEKRELIKRYELHLEPYKWLLRLFLSGYEGRDDGFYEELGNTNLDKE
       KFFEVTAGLRDALLRQSGSSRALKSSMLGKCPPSAAVGKAAKHIQALRDAGILPFKT
       GLTSGEDYNVLQQAVQQLRSWVACDHRTREAYAEQQEKTSQAEEAAKKAVNEVK
       PEDAKSLERHERALTKLRKQERRLERMRSHAQFSLDEMDCTGYSLCMGANYLKDY
       CLEKEGRGLRLTLKNSTMAGSYYVSVGDGQHAGMKNPGTPAGGSPEKGRRRNILF
       DFAVEKCGDNYLFRYDENGKRPRAGVVKEPRFCWRRKGNSVELYLAMPINIENSM
       RNIFVGKQKSGKHSAFTRQWPKEVEGLDELRDAVVLGVDIGINRAAFCAALKTSRF
       ENGLPADVQVMDTTCDALTEKGQEYRQLRKDATCLAWLIRTTRRFKADPGNKHNQ
       IKEKDVERFDSADGAYRRYMDAIAEMPSDPLQVWEAARITGYGEWAKEIFARFNHY
       KHEHACCTVSLSLSDRLVWCRLIDRILSLKKCLHFGGYESKHRKGFCKSLYRLRHN
       ARNDVRKKLARFVVDAAVDAGASVIAMEKLPSSGGKQSRDDNRIWDLMAPNTLAT
       TVCLMAKVEGIGFVQVDPEFTSQWVFEQRVIGDREGRIVSCLDAEGVRRDYDADEN
       AAKNIAWLALTREAEPFCMAFEKRNGVVEPKGFRFDIPEEPTREQDESNQDFKKRLE
       ERDKLIERLQAKSDRMRAIVRRLFGDRRPWDAFADRIPEGKSKRLFRHRDGLVLNK
       PFKGLCGSENSEQKASARNSRSRADPKKKRKV 64     Amino acid sequence of Casσ-11-NLS fusion protein
       MGPKKKRKVMDYKDHDGDYKDHDIDYKDDDDKMDTDTELSDEVELSDEVELSDE
       VELSDEVELTVKKVKTTTVKVDNNFKKELFELFNHFTSVASGIKDRLYDLQFDENT
       ASIFKGYIKEAKRGHGAATTVFTKLNPKKIYSGKKSFPRDYRDRGIFPFYNKESGKY
       DLSTCGYHYSANAEIHTQLNSHDECNKQCEKEYAALEKERNKYKHEFTRQFKAEN
       VEKFSNFVEKLTLMGWRYDATFRNFFELHMHPKLKTSETTYRATYKLPSGKSKRYS
       FSRDDIADEIAKNPEFWPMLESSNAVSWINSNNLLSRKKEKANYSSTSLIKSQIRLYL
       GDNGVPFTAREHDGRIYFSFRLPSINGEKGRNVEIPCSYKKVFNGKARKSCYLGGLTI
       ENTGGSKHIFKYSVNNKKPQVAELNECFLRLVVRNHGYFNKMVNGKLTDKDGKLH
       ADYPDFCIDLPLNVKEDPIHDLTYQEINGVKANPEKNIEKKVGLLGFYQSAYPEIKNL
       GSQIETGKNLTCPITKTHNIMGIDLGQRNPFAYCIKDNNGKFIAKDHMDGSKNETYK
       KYINFGKESTSVSHLIKETRSYLHGDPEAISKELYNEVSGLCNSPLSYEEYLKYLDSK
       KFLINKEDLNKNAMHLLRQKDHNWIGRDWLWYISKQYKKHNENRMQDADWRQT TABLE 1-continued Description of sequences

| SEQ ID NO: | Description |
|---|---|

LYWIDSLYRYIDVMKSFHNFGSFYDKNLKKKVNGTAVGFCKTIYDQINNNNKDMF
KKFTNELIPIIRKHKVSVVALEKMESMLGDKSRNTFENRNHNLWPVGQLKTFIENKL
DGFNVIVVEVDERNTSQMCDGNWSYREADDLYYVKDGELREVHADENAANNIVD
RCISRHTNIFSLYMTNPMDDYYVPACIWDRSENGKRGRGFLTKMYKNSDVVFTKKD
DKLVKSKMSVKELKKLVDKTKEKRGQYWYLFEGKSWINAADRDTIISNAKKLFRE
RDGGEQSTDTRSQNVTVSVLDVCETVEKKKLVLVSRADPKKKRKV

65  Amino acid sequence of Casσ-12-NLS fusion protein
MGPKKKRKVMDYKDHDGDYKDHDIDYKDDDDKMSTEVDVKTINLKIAKKGGVYP
ILEQSIKENCKSNDLLEFFMVLNRLQTYYIESNEEILVDFPKKYDELFDIVKNNDSSV
TREYFDSLCDKYITEVCANGFVNNVYIAHNKNQELNWAETSNDRKIKSNKTFMFGK
IKGLIRDKFGREELSDKDATKQLCEDIFNLFILNNANIELDEKYNIIKDELIQIWNERN
KEFIHIKDITLLFRQWGILPTYDNITHNCELKAIIAEPVRRFKSWLECNSEANKNYDTE
REKCTKYMDVMDSDLTVEFSKMVTELGNPFGANDKNIYKYFNQKFLLFFKQVVQP
KFVNGEPLDESNGSYSGEIKINSAGKVENYSIAVSVIDTIKKYPTIWSDRSWGESVIST
VAKIDPQYGIDDITDDMQVSPFYLFYGYFTAYNYIQQHKRNAKYTPISKDSLPSLYL
GNNYIPFKIDCENVDDDRFYITIKNMNNLKLNVLYRKPKLKFAKTKEKTKRNKCYF
DNLKITNTNNNFKFEYNINGDPNRSVVAYLKEPVIRYNNRKDYFYLSATISKDVETD
SELTSACWSKISNDTARRVNAEQYFNDNGVNIVGIDLGMNPIIAYSVLHYKNNEFID
LNITGKIADKDKHPNLNYKRMYEKRSEIKKLKTLIKMIPDYVNSDSNIFEGDNNVFK
QLDKKSKGRFRSSEYMGYYDKLNVDGKFISELEIVKKVVNTKHYKNDTEKNNDIM
RVYKGNKKNIIKKEIDTHRHQIHSIKDMNRRSDESNLCYVYDMVSYIDDFKKLVTSY
NKIGEDYNNPIKPLSDPMLFSKSKLYEYRQNIRDNFLKDICYQMVKIAKQYNAVLVH
EHFEQRKGGIDRVNNILMALFTPNDIIKKLKCVAKREGVLVFNTNKNHTSQYVYNK
NTVGYRDSNNKHNLYYIEDETTRKLGVVDSDINASKNIAARPFNKPLYAIKVKNYD
DGLFLSDYNNKYVLYKKDGDKYVAIGDTYRIDKKKIKQGSVTLYLHNGYYVDGEY
KNNYIENIKKLVLSRADPKKKRKV 66  Amino acid sequence of Casσ-13-NLS fusion protein
MGPKKKRKVMDYKDHDGDYKDHDIDYKDDDDKMAFQSKRRIVGNFVKEQCLKA
VDGKVILTDQEKRELIKRYELHLEPHKWLLRLFLSGYEGRDDGFYEELGNTNLDKE
KFFEVTAGLRDALLRQSGSSRALKSSMLGKCPPSAAVGKAAKHIQTLRDAGILPFKT
GLTSGEDYNVLQQAVQQLRSWVACDHRTREAYAEQQEKTSQAEEAAKKAANEVK
PEDAKSLERHERVLTKLRKQERRLERMKSHAQFSLDEMDCTGYSLCMGANYLKDY
CLEKEGRGLRLTLKNSTMAGSYYVSVGDGQHAGMKNPGTPAGGSPEKGRRRNILF
DFTVEKCGDNYLFRYDENGKRPRAGVVKEPRFCWRRKGNSVELYLAMPINIENSM
RNIFVGKQKSGKHSAFTRQWPKEVEGLDELRDAVVLGVDIGINRAAFCAALKTSRF
ENGLPADVQVMDTTCDALTEKGQEYRQLRKDATCLAWLIRTTRRFKADPGNKHNQ
IKEKDVERFDSADGAYRRYMDAIAEMPSDPLQVWEAARITGYGEWAKEIFARFNHY
KHEHACCAVSLSLSDRLVWCRLIDRILSLKKCLHFGGYESKHRKGFCKSLYRLRHN
ARNDVRKKLARFIVDAAVDAGASVIAMEKLPSSGGKQSKDDNRIWDLMAPNTLAT
TVCLMAKVEGIGFVQVDPEFTSQWVFEQRVIGDREGRIVSCLDAEGVRRDYDADEN
AAKNIAWLALTREAEPFCMAFEKRNGVVEPKGLRFDIPEEPTREQDESDQDFKKRLE
ERDKLIERLQAKADRMQAIVQRLFGDRRPWDAFADRIPEGKSKRLFRHRDGLVLNK
PFKGLCGSENSGQKASARNSRSRADPKKKRKV 67  Nucleotide sequence of Casσ-1 system expression cassette
ATGGGACCCAAGAAGAAGCGTAAGGTCATGGACTATAAAGATCACGACGGCGA
TTATAAAGACCACGACATTGATTACAAGGACGATGATGACAAGATGAGCAACTA
CAAAAACATTAAGTTCAAGTTGGTTCCGTTCAGTCAAAAGGATCTTATAAACAT
GCAGCTAAACGTGAATCTCCACCAGCAGTGTTATAGAGAGTTCGTGGAGCAGTT
CTGCGTCCTCTGTAATATCCCCTTTCCTGGGCTTAGTAAAGATCAAATTGAGCAG
AAGCGGAAACAATTAAATCTGTCTGAAGACGACGAGAAGGACATCAACTACATC
AAGGACCTTGTAAAAAATAAGAATAACATCGGCAATTCAATCTATGCTTTTTTCA
CTGGTACAAAGAAGGAAATGCCAAGCAGAAAGACTGATTTAACACCTCTTTACC
GCCTCCTTAAGGCTAACATACTGCCCTTTAGCCTCCTCAAAGGGCGAGAGAACT
ATAAGAAAAGCATATTCCAAACTGTTATTAACCAGACACTGGAAAAGTTTAAGT
CATATTTCAAGTGCAATGAATCAGTTGAAAACAACTTCAAACTGTCTCTGAACA
AGGACTCAAATGAGGAGCAAGTCCTGAATGAAAGCGAAATGAAAGACCTCCAA
AACCTATTCGAGAATTTGTCTAAAAATCAGTCTTTTTCCTTCTTCAACTTCAATAA
GAACTGGTTCTCCAAGGACAAGATCAAGACGAAACTCCTCAATAACGAGACCAA
CAAAATTAAGTCGTTGTCATCTGAAGAGATCGACCTGATCCTTAGTTATAAGGAT
AAGTTGTACTCCAACGAATTTGATCTGATTTCCATGTTCGTGGAGTTCAACTTAC
AGAAACAGAAGGCGGAGTCCTTGAAATCACAGGCGGACTTGAACCTCTTCAAGA
ACAACAACTATTCTTTTCGGATTGGAAGCAACTATGAAAACTTTAATCTAACTCA
AAATAACAAGGACATCCTGCTGGAAATCAATTCTTCAATGGGTGAGAAGATTAC
CTTTAAGATCATTCCGCATAAGAAAACCCAGATCTGGAATTTAGAGAAGAATAA
TGTTAAGATAACTTCGGGCGAGAACCTGGGGAATTACAAATCGGTGGACGTCAT
CAAGATGAAGCGGCCAGCAGACATTAAGGCAAAGCTGCTGAAGACGTCAGAGC
TGAATATCGAGATCAAGAACAACCAAATCTATTGCAACTTCATTTATGAGTACA
AGTGCTCCGATCATGGCGTGTACTTCTTTCACTGCAGTGGCAACAAGAAGCCAG
ATGAGAAGAATGAGAATATTCTAAAGGAGAGGGAGAGGACCTTTAGTTTCATTG
ATCTCCGGTCTTTTTCCGATGTATTCCATCTCCACATTTAAGTACAATAATAAGAG
CAATGATGGTGAGATCCTAGTCAAGTCGGGATCTGGGAACGAGAAACTCGACTT TABLE 1-continued Description of sequences

| SEQ ID NO: | Description |
|---|---|

CGGCTCTGCCTTCAAAATTCATTCAATCCAGATTGGAAAGAACAGCACAAATCT
CAACAAAATTAAGCAACTTCTTGAGAAGCTGAAAGACCTGAAGACCTACCTCAA
ATTCTCTAAGAGCATAAGCAGCTTCGACGAGAACAGCTACCAGCGCCAGCTTAA
AACGGGAGTGGAGATCAGCGAGCTGAACAGCCTGTCGTTCCAAAAAATATCAGA
AATTAAGTCCATTAATCTCGGCTTCAATGAATCCTTCAATAAAGAGTATTTTCTA
AAGCTGATCGAAAACCAAACATTCACGCAGAAGGAGTTACTACTGTTAAACTGC
AAGATCAAAGACCTCTTCAAAATTCTCTACAAAGAATATTCTAACATCAAAAAC
AGTCGCATATTTAAATTCAATAAAGAAGATGATCTCATCGTGACGGGTACTACT
GGCTGCAGGTCATTGATGAAATAATCAATATTAAAAAGTCGCTTACTTACTTCAA
CAGCAAGCCGTCGGAGAAGGGGAACAAAAGTAAGTTTATTTTCTTGAAGGATTT
TAACTACAAAAATAATTTTGCAAACAACTACGCGAAAATCGCTGCGTCACGTCT
CAAAAAATATTGTTTGGAGCACAAGGTTGACGTGTGTGTTTTTGAGAAGAACCT
CAACAACTTTCTGCAAAGCAAGGACAACGATAAAAAGACAAATAAGACCTTGAT
TAATTGGGCGAACCGCAATCTTTTTGAGAAAATTAAATTGGCGCTGGAAGAGCA
TGACATCTGCGTGAGTGAGGTTGATGGTAAGCATTCGTCCCAGCTGGACCCGCA
AACCATGAACTGGGGCGCTAGAGATAATCTTAATGGAAATGGTAACAAAGAAA
AGATCTTTTTTGAAAGGAACGGGCAGATAATCAACAGAACGCCGACCTCAGTG
CTTCTGAAGTCCTCGCAAAACGATTCTTCACCAGGTACGAGGACATCGTGCACA
TCTACATTGACCAGAAAATAAAGGATGACAAAACGATCCTTAAGTTGGTGAAGG
GTAAGGTGCGCGTAGAATCTTATCTGAAGAAGACTATAAATTCCTGCTACGCCA
TAGTAGATGAAAATGGCTTCCTTAAACCTATATCTAAGAAAGACTACAACAAGT
TCCAGGAGCTGCCGTCCAAGCCTCGCACAGATATTAAGTCGAATGAGATGTACA
GACATGGCAGCAAGTGGTATCACTTCCAGCAACATAGGGAGTTTCAGCAGGACC
TGTTGGCACGGGCAGAGAGCTGAAGAAGATAGCCGGCAGCGGCAGTAAAAGG
CCAGCCGCCACCAAGAAAGCCGGCCAGGCTAAAAAGAAGAAGTGA

68  Nucleotide sequence of Casσ-2 system expression cassette
    ATGGGCCCAAAGAAGAAGAGGAAGGTGATGGACTACAAGGACCACGACGGCGA
    CTACAAGGATCACGACATCGACTACAAGGACGACGACGACAAGATGAACAAGA
    CGGACACCCAGAACAACGAGCAGATCAACAAGCCGACGCAGCTGCTCAACAAC
    AAGGACATTGAGCTGACGGTGAAGACCGTGAAGTCCGCGACCGTGAAGGTGGA
    CAACAACAGCAAGAAGGAGCTGTTCGGCCTGTTCAACTACTTCACCAGCGTCGC
    CTCCGGCATCAAGGACAAGGTGTACAACCTGCAGTCCGATGAGAAGACCGCCCC
    GATCTTCAACGACTACGTGAAGCAGCCGCAGCGCGGCAGGTCTGCTGCTACTAC
    TCTGTTCACCAAGCTGGACGCGGAGAAGACCTACACCTCTCAGCACTCCTTCCCC
    GGCAAGTGGAGGGATTCCGGCATCTTCCCGCTGTACAACAAGGAGTCCGAGAAG
    TACGACCTGTCCACCCACGGCTACCACTACTCCGCTAACGCCGAGATCCACACC
    CAGCTGGACAGCCATGACGAGTGCAACAAGGAGTGCGAGAAGGAGTACGCCGC
    CCTTAGGGACGAGGTGAACAACTACAAGTACGAGTTCACGCTTCAGTTCAAGGC
    CGAGAACGCCGAGAAGTTCTACAACTTCGTGGAGAAGCTGACGCTGATGGGCTG
    GAGGTACGACGCTACGTTCAGGTCTTTCTTCGAGCTGCACATGCACCCAAAGCTC
    AAGACCGGCGAGACAACGTACAGGGCCACCTACAAGCTGCCGTCCGGCAAGTCT
    AAGAGGTACAGCTTCTTCAGGGACGACATCGCCGACGAGATTGCCAAGAACCCA
    GAGTTCTGGCCAATGCTGGAGTCCTCCAACGCCATCTCCTGGATCAACTCCAACA
    ACCTGCTCAGCAGGAAGAAGGACAAGGCCAACTACTCCTCAACCTCCCTCATCA
    AGTCCCAGATTCGCCTGTACCTGGGCAACAACGGCGTGCCATTCACCGCTAGGG
    AGCACGATGGCAGGATTTACTTCAGCTTCAGGCTCCCGGCCATCAACGGCGAGA
    AGGGCAGGATGGTCGAGATCCCATGCAGCTACAAGAAGGTGTTCAACGGCAAG
    GCCAGGAAGAGCTGCTACCTTGGCGGCCTTACCATCGAGAAGACCGACGCTGGC
    AAGCATATCTTCAAGTACTCCGTGAACAACAAGAAGCCGCAGGTGGCCGAGCTG
    AACGAGTGCTTCCTGAGGCTGGTTGTGAGGAATAGGGAGTACTTCAACAACGTG
    GTGGCCGGCAAGATCACCGACATCAACACCGATCACTTCGACTTCTACGTCGAT
    CTGCCGCTGAACGTGAAGGAGGACCCGATCCATGATCTGAGCAGCACGGAGGTG
    TTCGGCAAGAATGGCCTGAGGTCCTACTACTCCTCCGCCTACCCAGAGATTAAG
    AACCTGGGCTCCCAGATCGAGACGGGCAAGAACCTGACCTGCCCGATCACCAAG
    ACACACAACATCATGGGCATCGACCTTGGCCAGCGCAACCCATTCGCCTACTGC
    ATTAAGGACAACACCGGCAAGCTCATCGCCCAGGGCCATATGGACGGCTCTAAG
    AACGAGACGTACAAGAAGTACATCAATTTCGGCAAGGAGTCCACCTCCGTCTCC
    CACCTTATTAAGGAGACGAGGTCCTACCTGCACGGCGATCCAGAGGCTATCTCC
    AAGGAGCTGTACAATGAGGTCGCCGGCTTCTGCAACAACCCGGTTTCCTACGAG
    GAGTACCTTAAGTACCTGGACTCCAAGAAGTTCCTGATCAACAAGGAGGACCTG
    TCCAAGAATGCCATGCACCTGCTGAGGCAGAAGGACCACAACTGGATCGGCAGG
    GACTGGCTGTGGTACATCAGCAAGCAGTACAAGAAGCACAACGAGAACAGGAT
    GCAGGACGCCGACTGGAGGCAGACTCTGTACTGGATCGACAGCCTGTACAGGTA
    CATCGATGTGATGAAGTCCTTCCACAACTTCGGCAGCTTCTACGACAAGAACCT
    GAAGAAGAAGGTGAACGGCACCGTGGTGGGCTTCTGCAAGACGGTTCACGACC
    AGATCAACAACAACAACGATGACATGTTCAAGAAGTTCACCAACGAGCTGATGA
    GCGTGATCAGGGAGCACAAGGTGAGCGTGGTGGCGCTTGAGAAGATGGACAGC
    ATGCTGGGCGACAAGTCAAGGCACACGTTCGAGAACAGGAACTACAACCTGTGG
    CCGGTGGGCCAGCTGAAGACATTCATGGAGGGCAAGCTGGAGTCCTTCAACGTG
    GCCCTGATCGAGATCGATGAGAGGAACACCAGCCAGGTGTGCAAGGAGAACTG
    GTCCTACAGGGAGGCGGATGACCTGTACTACGTGACGGACGGCGAGTCCCACAA
    GGTGCATGCTGACGAGAACGCGGCCAACAACATCGTGGACAGGTGCATTTCCAG
    GCACACCAACATGTTCAGCCTGCACATGGTGAACCCAAAGGACGACTACTACGT TABLE 1-continued Description of sequences

| SEQ ID NO: | Description |
|---|---|

GCCGACCTGCATTTGGGACACCACGGAGGAGTCCGGCAAGAGGGTTAGGGGCTT
CCTGACCAAGCTCTACAAGAACTCCGACGTGGTCTTCACCAAGAAGGGCGACAA
GCTGGTGAAGAGCAAGACCTCCGTGAAGGAGCTGAAGAAGCTGGTGGGCAAGA
CCAAGGAGAAGAGGGGCCAGTACTGGTACAGGTTCGAGGGCAAGAGCTGGATC
AACGAGGCCGACAGGGACACCATCATCCTGAACGCCAAGAAGATCTCCAGGGA
AAGGGACAACGGCGAGCAGTCCACGGATACCAGGAGCCAGAACGTGACCGTGT
CCGTGCTGGACGTGTGCGAGACAGCTGAGAAGAAGAAGCTGGTCCTTGTGGGCA
GCGGCAGCAAGAGGCCAGCTGCTACTAAGAAGGCCGGCCAGGCTAAGAAGAAG
AAGTGA

69    Nucleotide sequence of Casσ-3 system expression cassette
ATGGGCCCAAAGAAGAAGAGGAAGGTGATGGACTACAAGGACCACGACGGGGA
CTACAAGGATCACGACATCGACTACAAGGACGACGACGACAAGATGAAGAGCA
TAAAGAGCATAAAAAGCATCAAGACGAAGGTGGTGAAGAACAACGAGCTGAAG
CTGATAGAGCTGAGTACGTGGTGCAGCAGCATATGCGAGCAGCTGGAGAGGTAC
ATATTCATCCTGGGGGGGGAAACAAATACACGACAGGGACGGCGTGGTGGTGCTG
GACGGCGCAGTGGAGAGGAAGATCTACTGTAAGAAAGACAAGAGCTTGATCGC
GGCCTGCGAGGTGGTGTACAAACACTTCACGGACAAGAGTTCCAAGTCCAGGAC
GTTTGGGTCCTGGTTCCTGGGTGGGAAGTCCGAGGGCGACAACACCAATAAGGG
AAGGAAGAGTACCAAGGAGAAGACCGAGAAACAAATCGCAAAGCAGATCGCCG
ACAAGAAGGAGCTGACGGACTCCCTGCAACTGCTGTGGGACAAGAAGCTGCTGC
CATTCCCGATAGACAACAAGGGCTACGACTTCATAAATACCCCAAGGGCCAAAT
CCTACAAGTGGGCGATCACGAAAACCATCCACGCTAAAATCAAATCCTACAACG
AGCAATGCGTGGAGACCAAAAAAGAGTACGACGCCCTGAACGCCGAGATCAAC
ACCTACAAGACCATCCTGTTCTCCGGCTACTCCGAAAAGGACATCGACGACCTG
CAGAAGTTCGTGGACATCTGCGAGGCAAACAACCACAGGATAAACTACAAATTC
ATATCCTTTCTCAAGAGGAAAGACCTCAATTTCGACGAACAAACAGGGAAATAC
AGGAAGGAAGGCAAGTGGATTCAACACAAGAACGGAAAGGAAGTCAAGAGCA
AGTACAGCATGAAGGACGAGATAGTGGAGGCCCTGTACAAGTACAAGTCCCTGA
CAAAGAACGACGTGAGCGTGCTGTGCAACGAGCACCAAAAAGAGGACGAAATG
GGCAAGGTGGTGCATTACAACATGAAGAGGTACTCTGATCTGCTGTTCAGAAAG
AAGAACAAAAAGGAAATCCCGAGTTACACGAAAATCAGCCTGGCCACCAGCAA
GATTGAGTTGGGGTTGAACAATGTGAAGTACAACGTGGAGCAGGTGGAGGACA
AACTGATATGGACCATATGCGACCAGACCGGCAAGGACATCCAGTTCGTGACCG
TGTACACCAGGAAGAAGGAGGATAACAGGACCAATGGCAAGAAAGGGGGGGGG
TTCTACAAGGGCAAACACCACCAGCTGGAGGACCTGAAAATAGTGCCGGTGGGC
GACATAGGGACCTACGACATCAGCTTCAAGGTGAACGGGAAGAGGCCGTTCACA
GGGACCCTGAAGGAACCGAACATCATATGCAGGGGCGGGAAGGTGTTCGTCCA
GATGCCGATCAACATCAACATCGACAAAACCCTGAACGACGCGAGGAAGAAGG
TGCTGTACGCATACCGGGAGACGTACTCCGGCTCCGTGAACGGCAAGAAGCAGA
AGATGATAAAGATCGAAAACTCCAAAATCGCCGAGTCCCTGAAATCCCTGGGGC
GGGACGCGATAGTCCTGGGCGTGGATCTGGGGCTGAGGGGGCTGGCTACAGCGG
TGGTGAGCCACAACGGGAAAAACGAGACAGTGAAGAGCAGCCAATACATTAAG
GGCGACATTGTGGAGTGGGAGAAGTACAGGGTGTTTAACGACAACATCAGGGA
GGTGAAGAAGTACATATTCCTGACCAAGAAGTCCTATACCGCCACGACGGAGGA
ATACACCGAGTTTTACAAGGAGTGCTCGAAGCCGGAGCAGGACTATCTGGACTC
CCTCAAGACCTATAAAGACAAGAACGTGAAACTCAACGAGCTGAAATACACGA
AGAACGCGTGGTCCGTGAGCAAGATGTTCGAAGACGTCTCCAAAATGTTCGAAA
CCCTCAAGCAGGACAGGCTGAAGTACTACGACATCTTCAACATGCCATACTGGG
CCGCCTCCCTGAAGAACTACATGAGCCTGATGAAGTCCTACAACTACGTCGGCG
TGGACATAAAGGTGTCCAAAGAATACATGAGCAAGTACCAGTCCCTGTACAACA
ACATCAAGGAAGATTACGCCAAAAAAATCGGCTCCTACATCGTGCAGCTCGCCG
TGGCCAAGAATTGCGACATCATTGTCCTGGAGGAGCTGAAATCCAACCTCGGCT
CCGTGGACAGGAAGAGCAAGAGAGACAACGAGATGTCCCTGATGTGGAACTGC
GGCCGCATCAAGACCCACGTCGAGAACATGGCAAAGGACTATGGGATGTTCATT
GACGAAGTCCCGGAGTATGGCACGTCCCAGGTGTATCACAAGACCGGCAACTAC
GGCTACAGGGATGAAGACAACAGGGAGATATTTTGGTACGAGGACAACAAGGA
CGTGGCCTACATACACGCCGACGAGAACGCGGCAATCAACATAGCCAAAAGATT
CCTGTCCCAACATACCGACAACTCCAGCTTCAGCGTTATCCTGAAGGGCGACGC
CTACTACCTGAACATCGCCTCCAACTCCAAACGCATGAGGGCCGCCGCACTGAA
AACCTTCGGCGACCTCAACAAACCGTTCAAAATCAACGCCAACGACAAAAACGG
AAACCTGTACAAGAAGACCAGGATCTTCAAGTCCGACTCCAGATGGATAGGCGT
CAACGACAAAGACCTCTACATAGAACACATCAAATCCCTCCGCAACCTCCGCGT
GCGCCAGGGTTCCGGTTCCAAGCGCCCAGCCGCCACCAAGAAGGCCGGCCAAGC
CAAGAAGAAAAAATGA 70    Nucleotide sequence of Casσ-4 system expression cassette
ATGGGCCCAAAGAAGAAGAGGAAGGTGATGGACTACAAGGACCACGACGGGGA
CTACAAGGATCACGACATCGACTACAAGGACGACGACGACAAGATGCCGAGCTT
CACGAAGGTGGACGAGGACAAAATAGTGCTGAAGCTGGGGAACAACTACATCC
CGTATGGGCTGAGCAGGATTTCCGAGGACAAGATGCTGTGGAGCTTTTCCTCCC
CGCAAAAAAAGAAGCTGTCTATAATAACGAACCACAGGCGCGTCGGCAAGGGC
AAACACTTTTACCTGGAAGGCTTGGAGATCGCCGACATTACCAAGGGCGACGGC
GACAAGACGTCCCCAAGCGGCAAATATACCATCTCCTTCAGCATCAACGGCAAG TABLE 1-continued Description of sequences

| SEQ ID NO: | Description |
|---|---|

CAGGACGTGAAGGGCGAGCTGAAGGAGCCGAGCTTCGGCCTGAGGAACGGCAA
CGTGTACATGTTTCTGCCAATCTCCATAAAGCAGACCGACGTGTTCGAGTCCAGG
GTGGAGATGAGGAGGTTGCTGTCTATGGCCTACCAGCCAACCACCGTGGAGGAT
CTGATCCTGGATGACGTGGAGACCAAGCAGAAGACCGTGAAGCAGGGGAAGAA
GGAGGTGAACACCACGAACATAGCGATTCAAGAGGCGATCAAGAAGCACGGCC
GCCTGCTGAAGGTGATGGGCGTGGACCTGGGGCTGAGGAACTTCGCGTTTGCCA
TCAAGAACTACGACGGCCACCACGACACCCTGTTGCGGCAGTTGTACTCCGAGT
CCGACCTGAACGAGAAACAGAGGTACACTACCCTGGCCAATGACTTGTCCAAGG
TGGGCAACCACATCAAGTTCGCCGCGGTCTTCTACGGCGCCAACGACACCGAGG
AGAACACCAAGATGTTCGACGCCGAGTGCACGGACGCCGAGTCCAGGACCCACC
TGGAGTGGCTGAGGAAAGCCAAGAAGTCCGGTGTGCTGCTCAAGGACCTGAGG
AAGGACAAGACGTGGATCGTGTCGATCAAGTATACCGAGTTGAGGAATAGGCTG
CACGCACTGAAATTCGGCAGGATGAAGAGCTACGACTACAGGAATAACCTCTAC
TGGGCCGCGACCATTAAGAAGTTCATCTCGCTCTCCGCCAGCTTCTACGGCGTGG
GGAGGCCTAGCCGCGGCAAGAAGGACGTGAGGGAGTTGAAGAAAAAGCACACC
TTCTTCTCCACGTATCAGGACCTGTACAACAACGTGAAGGAAGATTACGCGAAG
AAGGTGGCGAATCTGGTGGTGATGACGGCCAAAGAGAATAACGTGGACATCATC
GTGGTGGAGAACCTGACCGGGCACTGCGGGTCCAAGGACTACAAGACCAGGGC
CGAGAACGAGATGAGTATAATGTGGAATCATGGCAGGATCAAGACGTTCATCGA
TTGCATCGCCAATGCCAACGGCATGTTGTTGGCCGAGGTGTCCGAGTTCGAGAC
GTCCCAGGTGTACCACGAGACGAGGAACTACGGGTACAGGGACAAGAAGATGA
AAGAGATCCTGTGGTACATGGACTCCGAGGGGAACGTGCAGTATGCCCACGCCG
AGGTGAACGCCGCCATCAATATCGCCGACAGGTTCCTGTCCCAGCACACCAACC
TGTTCTCCTTCCCAGTGTGCAAGTCCAAGAAAGACGAGAATGTGTACGAGATCG
ACATCGCCGAGGGGAAAGAACTTGAGGGCCAGGATGAAGTGAAGAAGGCCAAG
AAACCGAAAGGCGGGAAGAGGCTGAACGGGGCGGTGGTGAAGACGTTTGGGAG
TACCAAGATCATGTTCAACGGGATAGTGGACAAAAACAAGAAGGGGCAGATAA
AGACGAAGACGAGGGTGTACAACATAGACGGGGAGTGGGGGGGGAAGACCCAG
AAAGACGAGTACGTGGACAAAATCAGGAAGGTGGTGGACGCGATGAGCCCGGA
GGAGAAAGCGAAGGTGAAGGCGGCGCTGAAGAAGTGCTTCAGCAGCGGCAGCG
GGAGCAAGAGGCCAGCCGCAACGAAGAAGGCGGGGCAGGCGAAGAAGAAGAA
GTGA

71   Nucleotide sequence of Cas0-5 system expression cassette
ATGGGCCCAAAGAAGAAGAGGAAGGTGATGGACTACAAGGACCACGACGGGGA
CTACAAGGATCACGACATCGACTACAAGGACGACGACGACAAGATGACGAAGG
AGCTGAGCGGGGTGAGGGTGATAGAGCTGAAGACCGACCTGAGGAAGGACCAG
TTCTGGGACAGGTACGAGAGGTGCTTCAAAACGTACCACGCCCTGTACAACGAG
GTGCCATGCTGGGGCCTGGACTGGGTGGAGCAGAAAACACAAAACCAAACCTCC
AGGGAACTCGGCTGCGAGAGAGTGGATCTGACCGCCCAACGCAAGGCACTGTAT
GAGAGGACGGACCGCACCATCTCTTACGAGCAGTTTAGCAACTGCCTCAAAGCC
CTCTGGCTGGGGCTGCTGAACTGTCAGCAGGGGAACCACATGTACACCAAACTG
TTTGAAGGCGCGATACAAACCGACCAGATGACCGCGGAGGACTGGGCCGTGCTG
ACCGAATACGTCGCGGACCCGAAGAGCCACAACTCCCAGTTCCTGTTCAGGGTG
TCCAACACCCTGAAGCACATCGGCTTCTTCTCCAGGCCGCCATTTACCGCCACCC
TGTTTGCCCCAGAGAGGAAGGCTATTACCAAGGACGTCATGTCCGACCTGAAAG
GATGGATTGAGATGAAGAGGATGACCGAGGAGTCTTACGCCGCGGAGGAGGTG
CAAATTCAACAAATGAAGGCCGAGGTGCCGGTGCGCATCAGGCAGAGCCTGCTG
AGGTTTTTCGACACCTGCATAGGCCTGAACCTCATCGGACACTTCGACGAAAGG
GTGCACCACTACCTGAGGGACTGCATAATACCGGCGCTGCAGCAAAGGACGATA
CCGACCGAACACTTCTACCTGAAATCCAACCGCAAAGACGTGGGCCAGAAACAC
ATAGACTTCAGCCTCGACATCAAATTCTACGAGCTGCTGGCTGAAATGCCAGAG
CTGTGGAACACCCTGGAGACCTCCGAGGACGACCTCATCCCCAAACCGCTGATC
CTCAAACACCTGCACCTGCTGGAAGCCATCATGTCCCACAGGGCCCACAGGAAG
ACCGCCGCCTACGCCTTCGTGGGCGAAGCCGACTACCACAGGTTCTACTACCTG
CTCGGCGGCAACTACACAAAACACCTCATCAGCGCCACCGGCTCCGAACTGCCG
GACAGGGTGATCTGGGACAACGACAAGGACGTTCTGATGAGGAACGGCAGGAA
GGTGGAGAGGCTGTACGTGAAAGTGGGCGACAGGAAAGAGAACTTCAACTTCG
AGGTGTACACGATAGCGATGAACACGAAGGGCCTGAGGGGGCACAGGAGCACG
CTGAAGCCGACGAGTTACTTGCAAGACCTGCAGATTTGGAGCAACCCGGAGGGC
GAGAGCACCTATCTGAACTTCGTGAGGAAGGGCACAGAGAGGAGCGCGATTTGC
AAAGAGCCAGTGCTGGTGTACAGGAACGGCGCCTTTTTTCTTAGGCTGAGCATG
AGCGTGGAAGGGATGCGGGCCTCCGAGGAGCATATCGCGCTGCAGTACTACCTT
TCTGCCGCGGCCACGGGCTCTGACTTGTCTAAGGACACGGAGAAGACCGTGGAG
AGGTTCAACTTGATCCAGGGAAGACATACAAGGTGATGTCCGTGGATCTCGGC
ATCCGCTCCCCCTTCGCCTGGGCTGTGACCGAGTCGACCATCACGGGCGTGGCC
AACCCGAGCCAGATCCTGAACAGCGGCGAGATGGAAATCGCGGACGACCCGGA
CTATACCGAGCTGTTCTACGCTTACAAAAACCTGGGGCACCTGATCGGCCAGGT
CAAGAGCAGCAGCAAGGGGAAAGGCCTCAAAGCGGACAGCCACCTGGTGGATA
TGATTCATACGGTGCAAAGGTTCTTCGCCGACTACAAAGTGGCCGGGCAGAGGA
GGAGTCAAATATTCGAGCAGTTCAGCAAGGACCCGGACCCGTTGTACCAGATGG
ACCAGATGATGAAGAGGTACGAGAACAACCTGGAGAGTGTGAAGAAGGATTTT
AGTTTCCTGATAAACATCCTGTTCAAGTACGTGACCCTGCAGTTCGGAGCCCTGA
GGAACCGGAGAAGGAGCTACCTGTCACAAAACCAGATGGCCGACCAGAAGTTC TABLE 1-continued Description of sequences SEQ
ID
NO:      Description GACCAAGACTTCAAGTGGCTGAACATCCTCGAGCAGAGGAAGCGCGTGACCAG
         GAGCCTGAGCTACCTGGGCACAGACAACAGCAGGATTCCTATCTGCCTGGAACA
         GCAGAAGCTGGACTACAACGGCTGCAAGGACAACTTCCTGAAGCAGCTGGCCTC
         CAAGATCGTGAGGATCGCCCACCAAAACGACTGCTGCCTGATTGTGCTGGAGGA
         CCTTGAGGGGTACGGGAAAACGCTCAACCAGAGGGACGAGAACTTCCTCACGGC
         CTTCTGGTCTCCGAAGAGGGTGAAGGATGCCATCATCAACGCCGCCCAATGGTA
         CGGCATTGGGGTGGTGACGGTGAGCGAGGCCCAGACGTCCCAGGTGCACCACGA
         GTCCGGCAGGATCGGCTATAGAAAGGGGAGGGACCTGTTTTTCCTGACCCCAGA
         CGGCCAGATCGAGTCCGTGCCGAGCGACATTAACGCCGCCAAGAACATTGGCCA
         TAGGTTCTTTTCCAGGCACACCGACCTGCACCAGGTGTACCTGAAGGGTTCCGAC
         GAGGGCGCCAAGAGGATGAAAGGCTGCCTTCTGTATCAGTTCGGGGAGTCTGGAG
         GCGGCCCGCACGCACCTTACCGGAACAGGACCGACCTGGTACTTGGACGGCGTG
         GAGTGGATAGACAAGACGGAGAGGAACCTGAGGGAGGGACCTGCTGAAGCAGAG
         GGTGGAAATCGAGAAAATGCCATTCGGCAGCGGGAGCAAGAGGCCGGCCGCTA
         CTAAGAAGGCGGGGCAGGCCAAGAAGAAGAAGTGA 72       Nucleotide sequence of CasΦ-6 system expression cassette
         ATGGGACCAAAGAAGAAACGGAAGGTTATGGATTACAAAGATCACGATGGCGA
         CTATAAAGACCATGACATCGATTACAAGGACGACGATGACAAGATGAAGAGCA
         TCAAGTCGATCAAGAGCATTAAGACTAAAGTTGTCAAGAACAACGAGCTGAAGC
         TCATCGAGCTGTCTACCTGGTGTAGCTCGATCTGCGAGCAGCTCGAGAGGTACA
         TCTTCATACTGGGCGGCAAGCAGATTCACGATCGCGATGGCGTCGTTGTTCTCGA
         TGGCGCCGTTGAGCGGAAGATCTACTGCAAGAAAGACAAGAGCCTGATCGCCGC
         CTGCGAGGTTGTCTATAAGCACTTTACCGACAAATCGTCCAAGTCTCGCACCTTT
         GGCAGCTGGTTCTTGGGCGGCAAGAGCGAGGGCGATAACACAAACAAGGGCAG
         AAAGTCCACCAAAGAGAAGACTGAGAAGCAGATCGCTAAGCAGATCGCCGACA
         AGAAGGAGCTGACCGATTCTCTGCAGCTCTTGTGGGATAAGAAACTGCTGCCAT
         TTCCGATTGATAACAAGGGTTACGACTTCATCAACACACCACGCGCCAAGAGCT
         ACAAGTGGGCTATCACCAAGACCATTCACGCGAAGATCAAGAGCTACAACGAGC
         AGTGTGTCGAGACGAAGAAAGAGTACGACGCGCTGAACGCCGAGATTAATACA
         TACAAGACTATTCTGTTCAGCGGTTACTCCGAGAAAGACATTGACGACCTCCAG
         AAGTTCGTCGATATATGTGAGGCCAACAACCACAGGATCAACTACAAGTTTATC
         AGCTTCTTGAAGCGCAAAGATTTGAATTTCGACGAGCAGACAGGCAAGTACCGC
         AAGGAGGGCAAGTGGATTCAGCACAAGAACGGCAAAGAAGTTAAGTCCAAGTA
         CAGCATGAAAGATGAGATCGTCGAGGCGCTGTACAAGTACAAGAGCCTGACTAA
         GAACGACGTGAGCGTGCTCTGCAACGAGCATCAGAAGGAGGACGAGATGGGTA
         AGGTGGTCCACTACAACATGAAGCGCTATTCCGACCTGCTGTTCCGCAAGAAGA
         ACAAGAAGGAAATACCAAGCTACACAAAGATCTCACTTGCCACGTCCAAGATCG
         AGCTGGGCCTCAACAACGTCAAGTACAACGTTGAGCAGGTTGAGGACAAGCTCA
         TCTGGACAATCTGCGATCAAACAGGCAAAGACATCCAGTTCGTGACTGTCTATA
         CAAGAAAGAAAGAAGATAACAGGACCAATGGCAAGAAGGGAGCGGGCTTCTAT
         AAGGGCAAGCATCACCAGCTCGAAGACCTGAAGATCGTGCCTGTGGGAGACATT
         GGCACTTACGACATCAGCTTCAAGGTCAACGGCAAGCGTCCGTTTACTGGCACT
         CTGAAAGAGCCGAACATCATTTGCCGCGGAGGCAAAGTGTTCGTGCAGATGCCA
         ATTAATATCAATATCGATAAGACTCTCAACGACGCTCGGAAGAAGGTTCTGTAC
         GCCTACAGGGAGACGTACAGCGGCTCCGTCAACGGTAAGAAACAGAAGATGAT
         CAAGATCGAGAACAGCAAGATCGCCGAGTCACTCAAGTCTTTGGGCAGAGACGC
         CATTGTGCTTGGCGTGGATTTGGGCTTGCGCGGACTTGCTACCGCCGTTGTGAGC
         CACAACGGAAAGAACGAGACTGTTAAGAGCAGCCAGTACATCAAGGGCGATAT
         TGTGGAGTGGGAGAAGTACAGGGTGTTCAATGATAATATCAGGGAGGTCAAGA
         AGTACATCTTCTTGACCAAGAAAAGCTACACCGCCACAACGGAAGAATACACAG
         AATTTTACAAGGAGTGCAGCAAGCCTGAGCAAGACTATCTTGATAGCCTCAAGA
         CGTACAAGGACAAGAACGTTAAACTGAACGAACTGAAGTACACCAAGAACGCC
         TGGAGCGTCTCGAAGATGTTTGAAGACGTTTCCAAGATGTTCGAGACACTCAAG
         CAAGACAGGCTCAAGTACTACGACATCTTCAATATGCCGTATTGGGCGGCCTCA
         CTGAAGAACTATATGTCGTTGATGAAGTCGTACAATTATGTTGGCGTGGACATC
         AAGGTCAGCAAAGAGTACATGTCCAAGTACCAATCCCTGTATAACAACATCAAG
         GAGGACTACGCCAAGAAGATCGGCAGCTACATTGTCCAGCTGGCTGTGGCAAAG
         AACTGCGACATCATCGTGCTTGAAGAGCTGAAGTCGAACCTGGGCAGCGTTGAT
         CGCAAGTCCAAGCGCGATAACGAAATGAGCCTCATGTGGAACTGCGGCGAAATC
         AAGACTCATGTCGAGAACATGGCCAAAGATTACGGCATGTTTATCGATGAGGTG
         CCTGAGTATGGTACTTCGCAGGTGTACCATAAGACCGGTAACTACGGCTATAGA
         GATGAAGACAACAGGGAAATCTTCTGGTACGAGGATAACAAAGACGTCGCCTAC
         ATCCATGCAGACGAGAATGCTGCCATCAACATCGCGAAGCGCTTTCTGTCACAG
         CATACCGACAACAGCTCATTCTCCGTGATTCTCAAGGGCGACGCTTACTACCTGA
         ACATCGCTTCCAACTCCAAGAGAATGCGCGCCGCCGCTCTCAAGACCTTTGGAG
         ATCTCAACAAGCCTTTCAAGATTAATGCCAACGATAAGAACGGCAACCTCTACA
         AGAAGACAAGAATCTTCAAGTCAGACTCTCGCTGGATCGGCGTGAACGACAAGG
         ACCTCTACATCGAGCACATCAAGAGCCTGAGAAATCTCAGGGTGAGGCAGGGCT
         CGGGCAGCAAGAGGCCGGCTGCCACTAAGAAGGCAGGTCAAGCGAAGAAGAAG
         AAGTGA TABLE 1-continued Description of sequences

| SEQ ID NO: | Description |
|---|---|

73    Nucleotide sequence of Casσ-7 system expression cassette
      ATGGGCCCAAAGAAGAAGAGGAAGGTGATGGACTACAAGGACCACGACGGCGA
      CTACAAGGATCACGACATCGACTACAAGGACGACGACGACAAGATGAACAAGA
      CGGACACCCAGAACAACGAGCAGATCAACAAGCCGACGCAGCTGCTCAACAAC
      AAGGACATTGAGCTGACGGTGAAGACCGTGAAGTCCGCGACCGTGAAGGTGGA
      CAACAACAGCAAGAAGGAGCTGTTCGGCCTGTTCAACTACTTCACCAGCGTCGC
      CTCCGGCATCAAGGACAAGGTGTACAACCTGCAGTCCGATGAGAAGACCGCCCC
      GATCTTCAACGACTACGTGAAGCAGCCGCAGCGCGGCAGGTCTGCTGCTACTAC
      TCTGTTCACCAAGCTGGACGCGGAGAAGACCTACACCTCTCAGCACTCCTTCCCC
      GGCAAGTGGAGGGATTCCGGCATCTTCCCGCTGTACAACAAGGAGTCCGAGAAG
      TACGACCTGTCCACCCACGGCTACCACTACTCCGCTAACGCCGAGATCCACACC
      CAGCTGGACAGCCATGACGAGTGCAACAAGGAGTGCGAGAAGGAGTACGCCGC
      CCTTAGGGACGAGGTGAACAACTACAAGTACGAGTTCACGCTTCAGTTCAAGGC
      CGAGAACGCCGAGAAGTTCTACAACTTCGTGGGAGAAGCTGACGCTGATGGGCTG
      GAGGTACGACGCTACGTTCAGGTCTTTCTTCGAGCTGCACATGCACCCAAAGCTC
      AAGACCGGCGAGACAACGTACAGGGCCACCTACAAGCTGCCGTCCGGCAAGTCT
      AAGAGGTACAGCTTCTTCAGGGACGACATCGCCGACGAGATTGCCAAGAACCCA
      GAGTTCTGGCCAATGCTGGAGTCCTCCAACGCCATCTCCTGGATCAACTCCAACA
      ACCTGCTCAGCAGGAAGAAGGACAAGGCCAACTACTCCTCAACCTCCCTCATCA
      AGTCCCAGATTCGCCTGTACCTGGGCAACAACGGCGTGCCATTCACCGCTAGGG
      AGCACGATGGCAGGATTTACTTCAGCTTCAGGCTCCCGGCCATCAACGGCGAGA
      AGGGCAGGATGGTCGAGATCCCATGCAGCTACAAGAAGGTGTTCAACGGCAAG
      GCCAGGAAGAGCTGCTACCTTGGCGGCCTTACCATCGAGAAGACCGACGCTGGC
      AAGCATATCTTCAAGTACTCCGTGAACAACAAGAAGCCGCAGGTGGCCGAGCTG
      AACGAGTGCTTCCTGAGGCTGGTTGTGAGGAATAGGGAGTACTTCAACAACGTG
      GTGGCCGGCAAGATCACCGACATCAACACCGATCACTTCGACTTCTACGTCGAT
      CTGCCGCTGAACGTGAAGGAGGACCCGATCCATGATCTGAGCAGCACGGAGGTG
      TTCGGCAAGAATGGCCTGAGGTCCTACTACTCCTCCGCCTACCCAGAGATTAAG
      AACCTGGGCTCCCAGATCGAGACCGGCAAGAACCTCACCTGCCCGATCACCAAG
      ACACACAACATCATGGGCATCGACCTTGGCCAGCGCAACCCATTCGCCTACTGC
      ATTAAGGACAACACCGGCAAGCTCATCGCCCAGGGCCATATGGACGGCTCTAAG
      AACGAGACCTACAAGAAGTACATCAATTTCGGCAAGGAGAGCACCTCAGTCTCC
      CACCTCATCAAGGAGACCAGGAGCTACCTGCACGGCGATCCAGAGGCTATCAGC
      AAGGAGCTGTACAACGAGGTGGCCGGCTTCTGCAACAACCCGGTTTCCTACGAG
      GAGTACCTCAAGTACCTGGACAGCAAGAAGTTCCTGATCAACAAGGAGGACCTG
      TCCAAGAACGCGATGCATCTCCTGAGGCAGAAGGATCACAACTGGATCGGCAGG
      GACTGGCTGTGGTACATCAGCAAGCAGTACAAGAAGCACAACGAGAACAGGAT
      GCAGGACGCCGACTGGAGGCAGACTCTTTACTGGATCGACAGCCTGTACCGCTA
      CATCGACGTGATGAAGTCCTTCCACAACTTCGGCTCCTTCTACGACAAGAACCTG
      AAGAAGAAGGTGAACGGCACGGTGGTGGGCTTCTGCAAGACGGTTCACGACCA
      GATCAATAACAACAACGACGACATGTTCAAGAAGTTCACGAATGAGCTGATGAG
      CGTGATCAGGGAGCACAAGGTGAGCGTGGTCGCCCTTGAGAAGATGGACTCCAT
      GCTCGGCGACAAGTCCAGGCACACCTTCGAGAACAGGAACTACAACCTGTGGCC
      GGTTGGCCAGCTGAAGACGTTCATGGAGGGCAAGCTGGAGTCCTTCAACGTGGC
      GCTTATCGAGATCGACGAGAGGAACACCTCCCAGGTTTGCAAGGAGAACTGGAG
      CTACAGGGAGGCGGACGACCTGTACTACGTGACGGACGGCGAGTCCCACAAGGT
      GCATGCTGACGAGAACGCCGCGAACAACATCGTCGACAGGTGCATCAGCAGGC
      ACACCAACATGTTCAGCCTGCACATGGTGAACCCGAAGGACGACTACTACGTGC
      CGACCTGCATCTGGGACACCACCGAGGAGAGCGGCAAGAGGGTTAGGGGCTTCC
      TCACGAAGCTCTACAAGAACTCCGACGTTGTCTTCACCAAGAAGGGCGACAAGC
      TGGTGAAGTCCAAGACCAGCGTGAAGGAGCTGAAGAAGCTGGTTGGCAAGACC
      AAGGAGAAGAGGGGCCAGTACTGGTACAGGTTCGAGGGCAAGAGCTGGATCAA
      CGAGGCCGACAGGGACACGATCATCCTGAACGCGAAGAAGATCAGCAGGGAGA
      GGGACAACGGCGAGCAGTCAACGGATACCCGGAGCCAGAACGTGACGGTGAGC
      GTTCTGGACGTGTGCGAGACCGCTGAGAAGAAGAAGCTGGTGCTGGTGGGCAGC
      GGCTCAAAGAGGCCAGCTGCTACTAAGAAGGCCGGCCAGGCTAAGAAGAAGAA
      GTGA 74    Nucleotide sequence of Casσ-8 system expression cassette
      ATGGGCCCAAAGAAGAAGAGGAAGGTGATGGACTACAAGGACCACGACGGCGA
      CTACAAGGATCACGACATCGACTACAAGGACGACGACGACAAGATGAAGAAGC
      CGAAGCAGAACATCGAGGAGACGGACCTGAAGATCACCACCCCAAAGACCGCG
      ACCATCAAGGCCACCAACCTGGACGACAAGATGAGGCTCTTCACCTTCTTCAAC
      GGCTTCACCACCGTGTGCTCCAAGGTGAAGGACGACATCTACAACTTCGGCCAG
      AACGAGGACACACTGCCGGTGTACACCGACTACATTAAGGCCTCCCAGAGGGCC
      AGGATGTGCGCTACTACCCTCGCTACCAAGAGCGAGTGCGACTTCGCCAAGAAG
      TACGGCGAGCACTTCCCGCTCCCCATTACAACCAGGAGGGCATGAACTACACC
      ACCCACCAGCACACCTACTCAGTGAACTCCGCCGTGCACACACAGCTCGACTCC
      CTTAACGAGTGCGACAAGCTCACCAACGGCGAGTACGTCAAGCTCAAGAAGACC
      GTCGACGAGCTGGAGGAGAAGCTGACCGAGGAGCACGGCAAGGAGCCACTTGA
      TTTCCTGGTGAAGTTCGTGGACGAGCAGATCCTCCTGGGCTGGAGGTTCGACGG
      CAAGTTCAGGCTGTTCTTCGAGGTGGCGATGCTGCCAGAGCTTAAGAACGGCAA
      CATCATCTACAAGAAGGCGTACAAGACCTCCGGCGGCAAGGGCAGGAGGTACTC TABLE 1-continued Description of sequences

| SEQ ID NO: | Description |
|---|---|

TTTCTACAACCCGTCCGTGGCCGATAACATTTCTAAGAACCCCACCGTGTGGAAC
CTGCTGAGCGACGTTAAGGCGGTGGACTACATCTCCCTGTCTAATTCCCTGCTGA
GGAAGAAGCCGCACGCCCAGTACACCAACACAACCCTGAACAGGGCCCAGGTG
AGGCCTACATTCGGCAACAACGGCGTGCCATTCTCCATCTCCGTCTCCGACGACG
ACTACGTGTACATCCGCTTCAGGCTGCCCAAGAAGGACGGCGAGGAGAAGGGCC
AGGAGATCTCAGTCAAGTGCAGCTACAAGACTTCATACAAGGGCAAGCGCAGCA
AGACGCTGAGGAAGAGCTGCTACCTGGGCAACCTGAAGATCGAGGAGAATGGC
AAGGGCAAGTACATTTGCAAGTACAACATCAACGGCAGGGAGACGACCACCGC
GGAGCTTAATGAGTGCTTCCTGAGGGTGAGGATCAACAACAACCGCTGGTTCAA
CAAGTACCTGAACGGCACGCTGACCAAGGAGGACGGCGTTCTTAAGAGCGAGTA
CTTCGACTTCTACTTCGACCTGTGCCTGAATGTGCATCAGAAGTCCATCCACGGC
CTGACCAACTCCGAGATTTTCGGCGGCAAGGGCAAGAGCATCAGGAGCTACTAC
TCCACCTCCTACCCGGAGGTGAAGAACCTGGACGGCCAGAAGAACATCAAGACC
GACTTCGGCTGCTACGTGGACAAGCCGCACAACATCATGGGCATCGACCTGGGC
CAGAGGAACCCATTCGCCTGGGCTGTTCTGGACCAGAACGGCAATGTGAAGGAC
GTGGGCCACCTGGACGGCGCTGAGAACGATACATACAAGGACTACCTGACGTTC
TCCAACAGGTGCAAGGACGTTAAGAATCTGATCCTGCAGTCCAGGGACTACCTG
TACGGCGACGATGAGGCCATTGACGAGACCCTGTTCGACTCCGTGGTGCAGTTC
GTGAACAGCAACATCACGCTGAACAAGTACAAGTCCTACCTGGACGAGAAGAA
GAGCCTGATCAACAAGGAGTCCCTGGAGAAGAACCGCCTGTACGAGCTGAAGA
AGAAGGACCACGGCTGGTTCGTGAGGGACTGCCTTTGGTTCCTGACCAAGGAGT
ACCACAGGATCAACTCCGAGCGCAAGACGCACTCCGACTGGAGGTACACCCTGT
ACTGGGTGGACGCCATTCACCGGTTCATTGACGTGAACAAGTCCTTCAACTCCCT
CGGCAGCTACTACGACAAGAAGCAGTCCAAGTCCATCAACGGCATCCAGAAGG
ACTTCTGCAGGAGCTACTGGAACCAGATCGACAACCTGAACGAGGACACCCTCA
AGAAGTTCGTGTTCGAGCTGCTGCCAGTGATCAAGAAGAACAACGTGTGCCTGA
TCGCCATCGAGGAGCTGAAGTCCATGCTGGGCGACGACGACAAGAGGGCTGAG
GATAACAGGCTGTACAACCTGTGGCCGGTGGGCCAGCTTAAGACGTTCCTGGAG
GGCAAGCTGCTGCCGTACAACGTGGCTGTGATGGAGGTGAGCGAGCAGAACAC
GAGCCAGATCGTGAACGGCCAGTGGTCCTACAGGGAGGGCGATGATCTCTACTA
CGTGAAGAACAACGACAACAACACCATGTGCAAGACCCACGCGGACGAGAACG
CGGCTATCAACATCGCCCTGAGGGCCTACTCCCACCACTAACCTGTACTCCAT
CTACATGATCAATCCGATCGACGACTACTACGTCCCGAGCTGCATCTGGAACAA
CAAGGACGAGGGCTCCAAGAGGATTAGGGGCTTCCTGACCAAGACCTACGGCAC
CTCCGACGTGGTGTTCATCAAGAAGAATGAGAAGCTGGTGAAGTCCGACGTGAG
CATCAAGGACGTGAAGAGGATCGTGAAGAACATCGGCAATGAGAAGAACAAGA
AGAGCGAGATCTGGTACAGGATGAACGACATCGAGTGGATCGACGAGGGCAGC
AGGGACATCATCATCAACACAATCAAGAGCAAGGTGAGGGGCTCCGGCAGCAA
GAGGCCAGCTGCTACTAAGAAGGCGGGCCAGGCTAAGAAGAAGAAGTGA

<table>
<tr><td>75</td><td>Nucleotide sequence of Casσ-9 system expression cassette</td></tr>
</table>

ATGGGCCCAAAGAAGAAGAGGAAGGTGATGGACTACAAGGACCACGACGGCGA
CTACAAGGATCACGACATCGACTACAAGGACGACGACGACAAGATGACGGACA
AGAGCATCAGCTTCAAGCAGTTCAGCCAGATCCTCAATGTGCTGTACAAGTGCA
TCGTGATTTCCGGCAAGGGCCGCGGCCTTACTTCCATTATCCTGGGCCAGCCGCA
GTGCAAGGACTCACTTACCTCCGCCGACTGGGGCAACCTGGAGACTCTTTCCGC
CAAGGACGAGCTGACCCCTGCTGAGGTTAAGGATATTACCAAGGACCTGATGTA
CAGGGCCAGCAACACCCTGGTCTCCATCGGCTTCAGGAACAGGTCCCCTTTCAA
GCTGACCCTGACCTCCGGCGAGAGGTACGCTGTTGTGGAGAACGTGCACCGCTC
CCTCAAGTCCTGGGTGGAGGTTGACAAGATTACCAGGGAGAACTACCTCAACGA
GGAGATCGCCCTGAGCGATGCCTTCAATAACATCGACGAGACGCTGCTGCCAAC
CCTTAAGGAGTTCTTCGACGCGTGCATGAATGAGAACATCATCCACCACTTCGA
CGCCAGGGTGTACGCCTACACGAGGGATTGCGTCATCCCAGCCCTGGTGGCTGG
CCTTGAGATCAAGGACCACTTCTACATCGACGGCCGCGACAAGGCCAAGAGGGA
TTACAGCCTGCAAGGTTACGCCGAGCTTCTGAAGGGCTTCCCGAAGCTCTGGCA
GGGCGTTGATCCGGAGATCCTGGCTAAGCTGTACATCCTGGAGGCCCAGATGGA
CCACAAGAAGCACAGGCCATGCGCCGCTTACGCGTTCATCGGCGAGGATTCCTA
CAGCAGGGTGCAGTACCTTCTGGGCAACAACTACACCTCCTTCAGCCCCTACGC
CCTCGGCGTTGATCTGGATGACGTGACCTGCGGCGATGACGCTGAGGCTGATAC
ACAGTTCCCCAAGAACAAGGTGATCCAGTTCAGCCAGGGCAAGAAGGTGACCA
AGCTGTCCCTGACCGTGAGCAGGGCAAGGAGGATACCAACAAGTACTCCTTCG
ATGTGTTCCTGGCCGACAAGTACAGCAACGGCTCCTACAAGCCAAGCCCGTACT
TCTCTGACCTGTCCGTTTGGGTGAGCGAGATCGGCATGCTGATGGAGTTCACCCG
CAAGGGCGAGAGGGTGCAGGCTATTGTGAAGGAGCCATCCCTGATTTACCGCAA
GGGCGCCTTCTACGTGAGGCTTAATATGGGCGTGATTCAGGACACCTCCCCGGA
GATCAACGACCTGTACTGGTACTTGTCCTCCGGCGCCCCAATGTCCATGACCGAT
AGGTCCAAGGCTTCCGAGACCCCGAAGAACACCGAGAGGCTGGAGTCAATTAA
GGGCAAGAGCTACCGCTTCCTGGGCATCGACCTGGGCCTTAGGTCCCCCATTCGC
CTGGGCTGTTGGCGAGGCTTCTATCTCCGGCGTCATCAACAAGCCGACGATCATT
GCCACCGGCGACTACACCACCGCCAGGGATACTAGGTACGACACGCTCTTCTTC
GCCCTCAAGAATGCGGGCAAGGTGATTGGCGTGACCAAGTCCCTCGCCAACGGC
AAGGACGCTTCTTTCAATGGCCTGATGGGCACCATCACCGCCGCTAGGGAGTAC
CTTGCGCACTACTCCGGCGTCGCTACCCATAAGGTGGCCGCTATCCAGGCCTTCT
GCCAGGATGACAACCCGCTGGAGACCCCTTAAGGGCCTGCTCAAGTCCTACAACA

TABLE 1-continued

Description of sequences

SEQ
ID
NO:    Description

ACGACCTCGTCACCCTCAAGAAGGACCCTAGGTTCATCGGCGGCATCCTGCTCA
       GGTACGCCAGGCTTCTGAAGGGCGAGCTTGTGACCTCCAGGAAGATGCACCTGC
       GGGAGCACTCCGTGGAGTCTAAGTTCGGCCAGGAGTACATGTGGCTGAATATTC
       TGGAGAGGGAGAAGAGGGTGTGCAGGAGCCTGTCCTACCTGGGCCTTGGCAACG
       ACAGGGACAGCGTTATCATGGGCAACCTGACCACGCCGTACAACCACTGCAAGG
       AGAACCTGCTTAAGCAGCTGGCCGCGAGGATTGTGTCACTGGCTGTGGAGAATA
       AGTGCCACGTTATCGTGATGGAGTCCCTGGGCGGCTCCAACAAGTCCATGAATA
       CCAGGGGCCAGAACTTCCTCGAGGCCTTCTGGTCCCCACAGAAGATCAAGGACA
       CCATCATCAACGCCGCCGCCTGGCATGGCATCATGGTTGCTGAGGTGAGCGAGA
       GCCAGACCTCCCAGGTTTGCTTCGAGACCGGCACCTTCGGCCACAGGGATAGGG
       CTTCTCTGTACTTCCTGGACAAGAACGGCGACCTCCAGGAGACGCATGCCGATA
       TGAACGCCGCCAAGAACCTCGTGGAGAGGTTCACCACCAGGCACACCAACCTGA
       GGCAGGTGAATATGGACTCCCTCCCCAAGGAGGGCCCGGATAAGACACCCAAAG
       AAGTCCCCGTCCAAGAAGAAGATGGAGAAGGCGAAGATGGACAACCCAGAGGA
       CCAGTCCAAGAGGCTCAAGGGCTTCCTGACCGTGAAGTTCGGCAATGTGAAGGC
       CGCCCAGGAGTACTTCGCCTCTAGGAAGCCGGAGCAGAGCTACAGCGGCAAGA
       AGGACGAGGCCATCTACTGGTACTTGGACGGCGACGAGTGGATCACCAAGAAG
       GAGAAGGAGTCCAGGGTCAGCGTGATTGAGGGCCTGGTGGGCCTTAAGGAGGT
       GGCTGTTGGCAGCGGCTCCAAGAGGCCAGCTGCTACTAAGAAGGCCGGCCAGGC
       TAAGAAGAAGAAGTGA

76     Nucleotide sequence of Casσ-10 system expression cassette
       ATGGGCCCAAAGAAGAAGAGGAAGGTGATGGACTACAAGGACCACGACGGCGA
       CTACAAGGATCACGACATCGACTACAAGGACGACGACGACAAGATGGCGTTCCA
       GAGCAAGAGGAGGATTGTGGGCAACCTGGTGAAGGAGCAGTGCCTCAAGGCCG
       TGGATGGCAAGGTGATCCTGACCGACCAGGAGAAGAGGGAGCTGATCAAGAGG
       TACGAGCTGCACCTGGAGCCGTACAAGTGGCTGCTGAGGCTGTTCCTGTCCGGC
       TACGAGGGCAGGGATGACGGCTTCTACGAGGAGCTGGGCAACACGAACCTGGA
       CAAGGAGAAGTTCTTCGAGGTCACCGCGGGCCTCAGGGATGCTCTTCTTAGGCA
       GTCTGGCTCCTCCAGGGCGCTTAAGTCCTCCATGCTGGGCAAGTGCCCGCCATCA
       GCTGCTGTTGGCAAGGCTGCTAAGCACATCCAGGCTCTGCGCGACGCTGGCATT
       CTTCCATTCAAGACGGGCCTCACCTCCGGCGAGGATTACAACGTGCTTCAGCAG
       GCCGTCCAGCAGCTGAGGTCATGGGTTGCTTGCGATCACAGGACCAGGGAGGCG
       TACGCTGAGCAGCAGGAGAAGACATCCCAGGCCGAGGAGGCTGCTAAGAAGGC
       TGTGAACGAGGTGAAGCCAGAGGACGCCAAGAGCCTGGAGAGGCATGAGAGGG
       CTCTGACGAAGCTGAGGAAGCAGGAGAGGAGGCTGGAGAGGATGAGGAGCCAC
       GCTCAGTTCAGCCTGGACGAGATGGACTGCACGGGCTACAGCCTGTGCATGGGC
       GCTAACTACCTGAAGGACTACTGCCTGGAGAAGGAGGGCAGGGGCCTTAGGCTT
       ACCCTGAAGAATAGCACTATGGCCGGCAGCTACTACGTTTCCGTGGGCGATGGC
       CAGCACGCTGGCATGAAGAACCCAGGTACTCCGGCGGGCGGCTCTCCAGAGAAG
       GGCAGGAGGAGGAACATCCTGTTCGACTTCGCGGTTGAGAAGTGCGGCGACAAC
       TACCTTTTCAGGTACGACGAGAACGGCAAGCGCCCGAGGGCTGGCGTTGTTAAG
       GAGCCAAGGTTCTGCTGGAGGCGGAAGGGCAACTCCGTGGAGCTTTACCTGGCC
       ATGCCGATCAACATCGAGAACAGCATGAGGAACATCTTCGTCGGCAAGCAGAAG
       AGCGGCAAGCACTCCGCTTTCACCCGGCAGTGGCCAAAGGAGGTGGAGGGCCTT
       GACGAGCTGAGGGATGCTGTGGTGCTGGGCGTTGACATCGGCATCAACAGGGCG
       GCTTTCTGCGCGGCTCTGAAGACTTCCCGCTTCGAGAACGGCCTGCCGGCTGATG
       TTCAGGTTATGGATACCACCTGCGATGCTCTGACCGAGAAGGGCCAGGAGTACA
       GGCAGCTGAGGAAGGACGCCACCTGCCTTGCTTGGCTGATCAGGACAACCAGGA
       GGTTCAAGGCCGACCCAGGTAACAAGCACAACCAGATCAAGGAGAAGGACGTG
       GAGAGGTTCGACAGCGCCGACGGCGCTTACAGGAGGTACATGGACGCCATCGCG
       GAGATGCCGTCCGATCCACTTCAGGTGTGGGAGGCTGCCAGGATCACCGGCTAC
       GGCGAGTGGGCTAAGGAGATTTTCGCCAGGTTCAATCACTACAAGCACGAGCAT
       GCCTGCTGCACCGTCTCCCTTTCCCTGTCTGACCGCCTGGTGTGGTGCAGGCTTA
       TCGATAGGATCTTGTCTCTCAAGAAGTGCCTTCACTTCGGCGGCTACGAGTCCAA
       GCACAGGAAGGGCTTCTGCAAGTCCCTCTACAGGCTTAGGCACAATGCCAGGAA
       CGACGTCAGGAAGAAGCTGGCCAGGTTCGTGGTGGACGCCGCTGTTGATGCGGG
       CGCTTCTGTTATCGCGATGGAAAAGCTCCCGTCCTCCGGCGGCAAGCAGTCTAG
       GGATGACAACCGGATCTGGGACCTGATGGCCCCAAACACCCTGGCTACCACCGT
       GTGCCTCATGGCTAAGGTTGAGGGCATCGGCTTCGTGCAGGTGGACCCAGAGTT
       CACCTCCCAGTGGGTGTTCGAGCAGAGGGTGATTGGCGATAGGGAGGGCAGGAT
       TGTGTCCTGCCTGGACGCTGAGGGCGTGAGGAGGGATTACGACGCTGACGAGAA
       CGCCGCGAAGAACATCGCCTGGCTGGCTCTTACTAGGGAGGCGGAGCCATTCTG
       CATGGCCTTCGAGAAGCGGAATGGCGTGGTGGAGCCGAAGGGCTTCAGGTTCGA
       CATTCCGGAGGAGCCGACCAGGGAGCAGGATGAGTCAAACCAGGACTTCAAGA
       AGAGGCTGGAGGAGAGGGACAAGCTGATCGAGAGGCTGCAGGCGAAGAGCGAT
       AGGATGAGGGCGATCGTGAGGAGGCTCTTCGGCGATAGGAGGCCGTGGGATGCT
       TTCGCTGACAGGATTCCTGAGGGCAAGTCCAAGAGGCTGTTCCGGCACAGGGAT
       GGCCTGGTTCTGAACAAGCCGTTCAAGGGCCTGTGCGGCTCCGAGAATAGCGAG
       CAGAAGGCCTCCGCCAGGAACTCTAGGGGCTCTGGCTCTAAGAGGCCTGCCGCT
       ACTAAGAAGGCGGGCCAGGCTAAGAAGAAGAAGTGA TABLE 1-continued Description of sequences SEQ
ID
NO:  Description 77    Nucleotide sequence of Casσ-11 system expression cassette
      ATGGGCCCAAAGAAGAAGAGGAAGGTGATGGACTACAAGGACCACGACGGCGA
      CTACAAGGATCACGACATCGACTACAAGGACGACGACGACAAGATGGACACGG
      ACACGGAGCTGAGCGACGAGGTTGAGCTGAGCGATGAGGTGGAGCTGAGCGAC
      GAGGTGGAGCTTTCCGACGAGGTGGAGCTGACGGTGAAGAAGGTGAAGACGAC
      GACGGTGAAGGTGGACAACAATTTCAAGAAGGAGCTGTTCGAGCTGTTCAATCA
      CTTCACCAGCGTGGCGAGCGGCATCAAGGACAGGCTTTACGACCTGCAGTTCGA
      TGAGAACACTGCCTCCATCTTCAAGGGCTACATCAAGGAGGCCAAGAGGGGCCA
      CGGCGCTGCTACTACTGTGTTCACTAAGCTGAACCCGAAGAAGATCTACTCCGG
      CAAGAAGTCCTTCCCAAGGGATTACAGGGACCGGGGCATCTTCCCGTTCTACAA
      CAAGGAGTCTGGCAAGTACGACCTGTCCACCTGCGGCTACCACTACAGCGCTAA
      CGCCGAGATTCACACCCAGCTCAACAGCCACGACGAGTGCAACAAGCAGTGCGA
      GAAGGAGTACGCGGCGCTGGAGAAGGAGAGGAACAAGTACAAGCATGAGTTCA
      CGAGGCAGTTCAAGGCCGAGAACGTGGAGAAGTTCAGCAACTTCGTGGAGAAG
      CTGACACTGATGGGCTGGAGGTACGATGCGACCTTCAGGAACTTCTTCGAGCTG
      CACATGCACCCAAAGCTCAAGACGTCCGAGACCACCTACAGGGCCACCTACAAG
      CTGCCGTCCGGCAAGTCTAAGCGGTACTCCTTCTCCAGGGACGATATTGCCGAC
      GAGATCGCCAAGAACCCCGAGTTCTGGCCAATGCTGGAGTCCTCCAACGCCGTT
      TCCTGGATCAACTCCAACAATCTGCTCTCCAGGAAGAAGGAGAAGGCCAATTAC
      TCCAGCACCAGCCTGATCAAGTCCCAGATTAGGCTGTACCTGGGCGACAACGGC
      GTGCCATTCACCGCTAGGGAGCACGATGGCAGGATCTACTTCAGCTTCAGGCTC
      CCGTCCATCAACGGCGAGAAGGGCAGGAACGTCGAGATCCCATGCTCCTACAAG
      AAGGTCTTCAATGGCAAGGCCAGGAAGTCCTGCTACCTGGGCGGCCTTACCATC
      GAGAACACCGGCGGCTCAAAGCACATTTTCAAGTACTCCGTGAACAACAAGAAG
      CCGCAGGTGGCGGAGCTGAACGAGTGCTTCCTGAGGCTGGTCGTGAGGAATCAT
      GGCTACTTCAACAAGATGGTGAACGGCAAGCTCACGGATAAGGACGGCAAGCT
      GCACGCCGACTACTTCGATTTCTGCATCGACCTGCCGCTTAACGTGAAGGAGGA
      CCCGATCCACGACCTGACCTACCAGGAGATTAACGGCGTGAAGGCCAACCCGGA
      GAAGAACATCGAGAAGAAGGTGGGCCTGCTGGGCTTCTACCAGTCCGCTTACCC
      AGAGATCAAGAACCTCGGCTCCCAGATCGAGACCGGCAAGAACCTGACCTGCCC
      GATCACCAAGACCCACAACATCATGGGCATCGACCTCGGCCAGCGCCAACCCATT
      CGCTTACTGCATCAAGGACAACAACGGCAAGTTCATCGCGAAGGACCACATGGA
      CGGCTCCAAGAACGAGACATACAAGAAGTACATCAATTTCGGCAAGGAGAGCA
      CCTCAGTCTCCCACCTGATCAAGGAGACCAGGTCCTACCTGCATGGCGATCCGG
      AGGCTATCTCCAAGGAGCTGTACAACGAGGTCAGCGGCCTGTGCAACTCTCCGC
      TTAGCTACGAGGAGTACCTTAAGTACCTGGACAGCAAGAAGTTCCTGATCAACA
      AGGAGGACCTGAACAAGAACGCCATGCACCTGCTGAGGCAGAAGGACCACAAC
      TGGATCGGCAGGGACTGGCTGTGGTACATCAGCAAGCAGTACAAGAAGCACAA
      CGAGAACAGGATGCAGGACGCCGACTGGAGGCAGACTCTGTACTGGATCGACA
      GCCTGTACAGGTACATCGATGTGATGAAGTCCTTCCACAACTTCGGCAGCTTCTA
      CGACAAGAACCTGAAGAAGAAGGTGAACGGCACCGCCGTGGGCTTCTGCAAGA
      CTATCTACGACCAGATCAACAACAACAACAAGGACATGTTCAAGAAGTTCACCA
      ATGAGCTGATCCCGATCATCCGCAAGCACAAGGTGTCCGTGGTGTTCACCAAGA
      AGATGGAGTCCATGCTGGGCGACAAGTCCAGGAACACATTCGAGAACAGGAAC
      CACAACCTGTGGCCAGTCGGCCAGCTGAAGACCTTCATCGAGAACAAGCTGGAT
      GGCTTCAACGTGATCGTGGTGGAGGTGGACGAGAGGAACACGAGCCAGATGTG
      CGACGGCAACTGGTCCTACAGGGAGGCTGACGACCTCTACTACGTCAAGGACGG
      CGAGCTGAGGGAGGTTCACGCTGATGAGAATGCGGCCAACAACATCGTCGACAG
      GTGCATCTCCAGGCATACCAACATCTTCAGCCTGTACATGACCAACCCGATGGA
      CGACTACTACGTGCCGGCGTGCATCTGGGACAGGTCAGAGAATGGCAAGAGGG
      GCAGGGGCTTCCTGACCAAGATGTACAAGAACAGCGACGTGGTGTTCACCAAGA
      AGGACGACAAGCTGGTGAAGTCCAAGATGTCCGTGAAGGAGCTGAAGAAGCTG
      GTGGACAAGACCAAGGAGAAGAGGGGCCAGTACTGGTACTTGTTCGAGGGCAA
      GAGCTGGATCAACGCCGCCGATAGGGATACCATTATCTCCAACGCGAAGAAGCT
      CTTCAGGGAGAGGGATGGCGGCGAGCAGTCAACTGATACCCGCTCTCAGAACGT
      GACGGTGTCCGTGCTGGACGTGTGCGAGACTGTGGAGAAGAAGAAGCTGGTCCT
      GGTGGGCTCCGGCTCAAAGAGGCCAGCTGCTACTAAGAAGGCCGGCCAGGCTAA
      GAAGAAGAAGTGA 78    Nucleotide sequence of Casσ-12 system expression cassette
      ATGGGCCCAAAGAAGAAGAGGAAGGTGATGGACTACAAGGACCACGACGGCGA
      CTACAAGGATCACGACATCGACTACAAGGACGACGACGACAAGATGAGCACGG
      AGGTGGACGTGAAGACGATCAACCTGAAGATCGCGAAGAAGGGCGGCGTGTAC
      CCGATTCTGGAGCAGTCAATTAAGGAGAACTGCAAGAGCAACGACCTGCTGGAG
      TTCTTCATGGTGCTGAACAGGCTGCAGACCTACTACATCGAGAGCAACGAGGAG
      ATTCTGGTGGACTTCCCCAAGAAGTACGACGAGCTGTTCGACATCGTGAAGAAC
      AACGACTCCTCCGTGACCAGGGAATACTTCGACTCCCTCTGCGACAAGTACATC
      ACAGAGGTGTGCGCCAATGGCTTCGTCAACAACGTGTACATTGCCCACAACAAG
      AACCAGGAGCTGAACTGGGCTGAGACGAGCAACGACCGCAAGATCAAGAGCAA
      CAAGACCTTCATGTTCGGCAAGATCAAGGGCCTGATCCGCGACAAGTTCGGCAG
      GGAGGAGCTGTCAGACAAGGACGCTACGAAGCAGCTGTGCGAGGACATCTTCA
      ACCTCTTCATCCTGAACAACGCCAACATCGAGCTGGACGAGAAGTACAACATCA
      TCAAGGACGAGCTGATCCAGATCTGGAACGAGAGGAACAAGGAGTTCATCCAC TABLE 1-continued Description of sequences

| SEQ ID NO: | Description |
|---|---|

ATCAAGGACATCACCCTGCTGTTCAGGCAGTGGGGCATCCTGCCTACCTACGAC
AACATCACCCACAACTGCGAGCTGAAGGCCATCATCGCCGAGCCAGTGAGGAGG
TTCAAGTCCTGGCTGGAGTGCAACTCTGAGGCGAACAAGAACTACGACACCGAG
AGGGAGAAGTGCACCAAGTACATGGACGTGATGGACTCCGACCTGACCGTGGA
GTTCAGCAAGATGGTGACGGAGCTGGGCAACCCATTCGGCGCTAACGACAAGAA
CATCTACAAGTACTTCAACCAGAAGTTCCTCCTGTTCTTCAAGCAGGTTGTGCAG
CCCAAGTTCGTTAACGGCGAGCCGCTGGACGAGTCTAATGGCTCTTACTCCGGC
GAGATCAAGATCAACTCCGCGGGCAAGGTGGAGAACTACTCCATCGCCGTGTCC
GTGATTGACACCATCAAGAAGTACCCGACGATCTGGTCCGACCGCTCCTGGGGC
GAGTCTGTTATCTCCACCGTGGCCAAGATTGATCCGCAGTACGGCATCGACGAC
ATCACCGACGATATGCAGGTGTCCCCGTTCTACCTCTTCTACGGCTACTTCACCG
CCTACAACTACATCCAGCAGCACAAGAGGAACGCCAAGTACACCCCGATCTCCA
AGGACTCCCTGCCATCCCTGTACCTCGGCAACAACTACATCCCATTCAAGATCGA
CTGCGAGAACGTCGACGACGACCGGTTCTACATCACCATCAAGAACATGAACAA
CCTGAAGCTGAACGTCCTCTACCGCAAGCCCAAGCTGAAGTTCGCCAAGACCAA
GGAGAAGACCAAGAGGAACAAGTGCTACTTCGACAACCTCAAGATCACCAACA
CCAACAACAACTTCAAGTTCGAGTACAACATCAACGGCGACCCAAACAGGTCCG
TGGTGGCTTACCTGAAGGAGCCAGTGATCCGCTACAACAACAGGAAGGACTACT
TCTACCTGAGCGCCACAATCAGCAAGGACGTGGAGACCGACTCCGAGCTGACCT
CTGCTTGCTGGTCGAAGATCTCCAACGACACCGCCCGCAGGGTCAACGCTGAGC
AGTACTTCAACGACAACGGCGTGAACATCGTGGGCATTGACCTGGGCATGAACC
CGATCATCGCCTACTCTGTTCTGCACTACAAGAACAACGAGTTCATTGACCTGAA
CATTACCGGCAAGATCGCCGACAAGGATAAGCACCCCAATCTGAACTACAAGAG
GATGTACGAGAAGAGGTCCGAGATCAAGAAGCTCAAGACCCTGATCAAGATGA
TCCCGGACTACGTGAACAGCGACAGCAACATCTTCGAGGGCGACAATAACGTGT
TCAAGCAGCTGGACAAGAAGAGCAAGGGCAGGTTCAGGTCCTCCGAGTACATG
GGCTACTACGACAAGCTGAACGTGGACGGCAAGTTCATCTCCGAGCTGGAGATC
GTGAAGAAGGTGGTGAACACAAAGCACTACAAGAATGACACCGAGAAGAACAA
CGATATTATGAGGGTGTACAAGGGCAATAAGAAGAACATCATCAAGAAGGAGA
TCGACACCCACAGGCACCAGATCCACTCCATCAAGGACATGAACAGGAGGTCCG
ACGAGAGCAACCTGTGCTACGTGTACGACATGGTGAGCTACATCGACGACTTCA
AGAAGCTGGTGACCTCCTACAACAAGATCGGCGAGGACTACAACAACCCGATCA
AGCCGCTGAGCGACCCGATGCTTTTCTCCAAGTCCAAGCTGTACGAGTACAGGC
AGAACATCAGGGACAATTTCCTGAAGGACATCTGCTACCAGATGGTGAAGATCG
CCAAGCAGTACAATGCCGTGCTGGTGCACGAGCACTTCGAGCAGAGGAAGGGC
GGCATTGACAGGGTGAACAACATCCTGATGGCCCTGTTCACGCCGAACGACATC
ATCAAGAAGCTGAAGTGCGTGGCCAAGAGGGAGGGCGTTCTGGTTTTCAACACC
AACAAGAACCATACCTCCCAGTACGTGTACAACAAGAACACCGTCGGCTACCGC
GACAGCAACAACAAGCACAACCTGTACTACATCGAGGACGAGACCACCAGGAA
GCTCGGCGTTGTGGACTCCGACATCAACGCCTCCAAGAACATCGCCGCCCGCCC
ATTCAACAAGCCACTCTACGCCATCAAGGTGAAGAACTACGATGACGGCCTGTT
CCTGTCAGACTACAACAATAAGTACGTTCTGTACAAGAAGGACGGCGACAAGTA
CGTGGCCATCGGCGATACATACAGGATCGACAAGAAGAAGATCAAGCAGGGCT
CCGTGACCCTGTACCTGCATAACGGCTACTACGTGGATGGCGAGTACAAGAACA
ATTACATCGAGAATATCAAGAAGCTGGTCCTGGGCAGCGGCAGCAAGAGGCCA
GCTGCTACTAAGAAGGCCGGCCAGGCTAAGAAGAAGAAGTGA

| 79 | Nucleotide sequence of Caso-13 system expression cassette |
|---|---|

ATGGGCCCAAAGAAGAAGAGGAAGGTGATGGACTACAAGGACCACGACGGCGA
CTACAAGGATCACGACATCGACTACAAGGACGACGACGACAAGATGGCGTTCCA
GAGCAAGAGGAGGATTGTGGGCAACTTCGTGAAGGAGCAGTGCCTGAAGGCCG
TGGATGGCAAGGTGATCCTGACGGACCAGGAGAAGAGGGAGCTGATTAAGAGG
TACGAGCTGCACCTGGAGCCGCATAAGTGGCTGCTGAGGCTGTTCCTGTCCGGC
TACGAGGGCAGGGATGACGGCTTCTACGAGGAGCTGGGCAACACGAACCTGGA
CAAGGAGAAGTTCTTCGAGGTCACCGCGGGCCTGAGGGATGCTCTTCTTAGGCA
GTCTGGCAGCAGCAGGGCGCTTAAGTCCTCCATGCTGGGCAAGTGCCCGCCATC
AGCTGCTGTTGGCAAGGCTGCTAAGCACATCCAGACCCTGAGGGACGCCGGCAT
TCTCCCATTCAAGACGGGCCTGACCTCCGGCGAGGATTACAACGTGCTGCAGCA
GGCCGTGCAGCAGCTTAGGTCATGGGTGGCTTGCGACCACAGGACGAGGGAGGC
TTACGCTGAGCAGCAGGAGAAGACAAGCCAGGCCGAGGAGGCTGCTAAGAAGG
CTGCTAACGAGGTGAAGCCGGAGGATGCGAAGTCTCTGGAGAGGCACGAGAGG
GTGCTGACGAAGCTGAGGAAGCAGGAGAGGAGGCTGGAGAGGATGAAGAGCCA
CGCGCAGTTCAGCCTGGACGAGATGGACTGCACGGGCTACTCCCTGTGCATGGG
CGCTAATTACCTGAAGGACTACTGCCTGGAGAAGGAGGGCAGGGGCCTTAGGCT
TACCCTGAAGAATAGCACGATGGCTGGCAGCTACTACGTTTCCGTGGGCGACGG
CCAGCACGCTGGCATGAAGAATCCGGGCACCCCAGCTGGCGGCTCTCCAGAGAA
GGGCAGGAGGAGGAATATCCTGTTCGACTTCACCGTGGAGAAGTGCGGCGACAA
TTACCTGTTCAGGTACGACGAGAACGGCAAGAGGCCGAGGGCTGGCGTTGTTAA
GGAGCCAAGGTTCTGCTGGAGGCGGAAGGGCAACAGCGTGGAGCTTTACCTGGC
GATGCCGATCAACATCGAGAACAGCATGAGGAACATCTTCGTGGGCAAGCAGA
AGTCCGGCAAGCACTCCGCTTTCACCCGGCAGTGGCCAAAGGAGGTCGAGGGCC
TTGACGAGCTTAGGGACGCTGTGGTGCTGGGCGTTGACATCGGCATCAACAGGG
CGGCTTTCTGCGCCGCTCTGAAGACTTCCAGGTTCGAGAATGGCCTGCCGGCCG
ATGTGCAGGTTATGGATACCACCTGCGATGCGCTGACCGAGAAGGGGCCAGGAGT

TABLE 1-continued

Description of sequences

SEQ
ID
NO: Description

```
    ACAGGCAGCTGAGGAAGGACGCCACCTGCCTTGCTTGGCTGATCAGGACGACCA
    GGAGGTTCAAGGCTGACCCAGGTAACAAGCACAACCAGATCAAGGAGAAGGAC
    GTGGAGAGGTTCGACAGCGCCGACGGCGCTTACAGGAGGTACATGGACGCCATC
    GCGGAGATGCCGAGCGATCCACTTCAGGTCTGGGAGGCTGCCAGGATCACCGGC
    TACGGCGAGTGGGCTAAGGAGATTTTCGCCAGGTTCAACCACTACAAGCATGAG
    CACGCCTGCTGCGCCGTGTCTCTTTCTCTTTCCGACAGGCTGGTGTGGTGCAGGC
    TCATCGACAGGATCTTGTCTCTGAAGAAGTGCCTCCACTTCGGCGGCTACGAGTC
    CAAGCACAGGAAGGGCTTCTGCAAGTCCCTGTACAGGCTGAGGCACAACGCCAG
    GAACGACGTGAGGAAGAAGCTGGCCAGGTTCATCGTGGATGCCGCCGTTGACGC
    GGGCGCTTCTGTTATTGCGATGGAGAAGCTGCCGTCCTCTGGCGGCAAGCAGTC
    AAAGGACGACAACAGGATCTGGGACCTGATGGCCCCGAACACCCTGGCTACTAC
    TGTGTGCCTGATGGCCAAGGTGGAGGGCATCGGCTTCGTCCAGGTCGATCCAGA
    GTTCACCTCCCAGTGGGTGTTCGAGCAGAGGGTGATTGGCGATAGGGAGGGCAG
    GATCGTGAGCTGCCTGGATGCTGAGGGCGTGAGGAGGGATTACGACGCTGACGA
    GAACGCCGCGAAGAACATCGCCTGGCTGGCTCTTACCAGGGAGGCTGAGCCATT
    CTGCATGGCGTTCGAGAAGAGGAACGGCGTGGTGGAGCCGAAGGGCCTTAGGTT
    CGACATCCCGGAGGAGCCTACCAGGGAGCAGGATGAGTCGGACCAGGACTTCA
    AGAAGAGGCTGGAGGAGAGGGACAAGCTGATCGAGAGGCTGCAGGCGAAGGCG
    GATAGGATGCAGGCTATCGTTCAGAGGCTTTTCGGCGACAGGAGGCCGTGGGAT
    GCTTTCGCTGACAGGATTCCTGAGGGCAAGAGCAAGAGGCTGTTCAGGCACAGG
    GACGGCCTGGTTCTGAACAAGCCGTTCAAGGGCCTGTGCGGCTCCGAGAATAGC
    GGCCAGAAGGCTTCTGCTAGGAACAGCCGCGGCTCCGGCTCTAAGAGGCCAGCT
    GCTACTAAGAAGGCGGGCCAGGCTAAGAAGAAGAAGTGA
```

80 PAM library sequence
   NNNNNNNNNGGTATAACAACTTCGACGAGCTCTACA

81 Target sequences for the recognition of PAM domain of Casσ
   GGUAUAACAACUUCGACGAGCUCUACA 82 Guide sequence of Casσ for eukaryotic editing
   GAGCCAGAGAGGAUCCUGGGAGGGAG 83 Guide sequence of Casσ
   CUUCCAUCAGAGAACCUCACUGCG

Specific Models for Carrying Out the Invention

The present invention is now described with reference to the following examples which are intended to illustrate the present invention (but not to limit the present invention).

Unless otherwise specified, the experiments and procedures described in the examples were basically performed according to the methods known in the art and using conventional methods described in various references. For example, conventional techniques of immunology, biochemistry, chemistry, molecular biology, microbiology, cell biology, genomics and recombinant DNA used in the present invention can be found in Sambrook, Fritsch, and Maniatis, MOLECULAR CLONING: A LABORATORY MANUAL, 2nd ed. (1989); CURRENT PROTOCOLS IN MOLECULAR BIOLOGY, edited by F. M. Ausubel et al. (1987)); METHODS IN ENZYMOLOGY series, Academic Press: PCR 2: A PRACTICAL METHOD APPROACH, edited by M. J. MacPherson, B. D. Hames, and G. R. Taylor (1995); ANTIBODIES, A LABORATORY MANUAL, edited by Harlow and Lane (1988); and, ANIMAL CELL CULTURE, edited by R. I. Freshney (1987).

In addition, when specific conditions were not specified in the examples, they were carried out under conventional conditions or conditions recommended by the manufacturer. The reagents or instruments used without indicating the manufacturer were all conventional products that could be obtained commercially. It is known to those skilled in the art that the examples describe the present invention by way of example, and are not intended to limit the scope sought to be protected by the present invention. All publications and other references mentioned herein are incorporated herein by reference in their entirety.

The sources of some reagents involved in the following examples were as follows:

LB liquid culture medium: 10 g of tryptone, 5 g of yeast extract, 10 g of NaCl, diluted to 1 L, and sterilized. If the addition of an antibiotic was required, it was added after the culture medium was cooled down, and its final concentration was 50 µg/mL.

Chloroform/isoamyl alcohol: 240 ml of chloroform was added with 10 mL of isoamyl alcohol, and mixed well.

RNP buffer: 100 mM sodium chloride, 50 mM Tris-HCl, 10 mM $MgCl_2$, 100 µg/mL BSA, pH 7.9.

Prokaryotic expression vectors pET-30a, pUC19, and pACYCDuet-1 were purchased from Beijing Quanshijin Biotechnology Co., Ltd.

*Escherichia coli* competent TSC-E03 was purchased from Beijing Qingke Biotechnology Co., Ltd.

Example 1. Acquisition of Casσ Sequences and Casσ Guide RNA

1. Annotation of CRISPR and genes: Prodigal was used to perform the gene annotation of the data of microbial genome and metagenome of NCBI and JGI databases to obtain all proteins, and Piler-CR was used to perform the annotation of CRISPR loci, and the parameters were all default parameters.

2. Protein filtering: The annotated proteins were subjected to redundancy removal through sequence consistency so as to remove proteins with completely identical sequences.

3. Acquisition of CRISPR-related proteins: Each CRISPR locus was extended by 10 Kb upstream and downstream, and the non-redundant proteins in the CRISPR adjacent interval were identified.

4. Clustering of CRISPR-related proteins: BLASTP was used to perform internal pairwise alignment of non-redundant CRISPR-related proteins, and the alignment results with Evalue<1E-10 were outputted. MCL was used to perform clustering analysis on the output results of BLASTP, CRISPR-related protein families.

5. Identification of CRISPR-enriched protein families: BLASTP was used to align the proteins of the CRISPR-related protein families to the non-redundant proteins databases from which the non-CRISPR-related proteins were removed, and the alignment results with Evalue<1E-10 were outputted. If the homologous proteins found in a non-CRISPR-related protein database were less than 100%, it meant that the proteins of this family were enriched in the CRISPR region. In this way, the CRISPR-enriched protein families were identified.

6. Annotation of protein functions and domains: The CRISPR-enriched protein family was annotated using the Pfam database, the NR database, and the Cas proteins collected from NCBI to obtain a new CRISPR/Cas protein family. Multiple sequence alignment of each CRISPR/Cas family protein was performed using Mafft, and then conserved domain analysis was performed using JPred and HHpred to identify the protein family containing RuvC domain.

On this basis, the inventors obtained a new Cas effector protein, which were named Casσ-1 to Casσ-13, respectively, the sequences of the proteins were set forth in SEQ ID NOs: 1 to 13, and the nucleotide sequences encoding the proteins were as set forth in SEQ ID NOs: 14 to 26. The direct repeat sequences (the repeat sequences contained in pre-crRNA) corresponding to Casσ-1 to Casσ-13 were set forth in SEQ ID NOs: 27 to 39.

Example 2. Description of Sequence Structure of Casσ Gene

1. The CRISPR/Casσ sequence fragment was synthesized by Beijing Qingke Biotechnology Co., Ltd. and constructed into the protein expression vector pET-30a (+), and the first generation sequencing was performed for confirmation. According to the sequencing results, the recombinant plasmid pET-30a+CRISPR/Casσ was described as follows:

(1) The recombinant plasmid pET-30a+CRISPR/Casσ-1 contained an expression cassette, and the expression cassette sequence was set forth in SEQ ID NO: 67. In the sequence as set forth in SEQ ID NO: 67, from the 5' end, positions 1 to 27 were the nucleotide sequence of SV40-NLS, positions 28 to 96 were the nucleotide sequence of 3×FLAG, positions 97 to 2742 are were nucleotide sequence of Casσ-1, and positions 2743 to 2802 were the nucleoplasmin NLS signal peptide.

(2) The recombinant plasmid pET-30a+CRISPR/Casσ-2 contained an expression cassette, and the expression cassette sequence was set forth in SEQ ID NO: 68. In the sequence as set forth in SEQ ID NO: 68, from the 5' end, positions 1 to 27 were the nucleotide sequence of SV40-NLS, positions 28 to 96 were the nucleotide sequence of 3×FLAG, positions 97 to 2901 were the nucleotide sequence of Casσ-2, and positions 2902 to 2961 were the nucleoplasmin NLS signal peptide.

(3) The recombinant plasmid pET-30a+CRISPR/Casσ-3 contained an expression cassette, and the expression cassette sequence was set forth in SEQ ID NO: 69. In the sequence as set forth in SEQ ID NO: 69, from the 5' end, positions 1 to 27 were the nucleotide sequence of SV40-NLS, positions 28 to 96 were the nucleotide sequence of 3×FLAG, positions 97 to 2700 were the nucleotide sequence of Casσ-3, and positions 2701 to 2856 were the nucleoplasmin NLS signal peptide.

(4) The recombinant plasmid pET-30a+CRISPR/Casσ-4 contained an expression cassette, and the expression cassette sequence was set forth in SEQ ID NO: 70. In the sequence as set forth in SEQ ID NO: 70, from the 5' end, positions 1 to 27 were the nucleotide sequence of SV40-NLS, positions 28 to 96 were the nucleotide sequence of 3×FLAG, positions 97 to 1977 were the nucleotide sequence of Casσ-4, and positions 1978 to 2037 were the nucleoplasmin NLS signal peptide.

(5) The recombinant plasmid pET-30a+CRISPR/Casσ-5 contained an expression cassette, and the expression cassette sequence was set forth in SEQ ID NO: 71. In the sequence as set forth in SEQ ID NO: 71, from the 5' end, positions 1 to 27 were the nucleotide sequence of SV40-NLS, positions 28 to 96 were the nucleotide sequence of 3×FLAG, positions 97 to 2877 were the nucleotide sequence of Casσ-5, and positions 2878 to 2937 were the nucleoplasmin NLS signal peptide.

(6) The recombinant plasmid pET-30a+CRISPR/Casσ-6 contained an expression cassette, and the expression cassette sequence was set forth in SEQ ID NO: 72. In the sequence as set forth in SEQ ID NO: 72, from the 5' end, positions 1 to 27 were the nucleotide sequence of SV40-NLS, positions 28 to 96 were the nucleotide sequence of 3×FLAG, positions 97 to 2796 were the nucleotide sequence of Casσ-6, and positions 2797 to 2856 were the nucleoplasmin NLS signal peptide.

(7) The recombinant plasmid pET-30a+CRISPR/Casσ-7 contained an expression cassette, and the expression cassette sequence was set forth in SEQ ID NO: 73. In the sequence as set forth in SEQ ID NO: 73, from the 5' end, positions 1 to 27 were the nucleotide sequence of SV40-NLS, positions 28 to 96 were the nucleotide sequence of 3×FLAG, positions 97 to 2901 were the nucleotide sequence of Casσ-7, and positions 2902 to 2961 were the nucleoplasmin NLS signal peptide.

(8) The recombinant plasmid pET-30a+CRISPR/Casσ-8 contained an expression cassette, and the expression cassette sequence was set forth in SEQ ID NO: 74. In the sequence as set forth in SEQ ID NO: 74, from the 5' end, positions 1 to 27 were the nucleotide sequence of SV40-NLS, positions 28 to 96 were the nucleotide sequence of 3×FLAG, positions 97 to 2784 were the nucleotide sequence of Casσ-8, and positions 2785 to 2844 were the nucleoplasmin NLS signal peptide.

(9) The recombinant plasmid pET-30a+CRISPR/Casσ-9 contained an expression cassette, and the expression cassette sequence was set forth in SEQ ID NO: 75. In the sequence as set forth in SEQ ID NO: 75, from the 5' end, positions 1 to 27 were the nucleotide sequence of SV40-NLS, positions 28 to 96 were the nucleotide sequence of 3×FLAG, positions 97 to 2757 were the nucleotide sequence of Casσ-9, and positions 2758 to 2817 were the nucleoplasmin NLS signal peptide.

(10) The recombinant plasmid pET-30a+CRISPR/Casσ-10 contained an expression cassette, and the expression cassette sequence was set forth in SEQ ID NO: 76. In the sequence as set forth in SEQ ID NO: 76, from the 5' end, positions 1 to 27 were the nucleotide sequence of SV40-NLS, positions 28 to 96 were the nucleotide sequence of 3×FLAG, positions 97 to 2559 were the nucleotide sequence of Casσ-10, and positions 2560 to 2619 were the nucleoplasmin NLS signal peptide.

(11) The recombinant plasmid pET-30a+CRISPR/Casσ-11 contained an expression cassette, and the expression cassette sequence was set forth in SEQ ID NO: 77. In the sequence as set forth in SEQ ID NO: 77, from the 5' end, positions 1 to 27 were the nucleotide sequence of SV40-NLS, positions 28 to 96 were the nucleotide sequence of 3×FLAG, positions 97 to 2958 were the nucleotide sequence of Casσ-11, and positions 2959 to 3018 were the nucleoplasmin NLS signal peptide.

(12) The recombinant plasmid pET-30a+CRISPR/Casσ-12 contained an expression cassette, and the expression cassette sequence was set forth in SEQ ID NO: 78. In the sequence as set forth in SEQ ID NO: 78, from the 5' end, positions 1 to 27 were the nucleotide sequence of SV40-NLS, positions 28 to 96 were the nucleotide sequence of 3×FLAG, positions 97 to 3099 were the nucleotide sequence of Casσ-12, and positions 3100 to 3159 were the nucleoplasmin NLS signal peptide.

(13) The recombinant plasmid pET-30a+CRISPR/Casσ-13 contained an expression cassette, and the expression cassette sequence was set forth in SEQ ID NO: 79. In the sequence as set forth in SEQ ID NO: 79, from the 5' end, positions 1 to 27 were the nucleotide sequence of SV40-NLS, positions 28 to 96 were the nucleotide sequence of 3×FLAG, positions 97 to 2559 were the nucleotide sequence of Casσ-13, and positions 2560 to 2619 were the nucleoplasmin NLS signal peptide.

Example 3. Identification of PAM and DNA Cleavage Mode of CRISPR/Casσ System I. In Vitro Expression and Purification of Casσ Protein The specific steps of in vitro expression and purification of Casσ protein were as follows:

1. Artificial synthesis of nucleotide sequences as set forth in SEQ ID NOs: 67 to 79.

2. The recombinant plasmids pET-30a-CRISPR/Casσ-1 to pET-30a-CRISPR/Casσ-13 were introduced into *E. coli* TSC-E03 to obtain recombinant bacteria, and the recombinant bacteria were named TSC-E03-CRISPR/Casσ-1 to TSC-E03-CRISPR/Casσ-13. The single clones of TSC-E03-CRISPR/Casσ-1 to TSC-E03-CRISPR/Casσ-13 were picked out, inoculated into 100 mL of LB liquid culture medium (containing 50 μg/mL kanamycin), and cultured under shaking at 37° C. and 200 rpm for 12 h to obtain culture solutions.

3. The culture solutions were taken and inoculated into 50 mL of LB liquid culture medium (containing 50 μg/mL kanamycin) at a volume ratio of 1:100, cultured under shaking at 37° C. and 200 rpm until the $OD_{600\ nm}$ value was 0.6, then IPTG was added to have a concentration of 1 mM, cultured under shaking at 18° C. and 220 rpm for 14 h, and centrifuged at 4° C. and 7000 rpm for 10 min to obtain bacterial precipitates.

5. The bacterial precipitates were taken, added with 100 mL of pH 8.0, 100 mM Tris-HCl buffer, resuspended and ultrasonically disrupted (ultrasonic power was 600 W, and cycle program was: disruption 4 s, stop 6 s, total 20 min), and then centrifuged at 4° C., 10000 rpm for 10 min to collect Supernatant A.

6. Supernatant A was taken, centrifuged at 4° C., 12000 rpm for 10 min to collect Supernatant B.

7. The nickel column produced by GE was used to purify Supernatant B (referring to the instructions of the nickel column for the specific steps of purification), and then the protein quantification kit produced by Thermo Fisher was used to quantify Casσ-1 to Casσ-13 proteins.

II. Transcription and Purification of Casσ Protein Guide RNA:

1. The templates for guide RNA transcription were designed respectively. The structure of the transcription templates was: (1) T7 promoter+direct repeat sequence of Casσ-1 to Casσ-13 (SEQ ID NOs: 27 to 39)+guide sequence (SEQ ID NO: 81). The primers were designed using Primer5.0 software to ensure that the Forward primer and Reward primer had at least 18 bp of overlapping sequence.

2. The following reaction system was prepared, gently blown and beaten and mixed well, then centrifuged briefly, and placed in a PCR instrument for slow annealing. The PCR system was as follows:

| Component | Volume (μL) |
| --- | --- |
| Forward Primer (100 nM) | 7.5 |
| Reward Primer (100 nM) | 7.5 |
| 2*KAPA Mix | 25 |
| ddH₂O | 10 |
| Total volume | 50 |

3. MinElute PCR Purification Kit was used to purify the template, and the steps were as follows:

1) The PCR product was added with PB of 5 times volume, and a MinElute column was placed on a 2 ml collection tube, allowed to stand at room temperature for 2 min, and centrifuged at 12000 g for 1 min;

2) The waste liquid was discarded, and 750 μL of Buffer PE (ethanol was added before use) was added and centrifuged at 12000 g/2 min;

3) The waste liquid was discarded, 350 μL of Buffer PE was added and centrifuged at 12000 g for 1 min, then the waste liquid was added, and centrifugation was performed at 12000 g for 2 min;

4) The MinElute column was placed on anew 1.5 ml centrifuge tube, the lid was opened, and standing was performed at 65° C. for 2 min;

5) 20 μL of preheated EB solution was added, allowed to stand for 2 min, and centrifuged at 12000 g for 1 min. In order to improve the recovery rate, the content of the centrifuge tube could pass through the MinElute centrifuge column 2 to 3 times;

6) The template was measured for concentration by Nanodrop, and frozen at −20° C. for later use.

4. Purification of guide RNA: DNaseI in the system was extracted and removed with phenol:chloroform:isoamyl alcohol (25:24:1);

1) 80 μL of RNA free H₂O was added to the post-transcription reaction system to adjust the volume to 100 μL;

2) 2 ml of Phase Lock Gel (PLG) Heavy was taken out, centrifuged at 15000 g for 2 min, and added with 100 μL of phenol:chloroform:isoamyl alcohol (25:24:1), and 100 μL of RNA digested with DNaseI, and the Phase-Lock tube was gently flicked 5 to 10 times by hand to mix evenly, and then centrifuged at 15° C. and 16000 g for 12 min;

3) A new RNA-free 1.5 ml centrifuge tube was taken, the supernatant was pipetted from the previous centrifugation and added to the centrifuge tube without pipetting the gel, then added with isopropanol of the same volume as the supernatant and sodium acetate solution of the one-tenth the volume, mixed well with a pipette tip, and placed into a −20° C. refrigerator for 1 h or overnight;

4) Centrifugation was performed at 4° C./16000 g for 30 min, the supernatant was discarded, 75% pre-cooled ethanol was added, the precipitate was mixed well by pipetting, and centrifuged at 4° C./16000 g for 12 min, the supernatant was discarded, then it was allowed to stand in a fume hood for 2 to 3 min, the ethanol on RNA surface was dried in the air, 100 μL of RNA free H₂O was added, and mixed well by pipetting.

5. The purified crRNA was measured for concentration by Nanodrop, and uniformly diluted to 250 ng/μL, divided into 200 μL PCR centrifuge tubes, and frozen at −80° C. for later use.

III. Casσ Protein In Vitro Enzyme Digestion and PAM Consumption:

1. Establishment of Double-Stranded DNA Enzyme Digestion System:

(1) The following reaction system was prepared, gently pipetted and mixed well, and then centrifuged briefly. It was placed at 37° C. for 15 min; and the DNA cleavage reaction system was as follows:

| Component | Sample amount |
|---|---|
| 120-crRNA (250 ng/μL) | 600 ng |
| 120 protein (0.5 μg/μL) | 0.5 μg |
| 10*DNA Cleavage buffer | 1 μL |
| RNA-Free H₂O | Supplemented to 7 μL |

(2) 300 ng of substrate DNA (100 ng/μL), 3 μL, was added, gently pipetted to mix well and then centrifuged briefly. It was placed at 37° C. for 8 hours;

(3) RNase was added, placed at 37° C. for 15 min to fully digest the RNA impurities in the system;

(4) Proteinase K was added, placed at 55° C. for 15 min to digest Casσ-1 to Casσ-13 proteins;

(5) Detection was performed by running agarose gel.

The gel results showed that Casσ-1 was capable of effectively cleaving double-stranded DNA.

2. Identification of PAM Site:

(1) The reaction system as in step 1 above was prepared, the substrate DNA was replaced with a plasmid library with 8 random bases before target, and placed at 37° C. for 8 hours, and the secondary control sample was a sample with Casσ added but no crRNA added. Three repeats were set for each protein;

(2) After the reaction, the reaction sample was subjected to column purification, and the purified product was used as a template to construct the second-generation library. The system and method for library construction were the same as the library construction method in step 2 of PAM library consumption in *Escherichia coli*. The specific operation process was as follows: (Each sample corresponded to one R-directed primer, and corresponded to multiple F-directed primers), the following reagents were prepared:

| Reagent | Usage amount |
|---|---|
| Template | 20 ng |
| High-fidelity PCR miX | 20 μL |
| NGS-Lib-Fwd-1-10 | 2 μL |
| NGS-Lib-Rev | 2 μL |
| distilled water | Supplemented to 40 μL |

The prepared reaction system was loaded in a PCR instrument, and the program was as follows:

| Temperature | Time |
|---|---|
| 98° C. | 3 min |
| 98° C. | 15 s |
| 60° C. | 30 s |
| 72° C. | 20 s |
| Go to step 2 | 20 cycles |
| 72° C. | 5 min |
| 10° C. | forever |

Sequencing 1 G for Each Sample;

(3) The numbers of occurrences of the combined PAM sequences in the experimental group and the control group were counted, respectively, and standardized with the number of all PAM sequences in each group. For any PAM sequence, when log 2(normalized value of the control group/normalized value of the experimental group) was greater than 3.5, it was believed that this PAM was significantly consumed. The significantly consumed PAM sequences were obtained from all PAM sequences. In addition, Weblogo was used to predict the significantly consumed PAM sequences, and finally the PAM domains of Casσ were obtained (FIG. 1).

Figure 2:
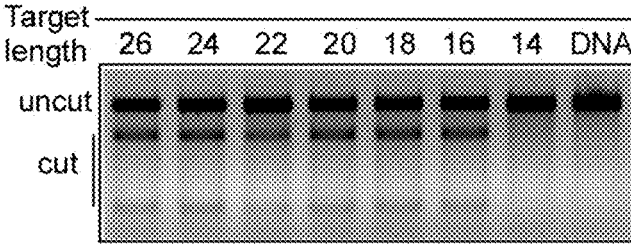
FIG. 2 shows the verification results of the in vitro cleavage activity of PAM in Example 3.
Figure 2:
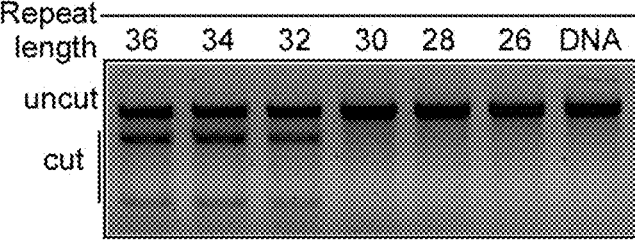

(4) Verification of PAM library domains: Through the PAM library consumption experiment, we obtained the PAM domain of Casσ-1. In order to verify the rigor of this domain, we set up TTT PAM for in vivo experiments to test the editing activity of Casσ-1 on this PAM. First, we integrated the 26 nt target of the T7 promoter with the corresponding PAM site and the sequence of the T7 terminator into the vector pET30a-Casσ-1, which was then co-transfected with the pACYCDuet-1 plasmid and coated on kanamycin and chloramphenicol resistance plates for screening. The monoclonal plaques with double resistance were selected for shaking bacteria, and IPTG induction was performed for 12 hours at an OD value of 1.0. Then, the bacteria before and after induction were observed by gradient dilution. If the chloramphenicol gene was edited, the growth on the chloramphenicol resistance plate was poor. Through the experimental results (FIG. 2 and FIG. 3), we could see that CRISPR/Casσ system could only effectively edit target sequences with specific PAM domains (e.g., TTT), but had no editing activity on the rest of the target sequences (e.g., CCC), thus verifying the accuracy of Casσ-1 for recognition of PAM domains. Through the above experimental results, it was confirmed that Casσ-1 had a rigorous PAM recognition mode (i.e. NTN; wherein, the two Ns may each be independently A or G or T or C), so Casσ-1 is easier in target selection.

Example 4. Analysis of Cleavage Activity of Casσ in Human Cell Lines

The eukaryotic expression vector containing the Casσ-1 gene and the PCR product containing the U6 promoter and guide RNA (containing a direct repeat sequence as shown in SEQ ID NO: 27 and a guide sequence for eukaryotic editing as shown in SEQ ID NO: 82) were transferred into human HELA cells by liposome transfection, and cultured at 37° C. and 5% carbon dioxide for 72 hours. DNA from all cells was extracted, and the sequence containing 700 bp of the target site was amplified. The PCR product was ligated to the B-simple vector for first-generation sequencing. The sequencing was completed by Thermo Fisher Scientific. The sequencing results were aligned to the AAVS1 gene of the human genome, and it was identified that Casσ-1 could perform double-stranded DNA editing on the target site, thereby causing base deletion (FIG. 4).

Although the specific models of the present invention have been described in detail, those skilled in the art will understand that various modifications and changes can be made to the details based on all the teachings that have been disclosed, and these changes are within the scope of protection of the present invention. All of the invention is given by the appended claims and any equivalents thereof.

What is claimed is:

1. A fusion protein, which comprises a first protein and a second protein or polypeptide; wherein the first protein consists of a sequence as set forth in SEQ ID NO: 1.

2. The fusion protein according to claim 1, the fusion protein is characterized by one or more of the following:

(1) the second protein or polypeptide is connected to the N-terminal or C-terminal of the first protein optionally via a linker; and (2) the second protein or polypeptide is selected from the group consisting of epitope tag, reporter gene sequence, nuclear localization signal (NLS) sequence, targeting moiety, transcription activation domain, transcription repression domain, nuclease domain, and any combination thereof.

3. The fusion protein according to claim 2, the fusion protein is characterized by one or more of the following:

(1) the NLS sequence is set forth in SEQ ID NO: 53;

(2) the NLS sequence is located at the N-terminal or C-terminal of the first protein; and, (3) the fusion protein has an amino acid sequence as set forth in SEQ ID NO: 54.

4. An isolated nucleic acid molecule, which comprises: a nucleotide sequence encoding the fusion protein according to claim 1.

5. A vector, which comprises the isolated nucleic acid molecule according to claim 4.

6. A host cell, which comprises the isolated nucleic acid molecule according to claim 4 or a vector comprising the isolated nucleic acid molecule.

7. A composition or complex, which comprises:

(i) a first component, which is selected from the group consisting of: the fusion protein according to claim 1, a nucleotide sequence encoding the fusion protein, and any combination thereof; and (ii) a second component, which is a nucleotide sequence for expressing a guide RNA;

wherein, the guide RNA comprises a direct repeat sequence and a guide sequence from the 5' to 3' direction, and the guide sequence is capable of hybridizing with a target sequence;

the guide RNA is capable of forming a complex with the fusion protein as described in (i).

8. The composition or complex according to claim 7 the composition or complex is characterized by one or more of the following:

(1) the guide sequence is linked to the 3' end of the direct repeat sequence;

(2) the guide sequence comprises a complementary sequence of the target sequence; and, (3) the composition or complex does not comprise a trans-activating crRNA (tracrRNA).

9. A composition or complex, which comprises one or more vectors, wherein the one or more vectors comprise:

(i) a first nucleic acid, which comprises a nucleotide sequence encoding the first protein or the fusion protein according to claim 1; optionally, the first nucleic acid is operably ligated to a first regulatory element; and (ii) a second nucleic acid, which comprises a nucleotide sequence for expressing a guide RNA; optionally, the second nucleic acid is operably ligated to a second regulatory element;

wherein:

the first nucleic acid and the second nucleic acid are present on the same vector or different vectors;

the guide RNA comprises a direct repeat sequence and a guide sequence from the 5' to 3' direction, and the guide sequence is capable of hybridizing with a target sequence;

the guide RNA is capable of forming a complex with the first protein or fusion protein as described in (i).

10. The composition or complex according to claim 7, wherein, when the target sequence is DNA, the target sequence is located at the 3' end of a protospacer adjacent motif (PAM), and the PAM has a sequence shown as 5'-NTN, wherein N is each independently selected from A, G, T, or C.

11. The composition or complex according to claim 7, wherein, the target sequence is a DNA or RNA sequence derived from a prokaryotic cell or a eukaryotic cell; or, the target sequence is a non-naturally occurring DNA or RNA sequence.

12. The composition or complex according to claim 9, wherein, the target sequence is present in a cell; or, the target sequence is present in a nucleic acid molecule in vitro.

13. The composition or complex according to claim 9, wherein, the fusion protein comprises one or more NLS sequences.

14. A delivery composition, which comprises a delivery vector and one or more selected from the following: the fusion protein according to claim 1, an isolated nucleic acid molecule comprising a nucleotide sequence encoding the fusion protein, a vector comprising the isolated nucleic acid molecule, a host cell comprising the vector, or a composition or complex comprising the fusion protein.

15. The delivery composition according to claim 14, the delivery composition is characterized by one or more of the following:

(1) the delivery vector is a particle;

(2) the delivery vector is selected from the group consisting of liposome, exosome and viral vector.

16. A method for modification of a target gene, which comprises: contacting the composition or complex according to claim 7 with the target gene, or delivering the composition or complex according to claim 10 to a cell containing the target gene; wherein a target sequence is present in the target gene.

17. The method according to claim 16, the method is characterized by one or more of the following:

(1) the target gene is present in a cell, or, the target gene is present in a nucleic acid molecule in vitro;

(2) the cell is a prokaryotic cell or eukaryotic cell;

(3) the modification refers to a break in the target sequence; and, (4) the modification further comprises inserting an exogenous nucleic acid into the break.

18. A method for changing the expression of a gene product, which comprises: contacting the composition or complex according to claim 7 with a nucleic acid molecule encoding the gene product, or delivering the composition or complex according to claim 10 to a cell containing the nucleic acid molecule; wherein a target sequence is present in the nucleic acid molecule.

19. The method according to claim 18, the method is characterized by one or more of the following:

(1) the nucleic acid molecule is present in a cell, or the nucleic acid molecule is present in a nucleic acid molecule in vitro;

(2) the cell is a prokaryotic cell or eukaryotic cell;

(3) the expression of the gene product is changed;

(4) the fusion protein, isolated nucleic acid molecule, vector, or composition or complex is contained in a delivery vehicle; and, (5) the method is used to modify a cell, cell line or organism by changing one or more target sequences in the nucleic acid molecule.

20. An in vitro, ex vivo or in vivo cell or cell line or progeny thereof, wherein the cell or cell line or progeny thereof comprises: the fusion protein according to claim 1, an isolated nucleic acid molecule comprising a nucleotide sequence encoding the fusion protein, a vector comprising the isolated nucleic acid molecule, or a composition or complex comprising the fusion protein;

optionally, the cell is a prokaryotic cell or a eukaryotic cell.

21. The method according to claim 16, the method is characterized by one or more of the following:

(1) the target gene is present in a plasmid;

(2) the cell is an animal cell or a plant cell; and, (3) the modification refers to a double-strand break in DNA or a single-strand break in RNA.

22. The method according to claim 19, the method is characterized by one or more of the following:

(1) the nucleic acid molecule is present in a plasmid;

(2) the cell is an animal cell or a plant cell;

(3) the gene product is a protein; and, (4) the delivery vehicle is selected from the group consisting of liposome, exosome and viral vector.

* * * * *

SEQUENCE LISTING

```
Sequence total quantity: 88
SEQ ID NO: 1            moltype = AA  length = 882
FEATURE                Location/Qualifiers
source                 1..882
                       mol_type = protein
                       organism = synthetic construct
SEQUENCE: 1
MSNYKNIKFK LVPFSQKDLI NMQLNVNLHQ QCYREFVEQF CVLCNIPFPG LSKDQIEQKR   60
KQLNLSEDDE KDINYIKDLV KNKNNIGNSI YAFFTGTKKE MPSRKTDLTP LYRLLKANIL  120
PFSLLKGREN YKKSIFQTVI NQTLEKFKSY FKCNESVENN FKLSLNKDSN EEQVLNESEM  180
KDLQNLFENL SKNQSFSFFN FNKNWFSKDK IKTKLLNNET NKIKSLSSEE IDLILSYKDK  240
LYSNEFDLIS MFVEFNLQKQ KAESLKSQAD LNLFKNNNYS FRIGSNYENF NLTQNNKDIL  300
LEINSSMGEK ITFKIIPHKK TQIWNLEKNN VKITSGENLG NYKSVDVIKM KRPADIKAKL  360
LKTSELNIEI KNNQIYCNFI YEYKCSDHGV YFFHCSGNKK PDEKNENILK ERERTFSFID  420
LGLFPMYSIS TFKYNNKSND GEILVKSGSG NEKLDFGSAF KIHSIQIGKN STNLNKIKQL  480
LEKLKDLKTY LKFSKSISSF DENSYQRQLK TGVEISELNS LSFQKISEIK SINLGFNESF  540
NKEYFLKLIE NQTFTQKELL LLNCKIKDLF KILYKEYSNI KNSRIFKFNK EDDLICDGYY  600
WLQVIDEIIN IKKSLTYFNS KPSEKGNKSK FIFLKDFNYK NNFANNYAKI AASRLKKYCL  660
EHKVDVCVFE KNLNNFLQSK DNDKKTNKTL INWANRNLFE KIKLALEEHD ICVSEVDGKH  720
SSQLDPQTMN WGARDNLNGN GNKEKIFFER NGQIIQQNAD LSASEVLAKR FFTRYEDIVH  780
IYIDQKIKDD KTILKLVKGK VRVESYLKKT INSCYAIVDE NGFLKPISKK DYNKFQELPS  840
KPRTDIKSNE MYRHGSKWYH FQQHREFQQD LLARGRELKK IA                     882

SEQ ID NO: 2            moltype = AA  length = 935
FEATURE                Location/Qualifiers
source                 1..935
                       mol_type = protein
                       organism = synthetic construct
SEQUENCE: 2
MNKTDTQNNE QINKPTQLLN NKDIELTVKT VKSATVKVDN NSKKELFGLF NYFTSVASGI   60
KDKVYNLQSD EKTAPIFNDY VKQPQRGRSA ATTLFTKLDA EKTYTSQHSF PGKWRDSGIF  120
PLYNKESEKY DLSTHGYHYS ANAEIHTQLD SHDECNKECE KEYAALRDEV NNYKYEFTLQ  180
FKAENAEKFY NFVEKLTLMG WRYDATFRSF FELHMHPKLK TGETTYRATY KLPSGKSKRY  240
SFFRDDIADE IAKNPEFWPM LESSNAISWI NSNNLLSRKK DKANYSSTSL IKSQIRLYLG  300
NNGVPPTARE HDGRIYFSFR LPAINGEKGR MVEIPCSYKK VFNGKARKSC YLGGLTIEKT  360
DAGKHIFKYS VNNKKPQVAE LNECFLRLVV RNREYFNNVV AGKITDINTD HFDFYVDLPL  420
NVKEDPIHDL SSTEVFGKNG LRSYYSSAYP EIKNLGSQIE TGKNLTCPIT KTHNIMGIDL  480
GQRNPFAYCI KDNTGKLIAQ GHMDGSKNET YKKYINFGKE STSVSHLIKE TRSYLHGDPE  540
AISKELYNEV AGFCNNPVSY EEYLKYLDSK KFLINKEDLS KNAMHLLRQK DHNWIGRDWL  600
WYISKQYKKH NENRMQDADW RQTLYWIDSL YRYIDVMKSF HNFGSFYDKN LKKKVNGTVV  660
GFCKTVHDQI NNNNDDMFKK FTNELMSVIR EHKVSVVALE KMDSMLGDKS RHTFENRNYN  720
LWPVGQLKTF MEGKLESFNV ALIEIDERNT SQVCKENWSY READDLYYVT DGESHKVHAD  780
ENAANNIVDR CISRHTNMFS LHMVNPKDDY YVPTCIWDTT EESGKRVRGF LTKLYKNSDV  840
VFTKKGDKLV KSKTSVKELK KLVGKTKEKR GQYWYRFEGK SWINEADRDT IILNAKKISR  900
ERDNGEQSTD TRSQNVTVSV LDVCETAEKK KLVLV                             935

SEQ ID NO: 3            moltype = AA  length = 900
FEATURE                Location/Qualifiers
source                 1..900
                       mol_type = protein
                       organism = synthetic construct
SEQUENCE: 3
MKSIKSIKSI KTKVVKNNEL KLIELSTWCS SICEQLERYI FILGGKQIHD RDGVVVLDGA   60
VERKIYCKKD KSLIAACEVV YKHFTDKSSK SRTFGSWFLG GKSEGDNTNK GRKSTKEKTE  120
KQIAKQIADK KELTDSLQLL WDKKLLPFPI DNKGYDFINT PRAKSYKWAI TKTIHAKIKS  180
YNEQCVETKK EYDALNAEIN TYKTILFSGY SEKDIDDLQK FVDICEANNH RINYKFISFL  240
KRKDLNFDEQ TGKYRKEGKW IQHKNGKEVK SKYSMKDEIV EALYKYKSLT KNDVSVLCNE  300
HQKEDEMGKV VHYNMKRYSD LLFRKKNKKE IPSYTKISLA TSKIELGLNN VKYNVEQVED  360
KLIWTICDQT GKDIQFVTVY TRKKEDNRTN GKKGAGFYKG KHHQLEDLKI VPVGDIGTYD  420
ISFKVNGKRP FTGTLKEPNI ICRGGKVFVQ MPININIDKT LNDARKKVLY AYRETYSGSV  480
NGKKQKMIKI ENSKIAESLK SLGRDAIVLG VDLGLRGLAT AVVSHNGKNE TVKSSQYIKG  540
DIVEWEKYRV FNDNIREVKK YIFLTKKSYT ATTEEYTEFY KECSKPEQDY LDSLKTYKDK  600
NVKLNELKYT KNAWSVSKMF EDVSKMFETL KQDRLKYYDI FNMPYWAASL KNYMSLMKSY  660
NYVGVDIKVS KEYMSKYQSL YNNIKEDYAK KIGSYIVQLA VAKNCDIIVL EELKSNLGSV  720
DRKSKRDNEM SLMWNCGRIK THVENMAKDY GMFIDEVPEY GTSQVYHKTG NYGYRDEDNR  780
```

```
EIFWYEDNKD VAYIHADENA AINIAKRFLS QHTDNSSFSV ILKGDAYYLN IASNSKRMRA    840
AALKTFGDLN KPFKINANDK NGNLYKKTRI FKSDSRWIGV NDKDLYIEHI KSLRNLRVRQ    900

SEQ ID NO: 4            moltype = AA  length = 627
FEATURE                 Location/Qualifiers
source                  1..627
                        mol_type = protein
                        organism = synthetic construct
SEQUENCE: 4
MPSFTKVDED KIVLKLGNNY IPYGLSRISE DKMLWSFSSP QKKKLSIITN HRRVGKGKHF     60
YLEGLEIADI TKGDGDKTSP SGKYTISFSI NGKQDVKGEL KEPSFGLRNG NVYMFLPISI    120
KQTDVFESRV EMRRLLSMAY QPTTVEDLIL DDVETKQKTV KQGKKEVNTT NIAIQEAIKK    180
HGRLLKVMGV DLGLRNFAFA IKNYDGHHDT LLRQLYSESD LNEKQRYTTL ANDLSKVGNH    240
IKFAAVFYGA NDTEENTKMF DAECTDAESR THLEWLRKAK KSGVLLKDLR KDKTWIVSIK    300
YTELRNRLHA LKFGRMKSYD YRNNLYWAAT IKKFISLSAS FYGVGRPSRG KKDVRELKKK    360
HTFFSTYQDL YNNVKEDYAK KVANLVVMTA KENNVDIIVV ENLTGHCGSK DYKTRAENEM    420
SIMWNHGRIK TFIDCIANAN GMLLAEVSEF ETSQVYHETR NYGYRDKKMK EILWYMDSEG    480
NVQYAHAEVN AAINIADRFL SQHTNLFSFP VCKSKKDENV YEIDIAEGKE LEGQDEVKKA    540
KKPKGGKRLN GAVVKTFGST KIMFNGIVDK NKKGQIKTKT RVYNIDGEWG GKTQKDEYVD    600
KIRKVVDAMS PEEKAKVKAA LKKCFSS                                        627

SEQ ID NO: 5            moltype = AA  length = 927
FEATURE                 Location/Qualifiers
source                  1..927
                        mol_type = protein
                        organism = synthetic construct
SEQUENCE: 5
MTKELSGVRV IELKTDLRKD QFWDRYERCF KTYHALYNEV PCWGLDWVEQ KTQNQTSREL     60
GCERVDLTAQ RKALYERTDR TISYEQFSNC LKALWLGLLN CQQGNHMYTK LFEGAIQTDQ    120
MTAEDWAVLT EYVADPKSHN SQFLFRVSNT LKHIGFFSRP PFTATLFAPE RKAITKDVMS    180
DLKGWIEMKR MTEESYAAEE VQIQQMKAEV PVRIRQSLLR FFDTCIGLNL IGHFDERVHH    240
YLRDCIIPAL QQRTIPTEHF YLKSNRKDVG QKHIDFSLDI KFYELLAEMP ELWNTLETSE    300
DDLIPKPLIL KHLHLLEAIM SHRAHRKTAA YAFVGEADYH RFYYLLGGNY TKHLISATGS    360
ELPDRVIWDN DKDVLMRNGR KVERLYVKVG DRKENFNFEV YTIAMNTKGL RGHRSTLKPT    420
SYLQDLQIWS NPEGESTYLN FVRKGTERSA ICKEPVLVYR NGAFFLRLSM SVEGMRASEE    480
HIALQYYLSA AATGSDLSKD TEKTVERFNL IQGKTYKVMS VDLGIRSPFA WAVTESTITG    540
VANPSQILNS GEMEIADDPD YTELFYAYKN LGHLIGQVKS SSKGKGKLAD SHLVDMIHTV    600
QRFFADYKVA GQRRSQIFEQ FSKDPDPLYQ MDQMMKRYEN NLESVKKDFS FLINILFKYV    660
TLQFGALRNR RRSYLSQNQM ADQKFDQDFK WLNILEQRKR VTRSLSYLGT DNSRIPICLE    720
QQKLDYNGCK DNFLKQLASK IVRIAHQNDC CLIVLEDLEG YGKTLNQRDE NFLTAFWSPK    780
RVKDAIINAA QWYGIGVVTV SEAQTSQVHH ESGRIGYRKG RDLFFLTPDG QIESVPSDIN    840
AAKNIGHRFF SRHTDLHQVY LKGSDEGAKR MKGCLLYQFG SLEAARTHLT GTGPTWYLDG    900
VEWIDKTERN LRRDLLKQRV EIEKMPF                                        927

SEQ ID NO: 6            moltype = AA  length = 900
FEATURE                 Location/Qualifiers
source                  1..900
                        mol_type = protein
                        organism = synthetic construct
SEQUENCE: 6
MKSIKSIKSI KTKVVKNNEL KLIELSTWCS SICEQLERYI FILGGKQIHD RDGVVVLDGA     60
VERKIYCKKD KSLIAACEVV YKHFTDKSSK SRTFGSWFLG GKSEGDNTNK GRKSTKEKTE    120
KQIAKQIADK KELTDSLQLL WDKKLLPFPI DNKGYDFINT PRAKSYKWAI TKTIHAKIKS    180
YNEQCVETKK EYDALNAEIN TYKTILFSGY SEKDIDDLQK FVDICEANNH RINYKFISFL    240
KRKDLNFDEQ TGKYRKEGKW IQHKNGKEVK SKYSMKDEIV EALYKYKSLT KNDVSVLCNE    300
HQKEDEMGKV VHYNMKRYSD LLFRKKNKKE IPSYTKISLA TSKIELGLNN VKYNVEQVED    360
KLIWTICDQT GKDIQFVTVY TRKKEDNRTN GKKGAGFYKG KHHQLEDLKI VPVGDIGTYD    420
ISFKVNGKRP FTGTLKEPNI ICRGGKVFVQ MPININIDKT LNDARKKVLY AYRETYSGSV    480
NGKKQKMIKI ENSKIAESLK SLGRDAIVLG VDLGLRGLAT AVVSHNGKNE TVKSSQYIKG    540
DIVEWEKYRV FNDNIREVKK YIFLTKKSYT ATTEEYTEFY KECSKPEQDY LDSLKTYKDK    600
NVKLNELKYT KNAWSVSKMF EDVSKMFETL KQDRLKYYDI FNMPYWAASL KNYMSLMKSY    660
NYVGVDIKVS KEYMSKYQSL YNNIKEDYAK KIGSYIVQLA VAKNCDIIVL EELKSNLGSV    720
DRKSKRDNEM SLMWNCGRIK THVENMAKDY GMFIDEVPEY GTSQVYHKTG NYGYRDEDNR    780
EIFWYEDNKD VAYIHADENA AINIAKRFLS QHTDNSSFSV ILKGDAYYLN IASNSKRMRA    840
AALKTFGDLN KPFKINANDK NGNLYKKTRI FKSDSRWIGV NDKDLYIEHI KSLRNLRVRQ    900

SEQ ID NO: 7            moltype = AA  length = 935
FEATURE                 Location/Qualifiers
source                  1..935
                        mol_type = protein
                        organism = synthetic construct
SEQUENCE: 7
MNKTDTQNNE QINKPTQLLN NKDIELTVKT VKSATVKVDN NSKKELFGLF NYFTSVASGI     60
KDKVYNLQSD EKTAPIFNDY VKQPQRGRSA ATTLFTKLDA EKTYTSQHSF PGKWRDSGIF    120
PLYNKESEKY DLSTHGYHYS ANAEIHTQLD SHDECNKECE KEYAALRDEV NNYKYEFTLQ    180
FKAENAEKFY NFVEKLTLMG WRYDATFRSF FELHMHPKLK TGETTYRATY KLPSGKSKRY    240
SFFRDDIADE IAKNPEFWPM LESSNAISWI NSNNLLSRKK DKANYSSTSL IKSQIRLYLG    300
NNGVPFTARE HDGRIYFSFR LPAINGEKGR MVEIPCSYKK VFNGKARKSC YLGGLTIEKT    360
DAGKHIFKYS VNNKKPQVAE LNECFLRLVV RNREYFNNVV AGKITDINTD HFDFYVDLPL    420
```

```
NVKEDPIHDL SSTEVFGKNG LRSYYSSAYP EIKNLGSQIE TGKNLTCPIT KTHNIMGIDL  480
GQRNPFAYCI KDNTGKLIAQ GHMDGSKNET YKKYINFGKE STSVSHLIKE TRSYLHGDPE  540
AISKELYNEV AGFCNNPVSY EEYLKYLDSK KFLINKEDLS KNAMHLLRQK DHNWIGRDWL  600
WYISKQYKKH NENRMQDADW RQTLYWIDSL YRYIDVMKSF HNFGSFYDKN LKKKVNGTVV  660
GFCKTVHDQI NNNNDDMFKK FTNELMSVIR EHKVSVVALE KMDSMLGDKS RHTFENRNYN  720
LWPVGQLKTF MEGKLESFNV ALIEIDERNT SQVCKENWSY READDLYYVT DGESHKVHAD  780
ENAANNIVDR CISRHTNMFS LHMVNPKDDY YVPTCIWDTT EESGKRVRGF LTKLYKNSDV  840
VFTKKGDKLV KSKTSVKELK KLVGKTKEKR GQYWYRFEGK SWINEADRDT IILNAKKISR  900
ERDNGEQSTD TRSQNVTVSV LDVCETAEKK KLVLV                            935

SEQ ID NO: 8            moltype = AA   length = 896
FEATURE                 Location/Qualifiers
source                  1..896
                        mol_type = protein
                        organism = synthetic construct
SEQUENCE: 8
MKKPKQNIEE TDLKITTPKT ATIKATNLDD KMRLFTFFNG FTTVCSKVKD DIYNFGQNED  60
TLPVYTDYIK ASQRARMCAT TLATKSECDF AKKYGEHFPL PHYNQEGMNY TTHQHTYSVN  120
SAVHTQLDSL NECDKLTNGE YVKLKKTVDE LEEKLTEEHG KEPLDFLVKF VDEQILLGWR  180
FDGKFRLFFE VAMLPELKNG NIIYKKAYKT SGGKGRRYSF YNPSVADNIS KNPTVWNLLS  240
DVKAVDYISL SNSLLRKKPH AQYTNTTLNR AQVRPTFGNN GVPFSISVSD DDYVYIRFRL  300
PKKDGEEKGQ EISVKCSYKT SYKGKRSKTL RKSCYLGNLK IEENGKGKYI CKYNINGRET  360
TTAELNECFL RVRINNNRWF NKYLNGTLTK EDGVLKSEYF DFYFDLCLNV HQKSIHGLTN  420
SEIFGGKGKS IRSYYSTSYP EVKNLDGQKN IKTDFGCYVD KPHNIMGIDL GQRNPFAWAV  480
LDQNGNVKDV GHLDGAENDT YKDYLTFSNR CKDVKNLILQ SRDYLYGDDE AIDETLFDSV  540
VQFVNSNITL NKYKSYLDEK KSLINKESLE KNRLYELKKK DHGWFVRDCL WFLTKEYHRI  600
NSERKTHSDW RYTLYWVDAI HRFIDVNKSF NSLGSYYDKK QSKSINGIQK DFCRSYWNQI  660
DNLNEDTLKK FVFELLPVIK KNNVCLIAIE ELKSMLGDDD KRAEDNRLYN LWPVGQLKTF  720
LEGKLLPYNV AVMEVSEQNT SQIVNGQWSY REGDDLYYVK NNDNNTMCKT HADENAAINI  780
ALRAYSHHTN LYSIYMINPI DDYYVPSCIW NNKDEGSKRI RGFLTKTYGT SDVVFIKKNE  840
KLVKSDVSIK DVKRIVKNIG NEKNKKSEIW YRMNDIEWID EGSRDIIINT IKSKVR      896

SEQ ID NO: 9            moltype = AA   length = 887
FEATURE                 Location/Qualifiers
source                  1..887
                        mol_type = protein
                        organism = synthetic construct
SEQUENCE: 9
MTDKSISFKQ FSQILNVLYK CIVISGKGRG LTSIILGQPQ CKDSLTSADW GNLETLSAKD  60
ELTPAEVKDI TKDLMYRASN TLVSIGFRNR SPFKLTLTSG ERYAVVENVH RSLKSWVEVD  120
KITRENYLNE EIALSDAFNN IDETLLPTLK EFFDACMNEN IIHHFDARVY AYTRDCVIPA  180
LVAGLEIKDH FYIDGRDKAK RDYSLQGYAE LLKGFPKLWQ GVDPEILAKL YILEAQMDHK  240
KHRPCAAYAF IGEDSYSRVQ YLLGNNYTSF SPYALGVDLD DVTCGDDAEA DTQFPKNKVI  300
QFSQGKKVTK LSLTVSRGKE DTNKYSFDVF LADKYSNGSY KPSPYFSDLS VWVSEIGMLM  360
EFTRKGERVQ AIVKEPSLIY RKGAFYVRLN MGVIQDTSPE INDLYWYLSS GAPMSMTDRS  420
KASETPKNTE RLESIKGKSY RFLGIDLGLR SPFAWAVGEA SISGVINKPT IIATGDYTTA  480
RDTRYDTLFF ALKNAGKVIG VTKSLANGKD ASFNGLMGTI TAAREYLAHY SGVATHKVAA  540
IQAFCQDDNP LETLKGLLKS YNNDLVTLKK DPRFIGGILL RYARLLKGEL VTSRKMHLRE  600
HSVESKFGQE YMWLNILERE KRVCRSLSYL GLGNDRDSVI MGNLTTPYNH CKENLLKQLA  660
ARIVSLAVEN KCHVIVMESL GGSNKSMNTR GQNFLEAFWS PQKIKDTIIN AAAWHGINVL  720
EVSESQTSQV CFETGTFGHR DRASLYFLDK NGDLQETHAD MNAAKNLVER FTTRHTNLRQ  780
VNMDSLPKEG PDKTPKKSPS KKKMEKAKMD NPEDQSKRLK GFLTVKFGNV KAAQEYFASR  840
KPEQSYSGKK DEAIYWYLDG DEWITKKEKE SRVSVIEGLV GLKEVAV              887

SEQ ID NO: 10           moltype = AA   length = 821
FEATURE                 Location/Qualifiers
source                  1..821
                        mol_type = protein
                        organism = synthetic construct
SEQUENCE: 10
MAFQSKRRIV GNLVKEQCLK AVDGKVILTD QEKRELIKRY ELHLEPYKWL RLRLFLSGYEG  60
RDDGFYEELG NTNLDKEKFF EVTAGLRDAL LRQSGSSRAL KSSMLGKCPP SAAVGKAAKH  120
IQALRDAGIL PFKTGLTSGE DYNVLQQAVQ QLRSWVACDH RTREAYAEQQ EKTSQAEEAA  180
KKAVNEVKPE DAKSLERHER ALTKLRKQER RLERMRSHAQ FSLDEMDCTG YSLCMGANYL  240
KDYCLEKEGR GLRLTLKNST MAGSYYVSVG DGQHAGMKNP GTPAGGSPEK GRRRNILFDF  300
AVEKCGDNYL FRYDENGKRP RAGVVKEPRF CWRRKGNSVE LYLAMPINIE NSMRNIFVGK  360
QKSGKHSAFT RQWPKEVEGL DELRDAVVLG VDIGINRAAF CAALKTSRFE NGLPADVQVM  420
DTTCDALTEK GQEYRQLRKD ATCLAWLIRT TRRFKADPGN KHNQIKEKDV ERFDSADGAY  480
RRYMDAIAEM PSDPLQVWEA ARITGYGEWA KEIFARFNHY KHEHACCTVS LSLSDRLVWC  540
RLIDRILSLK KCLHFGGYES KHRKGFCKSL YRLRHNARND VRKKLARFVV DAAVDAGASV  600
IAMEKLPSSG GKQSRDDNRI WDLMAPNTLA TTVCLMAKVE GIGFVQVDPE FTSQWVFEQR  660
VIGDREGRIV SCLDAEGVRR DYDADENAAK NIAWLALTRE AEPFCMAFEK RNGVVEPKGF  720
RFDIPEEPTR EQDESNQDFK KRLEEERDKLI ERLQAKSDRM RAIVRRLFGD RRPWDAFADR  780
IPEGKSKRLF RHRDGLVLNK PFKGLCGSEN SEQKASARNS R                     821

SEQ ID NO: 11           moltype = AA   length = 954
FEATURE                 Location/Qualifiers
```

```
source                  1..954
                        mol_type = protein
                        organism = synthetic construct
SEQUENCE: 11
MDTDTELSDE VELSDEVELS DEVELSDEVE LTVKKVKTTT VKVDNNFKKE LFELFNHFTS  60
VASGIKDRLY DLQFDENTAS IFKGYIKEAK RGHGAATTVF TKLNPKKIYS GKKSFPRDYR  120
DRGIFPFYNK ESGKYDLSTC GYHYSANAEI HTQLNSHDEC NKQCEKEYAA LEKERNKYKH  180
EFTRQFKAEN VEKFSNFVEK LTLMGWRYDA TFRNFFELHM HPKLKTSETT YRATYKLPSG  240
KSKRYSFSRD DIADEIAKNP EFWPMLESSN AVSWINSNNL LSRKKEKANY SSTSLIKSQI  300
RLYLGDNGVP FTAREHDGRI YFSFRLPSIN GEKGRNVEIP CSYKKVFNGK ARKSCYLGGL  360
TIENTGGSKH IFKYSVNNKK PQVAELNECF LRLVVRNHGY FNKMVNGKLT DKDGKLHADY  420
FDFCIDLPLN VKEDPIHDLT YQEINGVKAN PEKNIEKKVG LLGFYQSAYP EIKNLGSQIE  480
TGKNLTCPIT KTHNIMGIDL GQRNPFAYCI KDNNGKFIAK DHMDGSKNET YKKYINFGKE  540
STSVSHLIKE TRSYLHGDPE AISKELYNEV SGLCNSPLSY EEYLKYLDSK KFLINKEDLN  600
KNAMHLLRQK DHNWIGRDWL WYISKQYKKH NENRMQDADW RQTLYWIDSL YRYIDVMKSF  660
HNFGSFYDKN LKKKVNGTAV GFCKTIYDQI NNNNKDMFKK FTNELIPIIR KHKVSVVALE  720
KMESMLGDKS RNTFENRNHN LWPVGQLKTF IENKLDGFNV IVVEVDERNT SQMCDGNWSY  780
READDLYYVK DGELREVHAD ENAANNIVDR CISRHTNIFS LYMTNPMDDY YVPACIWDRS  840
ENGKRGRGFL TKMYKNSDVV FTKKDDKLVK SKMSVKELKK LVDKTKEKRG QYWYLFEGKS  900
WINAADRDTI ISNAKKLFRE RDGGEQSTDT RSQNVTVSVL DVCETVEKKK LVLV        954

SEQ ID NO: 12            moltype = AA   length = 1001
FEATURE                  Location/Qualifiers
source                   1..1001
                         mol_type = protein
                         organism = synthetic construct
SEQUENCE: 12
MSTEVDVKTI NLKIAKKGGV YPILEQSIKE NCKSNDLLEF FMVLNRLQTY YIESNEEILV  60
DFPKKYDELF DIVKNNDSSV TREYFDSLCD KYITEVCANG FVNNVYIAHN KNQELNWAET  120
SNDRKIKSNK TFMFGKIKGL IRDKFGREEL SDKDATKQLC EDIFNLFILN NANIELDEKY  180
NIIKDELIQI WNERNKEFIH IKDITLLFRQ WGILPTYDNI THNCELKAII AEPVRRFKSW  240
LECNSEANKN YDTEREKCTK YMDVMDSDLT VEFSKMVTEL GNPFGANDKN IYKYFNQKFL  300
LFFKQVVQPK FVNGEPLDES NGSYSGEIKI NSAGKVENYS IAVSVIDTIK KYPTIWSDRS  360
WGESVISTVA KIDPQYGIDD ITDDMQVSPF YLFYGYFTAY NYIQQHKRNA KYTPISKDSL  420
PSLYLGNNYI PFKIDCENVD DDRFYITIKN MNNLKLNVLY RKPKLKFAKT KEKTKRNKCY  480
FDNLKITNTN NNFKEYNIN  GDPNRSVVAY LKEPVIRYNN RKDYFYLSAT ISKDVETDSE  540
LTSACWSKIS NDTARRVNAE QYFNDNGVNI VGIDLGMNPI IAYSVLHYKN NEFIDLNITG  600
KIADKDKHPN LNYKRMYEKR SEIKKLKTLI KMIPDYVNSD SNIFEGDNNV FKQLDKKSKG  660
RFRSSEYMGY YDKLNVDGKF ISELEIVKKV VNTKHYKNDT EKNNDIMRVY KGNKKNIIKK  720
EIDTHRHQIH SIKDMNRRSD ESNLCYVYDM VSYIDDFKKL VTSYNKIGED YNNPIKPLSD  780
PMLFSKSKLY EYRQNIRDNF LKDICYQMVK IAKQYNAVLV HEHFEQRKGG IDRVNNILMA  840
LFTPNDIIKK LKCVAKREGV LVFNTNKNHT SQYVYNKNTV GYRDSNNKHN LYYIEDETTR  900
KLGVVDSDIN ASKNIAARPF NKPLYAIKVK NYDDGLFLSD YNNKYVLYKK DGDKYVAIGD  960
TYRIDKKKIK QGSVTLYLHN GYYVDGEYKN NYIENIKKLV L                    1001

SEQ ID NO: 13            moltype = AA   length = 821
FEATURE                  Location/Qualifiers
source                   1..821
                         mol_type = protein
                         organism = synthetic construct
SEQUENCE: 13
MAFQSKRRIV GNFVKEQCLK AVDGKVILTD QEKRELIKRY ELHLEPHKWL LRLFLSGYEG  60
RDDGFYEELG NTNLDKEKFF EVTAGLRDAL LRQSGSSRAL KSSMLGKCPP SAAVGKAAKH  120
IQTLRDAGIL PFKTGLTSGE DYNVLQQAVQ QLRSWVACDH RTREAYAEQQ EKTSQAEEAA  180
KKAANEVKPE DAKSLERHER VLTKLRKQER RLERMKSHAQ FSLDEMDCTG YSLCMGANYL  240
KDYCLEKEGR GLRLTLKNST MAGSYYVSVG DGQHAGMKNP GTPAGGSPEK GRRRNILFDF  300
TVEKCGDNYL FRYDENGKRP RAGVVKEPRF CWRRKGNSVE LYLAMPINIE NSMRNIFVGK  360
QKSGKHSAFT RQWPKEVEGL DELRDAVVLG VDIGINRAAF CAALKTSRFE NGLPADVQVM  420
DTTCDALTEK GQEYRQLRKD ATCLAWLIRT TRRFKADPGN KHNQIKEKDV ERFDSADGAY  480
RRYMDAIAEM PSDPLQVWEA ARITGYGEWA KEIFARFNHY KHEHACCAVS LSLSDRLVWC  540
RLIDRILSLK KCLHFGGYES KHRKGFCKSL YRLRHNARND VRKKLARFIV DAAVDAGASV  600
IAMEKLPSSG GKQSKDDNRI WDLMAPNTLA TTVCLMAKVE GIGFVQVDPE FTSQWVFEQR  660
VIGDREGRIV SCLDAEGVRR DYDADENAAK NIAWLALTEK AEPFCMAFEK RNGVVEPKGL  720
RFDIPEEPTR EQDESDQDFK KRLEERDKLI ERLQAKADRM QAIVQRLFGD RRPWDAFADR  780
IPEGKSKRLF RHRDGLVLNK PFKGLCGSEN SGQKASARNS R                     821

SEQ ID NO: 14            moltype = DNA   length = 2649
FEATURE                  Location/Qualifiers
source                   1..2649
                         mol_type = other DNA
                         organism = synthetic construct
SEQUENCE: 14
atgagcaact acaaaaacat taagttcaag ttggttccgt tcagtcaaaa ggatcttata  60
aacatgcagc taaacgtgaa tctccaccag cagtgttata gagagttcgt ggagcagttc  120
tgcgtcctct gtaatatccc ctttcctggg cttagtaaag atcaaattga gcagaagcgg  180
aaacaattaa atctgtctga agacgacgag aaggacatca actacatcaa ggaccttgta  240
aaaaataaga ataacatcgg caattcaatc tatgcttttt tcactggtac aaagaaggaa  300
atgccaagca gaaagactga tttaacacct ctttaccgcc tccttaaggc taacatactg  360
cccttTagc tcctcaaagg gcgagagaac tataagaaaa gcatattcca aactgttatt  420
```

```
aaccagacac tggaaaagtt taagtcatat ttcaagtgca atgaatcagt tgaaaacaac  480
ttcaaactgt ctctgaacaa ggactcaaat gaggagcaag tcctgaatga aagcgaaatg  540
aaaagacctcc aaaacctatt cgagaatttg tctaaaaatc agtctttttc cttcttcaac  600
ttcaataaga actggttctc caaggacaag atcaagacga aactcctcaa taacgagacc  660
aacaaaatta agtcgttgtc atctgaagag atcgacctga tccttagtta taaggataag  720
ttgtactcca acgaatttga tctgatttcc atgttcgtgg agttcaactt acagaaacag  780
aaggcggagt ccttgaaatc acaggcggac ttgaacctct tcaagaacaa caactattct  840
tttcggattg gaagcaacta tgaaaacttt aatctaactc aaaataacaa ggacatcctg  900
ctggaaatca attcttcaat gggtgagaag attacctta agatcattcc gcataagaaa  960
acccagatct ggaatttaga gaagaataat gttaagataa cttcgggcga gaacctgggg 1020
aattacaaat cggtggacgt catcaagatg aagcggccag cagacattaa ggcaaagctg 1080
ctgaagacgt cagagctgaa tatcgagatc aagaacaacc aaatctattg caacttcatt 1140
tatgagtaca agtgctccga tcatggcgtg tacttctttc actgcagtgg caacaagaag 1200
ccagatgaga agaatgagaa tattctaaag gagaggggaga ggaccttttag tttcattgat 1260
ctcggtcttt ttccgatgta ttccatctcc acatttaagt acaataataa gagcaatgat 1320
ggtgagatcc tagtcaagtc gggatctggg aacgagaaac tcgacttcgg ctctgccttc 1380
aaaattcatt caatccagat tggaaagaac agcacaaatc tcaacaaaat taagcaactt 1440
cttgagaagc tgaaagacct gaagacctac ctcaaattct ctaagagcat aagcagcttc 1500
gacgagaaca gctaccagcg ccagcttaaa acgggagtgg agatcagcga gctgaacagc 1560
ctgtcgttcc aaaaaaatatc agaaattaag tccattaatc tcggcttcaa tgaatccttc 1620
aataaagagt attttctaaa gctgatcgaa aaccaaacat tcacgcagaa ggagttacta 1680
ctgttaaact gcaagatcaa agacctcttc aaaattctct acaaagaata ttctaacatc 1740
aaaaacagtc gcatatttaa attcaataaa gaagatgatc tcatctgtga cgggtactac 1800
tggctgcagg tcattgatga aataatcaat attaaaaagt cgcttactta cttcaacagc 1860
aagccgtcgg agaaggggaa caaaagtaag tttattttct tgaaggattt taactacaaa 1920
aataattttg caaacaacta cgcgaaaatc gctgcgtcac gtctcaaaaa atattgtttg 1980
gagcacaagg ttgacgtgtg tgtttttgag aagaacctca acaactttct gcaaagcaag 2040
gacaacgata aaaagacaaa taagaccttg attaattggg cgaaccgcaa tctttttgag 2100
aaaattaaat tggcgctgga agagcatgac atctgcgtga gtgaggttga tggtaagcat 2160
tcgtcccagc tggacccgca aaccatgaac tggggcgaca gagataatct taatggaaat 2220
ggtaacaaag aaaagatctt ttttgaaagg aacgggcaga taatacaaca gaacgccgac 2280
ctcagtgctt ctgaagtcct cgcaaaacga ttcttcacca ggtacgagga catcgtgcac 2340
atctacattg accagaaaat aaaggatgac aaaacgatcc ttaagttggt gaagggtaag 2400
gtgcgcgtag aatcttatct gaagaagact ataaattcct gctacgccat agtagatgaa 2460
aatggcttcc ttaaacctat atctaagaaa gactacaaca agttccagga gctgccgtcc 2520
aagcctcgca cagatattaa gtcgaatgag atgtacagac atggcagcaa gtggtatcac 2580
ttccagcaac atagggagtt tcagcaggac ctgttggcac ggggcagaga gctgaagaag 2640
atagcctga                                                          2649
```

```
SEQ ID NO: 15          moltype = DNA  length = 2808
FEATURE                Location/Qualifiers
source                 1..2808
                       mol_type = other DNA
                       organism = synthetic construct
SEQUENCE: 15
atgaacaaga cggacaccca gaacaacgag cagatcaaca agccgacgca gctgctcaac  60
aacaaggaca ttgagctgac ggtgaagacc gtgaagtccg cgaccgtgaa ggtggacaac 120
aacagcaaga aggagctgtt cggcctgttc aactacttca ccagcgtcgc ctccggcatc 180
aaggacaagg tgtacaacct gcagtccgat gagaagaccg ccccgatctt caacgactac 240
gtgaagcagc cgcagcgcgg caggtctgct gctactactc tgttcaccaa gctggacgcg 300
gagagacct acacctctca gcactccttc cccggcaagt ggagggattc cggcatcttc 360
ccgctgtaca acaaggagtc cgagaagtac gacctgtcca cccacggcta ccactactcc 420
gctaacgccg agatccacac ccagctggac agccatgacg agtgcaacaa ggagtgcgag 480
aaggagtacg ccgcccttag ggacgaggtg aacaactaca gtacgagtt cacgcttcag 540
ttcaaggccg agaacgccga gaagttctac aacttcgtgg agaagctgac gctgatgggc 600
tggaggtacg acgctacgtt caggtctttc ttcgagctgc acatgcaccc aaagctcaag 660
accggcgaga caacgtacag ggccacctac aagctgccgt ccggcaagtc taagaggtac 720
agcttcttca gggacgacat cgccgacgag attgccaaga acccagagtt ctggccaatg 780
ctggagtcct ccaacgccat ctcctggatc aactccaaca acctgctcag caggaagaag 840
gacaaggcca actactcctc aacctccctc atcaagtccc agattcgcct gtacctgggc 900
aacaacggcg tgccattcac cgctagggag cacgatggca ggatttactt cagcttcagg 960
ctcccggcca tcaacggcga aagggcagg atggtcgaga tcccatgcag ctacaagaag 1020
gtgttcaacg gcaaggccag gaagagctgc taccttggcg ccttaccat cgagaagacc 1080
gacgctggca agcatatctt caagtactcc gtgaacaaca agaagccgca ggtgagccag 1140
ctgaacgagt gcttcctgag gctggttgtg aggaataggc agtacttcaa caacgtggtg 1200
gccggcaaga tcaccgacat caacaccgat cacttcgact tctacgtcga tctgccgctg 1260
aacgtgaagg aggacccgat ccatgatctg agcagcacgg aggtgttcgg caagaatggc 1320
ctgaggtcct actactcctc cgcctaccca gagattaaga acctgggctc ccagatcgag 1380
acgggcaaga acctgacctg cccgatcacc aagacacaca acatcatggg catcgacctt 1440
ggccagcgca acccattcgc ctactgcatt aaggacaaca ccggcaagct catcgcccag 1500
ggccatatgg acggctctaa gaacgagacg tacaagaagt acatcaattt cggcaaggag 1560
tccacctccg tctcccacct tattaaggag acgaggtcct acctgcacgg cgatccagag 1620
gctatctcca aggagctgta caatgaggtc gccggcttct gcaacaaccc ggtttcctac 1680
gaggagtacc ttaagtacct ggactccaag aagttcctga tcaacaagga ggacctgtcc 1740
aagaatgcca tgcacctgct gaggcagaag gaccacaact ggatcggcag ggactggctg 1800
tggtacatca gcaagcagta caagaagcac aacgagaaca ggatgcagga cgccgactgg 1860
aggcagactc tgtactggat cgacagcctg tacaggtaca tcgatgtgat gaagtccttc 1920
cacaacttcg gcagcttcta cgacaagaac ctgaagaaga aggtgaacgg caccgtggtg 1980
ggcttctgca agacggttca cgaccagatc aacaacaaca acgatgacat gttcaagaag 2040
```

```
ttcaccaacg agctgatgag cgtgatcagg gagcacaagg tgagcgtggt ggcgcttgag    2100
aagatggaca gcatgctggg cgacaagtca aggcacacgt tcgagaacag gaactacaac    2160
ctgtggccgg tgggccagct gaagacattc atggagggca agctggagtc cttcaacgtg    2220
gccctgatcg agatcgatga gaggaacacc agccaggtgt gcaaggagaa ctggtcctac    2280
agggaggcgg atgacctgta ctacgtgacg gacggcgagt cccacaaggt gcatgctgac    2340
gagaacgcgg ccaacaacat cgtggacagg tgcatttcca ggcacaccaa catgttcagc    2400
ctgcacatgt tgaacccaaa ggacgactac tacgtgccga cctgcatttg ggacaccacg    2460
gaggagtccg gcaagagggt taggggcttc ctgaccaagc tctacaagaa ctccgacgtg    2520
gtcttcacca agaagggcga caagctggtg aagagcaaac cctccgtgaa ggagctgaag    2580
aagctggtgg gcaagaccaa ggagaagagg ggccagtact ggtacaggtt cgagggcaag    2640
agctggatca acgaggccga cagggacacc atcatcctga acgcaagaa gatctccagg    2700
gaaaagggaca acggcgagca gtccacggat accaggagcc agaacgtgac cgtgtccgtg    2760
ctggacgtgt gcgagacagc tgagaagaag aagctggtcc ttgtgtga             2808

SEQ ID NO: 16              moltype = DNA   length = 2703
FEATURE                    Location/Qualifiers
source                     1..2703
                           mol_type = other DNA
                           organism = synthetic construct
SEQUENCE: 16
atgaagagca taaagagcat aaaaagcatc aagacgaagg tggtgaagaa caacgagctg    60
aagctgatag agctgagtac gtggtgcagc agcatatgcg agcagctgga ggtacata     120
ttcatcctgg gggggaaaca aatacacgac agggacggcg tggtggtgct ggacggcgca    180
gtggagagga agatctactg taagaaagac aagagcttga tcgcggcctg cgaggtggtg    240
tacaaacact tcacggacaa gagttccaag tccaggacgt ttgggtcctg gttcctgggt    300
gggaagtccg agggcgacaa caccaataag ggaaggaaga gtaccaagga agacaccgaa    360
aaacaaatcg caaagcagat cgccgacaag aaggagctga cggactccct gcaactgctg    420
tgggacaaga agctgctgcc attcccgata gacaacaagg gctacgactt cataaatacc    480
ccaagggcca aatcctacaa gtgggcgatc acgaaaacca tccacgctaa aatcaaatcc    540
tacaacgagc aatgcgtgga gaccaaaaaa gagtacgacg ccctgaacgc cgagatcaac    600
acctacaaga ccatcctgtt ctccggctac tccgaaaagg acatcgacga cctgcagaag    660
ttcgtggaca tctgcgaggc aaacaaccac aggataaact acaaattcat atcctttctc    720
aagaggaaag acctcaattt cgacgaacaa acagggaaat acaggaagga aggcaagtgg    780
attcaacaca agaacggaaa ggaagtcaag agcaagtaca gcatgaaaga cgagatagtg    840
gaggccctgt acaagtacaa gtccctgaca aagaacgacg tgagcgtgct gtgcaacgag    900
caccaaaaag aggacgaaat gggcaaggtg gtgcattaca acatgaagag gtactctgat    960
ctgctgttca gaaagaagaa caaaaaggaa atcccgagtt acacgaaaat cagcctggcc    1020
accagcaaga ttgagttggg gttgaacaat gtgaagtaca acgtggagca ggtggaggac    1080
aaactgatat ggaccatatg cgaccagacc ggcaaggaca tccagttcgt gaccgtgtac    1140
accaggaaga aggaggataa caggaccaat ggcaagaaag gggcggggtt ctacaagggc    1200
aaacaccacc agctggagga cctgaaaata tgtgccggtgg gcgacatagg gacctacgac    1260
atcagcttca aggtgaacgg gaagaggccg ttcacaggga ccctgaagga accgaacatc    1320
atatgcaggg gcgggaaggt gttcgtccag atgccgatca acatcaacat cgacaaaacc    1380
ctgaacgacg cgaggaagaa ggtgctgtac gcataccggg agacgtactc cggctccgtg    1440
aacggcaaga agcagaagat gataaagatc gaaaactcca aaatcgccga gtccctgaaa    1500
tccctggggc gggacgcgat agtcctgggc gtggatctgg ggctgagggg gctggctaca    1560
gcggtggtga gccacaacgg gaaaaacgag acagtgaaga gcagccaata cattaagggc    1620
gacattgtgg agtgggagaa gtacaggggt tttaacgaca acatcaggga ggtgaagaag    1680
tacatattcc tgaccaagaa gtcctatacc gccacgacgg aggaatacac cgagtttttac    1740
aaggagtgct cgaagccgga gcaggactat ctggactccc tcaagaccta taaagacaag    1800
aacgtgaaac tcaacgagct gaaatacacg aagaacgcgt ggtccgtgca caagatgttc    1860
gaagacgtct ccaaaatgtt cgaaaccctc aagcaggaca ggctgaagta ctacgacatc    1920
ttcaacatgc catactgggc cgcctccctg aagaactaca tgagcctgat gaagtcctac    1980
aactacgtcg gcgtggacat aaaggtgtcc aaagaataca tgagcaagta ccagtccctg    2040
tacaacaaca tcaaggaaga ttacgccaaa aaaatcggct cctacatcgt gcagctcgcc    2100
gtggccaaga attgcgacat cattgtcctg gaggagctga atccaacct cggctccgtg    2160
gacaggaaga gcaagagaga caacgagatg tccctgatgt ggaactgcgg ccgcatcaag    2220
acccacgtcg agaacatggc aaaggactat gggatgttca ttgacgaagt cccggagtat    2280
ggcacgtccc aggtgtatca caagaccggc aactacggct acaggggatga agacaacagg    2340
gagatatttt ggtacgagga caacaaggac gtggcctaca tacacgccga cgagaacgcg    2400
gcaatcaaca tagccaaaag attcctgtcc caacataccg acaactccag cttcagcgtt    2460
atcctgaagg gcgacgccta ctacctgaac atcgcctcca actccaaacg catgagggcc    2520
gccgcactga aaaccttcgg cgacctcaac aaaccgttca aaatcaacgc caacgacaaa    2580
aacggaaacc tgtacaagaa gaccaggatc ttcaagtccg actccagatg gatagccgtc    2640
aacgacaaag acctctacat agaacacatc aaatccctcc gcaacctccg cgtgcgccag    2700
tga                                                                 2703

SEQ ID NO: 17              moltype = DNA   length = 1884
FEATURE                    Location/Qualifiers
source                     1..1884
                           mol_type = other DNA
                           organism = synthetic construct
SEQUENCE: 17
atgccgagct tcacgaaggt ggacgaggac aaaaatagtgc tgaagctggg gaacaactac    60
atcccgtatg ggctgagcag gatttccgag gacaagatgc tgtggagctt ttcctccccg    120
caaaaaaaga agctgtctat aataacgaac cacaggcgcg tcggcaaggg caaacacttt    180
tacctggaag gcttggagat cgccgacatt accaagggcg acggcgacaa gacgtcccca    240
agcggcaaat ataccatctc cttcagcatc aacggcaagc aggacgtgaa gggcgagctg    300
aaggagccga gcttcggcct gaggaacggc aacgtgtaca tgtttctgcc aatctccata    360
```

-continued

```
aagcagaccg acgtgttcga gtccagggtg gagatgagga ggttgctgtc tatggcctac  420
cagccaacca ccgtggagga tctgatcctg gatgacgtgg agaccaagca gaagaccgtg  480
aagcagggga agaaggaggt gaacaccacg aacatagcga ttcaagaggc gatcaagaag  540
cacggccgcc tgctgaaggt gatgggcgtg gacctggggc tgaggaactt cgcgtttgcc  600
atcaagaact acgacggcca ccacgacacc ctgttgcgac agttgtactc cgagtccgac  660
ctgaacgaga aacagaggta cactaccctg gccaatgact tgtccaaggt gggcaaccac  720
atcaagttcg ccgcggtctt ctacggcgcc aacgacaccg aggagaacac caagatgttc  780
gacgccgagt gcacggacgc cgagtccagg acccacctgg agtggctgag gaaagccaag  840
aagtccggtg tgctgctcaa ggacctgagg aaggacaaga cgtggatcgt gtcgatcaag  900
tataccgagt tgaggaatag gctgcacgca ctgaaattcg gcaggatgaa gagctacgac  960
tacaggaata acctctactg ggccgcgacc attaagaagt tcatctcgct ctccgccagc  1020
ttctacggcg tggggaggcc tagccgccggc aagaaggacg tgagggagtt gaagaaaaag  1080
cacaccttct tctccacgta tcaggacctg tacaacaacg tgaaggaaga ttacgcgaag  1140
aaggtggcga atctggtggt gatgacggcc aaagagaata acgtggacat catcgtggtg  1200
gagaacctga ccgggcactg cgggtccaag gactacaaga ccagggccga gaacgagatg  1260
agtataatgt ggaatcatgg caggatcaag acgttcatcg attgcatcgc caatgccaac  1320
ggcatgttgt tggccgaggt gtccgagttc gagacgtccc aggtgtacca cgagacgagg  1380
aactacgggt acagggacaa gaagatgaaa gagatcctgt ggtacatgga ctccgagggg  1440
aacgtgcagt atgcccacgc cgaggtgaac gccgccatca atatcgccga caggttcctg  1500
tcccagcaca ccaacctgtt ctccttccca gtgtgcaagt ccaagaaaga cgagaatgtg  1560
tacgagatcg acatcgccga ggggaaagaa cttgagggcc aggatgaagt gaagaaggcc  1620
aagaaaccga aaggcgggaa gaggctgaac ggggcggtgg tgaagactt tgggagtacc  1680
aagatcatgt tcaacgggat agtggacaaa aacaagaagg ggcagataaa gacgaagacg  1740
agggtgtaca acatagacgg ggagtggggg gggaagaccc agaaagacga gtacgtggac  1800
aaaatcagga aggtggtgga cgcgatgagc ccggaggaga aagcgaaggt gaaggcggcg  1860
ctgaagaagt gcttcagcag ctga  1884
```

SEQ ID NO: 18             moltype = DNA  length = 2784
FEATURE                   Location/Qualifiers
source                    1..2784
                          mol_type = other DNA
                          organism = synthetic construct SEQUENCE: 18
```
atgacgaagg agctgagcgg ggtgagggtg atagagctga agaccgacct gaggaaggac  60
cagttctggg acaggtacga gaggtgcttc aaaacgtacc acgccctgta caacgaggtg  120
ccatgctggg gcctggactg ggtggagcag aaaacacaaa accaaacctc cagggaactc  180
ggctgcgaga gagtggatct gaccgcccaa cgcaaggcac tgtatgagag gacgtgaccgc  240
accatctctt acgagcagtt tagcaactgc ctcaaagccc tctggctggg gctgctgaac  300
tgtcagcagg ggaaccacat gtacaccaaa ctgtttgaag gcgcgataca aaccgaccag  360
atgaccgcgg aggactgggc cgtgctgacc gaatacgtcg cggacccgaa gagccacaac  420
tcccagttcc tgttcagggt gtccaacacc ctgaagcaca tcggcttctt ctccaggccg  480
ccatttaccg ccaccctgtt tgccccagag aggaaggcta ttaccaagga cgtcatgtcc  540
gacctgaaag gatggattga gatgaagagg atgaccgagg agtcttacgc cgcggaggag  600
gtgcaaattc aacaaatgaa ggccgaggtg ccggtgcgca tcaggcagag cctgctgagg  660
tttttcgaca cctgcatagg cctgaacctc atcggacact tcgacgaaag ggtgcaccac  720
tacctgaggg actgcataat accggcgctg cagcaaagga cgataccgac cgaacacttc  780
tacctgaaat ccaaccgcaa agacgtgggc cagaaacaca tagacttcag cctcgacatc  840
aaattctacg agctgctggc tgaaatgcca gagctgtgga cacccctgga gacctccgag  900
gacgacctca tccccaaacc gctgatcctc aaacacctgc acctgctgga agccatcatg  960
tcccacaggg cccacaggaa gaccgccgcc tacgccttcg tgggcgaagc cgactaccac  1020
aggttctact acctgctcgg cggcaactac acaaaacacc tcatcagcgc caccggtcc  1080
gaactgccgg acagggtgat ctgggacaac gacaaggacg ttctgatgag gaacggcagg  1140
aaggtggaga ggctgtacgt gaaagtgggc gacaggaaag agaacttcaa cttcgaggtg  1200
tacacgatag cgatgaacac gaagggcctg aggggggcaca ggagcacgct gaagccgacg  1260
agttacttgc aagacctgca gatttggagc aacccggagg cgagagcac ctatctgaac  1320
ttcgtgagga agggcacaga aggacgcgcg atttgcaaag agccagtgct ggtgtacagg  1380
aacggcgcct tttttcttag gctgagcatg agcgtggaag ggatgcgggc ctccgaggag  1440
catatcgcgc tgcagtacta cctttctgcc gcggccacgg gctctgactt gtctaaggac  1500
acggagaaga ccgtggagag gttcaacttg atccagggga agacatacaa ggtgatgtcc  1560
gtggatctcg gcatccgctc cccccttcgcc tgggctgtga ccgagtcgac catcacgggc  1620
gtggccaacc cgagccagat cctgaacagc ggcgagatgg aaatcgcgga cgacccggac  1680
tataccgagc tgttctacgc ttacaaaaac ctggggcacc tgatcggcca ggtcaagagc  1740
agcagcaagg ggaaaggcct caaagcggac agccacctgg tggatatgat tcatacggtg  1800
caaaggttct tcgccgacta caaagtggcc gggcagagga ggagtcaaat attcgagcag  1860
ttcagcaagg acccggaccc gttgtaccag atggaccaga tgatgaagag gtacgagaac  1920
aacctggaga gtgtgaagaa ggattttagt ttcctgataa acatcctgtt caagtacgtg  1980
accctgcagt tcggagccct gaggaaccgg agaaggagct acctgtcaca aaaccagatg  2040
gccgaccaga agttcgacca agacttcaag tggctgaaca tcctcgagca gaggaagcgc  2100
gtgaccagga gcctgagcta cctgggcaca gacaacagca ggattcctat ctgcctggaa  2160
cagcagaagc tggactacaa cggctgcaag gacaacttcc tgaagcagct ggcctccaag  2220
atcgtgagga tcgcccacca aaacgactgc tgcctgattg tgctggagga ccttgagggg  2280
tacggggaaa cgtctcaacca gagggacgag aacttcctca cggccttctg gtctccgaac  2340
agggtgaagg atgccatcat caacgccgcc caatgtacg gcattggggt ggtgacggtg  2400
agcgaggccc agacgtccca ggtgcaccac gagtccggca ggatcggcta tagaaagggg  2460
agggacctgt ttttcctgac cccagacggc cagatcgagt ccgtgccgag cgacattaac  2520
gccgccaaga acattggcca taggttcttt tccaggcaca ccgacctgca ccaggtgtac  2580
ctgaagggtt ccgacgaggg cgccaagagg atgaaaggct gccttctgta tcagttcggg  2640
```

-continued

```
agtctggagg cggcccgcac gcaccttacc ggaacaggac cgacctggta cttggacggc   2700
gtggagtgga tagacaagac ggagaggaac ctgaggaggg acctgctgaa gcagagggtg   2760
gaaatcgaga aaatgccatt ctga                                          2784

SEQ ID NO: 19            moltype = DNA   length = 2703
FEATURE                  Location/Qualifiers
source                   1..2703
                         mol_type = other DNA
                         organism = synthetic construct
SEQUENCE: 19
atgaagagca tcaagtcgat caagagcatt aagactaaag ttgtcaagaa caacgagctg   60
aagctcatcg agctgtctac ctggtgtagc tcgatctgcg agcagctcga gaggtacatc   120
ttcatactgg gcggcaagca gattcacgat cgcgatggcg tcgttgttct cgatggcgcc   180
gttgagcgga agatctactg caagaaagac aagagcctga tcgccgcctg cgaggttgtc   240
tataagcact ttaccgacaa atcgtccaag tctcgcacct ttggcagctg gttcttgggc   300
ggcaagagcg agggcgataa cacaaacaag ggcagaaagt ccaccaaaga gaagactgag   360
aagcagatcg ctaagcagat cgccgacaag aaggagctga ccgattctct gcagctcttg   420
tgggataaga aactgctgcc atttccgatt gataacaagg ttacgactt catcaacaca     480
ccacgcgcca agagctacaa gtgggctatc accaagacca ttcacgcgaa gatcaagagc   540
tacaacgagc agtgtgtcga gacgaagaaa gagtacgacg cgctgaacgc cgagattaat   600
acatacaaga ctattctgtt cagcggttac tccgagaaag acattgacga cctccagaag   660
ttcgtcgata tatgtgaggc caacaaccac aggatcaact acaagtttat cagcttcttg   720
aagcgcaaag atttgaattt cgacgagcag acaggcaagt accgcaagga gggcaagtgc   780
attcagcaca agaacggcaa agaagttaag tccaagtaca gcatgaaaga tgagatcgtc   840
gaggcgctgt acaagtacaa gagcctgact aagaacgacg tgagcgtgct ctgcaacgag   900
catcagaagg aggacgagat gggtaaggtg gtccataaca atactccgac ctattccgac   960
ctgctgttcc gcaagaagaa caagaaggaa ataccaagct acacaaagat ctcacttgcc   1020
acgtccaaga tcgagctggg cctcaacaac gtcaagtaca acgttgagca ggttgaggac   1080
aagctcatct ggacaatctg cgatcaaaca ggcaaagaca tccagttcgt gactgtctat   1140
acaagaagac aagaagataa caggaccaat ggcaagaagg gagcgggctt ctataagggc   1200
aagcatcacc agctcgaaga cctgaagatc gtgcctgtgg gagacattgg cacttacgac   1260
atcagcttca aggtcaacgg caagcgtccg tttactggca ctctgaaaga gccgaacatc   1320
atttgccgcg gaggcaaagt gttcgtgcag atgccaatta atatcaatat cgataagact   1380
ctcaacgacg ctcggaagaa ggttctgtac gcctacaggg agacgtacag cggctccgtc   1440
aacggtaaga aacagaagat gatcaagatc gagaacgaca agatcgccga gtcactcaag   1500
tctttgggca gagacgccat tgtgcttggc gtggatttgg gcttgcgcgg acttgctacc   1560
gccgttgtga gccacaacgg aaagaacgag actgttaaga gcagccagta catcaagggc   1620
gatattgtgt agtgggagaa gtacaggtg ttcaatgata atatcaggga ggtcaagaag    1680
tacatcttct tgaccaagaa aagctacacc gccacaacgg aagaatacac agaattttac   1740
aaggagtgca gcaagcctga gcaagactat cttgatagcc tcaagacgta caaggacaag   1800
aacgttaaac tgaacgaact gaagtacacc aagaacgcct ggagcgtctc gaagatgttt   1860
gaagacgttt ccaagatgtt cgagacactc aagcaagaca ggctcaagta ctacgacatc   1920
ttcaatatgc cgtattgggc ggcctcactg aagaactata tgtcgttgat gaagtcgtac   1980
aattatgttg gcgtggacat caaggtcagc aaagagtaca tgtccaagta ccaatccctg   2040
tataacaaca tcaaggagga ctacgccaag aagatcggca gctacattgt ccagctggct   2100
gtggcaaaga actgcgacat catcgtgctt gaagagctga gtcgaacct gggcagcgtt    2160
gatcgcaaat ccaagcgcga taacgaaatg agcctcatgt ggaactgcgg cagaatcaag   2220
actcatgtcg agaacatggc caaagattac ggcatgttta tcgatgaggt gcctgagtat   2280
ggtacttcgc aggtgtacca taagaccggt aactacggct atagagatga agacaacagg   2340
gaaatcttct ggtacgagga taacaaagac gtcgcctaca tccatgcaga cgagaatgct   2400
gccatcaaca tcgcgaagcg ctttctgtca cagcataccg acaacagctc attctccgtg   2460
attctcaagg gcgacgctta ctacctgaac atcgcttcca actccaagag aatgcgcgcc   2520
gccgctctca agacctttgg agatctcaac aagcctttca agattaatgc caacgataag   2580
aacggcaacc tctacaagaa gacaagaatc ttcaagtcag actctcgctg gatcggcgtg   2640
aacgacaagg acctctacat cgagcacatc aagagcctga gaaatctcag ggtgaggcag   2700
tga                                                                 2703

SEQ ID NO: 20            moltype = DNA   length = 2808
FEATURE                  Location/Qualifiers
source                   1..2808
                         mol_type = other DNA
                         organism = synthetic construct
SEQUENCE: 20
atgaacaaga cggacaccca gaacaacgag cagatcaaca agccgacgca gctgctcaac   60
aacaaggaca ttgagctgac ggtgaagacc gtgaagtccg cgaccgtgaa ggtggacaac   120
aacagcaaga ggagctgtt cggcctgttc aactacttca ccagcgtcgc ctccggcatc    180
aaggacaagg tgtacaacct gcagtccgat gagaagaccg ccccgatctt caacgactac   240
gtgaagcagc cgcagcgcgg caggtctgct gctactactc tgttcaccaa gctggacgcg   300
gagaagacct acacctctca gcactccttc cccggcaagt ggagggattc cggcatcttc   360
ccgctgtaca caaggagtc cgagaagtac gacctgtcca cccacggcta ccactactcc    420
gctaacgccg agatccacac ccagctggac agccatgacg agtgcaacaa gggagtgcgag   480
aaggagtacg ccgcccttag ggacgaggtg aacaactaca gtacgagtt cacgcttcag    540
ttcaaggccg agaacgccga gaagttctac aacttcgtgg agaagctgac gctgatgggc   600
tggaggtacg cgctacgtt caggtctttc ttcgagctgc acatgcaccc aaagctcaag    660
accggcgaga caacgtacag ggccacctac aagctgccgt ccggcaagtc taagaggtac   720
agcttcttca gggacgacat cgccgacgag attgccaaga cccagagtt ctggccaatg    780
ctggagtcct ccaacgccat ctcctggatc aactccaaca acctgctcag caggaagaag   840
gacaaggcca actactcctc aacctccctc atcaagtccc agattcgcct gtacctgggc   900
aacaacggcg tgccattcac cgctagggag cacgatggca ggatttactt cagcttcagg   960
```

-continued

```
ctcccggcca tcaacggcga gaagggcagg atggtcgaga tcccatgcag ctacaagaag   1020
gtgttcaacg gcaaggccag gaagagctgc taccttggcg gccttaccat cgagaagacc   1080
gacgctggca agcatatctt caagtactcc gtgaacaaca agaagccgca ggtggccgag   1140
ctgaacgagt gcttcctgag gctggttgtg aggaataggg agtacttcaa caacgtggtg   1200
gccggcaaga tcaccgacat caacaccgat cacttcgact tctacgtcga tctgccgctg   1260
aacgtgaagg aggacccgat ccatgatctg agcagcacgg aggtgttcgg caagaatggc   1320
ctgaggtcct actactcctc cgcctaccca gagattaaga acctgggctc ccagatcgag   1380
accggcaaga acctcacctg cccgatcacc aagacacaca acatcatggg catcgacctt   1440
ggccagcgca acccattcgc ctactgcatt aaggacaaca ccggcaagct catcgcccag   1500
ggccatatgg acggctctaa gaacgagacc tacaagaagt acatcaattt cggcaaggag   1560
agcacctcag tctcccacct catcaaggag accaggagct acctgcacgg cgatccagag   1620
gctatcagca aggagctgta caacgaggtg gccggcttct gcaacaaccc ggtttcctac   1680
gaggagtacc tcaagtacct ggacagcaag aagttcctga tcaacaagga ggacctgtcc   1740
aagaacgcga tgcatctcct gaggcagaag gatcacaact ggatcggcag ggactggctg   1800
tggtacatca gcaagcagta caagaagcac aacgagaaca ggatgcagga cgccgactgg   1860
aggcagactc tttactggat cgacagcctg taccgctaca tcgacgtgat gaagtccttc   1920
cacaacttcg gctccttcta cgacaagaac ctgaagaaga aggtgaacgg cacggtggtg   1980
ggcttctgca agacggttca cgaccagatc aataacaaca acgacgacat gttcaagaag   2040
ttcacgaatg agctgatgag cgtgatcagg gagcacaagg tgagcgatgg tcgcccttgag   2100
aagatggact ccatgctcgg cgacaagtcc aggcacacct tcgagaacag gaactacaac   2160
ctgtggccgg ttggccagct gaagacgttc atggagggca agctggagtc cttcaacgtg   2220
gcgcttatcg agatcgacga gaggaacacc tcccaggttt gcaaggagaa ctggagctac   2280
agggaggcgg acgaccgtgta ctacgtgacg gacggcgagt cccacaaggt gcatgctgac   2340
gagaacgccg cgaacaacat cgtcgacagg tgcatcagca ggcacaccaa catgttcagc   2400
ctgcacatgg tgaacccgaa ggacgactac tacgtgccga cctgcatctg ggacaccacc   2460
gaggagagcg gcaagagggt tagggggcttc ctcacgaagg tctacaagaa ctccgacgtt   2520
gtcttcacca agaagggcga caagctggtg aagtccaaga ccagcgtgaa ggagctgaag   2580
aagctggttg gcaagaccaa ggagaagagg ggccagtact ggtacaggtt cgagggcaag   2640
agctggatca acgaggccga cagggacacg atcatcctga acgcgaagaa gatcagcagg   2700
gagagggaca acggcgagca gtcaacggat acccggagcc agaacgtgac ggtgagcgtt   2760
ctggacgtgt gcgagaccgc tgagaagaag aagctggtgc tggtgtga   2808
```

```
SEQ ID NO: 21          moltype = DNA  length = 2691
FEATURE                Location/Qualifiers
source                 1..2691
                       mol_type = other DNA
                       organism = synthetic construct
SEQUENCE: 21
atgaagaagc cgaagcagaa catcgaggag acggacctga agatcaccac cccaaagacc   60
gcgaccatca aggccaccaa cctggacgac aagatgaggc tcttcacctt cttcaacggc   120
ttcaccaccg tgtgctccaa ggtgaaggac gacatctaca acttcggcca gaacgaggac   180
acactgccgg tgtacaccga ctacattaag gcctcccaga gggccaggat gtgcgctact   240
accctcgcta ccaagagcga gtgcgacttc gccaagaagt acggcgagca cttcccgctc   300
ccccattaca accaggaggg catgaactac accacccacc agcacaccta ctcagtgaac   360
tccgccgtgc acacacagct cgactccctt aacgagtgcg acaagctcac caacggcgag   420
tacgtcaagc tcaagaagac cgtcgacgag ctggaggaga agctgaccga ggagcacggc   480
aaggagccac ttgatttcct ggtgaagttc gtggacgagc agatcctcct gggctggagg   540
ttcgacggca agttcaggct gttcttcgag gtggcgatgc tgccagagct taagaacggc   600
aacatcatct acaagaaggc gtacaagacc tccggcggca agggcaggag gtactctttc   660
tacaacccgt ccgtggccga taacatttct aagaacccca ccgtgtggaa cctgctgagc   720
gacgttaagg cggtggacta catctccctg tctaattccc tgctgaggaa gaagccgcac   780
gcccagtaca ccaacacaac cctgaacagg gcccaggtga ggcctacatt cggcaacaac   840
ggcgtgccat ctccatctc cgtctccgac gacgactacg tgtacatccg cttcaggctg   900
cccaagaagg acggcgagga aagggccag gagatctcag tcaagtgcag ctacaagact   960
tcatacaagg gcaagcgcag caagacgctg aggaagagct gctacctggg caacctgaag   1020
atcgaggaga atggcaaggg caagtacatt tgcaagtaca acatcaacgg cagggagacg   1080
accaccgcgg agcttaatga gtgcttcctg agggtgagga tcaacaacaa ccgctggttc   1140
aacaagtacc tgaacggcac gctgaccaag gaggacggcg ttcttaagag cgagtacttc   1200
gacttctact tcgacctgtg cctgaatgtg catcagaagt ccatccacgg cctgaccaac   1260
tccgagattt tcggcggcaa gggcaagagc atcaggagct actactccac ctcctacccg   1320
gaggtgaaga acctggacgg ccagaagaac atcaagaccg acttcggctg ctacgtggac   1380
aagccgcaca acatcatggg catcgacctg gccagagga acccattcgc ctgggctgtt   1440
ctggaccaga acggcaatgt gaaggacgtg ggccacctgg acggcgctga acgatacag   1500
tacaaggact acctgacgtt ctccaacagg tgcaaggacg ttaagaatct gatcctgcag   1560
tccagggact acctgtacgg cgacgatgag gccattgacg agaccctgtt cgactccgtg   1620
gtgcagttcg tgaacagcaa catcacgctg aacaagtaca gtcctacctt ggacgagaag   1680
aagagcctga tcaacaagga gtccctggag aagaaccgcc tgtacgagct gaagaagaag   1740
gaccacggct ggttcgtgag ggactgcctt tggttcctga ccaaggagta ccacaggatc   1800
aactccgagc gcaagacgca ctccgactgg aggtacacc tgctctgggt ggacgccatt   1860
caccggttca ttgacgtgaa caagtccttc aactccctcg gcagctacta cgacaagaag   1920
cagtccaagt ccatcaacgg catccagaag gacttctgca ggagctactg gaaccagatc   1980
gacaacctga acgaggacac cctcaagaag ttcgtgttcg agctgctgcc agtgatcaag   2040
aagaacaacg tgtgcctgat cgccatcgag gagctgaagt ccatgctggg cgacgacgac   2100
aagagggctg aggataacag gctgtacaac ctgtgccgag ctacagct taagacgttc   2160
ctggagggca gctgctgcc gtacaacgtg ctgtgatgg aggtgagcga gcagaacacg   2220
agccagatct gaacggcca gtggtcctac agggagggcg atgatctcta ctacgtgaag   2280
aacaacgaca acaacaccat gtgcaagacc cacgcggacg agaacgcggc tatcaacatc   2340
gccctgaggg cctactccca ccacactaac ctgtactcca tctacatgat caatccgatc   2400
gacgactact acgtcccgag ctgcatctgg aacaacaagg acgagggctc caagaggatt   2460
```

```
aggggcttcc tgaccaagac ctacggcacc tccgacgtgg tgttcatcaa gaagaatgag    2520
aagctggtga agtccgacgt gagcatcaag gacgtgaaga ggatcgtgaa gaacatcggc    2580
aatgagaaga acaagaagag cgagatctgg tacaggatga acgacatcga gtggatcgac    2640
gagggcagca gggacatcat catcaacaca atcaagagca aggtgaggtg a              2691

SEQ ID NO: 22           moltype = DNA   length = 2664
FEATURE                 Location/Qualifiers
source                  1..2664
                        mol_type = other DNA
                        organism = synthetic construct
SEQUENCE: 22
atgacggaca agagcatcag cttcaagcag ttcagccaga tcctcaatgt gctgtacaag    60
tgcatcgtga tttccggcaa gggccgcggc cttacttcca ttatcctggg ccagccgcag    120
tgcaaggact cacttacctc cgccgactgg ggcaacctgg agactctttc cgccaaggac    180
gagctgaccc ctgctgaggt taaggatatt accaaggacc tgatgtacag ggccagcaac    240
accctggtct ccatcggctt caggaacagg tcccctttca agctgaccct gacctccggc    300
gagaggtacg ctgttgtgga gaacgtgcac cgctccctca agtcctgggt ggaggttgac    360
aagattacca gggagaacta cctcaacgag gagatcgccc tgagcgatgc cttcaataac    420
atcgacgaga cgctgctgcc aaccccttaag gagttcttcg acgcgtgcat gaatgagaac    480
atcatccacc acttcgacgc cagggtgtac gcctacacga gggattgcgt catcccagcc    540
ctggtggctg gccttgagat caaggaccac ttctacatcg acggccgcga caaggccaag    600
agggattaca gcctgcaagg ttacgccgag cttctgaagg gcttcccgaa gctctggcag    660
ggcgttgatc cggagatcct ggctaagctg tacatcctgg aggcccagat ggaccacaag    720
aagcacaggc catgcgccgc ttacgcgttc atcggcgagg attcctacag cagggtgcag    780
taccttctgg gcaacaacta cacctccttc agcccctacg ccctcggcgt tgatctggat    840
gacgtgacct gcgggcatga cgctgaggct gatacacagt tccccaagaa caaggtgatc    900
cagttcagcc agggcaagaa ggtgaccaag ctgtccctga ccgtgagcag gggcaaggag    960
gataccaaca agtactcctt cgatgtgttc ctggccgaca agtacagcaa cggctcctac    1020
aagccaagcc cgtacttctc tgacctgtcc gtttgggtga gcgagatcgg catgctgatg    1080
gagttcaccc gcaagggcga gagggtgcag gctattgtga aggagccatc cctgatttac    1140
cgcaagggcg ccttctacgt gaggcttaat atgggcgtga ttcaggacac ctccccggag    1200
atcaacgacc tgtactggta cttgtcctcc ggcgccccaa tgtccatgac cgataggtcc    1260
aaggcttccg agaccccgaa gaacaccgag aggctggagt caattaaggg caagagctac    1320
cgcttcctgg gcatcgacct gggccttagg tccccattcg cctgggctgt tggcgaggct    1380
tctatctccg gcgtcatcaa caagccgaca atcattgcca ccggcgacta caccaccgcc    1440
agggatacta ggtacgacac gctcttcttc gccctcaaga atgcgggcaa ggtgattggc    1500
gtgaccaagt ccctcgccaa cggcaaggac gcttctttca atggcctgat gggcaccatc    1560
accgccgcta gggagtacct tgcgcactac tccggcgtcg ctacccataa ggtggccgct    1620
atccaggcct tctgccagga tgacaacccg ctggagaccc ttaaggcct gctcaagtcc    1680
tacaacaacg acctcgtcac cctcaagaag gaccctaggt tcatcggcgg catcctgctc    1740
aggtacgcca ggcttctgaa gggcgagctt gtgacctcca ggaagatgca cctgcgggag    1800
cactccgtgg agtctaagtt cggccaggag tacatgtggc tgaatattct ggagagggag    1860
aagaggtgt gcaggagcct gtcctacctg ggccttgaca acgacaggga cagcgttatc    1920
atgggcaacc tgaccacgcc gtacaaccac tgcaaggaga acctgcttaa gcagctggcc    1980
gcgaggattg tgtcactggc tgtggagaat aagtgccacg ttatcgtgat ggagtccctg    2040
ggcggctcca acaagtccat gaataccagg ggccagaact tcctcgaggc cttctggtcc    2100
ccacagagaa tcaaggacac catcatcaac gccgccgcct ggcatggcat catggtttgct    2160
gaggtgagcg agagccagac ctcccaggtt tgcttcgaga ccggcacctt cggccacagg    2220
gatagggctt ctctgtactt cctggacaag aacggcgacc tccaggagac gcatgccgat    2280
atgaacgccg ccaagaacct cgtggagagg ttcaccacca ggcacaccaa cctgaggcag    2340
gtgaatatgg actccctccc caaggagggc ccggataaga caccaaagaa gtccccgtcc    2400
aagaagaaga tggagaaggc gaagatggac aacccagagg accagtccaa gaggctcaag    2460
ggcttcctga ccgtgaagtt cggcaatgtg aaggccgccc aggagtactt cgcctctagg    2520
aagccggagc agagctacag cggcaagaag gacgaggcca tctactggta cttggacggc    2580
gacgagtgga tcaccaagaa ggagaaggag tccaggatca gcgtgattga gggcctggtg    2640
ggccttaagg aggtggctgt ttga                                           2664

SEQ ID NO: 23           moltype = DNA   length = 2466
FEATURE                 Location/Qualifiers
source                  1..2466
                        mol_type = other DNA
                        organism = synthetic construct
SEQUENCE: 23
atggcgttcc agagcaagag gaggattgtg ggcaacctgg tgaaggagca gtgcctcaag    60
gccgtggatg gcaaggtgat cctgaccgac caggagaaga gggagctgat caagaggtac    120
gagctgcacc tggagccgta caagtggctg ctgaggctgt tcctgtccgg ctacgagggc    180
agggatgacg gcttctacga ggagctgggc aacacgaacc tggacaagga gaagttcttc    240
gaggtcaccg cgggcctcag ggatgctctt cttaggcagt ctggctcctc cagggcgctt    300
aagtcctcca tgctgggcaa gtgcccgcca tcagctgctg ttggcaaggc tgctaagcac    360
atccaggctc tgcgcgacgc tggcattctt ccattcaaga cggdcctcac ctccggcgag    420
gattacaacg tgcttcagca ggccgtccag cagctgaggg catgggttgc ttgcgatcac    480
aggaccaggg aggcgtacgc tgagcagcag gagaagacat cccaggccga ggaggctgct    540
aagaaggctg tgaacgaggt gaagccagag gacgccaaga gcctggagag gcatgagagg    600
gctctgacga agctgaggaa gcaagaagg aggctggagg ggatgaggag cacgctgcag    660
ttcagcctgg acgagatgga ctgcacgggc tacagcctgt gcatgggcgc taactacctg    720
aaggactact gcctggagaa gggaggcagg ggccttaggc ttaccctgaa gaatagcact    780
atggccggca gctactacgt ttccgtgggc gatggccagc acgctggcat gaagaaccca    840
ggtactccgc ggggcggctc tccagagaag ggcaggagga ggaacatcct gttcgacttc    900
gcggttgaga agtgcggcga caactacctt ttcaggtacg acgagaacgg caagcgcccg    960
```

-continued

```
agggctggcg ttgttaagga gccaaggttc tgctggaggc ggaagggcaa ctccgtggag    1020
ctttacctgg ccatgccgat caacatcgag aacagcatga ggaacatctt cgtcggcaag    1080
cagaagagcg gcaagcactc cgctttcacc cggcagtggc caaaggaggt ggagggcctt    1140
gacgagctga gggatgctgt ggtgctgggc gttgacatcg gcatcaacag ggcggctttc    1200
tgcgcggctc tgaagacttc ccgcttcgag aacggcctgc cggctgatgt tcaggttatg    1260
gataccacct gcgatgctct gaccgagaag ggccaggagt acaggcagct gaggaaggac    1320
gccacctgcc ttgcttggct gatcaggaca accaggaggt tcaaggccga cccaggtaac    1380
aagcacaacc agatcaagga gaaggacgtg gagaggttcg acagcgccga cggcgcttac    1440
aggaggtaca tggacgatcat cgcggaggatg ccgtccgatc cacttcaggt gtgggaggcg    1500
gccaggatca ccggctacgg cgagtgggct aaggagattt tcgccaggtt caatcactac    1560
aagcacgagc atgcctgctg caccgtctcc ctttccctgt ctgaccgcct ggtgtggtgc    1620
aggcttatcg ataggatctt gtctctcaag aagtgccttc acttcggcgg ctacgagtcc    1680
aagcacagga agggcttctg caagtccctc tacaggctta ggcacaatgc caggaacgac    1740
gtcaggaaga agctggccag gttcgtggtg gacgccgctg ttgatgcggg cgcttctgtt    1800
atcgcgatgg aaaagctccc gtcctccggc ggcaagcagt ctaggggatga caaccggatc    1860
tgggacctga tggccccaaa caccctggct accaccgtgt gcctcatggc taaggttgag    1920
ggcatcggct tcgtgcaggt ggacccagag ttcacctccc agtgggtgtt cgagcagagg    1980
gtgattggcg ataggggaggg caggattgtg tcctgcctgg acgctgaagt cgtgaggagg    2040
gattacgacg ctgacgagaa cgccgcgaag aacatcgcct ggctggctct tactagggag    2100
gcggagccat tctgcatggc cttcgagaag cggaatggcg tggtggagcc gaagggcttc    2160
aggttcgaca ttccggagga gccgaccagg gagcaggatg agtcaaacca ggacttcaag    2220
aagaggctgg aggagaggga caagctgatc gagaggctgc aggaggaagag cgataggatg    2280
agggcgatcg tgaggaggct cttcggcgat aggaggccgt gggatgcttt cgctgacagg    2340
attcctgagg gcaagtccaa gaggctgttc cggcacaggg atggcctggt tctgaacaag    2400
ccgttcaagg gcctgtgcgg ctccgagaat agcgagcaga aggcctccgc caggaactct    2460
aggtga                                                               2466
```

SEQ ID NO: 24       moltype = DNA   length = 2865
FEATURE            Location/Qualifiers
source             1..2865
                       mol_type = other DNA
                       organism = synthetic construct

```
SEQUENCE: 24
atggacacgg acacggagct gagcgacgag gttgagctga gcgatgaggt ggagctgagc    60
gacgaggtgg agctttccga cgaggtggag ctgacggtga agaaggtgaa gacgacgacg    120
gtgaaggtgg acaacaattt caagaaggag ctgttcgagc tgttcaatca cttcaccagc    180
gtggcgagcg gcatcaagga caggctttac gacctgcagt tcgatgagaa cactgcctcc    240
atcttcaagg gctacatcaa ggaggccaag aggggccacg gcgctgctac tactgtgttc    300
actaagctga acccgaagaa gatctactcc ggcaagaagt cctteccaag ggattacagg    360
gaccgggggca tcttcccgtt ctacaacaag gagtctggca agtacggacct gtccacctgt    420
ggctaccact acagcgctaa cgccgagatt cacacccagc tcaacagcca cgacgagtgc    480
aacaagcagt gcgagaagga gtacgcggcg ctggagaagg agaggaacaa gtacaagcat    540
gagttcacga ggcagttcaa ggccgagaac gtggagaagt tcagcaactt cgttggagaag    600
ctgacactga tgggctggag gtacgatgcg accttcagga acttcttcga gctgcacatg    660
cacccaaagc tcaagacgtc cgagaccacc tacaggggcca cctacaagct gccgtccggc    720
aagtctaagc ggtactcctt ctccagggac gatattgccg acgagatcgc caagaacccc    780
gagttctggc caatgctgga gtcctccaac gccgtttcct ggatcaactc caacaatctg    840
ctctccagga agaaggagaa ggccaattac tccagcacca gcctgatcaa gtcccagatt    900
aggctgtacc tgggcgacaa cggcgtgcca ttcaccgcta gggagcacga tggcaggatc    960
tacttcagct tcaggctccc gtccatcaac ggcgagaagg gcaggaacgt cgagatccca    1020
tgctcctaca agaaggtctt caatggcaag gccaggaagt cctgctacct gggcggcctt    1080
accatcgaga acaccggcgg ctcaaagcac attttcaagt actccgtgaa caacaagaag    1140
ccgcaggtgg cggagctgaa cgagtgcttc ctgaggctgg tcgtgaggaa tcatggctac    1200
ttcaacaaga tggtgaacgg caagctcacg gataaggacg gcaagctgca cgccgactac    1260
ttcgatttct gcatcgacct gccgcttaac gtgaaggagg acccgatcca cgacctgacc    1320
taccaggaga ttaacggcgt gaaggccaac ccggacgaga acatcgagaa gaaggtgggc    1380
ctgctgggct ctaccagtc cgcttaccca gagatcaaga acctcggctc ccagatcgag    1440
accggcaaga acctgacctg cccgatcacc aagacccaca acatcatggg catcgacctc    1500
ggccagcgca acccattcgc ttactgcatc aaggacaaca acggcaagtt catcgcgaag    1560
gaccacatgg acggctccaa gaacgagaca tacaagaagt acatcaattt cggcaaggag    1620
agcacctcag tctcccacct gatcaaggag accaggtcct acctgcatgg cgatccggag    1680
gctatctcca aggagctgta caacgaggtc agcggcctgt gcaactctcc gcttagctac    1740
gaggagtacc ttaagtacct ggacagcaag aagttcctga tcaacaagga ggacctgaac    1800
aagaacgcca tgcacctgct gaggcagaag gaccacaact ggatcggcag ggactggctg    1860
tggtacatca gcaagcagta caagaagcac aacgagaaca ggatgcagga cgccgactgg    1920
aggcagactc tgtactggat cgacagcctg tacaggtaca tcgatgtgat gaagtccttc    1980
cacaacttcg gcagcttcta cgacaagaac ctgaagaaga aggtgaacgg caccgccgtg    2040
ggcttctgca gagactatcta cgaccagatc aacaacaaca acaaggacat gttcaagaag    2100
ttcaccaatg agctgatccc gatcatccgc aagcacaagg tgtccgtggt ggcccttgag    2160
aagatggagt ccatgctggg cgacaagtcc aggaacacat cgagaacag gaaccacaac    2220
ctgtggccag tcgccagct gaagaccttc atcgagaaca agctggatgg cttcaacgtg    2280
atcgtggtgg aggtggacga gaggaacacg agccagatgt gcgacggcaa ctggtcctac    2340
agggaggctg acgacctcta ctacgtcaag gacggcgagc tgagggaggt tcacgctgat    2400
gagaatgcgg ccaacaacat cgtcgacaag tgcatctcca agcataccaa catcttcagc    2460
ctgtacatga ccaacccgat ggacgactac tacgtgccgg cgtgcatctg ggacaggtca    2520
gagaatggca gagggggcag gggcttcctg accaagatgt acaagaacag cgacgtggtg    2580
ttcaccaaga aggacgacaa gctggtgaag tccaagatgt ccgtgaagga gctgaagaag    2640
ctggtggaca agaccaagga gaagaggggc cagtactggt acttgttcga gggcaagagc    2700
tggatcaacg ccgccgatag ggataccatt atctccaacg cgaagaagct cttcagggag    2760
```

-continued

```
agggatggcg gcgagcagtc aactgatacc cgctctcaga acgtgacggt gtccgtgctg    2820
gacgtgtgcg agactgtgga gaagaagaag ctggtcctgg tgtga                    2865

SEQ ID NO: 25          moltype = DNA  length = 3006
FEATURE                Location/Qualifiers
source                 1..3006
                       mol_type = other DNA
                       organism = synthetic construct
SEQUENCE: 25
atgagcacgg aggtggacgt gaagacgatc aacctgaaga tcgcgaagaa gggcggcgtg    60
tacccgattc tggagcagtc aattaaggag aactgcaaga gcaacgacct gctggagttc    120
ttcatggtgc tgaacaggct gcagacctac tacatcgaga gcaacgagga gattctggtg    180
gacttcccca agaagtacga cgagctgttc gacatcgtga agaacaacga ctcctccgtg    240
accagggaat acttcgactc cctctgcgac aagtacatca cagaggtgtg cgccaatggc    300
ttcgtcaaca acgtgtacat tgcccacaac aagaaccagg agctgaactg ggctgagacg    360
agcaacgacc gcaagatcaa gagcaacaag accttcatgt tcggcaagat caagggcctg    420
atccgcgaca agttcggcag gggaggagtg tcagacaagg acgctacgaa gcagctgtgc    480
gaggacatct tcaacctctt catcctgaac aacgccaaca tcgagctgga cgagaagtac    540
aacatcatca aggacgagct gatccagatc tggaacgaga ggaacaagga gttcatccac    600
atcaaggaca tcaccctgct gttcaggcag tggggcatcc tgcctaccta cgacaacatc    660
acccacaact gcgagctgaa ggccatcatc gccgagccag tgaggaggtt caagtcctgg    720
ctggagtgca actctgaggc gaacaagaac tacgacaccg agaggagaa gtgcaccaag    780
tacatggacg tgatggactc cgacctgacc gtggagttca gcaagatggt gacggagctg    840
ggcaacccat tcggcgctaa cgacaagaac atctacaagt acttcaacca gaagttcctc    900
ctgttcttca agcaggttgt gcagcccaag ttcgttaacg gcgagccgct ggacgagtct    960
aatggctctt actccggcga gatcaagatc aactccgcga caaggtgga gaactactcc    1020
atcgccgtgt ccgtgattga caccatcaag aagtacccga cgatctggtc cgaccgctcc    1080
tggggcgagt ctgttatctc caccgtggcc aagattgatc cgcagtacgg catcgacgac    1140
atcaccgacg atatgcaggt gtccccgttc tacctcttct acggctactt caccgcctac    1200
aactacatcc agcagcacaa gaggaacgcc aagtacaccc agactccaa ggactccctg    1260
ccatccctgt acctcggcaa caactcatc ccattcaaga tcgactgcga gaacgtcgac    1320
gacgaccggt tctacatcac catcaagaac atgaacaacc tgaagctgaa cgtcctctac    1380
cgcaagccca agctgaagtt cgccaagacc aaggagaaga ccaagaggaa caagtgctac    1440
ttcgacaacc tcaagatcac caacaccaac aacaacttca agttcgagta caacatcaac    1500
ggcgacccaa acaggtccgt ggtggcttac ctgaaggagc cagtgatccg ctacaacaac    1560
aggaaggact acttctacct gagcgccaca atcagcaagg acgtggagac cgactccgag    1620
ctgacctctg cttgctggtc gaagatctcc aacgacaccg cccgcagggt caacgctgag    1680
cagtacttca acgacaacgg cgtgaacatc gtgggcattg acctgggcat gaacccgatc    1740
atcgcctact ctgttctgca ctacaagaac aacgagttca ttgacctgaa cattaccggc    1800
aagatcgccg acaaggataa gcaccccaat ctgaactaca agaggatgta cgagaagagg    1860
tccgagatca agaagctcaa gaccctgatc aagatgatcc cggactacgt gaacagcgac    1920
agcaacatct cgagggcga caataacgtg ttcaagcagc tggacaagaa gagcaagggc    1980
aggttcaggt cctccgagta catggctac tacgacaagc tgaacgtgga cggcaagttc    2040
atctccgagc tggagatcgt gaagaaggtg gtgaacacaa agcactacaa gaatgacacc    2100
gagaagaaca acgatattat gagggtgtac aagggcaata agaagaacat catcaagaag    2160
gagatcgaca cccacaggca ccagatccac tccatcaagg acatgaacag gaggtccgac    2220
gagagcaacc tgtgctacgt gtacgacatg gtgagctaca tcgacgactt caagaagctg    2280
gtgacctcct acaacaagat cggcgaggac tacaacaacc cgatcaagcc gctgagcgac    2340
ccgatgcttt tctccaagtc caagctgtac gagtacaggc agaacatcag ggacaatttc    2400
ctgaaggaca tctgctacca gatggtgaag atcgccaagc agtacaatgc cgtgctggtg    2460
cacgagcact tcgagcagag gaagggcggc attgacaggg tgaacaacat cctgatggcc    2520
ctgttcacgc cgaacgacat catcaagaag ctgaagtgcg tggccaagag ggagggcgtt    2580
ctggtttca acaccaacaa gaaccatacc tcccagtacg tgtacaacaa gaacaccgtc    2640
ggctaccgcg acagcaacaa caagcacaac ctgtactaca tcgaggacga gaccaccagg    2700
aagctcggcg ttgtggactc cgacatcaac gcctccaaga acatcgccgc ccgcccattc    2760
aacaagccac tctacgccat caaggtgaag aactacgatg acggcctgtt cctgtcagac    2820
tacaacaata agtacgttct gtacaagaag acggcgaca agtacgtggc catcggcgat    2880
acatacagga tcgacaagaa gaagatcaag cagggctccg tgaccctgta cctgcataac    2940
ggctactacg tggatggcga gtacaagaac aattacatcg agaatatcaa gaagctggtc    3000
ctgtga                                                               3006

SEQ ID NO: 26          moltype = DNA  length = 2466
FEATURE                Location/Qualifiers
source                 1..2466
                       mol_type = other DNA
                       organism = synthetic construct
SEQUENCE: 26
atggcgttcc agagcaagag gaggattgtg ggcaacttcg tgaaggagca gtgcctgaag    60
gccgtggatg gcaaggtgat cctgacggac caggagaaga gggagctgat taagaggtac    120
gagctgcacc tggagccgca taagtggctg ctgaggctgt tcctgtccgg ctacgagggc    180
agggatgacg gcttctacga ggagctgggc aacacgaacc tggacaagga gaagttcttc    240
gaggtcaccg cgggcctgag ggatgctctt cttaggcagt ctggcagcag cagggcgctt    300
aagtcctcca tgctgggcaa gtgcccgcca tcagctgctg ttggcaaggc tgctaagcac    360
atccagaccc tgagggacgc cggcattctc ccattcaaga cggcctgac ctccggcgag    420
gattacaacg tgctgcagca ggccgtgcag cagcttaggt catgggtggc ttgcgaccac    480
aggacgaggg aggcttacgc tgagcagcag gagaagacaa gccaggccga ggaggctgct    540
aagaaggctg ctaacgaggt gaagccggag gatgcgaagt ctctggagag gcacgagagg    600
gtgctgacga agctgaggaa gcaggagagg aggctggaga ggatgaagag ccacgcgcag    660
ttcagcctgg acgagatgga ctgcacgggc tactccctgt gcatgggcgc taattacctg    720
```

```
aaggactact gcctggagaa ggagggcagg ggccttaggc ttaccctgaa gaatagcacg   780
atggctggca gctactacgt ttccgtgggc gacggccagc acgctggcat gaagaatccg   840
ggcaccccag ctggcggctc tccagagaag ggcaggagga ggaatatcct gttcgacttc   900
accgtgagag agtgcggcga caattacctg ttcaggtacg acgagaacgg caagaggccg   960
agggctggcg ttgttaagga gccaaggttc tgctgtgggc ggaagggcaa cagcgtggag  1020
ctttacctgg cgatgccgat caacatcgag aacagcatga ggaacatctt cgtgtgggcaag  1080
cagaagtccg gcaagcactc cgctttcacc cggcagtggc caaaggaggt cgagggcctt  1140
gacgagctta gggacgctgt ggtgctgggc gttgacatcg gcatcaacag ggcggctttc  1200
tgcgccgctc tgaagacttc caggttcgag aatggcctgc cggccgatgt gcaggttatg  1260
gataccacct gcgatgcgct gaccgagaag ggccaggagt acaggcagct gaggaaggac  1320
gccacctgcc ttgcttggct gatcaggacg accaggaggt tcaaggctga cccaggtaac  1380
aagcacaacc agatcaagga gaaggacgtg gagaggttcg acagcgccga cggcgcttac  1440
aggaggtaca tggacgccat cgcggagatg ccgagcgatc cacttcaggt ctgggaggct  1500
gccaggatca ccggctacgg cgagtgggct aaggagattt tcgccaggtt caaccactac  1560
aagcatgagc acgcctgctg cgccgtgtct ctttctcttt ccgacaggct ggtgtggtgc  1620
aggctcatcg acaggatctt gtctctgaag aagtgcctcc acttcggcgg ctacgagtcc  1680
aagcacagga agggcttctg caagtccctg tacaggctga ggcacaacgc caggaacgac  1740
gtgaggaaga agctggccag gttcatcgtg gatgccgccg ttgacgcggg cgcttctgtt  1800
attgcgatgg agaagctgcc gtcctctggc ggcaagcagt caaaggacga caacaggatc  1860
tgggacctga tggccccgaa caccctggct actactgtgt gcctgatggc caaggtggag  1920
ggcatcggct tcgtccaggt cgatccagag ttcacctccc agtgggtgtt cgagcagagg  1980
gtgattggcg atagggaggg caggatcgtg agctgcctgg atgctgaggg cgtgagaggg  2040
gattacgacg ctgacgagaa cgccgcgaag aacatcgcct ggctggctct taccaggag  2100
gctgagccat tctgcatggc gttcgagaag aggaacggcg tggtggagcc gaagggcctt  2160
aggttcgaca tcccggagga gcctaccagg gagcaggatg agtcggacca ggacttcaag  2220
aagaggctgg aggagaggga caagctgatc gagaggctga ggcgaaggc ggataggatg  2280
caggctatcg ttcagaggct tttcggcgac aggaggccgt gggatgcttt cgctgacagg  2340
attcctgagg gcaagagcaa gaggctgttc aggcacaggg acggcctggt tctgaacaag  2400
ccgttcaagg gcctgtgcgg ctccgagaat agcggccaga aggcttctgc taggaacagc  2460
cgctga                                                              2466

SEQ ID NO: 27            moltype = RNA   length = 36
FEATURE                  Location/Qualifiers
source                   1..36
                         mol_type = other RNA
                         organism = synthetic construct
SEQUENCE: 27
agtgcaatag ttacagaata gtaattatat tcgcac                                36

SEQ ID NO: 28            moltype = RNA   length = 34
FEATURE                  Location/Qualifiers
source                   1..34
                         mol_type = other RNA
                         organism = synthetic construct
SEQUENCE: 28
tgttggtatc tagtaaaatc tagagccgtt gaca                                  34

SEQ ID NO: 29            moltype = RNA   length = 30
FEATURE                  Location/Qualifiers
source                   1..30
                         mol_type = other RNA
                         organism = synthetic construct
SEQUENCE: 29
gtgtcaacgc atcctctata gttgaggaag                                       30

SEQ ID NO: 30            moltype = RNA   length = 36
FEATURE                  Location/Qualifiers
source                   1..36
                         mol_type = other RNA
                         organism = synthetic construct
SEQUENCE: 30
gtgttgtcct cattataata tgatggacag agacac                                36

SEQ ID NO: 31            moltype = RNA   length = 36
FEATURE                  Location/Qualifiers
source                   1..36
                         mol_type = other RNA
                         organism = synthetic construct
SEQUENCE: 31
ctaactgtgt gagcttctaa ccgaagctaa tgacac                                36

SEQ ID NO: 32            moltype = RNA   length = 36
FEATURE                  Location/Qualifiers
source                   1..36
                         mol_type = other RNA
                         organism = synthetic construct
SEQUENCE: 32
gtgtcaacgc atcctctata gttgaggaag caacac                                36
```

-continued

```
SEQ ID NO: 33              moltype = RNA   length = 37
FEATURE                    Location/Qualifiers
source                     1..37
                           mol_type = other RNA
                           organism = synthetic construct
SEQUENCE: 33
gtgtcaacgg ctctagattt tactagatac caacaca                                37

SEQ ID NO: 34              moltype = RNA   length = 36
FEATURE                    Location/Qualifiers
source                     1..36
                           mol_type = other RNA
                           organism = synthetic construct
SEQUENCE: 34
gtgttagtat cttgtagaat caggagctat tgacac                                 36

SEQ ID NO: 35              moltype = RNA   length = 36
FEATURE                    Location/Qualifiers
source                     1..36
                           mol_type = other RNA
                           organism = synthetic construct
SEQUENCE: 35
gtgtcaatga tccattttat ggatccacac tgagat                                 36

SEQ ID NO: 36              moltype = RNA   length = 36
FEATURE                    Location/Qualifiers
source                     1..36
                           mol_type = other RNA
                           organism = synthetic construct
SEQUENCE: 36
gtgtcattag ccaccccatt cagaggaggc ctacac                                 36

SEQ ID NO: 37              moltype = RNA   length = 36
FEATURE                    Location/Qualifiers
source                     1..36
                           mol_type = other RNA
                           organism = synthetic construct
SEQUENCE: 37
gtgttggtat ctagtaaaat ctagagccgt tgacac                                 36

SEQ ID NO: 38              moltype = RNA   length = 36
FEATURE                    Location/Qualifiers
source                     1..36
                           mol_type = other RNA
                           organism = synthetic construct
SEQUENCE: 38
atagtcgagg gtgtaataat atgcacctaa tgcgac                                 36

SEQ ID NO: 39              moltype = RNA   length = 36
FEATURE                    Location/Qualifiers
source                     1..36
                           mol_type = other RNA
                           organism = synthetic construct
SEQUENCE: 39
gtgtaggcct cctctgaatg gggtggctaa tgacac                                 36

SEQ ID NO: 40              moltype = DNA   length = 36
FEATURE                    Location/Qualifiers
source                     1..36
                           mol_type = other DNA
                           organism = synthetic construct
SEQUENCE: 40
agtgcaatag ttacagaata gtaattatat tcgcac                                 36

SEQ ID NO: 41              moltype = DNA   length = 34
FEATURE                    Location/Qualifiers
source                     1..34
                           mol_type = other DNA
                           organism = synthetic construct
SEQUENCE: 41
tgttggtatc tagtaaaatc tagagccgtt gaca                                   34

SEQ ID NO: 42              moltype = DNA   length = 30
FEATURE                    Location/Qualifiers
source                     1..30
                           mol_type = other DNA
                           organism = synthetic construct
SEQUENCE: 42
gtgtcaacgc atcctctata gttgaggaag                                        30
```

```
SEQ ID NO: 43           moltype = DNA   length = 36
FEATURE                 Location/Qualifiers
source                  1..36
                        mol_type = other DNA
                        organism = synthetic construct
SEQUENCE: 43
gtgttgtcct cattataata tgatggacag agacac                              36

SEQ ID NO: 44           moltype = DNA   length = 36
FEATURE                 Location/Qualifiers
source                  1..36
                        mol_type = other DNA
                        organism = synthetic construct
SEQUENCE: 44
ctaactgtgt gagcttctaa ccgaagctaa tgacac                              36

SEQ ID NO: 45           moltype = DNA   length = 36
FEATURE                 Location/Qualifiers
source                  1..36
                        mol_type = other DNA
                        organism = synthetic construct
SEQUENCE: 45
gtgtcaacgc atcctctata gttgaggaag caacac                              36

SEQ ID NO: 46           moltype = DNA   length = 37
FEATURE                 Location/Qualifiers
source                  1..37
                        mol_type = other DNA
                        organism = synthetic construct
SEQUENCE: 46
gtgtcaacgg ctctagattt tactagatac caacaca                             37

SEQ ID NO: 47           moltype = DNA   length = 36
FEATURE                 Location/Qualifiers
source                  1..36
                        mol_type = other DNA
                        organism = synthetic construct
SEQUENCE: 47
gtgttagtat cttgtagaat caggagctat tgacac                              36

SEQ ID NO: 48           moltype = DNA   length = 36
FEATURE                 Location/Qualifiers
source                  1..36
                        mol_type = other DNA
                        organism = synthetic construct
SEQUENCE: 48
gtgtcaatga tccattttat ggatccacac tgagat                              36

SEQ ID NO: 49           moltype = DNA   length = 36
FEATURE                 Location/Qualifiers
source                  1..36
                        mol_type = other DNA
                        organism = synthetic construct
SEQUENCE: 49
gtgtcattag ccaccccatt cagaggaggc ctacac                              36

SEQ ID NO: 50           moltype = DNA   length = 36
FEATURE                 Location/Qualifiers
source                  1..36
                        mol_type = other DNA
                        organism = synthetic construct
SEQUENCE: 50
gtgttggtat ctagtaaaat ctagagccgt tgacac                              36

SEQ ID NO: 51           moltype = DNA   length = 36
FEATURE                 Location/Qualifiers
source                  1..36
                        mol_type = other DNA
                        organism = synthetic construct
SEQUENCE: 51
atagtcgagg gtgtaataat atgcacctaa tgcgac                              36

SEQ ID NO: 52           moltype = DNA   length = 36
FEATURE                 Location/Qualifiers
source                  1..36
                        mol_type = other DNA
                        organism = synthetic construct
```

```
SEQUENCE: 52
gtgtaggcct cctctgaatg gggtggctaa tgacac                              36

SEQ ID NO: 53          moltype = AA  length = 11
FEATURE                Location/Qualifiers
source                 1..11
                       mol_type = protein
                       organism = synthetic construct
SEQUENCE: 53
SRADPKKKRK V                                                          11

SEQ ID NO: 54          moltype = AA  length = 925
FEATURE                Location/Qualifiers
source                 1..925
                       mol_type = protein
                       organism = synthetic construct
SEQUENCE: 54
MGPKKKRKVM DYKDHDGDYK DHDIDYKDDD DKMSNYKNIK FKLVPFSQKD LINMQLNVNL     60
HQQCYREFVE QFCVLCNIPF PGLSKDQIEQ KRKQLNLSED DEKDINYIKD LVKNKNNIGN     120
SIYAFFTGTK KEMPSRKTDL TPLYRLLKAN ILPFSLLKGR ENYKKSIFQT VINQTLEKFK     180
SYFKCNESVE NNFKLSLNKD SNEEQVLNES EMKDLQNLFE NLSKNQSFSF FNFNKNWFSK     240
DKIKTKLLNN ETNKIKSLSS EEIDLILSYK DKLYSNEFDL ISMFVEFNLQ KQKAESLKSQ     300
ADLNLFKNNN YSFRIGSNYE NFNLTQNNKD ILLEINSSMG EKITFKIIPH KKTQIWNLEK     360
NNVKITSGEN LGNYKSVDVI KMKRPADIKA KLLKTSELNI EIKNNQIYCN FIYEYKCSDH     420
GVYFFHCSGN KKPDEKNENI LKERERTFSF IDLGLFPMYS ISTFKYNNKS NDGEILVKSG     480
SGNEKLDFGS AFKIHSIQIG KNSTNLNKIK QLLEKLKDLK TYLKFSKSIS SFDENSYQRQ     540
LKTGVEISEL NSLSFQKISE IKSINLGFNE SFNKEYFLKL IENQTFTQKE LLLLNCKIKD     600
LPFKILYKEYS NIKNSRIFKF NKEDDLICDG YYWLQVIDEI INIKKSLTYF NSKPSEKGNK     660
SKFIFLKDFN YKNNFANNYA KIAASRLKKY CLEHKVDVCV FEKNLNNFLQ SKDNDKKTNK     720
TLINWANRNL FEKIKLALEE HDICVSEVDG KHSSQLDPQT MNWGARDNLN GNGNKEKIFF     780
ERNGQIIQQN ADLSASEVLA KRFFTRYEDI VHIYIDQKIK DDKTILKLVK GKVRVESYLK     840
KTINSCYAIV DENGFLKPIS KKDYNKFQEL PSKPRTDIKS NEMYRHGSKW YHFQQHREFQ     900
QDLLARGREL KKIASRADPK KKRKV                                           925

SEQ ID NO: 55          moltype = AA  length = 978
FEATURE                Location/Qualifiers
source                 1..978
                       mol_type = protein
                       organism = synthetic construct
SEQUENCE: 55
MGPKKKRKVM DYKDHDGDYK DHDIDYKDDD DKMNKTDTQN NEQINKPTQL LNNKDIELTV     60
KTVKSATVKV DNNSKKELFG LFNYFTSVAS GIKDKVYNLQ SDEKTAPIFN DYVKQPQRGR     120
SAATTLFTKL DAEKTYTSQH SFPGKWRDSG IFPLYNKESE KYDLSTHGYH YSANAEIHTQ     180
LDSHDECNKE CEKEYAALRD EVNNYKYEFT LQFKAENAEK FYNFVEKLTL MGWRYDATFR     240
SFFELHMHPK LKTGETTYRA TYKLPSGKSK RYSFFRDDIA DEIAKNPEFW PMLESSNAIS     300
WINSNNLLSR KKDKANYSST SLIKSQIRLY LGNNGVPFTA REHDGRIYFS FRLPAINGEK     360
GRMVEIPCSY KKVFNGKARK SCYLGGLTIE KTDAGKHIFK YSVNNKKPQV AELNECFLRL     420
VVRNREYFNN VVAGKITDIN TDHFDFYVDL PLNVKEDPIH DLSSTEVFGK NGLRSYYSSA     480
YPEIKNLGSQ IETGKNLTCP ITKTHNIMGI DLGQRNPFAY CIKDNTGKLI AQGHMDGSKN     540
ETYKKYINFG KESTSVSHLI KETRSYLHGD PEAISKELYN EVAGFCNNPV SYEEYLKYLD     600
SKKFLINKED LSKNAMHLLR QKDHNWIGRD WLWYISKQYK KHNENRMQDA DWRQTLYWID     660
SLYRYIDVMK SFHNFGSFYD KNLKKKVNGT VVGFCKTVHD QINNNNDDMF KKFTNELMSV     720
IREHKVSVVA LEKMDSMLGD KSRHTFENRN YNLWPVGQLK TFMEGKLESF NVALIEIDER     780
NTSQVCKENW SYREADDLYY VTDGESHKVH ADENAANNIV DRCISRHTNM FSLHMVNPKD     840
DYYVPTCIWD TTEESGKRVR GFLTKLYKNS DVVFTKKGDK LVKSKTSVKE LKKLVGKTKE     900
KRGQYWYRFE GKSWINEADR DTIILNAKKI SRERDNGEQS TDTRSQNVTV SVLDVCETAE     960
KKKLVLVSRA DPKKKRKV                                                   978

SEQ ID NO: 56          moltype = AA  length = 943
FEATURE                Location/Qualifiers
source                 1..943
                       mol_type = protein
                       organism = synthetic construct
SEQUENCE: 56
MGPKKKRKVM DYKDHDGDYK DHDIDYKDDD DKMSIKSIK SIKTKVVKNN ELKLIELSTW      60
CSSICEQLER YIFILGGKQI HDRDGVVVLD GAVERKIYCK KDKSLIAACE VVYKHFTDKS     120
SKSRTFGSWF LGGKSEGDNT NKGRKSTKEK TEKQIAKQIA DKKELTDSLQ LLWDKKLLPF     180
PIDNKGYDFI NTPRAKSYKW AITKTIHAKI KSYNEQCVET KKEYDALNAE INTYKTILFS     240
GYSEKDIDDL QKFVDICEAN NHRINYKFIS FLKRKDLNFD EQTGKYRKEG KWIQHKNGKE     300
VKSKYSMKDE IVEALYKYKS LTKNDVSVLC NEHQKEDEMG KVVHYNMKRY SDLLFRKKNK     360
KEIPSYTKIS LATSKIELGL NNVKYNVEQV EDKLIWTICD QTGKDIQFVT VYTRKKEDNR     420
TNGKKGAGFY KGKHHQLEDL KIVPVGDIGT YDISFKVNGK RPFTGTLKEP NIICRGGKVF     480
VQMPININID KTLNDARKKV LYAYRETYSG SVNGKKQKMI KIENSKIAES LKSLGRDAIV     540
LGVDLGLRGL ATAVVSHNGK NETVKSSQYI KGDIVEWEKY RVPNDNIREV KKYIFLTKKS     600
YTATTEEYTE FYKECSKPEQ DYLDSLKTYK DKNVKLNELK YTKNAWVSK MFEDVSKMFE      660
TLKQDRLKYY DIFNMPYWAA SLKNYMSLMK SYNYVGVDIK VSKEYMSKYQ SLYNNIKEDY     720
AKKIGSYIVQ LAVAKNCDII VLEELKSNLG SVDRKSKRDN EMSLMWNCGR IKTHVENMAK     780
```

-continued

```
DYGMFIDEVP EYGTSQVYHK TGNYGYRDED NREIFWYEDN KDVAYIHADE NAAINIAKRF   840
LSQHTDNSSF SVILKGDAYY LNIASNSKRM RAAALKTFGD LNKPFKINAN DKNGNLYKKT   900
RIFKSDSRWI GVNDKDLYIE HIKSLRNLRV RQSRADPKKK RKV                     943

SEQ ID NO: 57          moltype = AA  length = 670
FEATURE                Location/Qualifiers
source                 1..670
                       mol_type = protein
                       organism = synthetic construct
SEQUENCE: 57
MGPKKKRKVM DYKDHDGDYK DHDIDYKDDD DKMPSFTKVD EDKIVLKLGN NYIPYGLSRI   60
SEDKMLWSFS SPQKKKLSII TNHRRVGKGK HFYLEGLEIA DITKGDGDKT SPSGKYTISF   120
SINGKQDVKG ELKEPSFGLR NGNVYMFLPI SIKQTDVFES RVEMRRLLSM AYQPTTVEDL   180
ILDDVETKQK TVKQGKKEVN TTNIAIQEAI KKHGRLLKVM GVDLGLRNFA FAIKNYDGHH   240
DTLLRQLYSE SDLNEKQRYT TLANDLSKVG NHIKFAAVFY GANDTEENTK MFDAECTDAE   300
SRTHLEWLRK AKKSGVLLKD LRKDKTWIVS IKYTELRNRL HALKFGRMKS YDYRNNLYWA   360
ATIKKFISLS ASFYGVGRPS RGKKDVRELK KKHTFFSTYQ DLYNNVKEDY AKKVANLVVM   420
TAKENNVDII VVENLTGHCG SKDYKTRAEN EMSIMWNHGR IKTFIDCIAN ANGMLLAEVS   480
EFETSQVYHE TRNYGYRDKK MKEILWYMDS EGNVQYAHAE VNAAINIADR FLSQHTNLFS   540
FPVCKSKKDE NVYEIDIAEG KELEGQDEVK KAKKPKGGKR LNGAVVKTFG STKIMFNGIV   600
DKNKKGQIKT KTRVYNIDGE WGGKTQKDEY VDKIRKVVDA MSPEEKAKVK AALKKCFSSS   660
RADPKKKRKV                                                         670

SEQ ID NO: 58          moltype = AA  length = 970
FEATURE                Location/Qualifiers
source                 1..970
                       mol_type = protein
                       organism = synthetic construct
SEQUENCE: 58
MGPKKKRKVM DYKDHDGDYK DHDIDYKDDD DKMTKELSGV RVIELKTDLR KDQFWDRYER   60
CFKTYHALYN EVPCWGLDWV EQKTQNQTSR ELGCERVDLT AQRKALYERT DRTISYEQFS   120
NCLKALWLGL LNCQQGNHMY TKLFEGAIQT DQMTAEDWAV LTEYVADPKS HNSQFLFRVS   180
NTLKHIGFFS RPPFTATLFA PERKAITKDV MSDLKGWIEM KRMTEESYAA EEVQIQQMKA   240
EVPVRIRQSL LRFFDTCIGL NLIGHFDERV HHYLRDCIIP ALQQRTIPTE HFYLKSNRKD   300
VGQKHIDFSL DIKFYELLAE MPELWNTLET SEDDLIPKPL ILKHLHLLEA IMSHRAHRKT   360
AAYAFVGEAD YHRFYYLLGG NYTKHLISAT GSELPDRVIW DNDKDVLMRN GRKVERLYVK   420
VGDRKENFNF EVYTIAMNTK GLRGHRSTLK PTSYLQDLQI WSNPEGESTY LNFVRKGTER   480
SAICKEPVLV YRNGAFFLRL SMSVEGMRAS EEHIALQYYL SAAATGSDLS KDTEKTVERF   540
NLIQGKTYKV MSVDLGIRSP FAWAVTESTI TGVANPSQIL NSGEMEIADD PDYTELFYAY   600
KNLGHLIGQV KSSSKGKGLK ADSHLVDMIH TVQRFFADYK VAGQRRSQIF EQFSKDPDPL   660
YQMDQMMKRY ENNLESVKKD FSFLINILFK YVTLQFGALR NRRRSYLSQN QMADQKFDQD   720
FKWLNILEQR KRVTRSLSYL GTDNSRIPIC LEQQKLDYNG CKDNFLKQLA SKIVRIAHQN   780
DCCLIVLEDL EGYGKTLNQR DENFLTAFWS PKRVKDAIIN AAQWYGIGVV TVSEAQTSQV   840
HHESGRIGYR KGRDLFFLTP DGQIESVPSD INAAKNIGHR FFSRHTDLHQ VYLKGSDEGA   900
KRMKGCLLYQ FGSLEAARTH LTGTGPTWYL DGVEWIDKTE RNLRRDLLKQ RVEIEKMPFS   960
RADPKKKRKV                                                         970

SEQ ID NO: 59          moltype = AA  length = 943
FEATURE                Location/Qualifiers
source                 1..943
                       mol_type = protein
                       organism = synthetic construct
SEQUENCE: 59
MGPKKKRKVM DYKDHDGDYK DHDIDYKDDD DKMKSIKSIK SIKTKVVKNN ELKLIELSTW   60
CSSICEQLER YIFILGGKQI HDRDGVVVLD GAVERKIYCK KDKSLIAACE VVYKHFTDKS   120
SKSRTFGSWF LGGKSEGDNT NKGRKSTKEK TEKQIAKQIA DKKELTDSLQ LLWDKKLLPF   180
PIDNKGYDFI NTPRAKSYKW AITKTIHAKI KSYNEQCVET KKEYDALNAE INTYKTILFS   240
GYSEKDIDDL QKFVDICEAN NHRINYKFIS FLKRKDLNFD EQTGKYRKEG KWIQHKNGKE   300
VKSKYSMKDE IVEALYKYKS LTKNDVSVLC NEHQKEDEMG KVVHYNMKRY SDLLFRKKNK   360
KEIPSYTKIS LATSKIELGL NNVKYNVEQV EDKLIWTICD QTGKDIQFVT VYTRKKEDNR   420
TNGKKGAGFY KGKHHQLEDL KIVPVGDIGT YDISFKVNGK RPFTGTLKEP NIICRGGKVF   480
VQMPININID KTLNDARKKV LYAYRETYSG SVNGKKQKMI KIENSKIAES LKSLGRDAIV   540
LGVDLGLRGL ATAVVSHNGK NETVKSSQYI KGDIVEWEKY RVFNDNIREV KKYIFLTKKS   600
YTATTEEYTE FYKECSKPEQ DYLDSLKTYK DKNVKLNELK YTKNAWSVSK MFEDVSKMFE   660
TLKQDRLKYY DIFNMPYWAA SLKNYMSLMK SYNYVGVDIK VSKEYMSKYQ SLYNNIKEDY   720
AKKIGSYIVQ LAVAKNCDII VLEELKSNLG SVDRKSKRDN EMSLMWNCGR IKTHVENMAK   780
DYGMFIDEVP EYGTSQVYHK TGNYGYRDED NREIFWYEDN KDVAYIHADE NAAINIAKRF   840
LSQHTDNSSF SVILKGDAYY LNIASNSKRM RAAALKTFGD LNKPFKINAN DKNGNLYKKT   900
RIFKSDSRWI GVNDKDLYIE HIKSLRNLRV RQSRADPKKK RKV                     943

SEQ ID NO: 60          moltype = AA  length = 978
FEATURE                Location/Qualifiers
source                 1..978
                       mol_type = protein
                       organism = synthetic construct
SEQUENCE: 60
MGPKKKRKVM DYKDHDGDYK DHDIDYKDDD DKMNKTDTQN NEQINKPTQL LNNKDIELTV   60
KTVKSATVKV DNNSKKELFG LFNYFTSVAS GIKDKVYNLQ SDEKTAPIFN DYVKQPQRGR   120
SAATTLFTKL DAEKTYTSQH SFPGKWRDSG IFPLYNKESE KYDLSTHGYH YSANAEIHTQ   180
```

```
LDSHDECNKE CEKEYAALRD EVNNYKYEFT LQFKAENAEK FYNFVEKLTL MGWRYDATFR   240
SFFELHMHPK LKTGETTYRA TYKLPSGKSK RYSFFRDDIA DEIAKNPEFW PMLESSNAIS   300
WINSNNLLSR KKDKANYSST SLIKSQIRLY LGNNGVPFTA REHDGRIYFS FRLPAINGEK   360
GRMVEIPCSY KKVFNGKARK SCYLGGLTIE KTDAGKHIFK YSVNNKKPQV AELNECFLRL   420
VVRNREYFNN VVAGKITDIN TDHFDFYVDL PLNVKEDPIH DLSSTEVFGK NGLRSYYSSA   480
YPEIKNLGSQ IETGKNLTCP ITKTHNIMGI DLGQRNPFAY CIKDNTGKLI AQGHMDGSKN   540
ETYKKYINFG KESTSVSHLI KETRSYLHGD PEAISKELYN EVAGFCNNPV SYEEYLKYLD   600
SKKFLINKED LSKNAMHLLR QKDHNWIGRD WLWYISKQYK KHNENRMQDA DWRQTLYWID   660
SLYRYIDVMK SFHNFGSFYD KNLKKKVNGT VVGFCKTVHD QINNNNDDMF KKFTNELMSV   720
IREHKVSVVA LEKMDSMLGD KSRHTFENRN YNLWPVGQLK TFMEGKLESF NVALIEIDER   780
NTSQVCKENW SYREADDLYY VTDGESHKVH ADENAANNIV DRCISRHTNM FSLHMVNPKD   840
DYYVPTCIWD TTEESGKRVR GFLTKLYKNS DVVFTKKGDK LVKSKTSVKE LKKLVGKTKE   900
KRGQYWRFE GKSWINEADR DTIILNAKKI SRERDNGEQS TDTRSQNVTV SVLDVCETAE    960
KKKLVLVSRA DPKKKRKV                                                 978
```

```
SEQ ID NO: 61            moltype = AA   length = 939
FEATURE                  Location/Qualifiers
source                   1..939
                         mol_type = protein
                         organism = synthetic construct
SEQUENCE: 61
MGPKKKRKVM DYKDHDGDYK DHDIDYKDDD DKMKKPKQNI EETDLKITTP KTATIKATNL   60
DDKMRLFTFF NGFTTVCSKV KDDIYNFGQN EDTLPVYTDY IKASQRARMC ATTLATKSEC   120
DFAKKYGEHF PLPHYNQEGM NYTTHQHTYS VNSAVHTQLD SLNECDKLTN GEYVKLKKTV   180
DELEEKLTEE HGKEPLDFLV KFVDEQILLG WRFDGKFRLF FEVAMLPELK NGNIIYKKAY   240
KTSGGKGRRY SFYNPSVADN ISKNPTVWNL LSDVKAVDYI SLSNSLLRKK PHAQYTNTTL   300
NRAQVRPTFG NNGVPFSISV SDDDYVYIRF RLPKKDGEEK GQEISVKCSY KTSYKGKRSK   360
TLRKSCYLGN LKIEENGKGK YICKYNINGR ETTTAELNEC FLRVRINNNR WFNKYLNGTL   420
TKEDGVLKSE YFDFYFDLCL NVHQKSIHGL TNSEIFGGKG KSIRSYYSTS YPEVKNLDGQ   480
KNIKTDFGCY VDKPHNIMGI DLGQRNPFAW AVLDQNGRVK DVGHLDGAEN DTYKDYLTFS   540
NRCKDVKNLI LQSRDYLYGD DEAIDETLFD SVVQFVNSNI TLNKYKSYLD EKKSLINKES   600
LEKNRLYELK KKDHGWFVRD CLWFLTKEYH RINSERKTHS DWRYTLYWVD AIHRFIDVNK   660
SFNSLGSYYD KKQSKSINGI QKDFCRSYWN QIDNLNEDTL KKFVFELLPV IKKNNVCLIA   720
IEELKSMLGD DDKRAEDNRL YNLWPVGQLK TFLEGKLLPY NVAVMEVSEQ NTSQIVNGQW   780
SYREGDDLYY VKNNDNNTMC KTHADENAAI NIALRAYSHH TNLYSIYMIN PIDDYYVPSC   840
IWNNKDEGSK RIRGFLTKTY GTSDVVFIKK NEKLVKSDVS IKDVKRIVKN IGNEKNKKSE   900
IWYRMNDIEW IDEGSRDIII NTIKSKVRSR ADPKKKRKV                          939
```

```
SEQ ID NO: 62            moltype = AA   length = 930
FEATURE                  Location/Qualifiers
source                   1..930
                         mol_type = protein
                         organism = synthetic construct
SEQUENCE: 62
MGPKKKRKVM DYKDHDGDYK DHDIDYKDDD DKMTDKSISF KQFSQILNVL YKCIVISGKG   60
RGLTSIILGQ PQCKDSLTSA DWGNLETLSA KDELTPAEVK DITKDLMYRA SNTLVSIGFR   120
NRSPFKLTLT SGERYAVVEN VHRSLKSWVE VDKITRENYL NEEIALSDAF NNIDETLLPT   180
LKEFFDACMN ENIIHHFDAR VYAYTRDCVI PALVAGLEIK DHFYIDGRDK AKRDYSLQGY   240
AELLKGFPKL WQGVDPEILA KLYILEAQMD HKKHRPCAAY AFIGEDSYSR VQYLLGNNYT   300
SFSPYALGVD LDDVTCGDDA EADTQFPKNK VIQFSQGKKV TKLSLTVSRG KEDTNKYSFD   360
VPLADKYSNG SYKPSPYFSD LSVWVSEIGM LMEFTRKGER VQAIVKEPSL IYRKGAFYVR   420
LNMGVIQDTS PEINDLYWYL SSGAPMSMTD RSKASETPKN TERLESIKGK SYRFLGIDLG   480
LRSPFAWAVG EASISGVINK PTIIATGDYT TARDTRYDTL FFALKNAGKV IGVTKSLANG   540
KDASFNGLMG TITAAREYLA HYSGVATHKV AAIQAFCQDD NPLETLKGLL KSYNNDLVTL   600
KKDPRFIGGI LLRYARLLKG ELVTSRKMHL REHSVESKFG QEYMWLNILE REKRVCRSLS   660
YLGLGNDRDS VIMGNLTTPY NHCKENLLKQ LAARIVSLAV ENKCHVIVME SLGGSNKSMN   720
TRGQNFLEAF WSPQKIKDTI INAAAWHGIM VAEVSESQTS QVCFETGTFG HRDRASLYFL   780
DKNGDLQETH ADMNAAKNLV ERFTTRHTNL RQVNMDSLPK EGPDKTPKKS PSKKKMEKAK   840
MDNPEDQSKR LKGFLTVKFG NVKAAQEYFA SRKPEQSYSG KKDEAIYWYL DGDEWITKKE   900
KESRVSVIEG LVGLKEVAVS RADPKKKRKV                                    930
```

```
SEQ ID NO: 63            moltype = AA   length = 864
FEATURE                  Location/Qualifiers
source                   1..864
                         mol_type = protein
                         organism = synthetic construct
SEQUENCE: 63
MGPKKKRKVM DYKDHDGDYK DHDIDYKDDD DKMAFQSKRR IVGNLVKEQC LKAVDGKVIL   60
TDQEKRELIK RYELHLEPYK WLLRLFLSGY EGRDDGFYEE LGNTNLDKEK FFEVTAGLRD   120
ALLRQSGSSR ALKSSMLGKC PPSAAVGKAA KHIQALRDAG ILPFKTGLTS GEDYNVLQQA   180
VQQLRSWVAC DHRTREAYAE QQEKTSQAEE AAKKAVNEVK PEDAKSLERH ERALTKLRKQ   240
ERRLERMRSH AQFSLDEMDC TGYSLCMGAN YLKDYCLEKE GRGLRLTLKN STMAGSYYVS   300
VGDGQHAGMK NPGTPAGGSP EKGRRRNILF DFAVEKCGDN YLFRYDENGK RPRAGVVKEP   360
RFCWRRKGNS VELYLAMPIN IENSMRNIFV GKQKSGKHSA FTRQWPKEVE GLDELRDAVV   420
LGVDIGINRA AFCAALKTSR FENGLPADVQ VMDTTCDALT EKGQEYRQLR KDATCLAWLI   480
RTTRRFKADP GNKHNQIKEK DVERFDSADG AYRRYMDAIA EMPSDPLQVW EAARITGYGE   540
WAKEIFARFN HYKHEHACCT VSLSLSDRLV WCRLIDRILS LKKCLHFGGY ESKHRKGFCK   600
SLYRLRHNAR NDVRKKLARF VVDAAVDAGA SVIAMEKLPS SGGKQSRDDN RIWDLMAPNT   660
LATTVCLMAK VEGIGFVQVD PEFTSQWVFE QRVIGDREGR IVSCLDAEGV RRDYDADENA   720
```

```
AKNIAWLALT REAEPFCMAF EKRNGVVEPK GFRFDIPEEP TREQDESNQD FKKRLEERDK 780
LIERLQAKSD RMRAIVRRLF GDRRPWDAFA DRIPEGKSKR LFRHRDGLVL NKPFKGLCGS 840
ENSEQKASAR NSRSRADPKK KRKV                                        864
```

```
SEQ ID NO: 64              moltype = AA   length = 997
FEATURE                    Location/Qualifiers
source                     1..997
                           mol_type = protein
                           organism = synthetic construct
SEQUENCE: 64
MGPKKKRKVM DYKDHDGDYK DHDIDYKDDD DKMDTDTELS DEVELSDEVE LSDEVELSDE 60
VELTVKKVKT TTVKVDNNFK KELFELFNHF TSVASGIKDR LYDLQFDENT ASIFKGYIKE 120
AKRGHGAATT VFTKLNPKKI YSGKKSFPRD YRDRGIFPFY NKESGKYDLS TCGYHYSANA 180
EIHTQLNSHD ECNKQCEKEY AALEKERNKY KHEFTRQFKA ENVEKFSNFV EKLTLMGWRY 240
DATFRNFFEL HMHPKLKTSE TTYRATYKLP SGKSKRYSFS RDDIADEIAK NPEFWPMLES 300
SNAVSWINSN NLLSRKKEKA NYSSTSLIKS QIRLYLGDNG VPFTAREHDG RIYFSFRLPS 360
INGEKGRNVE IPCSYKKVFN GKARKSCYLG GLTIENTGGS KHIFKYSVNN KKPQVAELNE 420
CFLRLVVRNH GYFNKMVNGK LTDKDGKLHA DYFDFCIDLP LNVKEDPIHD LTYQEINGVK 480
ANPEKNIEKK VGLLGFYQSA YPEIKNLGSQ IETGKNLTCP ITKTHNIMGI DLGQRNPFAY 540
CIKDNNGKFI AKDHMDGSKN ETYKKYINFG KESTSVSHLI KETRSYLHGD PEAISKELYN 600
EVSGLCNSPL SYEEYLKYLD SKKFLINKED LNKNAMHLLR QKDHNWIGRD WLWYISKQYK 660
KHNENRMQDA DWRQTLYWID SLYRYIDVMK SFHNFGSFYD KNLKKKVNGT AVGFCKTIYD 720
QINNNNKDMF KKFTNELIPI IRKHKVSVVA LEKMESMLGD KSRNTFENRN HNLWPVGQLK 780
TFIENKLDGF NVIVVEVDER NTSQMCDGNW SYREADDLYY VKDGELREVH ADENAANNIV 840
DRCISRHTNI FSLYMTNPMD DYYVPACIWD RSENGKRGRG FLTKMYKNSD VVFTKKDDKL 900
VKSKMSVKEL KKLVDKTKEK RGQYWYLFEG KSWINAADRD TIISNAKKLF RERDGGEQST 960
DTRSQNVTVS VLDVCETVEK KKLVLVSRAD PKKKRKV                          997
```

```
SEQ ID NO: 65              moltype = AA   length = 1044
FEATURE                    Location/Qualifiers
source                     1..1044
                           mol_type = protein
                           organism = synthetic construct
SEQUENCE: 65
MGPKKKRKVM DYKDHDGDYK DHDIDYKDDD DKMSTEVDVK TINLKIAKKG GVYPILEQSI 60
KENCKSNDLL EFFMVLNRLQ TYYIESNEEI LVDFPKKYDE LFDIVKNNDS SVTREYFDSL 120
CDKYITEVCA NGFVNNVYIA HNKNQELNWA ETSNDRKIKS NKTFMFGKIK GLIRDKFGRE 180
ELSDKDATKQ LCEDIFNLFI LNNANIELDE KYNIIKDELI QIWNERNKEF IHIKDITLLF 240
RQWGILPTYD NITHNCELKA IIAEPVRRFK SWLECNSEAN KNYDTEREKC TKYMDVMDSD 300
LTVEFSKMVT ELGNPFGAND KNIYKYFNQK FLLFFKQVVQ PKFVNGEPLD ESNGSYSGEI 360
KINSAGKVEN YSIAVSVIDT IKKYPTIWSD RSWGESVIST VAKIDPQYGI DDITDDMQVS 420
PFYLFYGYFT AYNYIQQHKR NAKYTPISKD SLPSLYLGNN YIPFKIDCEN VDDDRFYITI 480
KNMNNLKLNV LYRKPKLKFA KTKEKTKRNK CYFDNLKITN TNNNFKFEYN INGDPNRSVV 540
AYLKEPVIRY NNRKDYFYLS ATISKDVETD SELTSACWSK ISNDTARRVN AEQYFNDNGV 600
NIVGIDLGMN PIIAYSVLHY KNNEFIDLNI TGKIADKDKH PNLNYKRMYE KRSEIKKLKT 660
LIKMIPDYVN SDSNIFEGDN NVFKQLDKKS KGRFRSSEYM GYYDKLNVDG KFISELEIVK 720
KVVNTKHYKN DTEKNNDIMR VYKGNKKNII KKEIDTHRHQ IHSIKDMNRR SDESNLCYVV 780
DMVSYIDDFK KLVTSYNKIG EDYNNPIKPL SDPMLFSKSK LYEYRQNIRD NFLKDICYQM 840
VKIAKQYNAV LVHEHFEQRK GGIDRVNNIL MALFTPNDII KKLKCVAKRE GVLVFNTNKN 900
HTSQYVYNKN TVGYRDSNNK HNLYYIEDET TRKLGVVDSD INASKNIAAR PFNKPLYAIK 960
VKNYDDGLFL SDYNNKYVLY KKDGDKYVAI GDTYRIDKKK IKQGSVTLYL HNGYYVDGEY 1020
KNNYIENIKK LVLSRADPKK KRKV                                        1044
```

```
SEQ ID NO: 66              moltype = AA   length = 864
FEATURE                    Location/Qualifiers
source                     1..864
                           mol_type = protein
                           organism = synthetic construct
SEQUENCE: 66
MGPKKKRKVM DYKDHDGDYK DHDIDYKDDD DKMAFQSKRR IVGNFVKEQC LKAVDGKVIL 60
TDQEKRELIK RYELHLEPHK WLLRLFLSGY EGRDDGFYEE LGNTNLDKEK FFEVTAGLRD 120
ALLRQSGSSR ALKSSMLGKC PPSAAVGKAA KHIQTLRDAG ILPFKTGLTS GEDYNVLQQA 180
VQQLRSWVAC DHRTREAYAE QQEKTSQAEE AAKKAANEVK PEDAKSLERH ERVLTKLRKQ 240
ERRLERMKSH AQFSLDEMDC TGYSLCMGAN YLKDYCLEKE GRGLRLTLKN STMAGSYYVS 300
VGDGQHAGMK NPGTPAGGSP EKGRRRNILF DFTVEKCGDN YLFRYDENGK RPRAGVVKEP 360
RFCWRRKGNS VELYLAMPIN IENSMRNIFV GKQKSGKHSA FTRQWPKEVE GLDELRDAVV 420
LGVDIGINRA AFCAALKTSR FENGLPADVQ VMDTTCDALT EKGQEYRQLR KDATCLAWLI 480
RTTRRFKADP GNKHNQIKEK DVERFDSADG AYRRYMDAIA EMPSDPLQVW EAARITGYGE 540
WAKEIFARFN HYKHEHACCA VSLSLSDRLV WCRLIDRILS LKKCLHFGGY ESKHRKGFCK 600
SLYRLRHNAR NDVRKKLARF IVDAAVDAGA SVIAMEKLPS SGGKQSKDDN RIWDLMAPNT 660
LATTVCLMAK VEGIGFVQVD PEFTSQWVFE QRVIGDREGR IVSCLDAEGV RRDYDADENA 720
AKNIAWLALT REAEPFCMAF EKRNGVVEPK GLRFDIPEEP TREQDESDQD FKKRLEERDK 780
LIERLQAKAD RMQAIVQRLF GDRRPWDAFA DRIPEGKSKR LFRHRDGLVL NKPFKGLCGS 840
ENSGQKASAR NSRSRADPKK KRKV                                        864
```

```
SEQ ID NO: 67              moltype = DNA   length = 2805
FEATURE                    Location/Qualifiers
```

-continued

```
source                  1..2805
                        mol_type = other DNA
                        organism = synthetic construct
SEQUENCE: 67
atgggaccca agaagaagcg taaggtcatg gactataaag atcacgacgg cgattataaa  60
gaccacgaca ttgattacaa ggacgatgat gacaagatga gcaactacaa aaacattaag  120
ttcaagttgg ttccgttcag tcaaaaggat cttataaaca tgcagctaaa cgtgaatctc  180
caccagcagt gttatagaga gttcgtggag cagttctgcg tcctctgtaa tatccccttt  240
cctgggctta gtaaagatca aattgagcag aagcggaaac aattaaatct gtctgaagac  300
gacgagaagg acatcaacta catcaaggac cttgtaaaaa ataagaataa catcggcaat  360
tcaatctatg cttttttcac tggtacaaag aaggaaatgc caagcagaaa gactgattta  420
acacctcttt accgcctcct taaggctaac atactgccct ttagcctcct caaagggcga  480
gagaactata agaaaagcat attccaaact gttattaacc agacactgga aaagtttaag  540
tcatatttca agtgcaatga atcagttgaa aacaacttca aactgtctct gaacaaggac  600
tcaaatgagg agcaagtcct gaatgaaagc gaaatgaaag acctccaaaa cctattcgag  660
aatttgtcta aaaatcagtc ttttttccttc ttcaacttca ataagaactg gttctccaag  720
gacaagatca agacgaaact cctcaataac gagaccaaca aaattaagtc gttgtcatct  780
gaagagatcg acctgatcct tagttataag gataagttgt actccaacga atttgatctg  840
atttccatgt tcgtggagtt caacttacag aaacagaagg cggagtcctt gaaatcacag  900
gcggacttga acctcttcaa gaacaacaac tattcttttc ggattggaag caactatgaa  960
aactttaatc taactcaaaa taacaaggac atcctgctgg aaatcaattc ttcaatgggt  1020
gagaagatta cctttaagat cattccgcat aagaaaaccc agatctggaa tttagagaag  1080
aataatgtta agataaacttc gggcgagaac ctggggaatt acaaatcggt ggacgtcatc  1140
aagatgaagc ggccagcaga cattaaggca aagctgctga agacgtcaga gctgaatatc  1200
gagatcaaga acaaccaaat ctattgcaac ttcatttatg agtacaagtg ctccgatcat  1260
ggcgtgtact tctttcactg cagtggcaac aagaagccag atgagaagaa tgagaatatt  1320
ctaaaggaga gggagaggac ctttagtttc attgatctcg gtcttttttcc gatgtattcc  1380
atctccacat ttaagtacaa taataagagc aatgatggtg agatcctagt caagtcggga  1440
tctgggaacg agaaactcga cttcggctct gccttcaaaa ttcattcaat ccagattgga  1500
aagaacagca caaatctcaa caaaattaag caacttcttg agaagctgaa agacctgaag  1560
acctacctca aattctctaa gagcataagc agcttcgacg agaacagcta ccagcgccag  1620
cttaaaacgg gagtggagat cagcgagctg aacagcctgt cgttccaaaa aatatcagaa  1680
attaagtcca ttaatctcgg cttcaatgaa tccttcaata aagagtattt tctaaagctg  1740
atcgaaaccc aaacattcac gcagaaggag ttactactgt taaactgcaa gatcaaagac  1800
ctcttcaaaa ttctctacaa agaatattct aacatcaaaa acagtcgcat atttaaattc  1860
aataaagaag atgatctcat ctgtgacggg tactactggc tgcaggtcat tgatgaaata  1920
atcaatatta aaaagtcgct tacttacttc aacagcaagc cgtcggagaa ggggaacaaa  1980
agtaagttta ttttcttgaa ggattttaac tacaaaaata attttgcaaa caactacgcg  2040
aaaatcgctg cgtcacgtct caaaaaatat tgtttggagc acaaggttga cgtgtgtgtt  2100
tttgagaaga acctcaacaa ctttctgcaa agcaaggaca acgataaaaa gacaaataag  2160
accttgatta attgggcgaa ccgcaatctt tttgagaaaa ttaaattggc gctggaagag  2220
catgacatct gcgtgagtga ggttgatggt aagcattcgt cccagctgga cccgcaaacc  2280
atgaactggg gcgctagaga taatcttaat ggaaatggta acaaagaaaa gatctttttt  2340
gaaaggaacg ggcagataat acaacagaac gccgacctca gtgcttctga agtcctcgca  2400
aaacgattct tcaccaggta cgaggacatc gtgcacatct acattgacca gaaaataaag  2460
gatgacaaaa cgatccttaa gttggtgaag ggtaaggtgc gcgtagaatc ttatctgaag  2520
aagactataa attcctgcta cgccatagta gatgaaaatg gcttccttaa acctatatct  2580
aagaaagact acaacaagtt ccaggagctg ccgtccaagc ctcgcacaga tattaagtcg  2640
aatgagatgt acagacatgg cagcaagtgg tatcacttcc agcaacatag ggagtttcag  2700
caggacctgt tggcacgggg cagagagctg aagaagatag ccggcagcgg cagtaaaagg  2760
ccagccgcca ccaagaaagc cggccaggct aaaaagaaga agtga  2805

SEQ ID NO: 68          moltype = DNA   length = 2964
FEATURE                Location/Qualifiers
source                 1..2964
                       mol_type = other DNA
                       organism = synthetic construct
SEQUENCE: 68
atgggcccaa agaagaagag gaaggtgatg gactacaagg accacgacgg cgactacaag  60
gatcacgaca tcgactacaa ggacgacgac gacaagatga acaagacgga cacccagaac  120
aacgagcaga tcaacaagcc gacgcagctg ctcaacaaca aggacattga gctgacggtg  180
aagaccgtga agtccgcgac cgtgaaggtg gacaacaaca gcaagaagga gctgttcggc  240
ctgttcaact acttcaccag cgtcgcctcc ggcatcaaga caaggtgta caacctgcag  300
tccgatgaga agaccgcccc gatcttcaac gactacgtga agcagccgca gcgcggcgag  360
tctgctgcta ctactctgtt caccaagctg gacgcggaga agacctacac ctctcagcac  420
tccttcccg gcaagtggag ggattccggc atcttcccgc tgtacaacaa gggtccgag  480
aagtacgacc tgtccaccca cggctaccac tactccgcta cgccgagat ccacacccag  540
ctggacagcc atgacgagtg caacaaggag tgcgagaagg agtacgccgc cctagggac  600
gaggtgaaca actacaagta cgagttcacg cttcagttca agccgagaa cgccgagaag  660
ttctacaact cgtggagaa gctgacgctg atgggctgga ggtacgacgc tacgttcagg  720
tctttcttcg agctgcacat gcacccaaag ctcaagaccg gcgagacaac gtacagggcc  780
acctacagc tgccgtccgg caagtctaag aggtacagct tcttcaggga cgacatcgcc  840
gacgagattg ccaagaaccc agagttctgg ccaatgctgg agtcctccaa cgccatctcc  900
tggatcaact caacaacct gctcagcagg aagaaggaca agccaacta ctcctcaacc  960
tccctcatca agtcccagat cgcctgtac ctgggcaaca acggcgtgcc attcaccgct  1020
agggagcacg atggcaggat ttacttcagc ttcaggctcc cggccatcaa cggcgagaag  1080
ggcaggatgt cgagatcccc atgcagctac aagaaggtgt caacggcaa ggccaggaag  1140
agctgctacc ttgcggcct taccatcgag aagaccacg ctggcaagca tatcttcaag  1200
tactccgtga acaacaagaa gccgcaggtg gccgagctga cgagtgctt cctgaggctg  1260
```

```
gttgtgagga atagggagta cttcaacaac gtggtggccg gcaagatcac cgacatcaac   1320
accgatcact tcgacttcta cgtcgatctg ccgctgaacg tgaaggagga cccgatccat   1380
gatctgagca gcacggaggt gttcggcaag aatggcctga ggtcctacta ctcctccgcc   1440
tacccagaga ttaagaacct gggctcccag atcgagacgg gcaagaacct gacctgcccg   1500
atcaccaaga cacacaacat catgggccatc gaccttggac agcgcaacc attcgcctac   1560
tgcattaagg acaacaccgg caagctcatc gcccagggcc atatggacgg ctctaagaac   1620
gagacgtaca agaagtacat caatttcggc aaggagtcca cctccgtctc ccaccttatt   1680
aaggagacga ggtcctacct gcacggcgat ccagaggcta tctccaagga gctgtacaat   1740
gaggtcgccg gcttctgcaa caacccggtt tcctacgagg agtaccttaa gtacctggac   1800
tccaagaagt tcctgatcaa caaggaggac ctgtccaaga atgccatgca cctgctgagg   1860
cagaaggacc acaactggat cggcagggac tggcctgtgg acatcagcaa gcagtacaag   1920
aagcacaacg agaacaggat gcaggacgcc gactggaggc agactctgta ctggatcgac   1980
agcctgtaca ggtacatcga tgtgatgaag tccttccaca acttcggcag cttctacgac   2040
aagaacctga agaagaaggt gaacggcacc gtggtgggct tctgcaagac ggttcacgac   2100
cagatcaaca acaacaacga tgacatgttc aagaagttca ccaacgagct gatgagcgtg   2160
atcagggagc acaaggtgag cgtggtggcg cttgagaaga tggacagcat gctgggcgac   2220
aagtcaaggc acacgttcga gaacaggaac tacaacctgt ggccggtggg ccagctgaag   2280
acattcatgg agggcaagct ggagtccttc aacgtggccc tctgcgagat cgatgagagg   2340
aacaccagcc aggtgtgcaa ggagaactgg tcctacaggg aggcggatga cctgtactac   2400
gtgacggacg gcgagtccca caaggtgcat gctgacgaga acgcggccaa caacatcgtg   2460
gacaggtgca tttccaggca caccaacatg ttcagcctgc acatggtgaa cccaaaggac   2520
gactactacg tgccgacctg catttgggac accacggagg atccggccaa gagggttagg   2580
ggcttcctga ccaagctcta caagaactcc gacgtggtct tcaccaagaa gggcgacaag   2640
ctggtgaaga gcaagacctc cgtgaaggag ctgaagaagc tggtgggcaa gaccaaggag   2700
aagaggggc agtactggta caggttcgag ggcaagagct ggatcaacga ggccgacagg   2760
gacaccatca tcctgaacgc caagaagatc tccaggaaga agcaacggc cgagcagtcc   2820
acggatacca ggagccagaa cgtgaccgtg tccgtgctgg acgtgtgcga gacagctgag   2880
aagaagaagc tggtccttgt gggcagcggc agcaagaggc cagctgctac taagaaggcc   2940
ggccaggcta agaagaagaa gtga                                          2964
```

SEQ ID NO: 69         moltype = DNA  length = 2859
FEATURE               Location/Qualifiers
source                1..2859
                      mol_type = other DNA
                      organism = synthetic construct
SEQUENCE: 69

```
atgggcccaa agaagaagag gaaggtgatg gactacaagg accacgacgg ggactacaag    60
gatcacgaca tcgactacaa ggacgacgac gacaagatga gagcataaa gagcataaa    120
agcatcaaga cgaaggtggt gaagaacaac gagctgaagc tgatagagct gagtacgtgg   180
tgcagcagca tatgcgagca gctggagagg tacatattca tcctgggggg gaaacaaata   240
cacgacaggg acggcgtggt ggtgctggac ggcgcagtgg agaggaagat ctactgtaag   300
aaagacaaga gcttgatcgc ggcctgcgag gtggtgtaca aacacttcac ggacaagagt   360
tccaagtcca ggacgtttgg gtcctggttc ctgggtggga agtccgaggg cgacaacacc   420
aataagggaa ggaagagtac caaggagaag accgagaaac aaatcgcaaa gcagatcgcc   480
gacaagaagg agctgacgga ctccctgcaa ctgctgtggg acaagaagct gctgccattc   540
ccgatagaca acaagggcta cgacttcata aataccccaa gggccaaatc ctacaagtgg   600
gcgatcacga aaccatcca cgctaaaatc aaatcctaca acgagcaatg cgtggagacc   660
aaaaaagagt acgacgccct gaacgccgag atcaacacct acaagaccat cctgttctcc   720
ggctactccg aaaaggacat cgacgacctg cagaagttcg tggacatctg cgaggcaaac   780
aaccacagga taaactacaa attcatatcc tttctcaaga ggaaagacct caatttcgac   840
gaacaaacag ggaaatacag gaaggaaggc aagtggattc aacacaagaa cggaaaggaa   900
gtcaagagca agtacagcat gaaggacgag atagtggagg ccctgtacaa gtacaagtcc   960
ctgacaaaga cgacgtgag cgtgctgtgc aacgagcacc aaaaagagga cgaaatgggc   1020
aaggtggtgc attacaacat gaagaggtac tctgatctgc tgttcagaaa gaagaacaaa   1080
aaggaaatcc cgagttacac gaaaatcagc ctggccaaca gcgcagattga gttggggttg   1140
aacaatgtga agtacaacgt gggagcaggtg gaggacaaac tgatatggac catatgcgac   1200
cagaccggca aggacatcca gttcgtgacc gtgtacacca ggaagaagga ggataacagg   1260
accaatggca agaaaggggc ggggttctac aagggcaaac accaccagct ggaggacctg   1320
aaaatagtgc cggtgggcga catagggacc tacgacatca gcttcaaggt gaacgggaag   1380
aggccgttca cagggaccct gaaggaaccg aacatcatat gcaggggcgg gaaggtgttc   1440
gtccagatgc cgatcaacat caacatcgac aaaaccctga acgacgcgag gaagaaggtg   1500
ctgtacgcat accgggagac gtactccggc tccgtgaacg gcaagaagca gaagatgata   1560
aagatcgaaa actccaaaat cgccgagtcc ctgaaatccc tggggcggga cgcgatagtc   1620
ctgggcgtgg atctggggct gaggggctg gctacagcgg tggtgagcca caacgggaaa   1680
aacgagacag tgaagagcag ccaatacatt aagggcgaca ttgtggagtg ggagaagtac   1740
agggtgttta acgacaacat cagggaggtg aagaagtaca tattcctgac caagaagtcc   1800
tataccgcca cgacggagga atacaccgag ttttacaagg agtgctcgaa gccggagcag   1860
gactatctgg actccctcaa gacctataaa gacaagaacg tgaaactcaa cgagctgaaa   1920
tacacgaaga acgcgtggtc cgtgagcaag atgttcggac acgtctccaa aatgttcgaa   1980
accctcaagc aggacaggct gaagtactac gacatcttca acatgccata ctgggccgcc   2040
tccctgaaga actacatgag cctgatgaag tcctacaact acgtcggcgt ggacataaag   2100
gtgtccaaga aatacatgag caagtaccag tccctgtaca caacatcaa ggaagattac   2160
gccaaaaaaa tcggctccta catcgtgcag ctcgccgtgg ccaagaattg cgacatcatt   2220
gtcctggagg agctgaaatc caacctcggc tccgtgaca ggagagcaa gagagacaac   2280
gagatgtccc tgatgtggaa ctgcggccgc atcaagaccc acgtcgagaa catggcaaag   2340
gactatggga tgttcattga cgaagtcccg gagtatggca cgtcccaggt gtatcacaag   2400
accggcaact acggctacag ggatgaagac aacaggggaga tattttggta cgaggacaac   2460
aaggacgtgg cctacataca cgccgacgag aacgcggcaa tcaacatagc caaaagattc   2520
ctgtcccaac ataccgacaa ctccagcttc agcgttatc tgaagggcga cgcctactac   2580
```

-continued

```
ctgaacatcg cctccaactc caaacgcatg agggccgccg cactgaaaac cttcggcgac  2640
ctcaacaaac cgttcaaaat caacgccaac gacaaaaacg gaaacctgta caagaagacc  2700
aggatcttca agtccgactc cagatggata ggcgtcaacg acaaagacct ctacatagaa  2760
cacatcaaat ccctccgcaa cctccgcgtg cgccagggtt ccggttccaa gcgcccagcc  2820
gccaccaaga aggccggcca agccaagaag aaaaaatga                          2859

SEQ ID NO: 70             moltype = DNA   length = 2040
FEATURE                   Location/Qualifiers
source                    1..2040
                          mol_type = other DNA
                          organism = synthetic construct
SEQUENCE: 70
atgggcccaa agaagaagag gaaggtgatg gactacaagg accacgacgg ggactacaag  60
gatcacgaca tcgactacaa ggacgacgac gacaagatgc cgagcttcac gaaggtggac  120
gaggacaaaa tagtgctgaa gctggggaac aactacatcc cgtatgggct gagcaggatt  180
tccgaggaca agatgctgtg gagcttttcc tccccgcaaa aaaagaagct gtctataata  240
acgaaccaca ggcgcgtcgg caagggcaaa cacttttacc tggaaggctt ggagatcgcc  300
gacattacca agggcgacgg cgacaagacg tccccaagcg gcaaatatac catctccttc  360
agcatcaacg gcaagcagga cgtgaagggc gagctgaagg agccgagctt cggcctgagg  420
aacggcaacg tgtacatgtt tctgccaatc tccataaagc agaccgacgt gttcgagtcc  480
agggtggaga tgaggaggtt gctgtctatg gcctaccagc caaccaccgt ggaggatctg  540
atcctggatg acgtggagac caagcagaag accgtgaagc ggggtgaagaa ggaggtgaac  600
accacgaaca tagcgattca agaggcgatc aagaagcacg gccgcctgct gaaggtgatg  660
ggcgtggacc tggggctgag gaacttcgcg tttgccatca agaactacga cggccaccac  720
gacaccctgt tgcggcagtt gtactccgag tccgacctga acgagaaaca gaggtacact  780
accctggcca atgacttgtc caaggtgggc aaccacatca agttcgccgc ggtcttctac  840
ggcgccaacg acaccgagga gaacaccaag atgttcgacg ccgagtgcac ggacgccgag  900
tccaggaccc acctggagtg gctgaggaaa gccaagaagt ccggtgtgct gctcaaggac  960
ctgaggaagg acaagacgtg gatcgtgtcg atcaagtata ccgagttgag gaataggctg  1020
cacgcactga aattcggcag gatgaagagc tacgactaca ggaataacct ctactgggcc  1080
gcgaccatta agaagttcat ctcgctctcc gccagcttct acggcgtggg gaggcctagc  1140
cgcggcaaga aggacgtgag gggagttgaag aaaaagcaca ccttcttctc cacgtatcag  1200
gacctgtaca acaacgtgaa ggaagattac gcgaagaagg tggcgaatct ggtggtgatg  1260
acggccaaag agaataacgt ggacatcatc gtggtggaga acctgaccgg gcactgcggg  1320
tccaaggact acaagaccag ggccgagaac gagatgagta taatgtggaa tcatggcagc  1380
atcaagacgt tcatcgattg catcgccaat gccaacggca tgttgttggc cgaggtgtcc  1440
gagttcgaga cgtcccaggt gtaccacgag acgaggaact acgggtacag ggacaagaag  1500
atgaaagaga tcctgtggta catggactcc gaggggaacg tgcagtatgc ccacgccgag  1560
gtgaacgccg ccatcaatat cgccgacagg ttcctgtccc agcacaccac cctgttctcc  1620
ttcccagtgt gcaagtccaa gaaagacgag aatgtgtacg agatcgacat cgccgagggg  1680
aaagaacttg agggccagga tgaagtgaag aaggccaaga accgaaagg cgggaagagg  1740
ctgaacgggg cggtggtgaa gacgtttggg agtaccaaga tcatgttcaa cgggatagtg  1800
gacaaaaaca agaaggggca gataaagacg aagacgaggc tgtacaacat agacggggag  1860
tggggggggga agacccagaa agacgagtac gtggacaaaa tcaggaaggt ggtggacgcg  1920
atgagcccgg aggagaaagc gaaggtgaag gcggcgctga agaagtgctt cagcagcggc  1980
agcgggagca agaggccagc cgcaacgaag aaggcggggc aggcgaagaa gaagaagtga  2040

SEQ ID NO: 71             moltype = DNA   length = 2940
FEATURE                   Location/Qualifiers
source                    1..2940
                          mol_type = other DNA
                          organism = synthetic construct
SEQUENCE: 71
atgggcccaa agaagaagag gaaggtgatg gactacaagg accacgacgg ggactacaag  60
gatcacgaca tcgactacaa ggacgacgac gacaagatga cgaaggagga gagcgggggtg  120
agggtgatga agctgaagac cgacctgagg aaggaccagt tctgggacag gtacgagagg  180
tgcttcaaaa cgtaccacgc cctgtacaac gaggtgccat gctggggcct ggactggggtg  240
gagcagaaaa cacaaaacca aacctccagg gaactcggct cgagagagt ggatctgacc  300
gcccaacgca aggcactgta tgagaggacg gaccgcacca tctcttacga gcagtttagc  360
aactgcctca aagccctctg gctggggctg ctgaactgtc agcagggaa ccacatgtat  420
accaaactgt ttgaaggcgc gatacaaacc gaccagatga ccgcggagga ctgggccgtg  480
ctgaccgaat acgtcgcgga cccgaagagc cacaactccc agttcctgtt cagggtgtcc  540
aacaccctga agcacatcgg cttcttctcc aggccgccat ttaccgccac cctgtttgcc  600
ccagagagga aggctattac caaggacgtc atgtccgacc tgaaaggatg gattgagatg  660
aagaggatga ccgaggagtc ttacgccgcg gaggaggtgc aaattcaaca aatgaaggcc  720
gaggtgccgg tgcgcatcag gcagagcctg ctgaggtttt tcgacacctg cataggcctg  780
aacctcatcg gacacttcga cgaaagggtg caccactacc tgagggactg cataataccg  840
gcgctgcagc aaaggacgat accgaccgaa cacttctacc tgaaatccaa ccgcaaagac  900
gtgggccgaa aacacataga cttcagcctc gacatcaaat tctacgagct gctggctagc  960
atgccagagc tgtggaacac cctggagacc tccgaggacg acctcatccc caaaccgctg  1020
atcctcaaac acctgcacct gctggaagcc atcatgtccc acagggccca caggaagacc  1080
gccgcctacc ccttcgtggg cgaagccgac taccacaggt tctactacct gctcggcggc  1140
aactacacaa aacacctcat cagcgccacc ggctccgaac tgccggacag ggtgatctgg  1200
gacaacgaca aggacgttct gatgaggaac gcgatggaag tggagaggct gtacgtgaaa  1260
gtgggcgaca ggaaagagaa cttcaacttc gaggtgtaca cgatagcgat gaacacgaag  1320
ggcctgaggg gcacaggag cacgctgaag ccgacgagtt acttgcaaga cctgcagatt  1380
tggagcaacc cggagggcga gagcaccctat ctgaacttcg tgaggaaggg cacagagagg  1440
agcgcgattt gcaaagagcc agtgctggtg tacaggaacg gcgccttttt tcttaggctg  1500
agcatgagcg tggaagggat gcggggcctcc gaggagcata tcgcgctgca gtactaccctt  1560
```

-continued

```
tctgccgcgg ccacgggctc tgacttgtct aaggacacgg agaagaccgt ggagaggttc    1620
aacttgatcc aggggaagac atacaaggtg atgtccgtgg atctcggcat ccgctccccc    1680
ttcgcctggg ctgtgaccga gtcgaccatc acgggcgtgg ccaacccgag ccagatcctg    1740
aacagcggcg agatggaaat cgcggacgac ccggactata ccgagctgtt ctacgcttac    1800
aaaaacctgg ggcacctgat cggccaggtc aagagcagca gcaaggggaa aggcctcaaa    1860
gcggacagcc acctggtgga tatgattcat acggtgcaaa ggttcttcgc cgactacaaa    1920
gtggccgggc agaggaggag tcaaatattc gagcagttca gcaaggaccc ggacccgttg    1980
taccagatgg accagatgat gaagaggtac gagaacaacc tggagagtgt gaagaaggat    2040
tttagtttcc tgataaacat cctgttcaag tacgtgaccc tgcagttcgg agccctgagg    2100
aaccggagaa ggagctacct gtcacaaaac cagatggccg accagaagtt cgaccaagac    2160
ttcaagtggc tgaacatcct cgagcagagg aagcgcgtga ccaggagcct gagctacctg    2220
ggcacagaca acagcaggat tcctatctgc ctggaacagc agaagctgga ctacaacggc    2280
tgcaaggaca acttcctgaa gcagctggcc tccaagatcg tgaggatcgc ccaccaaaac    2340
gactgctgcc tgattgtgct ggaggacctt gagggg tacg ggaaaacgct caaccagagg    2400
gacgagaact tcctcacggc cttctggtct ccgaagaggg tgaaggatgc catcatcaac    2460
gccgcccaat ggtacggcat tggggtggtg acggtgagcg aggcccagac gtcccaggtg    2520
caccacgagt ccggcaggat cggctataga aagggg aggg acctgttttt cctgacccca    2580
gacggccaga tcgagtccgt gccgagcgac attaacgccg ccaagaacat tggccatagg    2640
ttcttttcca ggcacaccga cctgcaccag gtgtacctga agggttccga cgagggcgcc    2700
aagaggatga aaggctgcct tctgtatcag ttcgggagtc tggaggcggc ccgcacgcac    2760
cttaccggaa caggaccgac ctggtacttg gacgcgcgtgg agtggataga caagacggag    2820
aggaacctga ggagggacct gctgaagcag agggtgaaa tcgagaaaat gccattcggc    2880
agcgggagca agagccggc cgctactaag aaggcgggc aggccaagaa gaagaagtga    2940
```

```
SEQ ID NO: 72            moltype = DNA   length = 2859
FEATURE                  Location/Qualifiers
source                   1..2859
                         mol_type = other DNA
                         organism = synthetic construct
SEQUENCE: 72
atgggaccaa agaagaaacg gaaggttatg gattacaaag atcacgatgg cgactataaa      60
gaccatgaca tcgattacaa ggacgacgat gacaagatga gagcatcaa gtcgatcaag     120
agcattaaga ctaaagttgt caagaacaac gagctgaagc tcatcgagct gtctacctgg     180
tgtagctcga tctgcgagca gctcgagagg tacatcttca tactgggcgg caagcagatt     240
cacgatcgcg atggcgtcgt tgttctcgat ggcgccgttg agcggaagat ctactgcaag     300
aaagacaaga gcctgatcgc cgcctgcgag gttgtctata agcactttac cgacaaatcg     360
tccaagtctc gcacctttgg cagctggttc ttgggcggca agagcgaggg cgataacaca     420
aacaagggca gaaagtccac caaagagaag actgagaagc agatcgctaa gcagatcgcc     480
gacaagaagg agctgaccga ttctctgcag ctcttgtggg ataagaaact gctgccattt     540
ccgattgata caagggtta cgacttcatc aacacaccac gcgccaagag ctacaagtgg     600
gctatcacca agaccattca cgcgaagatc aagagctaca acgagcagtg tgtcgagacg     660
aagaaagagt acgacgcgct gaacgccgag attaatacat acaagactat tctgttcagc     720
ggttactccg agaaagacat tgacgacctc cagaagttcg tcgtatatatg tgaggccaac     780
aaccacagga tcaactacaa gtttatcagc ttcttgaagc gcaaagattt gaatttcgac     840
gagcagacag gcaagtaccg caaggagggc aagtggattc agcacaagaa cggcaaagaa     900
gttaagtcca agtacagcat gaaagatgag atcgtcgagg cgctgtacaa gtacaagagc     960
ctgactaaga acgacgtgag cgtgtctctgc aacgagcatc agaaggagga cgagatgggt    1020
aaggtggtcc actacaacat gaagcgctat tccgacctgc tgttccgcaa gaagaacaag    1080
aaggaaatac caagctacac aaagatctca cttgccacgt ccaagatcga gctggggcctc    1140
aacaacgtca agtacaacgt tgagcaggtt gaggacaagc tcatctggac aatctgcgat    1200
caaacaggca aagacatcca gttcgtgact gtctatacaa gaaagaaaga agataacgag    1260
accaatggca agaagggagc gggcttctat aagggcaagc atcaccagct cgaagacctg    1320
aagatcgtgc ctgtgggaga cattggcact tacgacatca gcttcaaggt caacggcaag    1380
cgtccgttta ctggcactct gaaagagccg aacatcattt gccgcggagg caaagtgttc    1440
gtgcagatgc aattaatat caatatcgat aagactctca acgacgctcg gaagaaggtt    1500
ctgtacgcct acagggagac gtacagcggc tccgtcaacg gtaagaaaca gaagatgatc    1560
aagatcgaga acagcaagat cgccgagtca ctcaagtctt tgggcagaga cgccattgtg    1620
cttggcgtgg atttgggctt gcgcggactt gctaccgccg ttgtgagcca aacggaaag    1680
aacgagactg ttaagagcag ccagtacatc aagggcgata ttgtggagtg ggagaagtac    1740
agggtgttca atgataatat cagggaggtc tcttcttgac caagaaaagc                1800
tacaccgcca caacggaaga atacacagaa ttttacaagg agtgcagcaa gcctgagcaa    1860
gactatcttg atagcctcaa gacgtacaag gacaagaacg ttaaactgaa cgaactgaag    1920
tacaccaaga acgcctggag cgtctcgaag atgtttgaag acgtttccaa gatgttcgag    1980
acactcaagc aagacaggct caagtactac gacatcttca atatgccgta ttgggcgaac    2040
tcactgaaga actatatgtc gttgatgaag tcgtacaatt atgttggcgt ggacatcaag    2100
gtcagcaaag agtacatgtc caagtaccaa tccctgtata caacatcaa ggaggactac    2160
gccaagaaga tcggcagcta cattgtccag ctggctgtgg caaagaactg cgacatcatc    2220
gtgcttgaag agctgaagtc gaacctgggc agcgttgatc gcaaagtcaa gcgcgataac    2280
gaaatgagcc tcatgtggaa ctgcgggcaga atcaagactc atgtcgagaa catggccaaa    2340
gattacggca tgtttatcga tgaggtgcct gagtatggta cttcgcaggt gtaccataag    2400
accggtaact acggctatag agatgaagac aacaggaaa tcttctggta cgaggataac    2460
aaagacgtcg cctacatcca tgcagacgag aatgctgcca tcaacatcgc gaagcgcttt    2520
ctgtcacagc ataccgacaa cagctcattc tccgtgattc tcaagggcga cgcttactac    2580
ctgaacatcg cttccaactc caagagaatg cgcgccgacg ctctcaagac ctttggagat    2640
ctcaacaagc ctttcaagat taatgccaac gataagaacg gcaacctcta caagaagaca    2700
agaatcttca gtcagactc tcgctggatc ggcgtgaacg acaaggacct ctacatcgag    2760
cacatcaaga gcctgagaaa tctcagggtg aggcagggct cgggcagcaa gaggccggct    2820
gccactaaga aggcaggtca agcgaagaag aagaagtga                           2859
```

-continued

```
SEQ ID NO: 73            moltype = DNA   length = 2964
FEATURE                  Location/Qualifiers
source                   1..2964
                         mol_type = other DNA
                         organism = synthetic construct
SEQUENCE: 73
atgggcccaa agaagaagag gaaggtgatg gactacaagg accacgacgg cgactacaag    60
gatcacgaca tcgactacaa ggacgacgac gacaagatga acaagacgga cacccagaac   120
aacgagcaga tcaacaagcc gacgcagctg ctcaacaaca aggacattga gctgacggtg   180
aagaccgtga agtccgcgac cgtgaaggtg gacaacaaca gcaagaagga gctgttcggc   240
ctgttcaact acttcaccag cgtcgcctcc ggcatcaagg acaaggtgta caacctgcag   300
tccgatgaga agaccgcccc gatcttcaac gactacgtga agcagccgca gcgcggcagg   360
tctgctgcta ctactctgtt caccaagctg gacgcggaga agacctacac ctctcagcac   420
tccttccccg gcaagtggag ggattccggc atcttcccgc tgtacaacaa ggagtccgag   480
aagtacgacc tgtccaccca cggctaccac tactccgcta acgccgagat ccacacccag   540
ctggacagcc atgacgagtg caacaaggag tgcgagaagg agtacgccgc ccttagggac   600
gaggtgaaca actacaagta cgagttcacg cttcagttca aggccgagaa cgccgagaag   660
ttctacaact tcgtggagaa gctgacgctg atgggctgga ggtacgacgc tacgttcggc   720
tctttcttcg agctgcacat gcacccaaag ctcaagaccg gcgagacaac gtacagggcc   780
acctacaagc tgccgtccgg caagtctaag aggtacagct tcttcaggga cgacatcgcc   840
gacgagattg ccaagaaccc agagttctgg ccaatgctgg agtcctccaa cgccatcctc   900
tggatcaact ccaacaacct gctcagcagg aagaaggaca aggccaacta ctcctcaacc   960
tccctcatca agtcccagat tcgcctgtac ctgggcaaca acggcgtgcc attcaccgct  1020
agggagcacg atggcaggat ttacttcagc ttcaggctcc cggccatcaa cggcgagaag  1080
ggcaggatgg tcgagatccc catgcagcta caagaaggtgt tcaacggcaa ggccaggaag  1140
agctgctacc ttggcggcct taccatcgag aagaccgacg ctggcaagca tatcttcaag  1200
tactccgtga acaacaagaa gccgcaggtg gccgagctga acgagtgctt cctgaggctg  1260
gttgtgagga ataggggagta cttcaacaac gtggtggccg gcaagatcac cgacatcaac  1320
accgatcact tcgacttcta cgtcgatctg ccgctgaacg tgaaggagga cccgatccat  1380
gatctgacga gcacggaggt gttcggcaag aatggcctga ggtcctacta ctcctccgcc  1440
tacccagaga ttaagaacct gggctcccag atcgagaccg gcaagaacct cacctgcccg  1500
atcaccaaga cacacaacat catgggcatc gaccttggcc agcgcaaccc attcgcctac  1560
tgcattaagg acaacaccgg caagctcatc gcccagggcc atatggacgg ctctaagaac  1620
gagacctaca agagtacat caatttcggc aaggagagca cctcagtctc ccacctcatc  1680
aaggagacca ggagctacct gcacggcgat ccagaggcta tcagcaagga gctgtacaac  1740
gaggtggccg gcttctgcaa caacccggtt tcctacgagg agtacctcaa gtacctggac  1800
agcaagaagt tcctgatcaa caaggaggac ctgtccaaga acgcgatgca tctcctgagg  1860
cagaaggatc acaactggat cggcagggac tggctgtggt acatcagcaa gcagtacaag  1920
aagcacaacg agaacaggat gcaggacgcc gactggaggc agactctta ctggatcgac  1980
agcctgtacc gctacatcga cgtgatgaag tccttccaca acttcggctc cttctacgac  2040
aagaacctga agaagaaggt gaacggcacg gtggtgggct tctgcaagac ggttcacgac  2100
cagatcaata caacaacga cgacatgttc aagaagttca cgaatgagct gatgagcgtg  2160
atcagggagc acaaggtgag cgtggtcgcc cttgagaaga tggactccat gctcggcgac  2220
aagtccaggc acaccttcga gaacaggaac tacaacctgt ggccggttgg ccagctgaag  2280
acgttcatgg agggcaagct ggagtccttc aacgtggcgc ttatcgagat cgacgagagg  2340
aacacctccc aggtttgcaa ggagaactgg agctacaggg aggcggacga cctgtactac  2400
gtgacggacg gcgagtccca caaggtgcat gctgacgaga acgccgcaa caacatcgtc  2460
gacaggtgca tcagcaggca caccaacatg ttcagcctgc acatggtgaa cccgaaggac  2520
gactactacg tgccgacctg catctgggac accaccgagg agagcggcaa gagggttagg  2580
ggcttcctca cgaagctcta caagaactcc gacgttgtct tcaccaagaa gggcgacaag  2640
ctggtgaagt ccaagaccag cgtgaaggag ctgaagaagc tggttggcaa gaccaaggag  2700
aagaggggcc agtactggta caggttcgag ggcaagagct ggatcaacga ggccgacagg  2760
gacacgatca tcctgaacgc gaagaagatc agcagggaga gggacaacgg cgagcagtca  2820
acggataccc ggagccagaa cgtgacggtg agcgttctgg acgtgtgcga gaccgctgag  2880
aagaagaagc tggtgctggt gggcagcggc tcaaagaggc cagctgctac taagaaggcc  2940
ggccaggcta agaagaagaa gtga                                          2964

SEQ ID NO: 74            moltype = DNA   length = 2847
FEATURE                  Location/Qualifiers
source                   1..2847
                         mol_type = other DNA
                         organism = synthetic construct
SEQUENCE: 74
atgggcccaa agaagaagag gaaggtgatg gactacaagg accacgacgg cgactacaag    60
gatcacgaca tcgactacaa ggacgacgac gacaagatga agaagccgaa gcagaacatc   120
gaggagacgg acctgaagat caccaccccca aagaccgcga ccatcaaggc caccaacctg   180
gacgacaaga tgaggctctt caccttcttc aacggcttca ccaccgtgtg ctccaaggtg   240
aaggacaaca tctacaactt cggccagaac gaggacacac tgccggtgta caccgactac   300
attaaggcct cccagagggc caggatgtgc gctactaccc tcgctaccaa gagcgagtgc   360
gacttcgcca agaagtacgg cgagcacttc ccgctccccc attacaacca ggagggcatg   420
aactacacca cccaccagca cacctactca gtgaactccg ccgtgcacac acagctcgac   480
tcccttaacg agtgcgacaa gctcaccaac ggcgagtacg tcaagctcaa gaagaccgtc   540
gacgagctgg aggagaagct gaccgaggag cacggcaagg agccacttga tttcctggtg   600
aagttcgtgg acgacgagat cctcctgggc tggaggttcg acggcaagtt caggctgttc   660
ttcgaggtgg cgatgctgcc agagcttaag aacggcaaca tcatctacaa gaaggcgtac   720
aagacctccg cgcgcaaggg caggaggtac tctttctaca accgtccgt ggccgataac   780
atttctaaga accccaccgt gtggaacctg ctgagcgacg ttaaggcggt ggactacatc   840
tccctgtcta attccctgct gaggaagaag ccgcacgccc agtacaccaa cacaaccctg   900
aacagggccc aggtgaggc tacattcggc aacaacggcg tgccattctc catctccgtc   960
```

```
tccgacgacg actacgtgta catccgcttc aggctgccca agaaggacgg cgaggagaag   1020
ggccaggaga tctcagtcaa gtgcagctac aagacttcat acaagggcaa gcgcagcaag   1080
acgctgagga agagctgcta cctgggcaac ctgaagatcg aggagaatgg caagggcaag   1140
tacatttgca agtacaacat caacggcagg gagacgacca ccgcggagct taatgagtgc   1200
ttcctgaggg tgaggatcaa caacaaccgc tggttcaaca agtacctgaa cggcacgctg   1260
accaaggagg acggcgttct taagagcgag tacttcgact tctacttcga cctgtgcctg   1320
aatgtgcatc agaagtccat ccacggcctg accaactccg agattttcgg cggcaagggc   1380
aagagcatca ggagctacta ctccacctcc tacccggagg tgaagaacct ggacggccag   1440
aagaacatca agaccgactt cggctgctac gtggacaagc cgcacaacat catgggcatc   1500
gacctgggcc agaggaaccc attcgcctgg gctgttctgg accagaacgg caatgtgaag   1560
gacgtgggcc acctggacgg cgctgagaac gatacataca aggactacct gacgttctcc   1620
aacaggtgca aggacgttaa gaatctgatc ctgcagtcca gggactacct gtacggcgac   1680
gatgaggcca ttgacgagac cctgttcgac tccgtggtgc agttcgtgaa cagcaacatc   1740
acgctgaaca agtacaagtc ctacctggac gagaagaaga gcctgatcaa caaggagtcc   1800
ctggagaaga accgcctgta cgagctgaag aagaaggacc acggctggtt cgtgagggac   1860
tgcctttggt tcctgaccaa ggagtaccac aggatcaact ccgagcgcaa gacgcactcc   1920
gactggaggt acaccctgta ctgggtggac gccattcacc ggttcattga cgtgaacaag   1980
tccttcaact ccctcggcag ctactacgac aagaagcagt ccaagtccat caacggcatc   2040
cagaaggact tctgcaggag ctactggaac cagatcgaca acctgaacga ggacaccctc   2100
aagaagttcg tgttcgagct gctgccagtg atcaagaaga caacgtgtg cctgatcgcc   2160
atcgaggagc tgaagtccat gctgggcgac gacgacaaga gggctgagga taacaggctg   2220
tacaacctgt ggccggtggg ccagcttaag acgttcctgg agggcaagct gctgccgtac   2280
aacgtggctg tgatggaggt gagcgagcag aacacgagcc agatcgtgaa cggccagtgg   2340
tcctacaggg agggcgatga tctctactac gtgaagaaca acgacaacaa caccatgtgc   2400
aagacccacg cggacgagaa cgcggctatc aacatcgccc tgagggccta ctcccaccac   2460
actaacctgt actccatcta catgatcaat ccgatcgacg actactacgt cccgagctgc   2520
atctggaaca acaaggacga gggctccaag aggattaggg gcttcctgac caagacctac   2580
ggcacctccg acgtggtgtt catcaagaag aatgagaagc tggtgaagtc cgacgtgagc   2640
atcaaggacg tgaagaggat cgtgaagaac atcggcaatg agaagaacaa gaagagcgag   2700
atctggtaca ggatgaacga catcgagtgg atcgacgagg gcagcaggga catcatcatc   2760
aacacaatca agagcaaggt gagggggctcc ggcagcaaga ggccagctgc tactaagaag   2820
gcgggccagg ctaagaagaa gaagtga                                       2847
```

SEQ ID NO: 75            moltype = DNA   length = 2820
FEATURE                  Location/Qualifiers
source                   1..2820
                         mol_type = other DNA
                         organism = synthetic construct
SEQUENCE: 75

```
atgggcccaa agaagaagag gaaggtgatg gactacaagg accacgacgg cgactacaag   60
gatcacgaca tcgactacaa ggacgacgac gacaagatga cggacaagag catcagcttc   120
aagcagttca gccagatcct caatgtgctg tacaagtgca tcgtgatttc cggcaagggc   180
cgcggcctta cttccattat cctgggccag ccgcagtgca aggactcact tacctccgcc   240
gactgggggca acctggagac tctttccgcc aaggacgagc tgacccctgc tgaggttaag   300
gatattacca aggacctgat gtacagggcc agcaacaccc tggtctccat cggcttcagg   360
aacaggtccc ctttcaagct gaccctgacc tccggcgaga ggtacgctgt tgtggagaac   420
gtgcaccgct ccctcaagtc ctgggtggag gttgacaaga ttacccctc gaactacctc   480
aacgaggaga tcgccctgag cgatgccttc aataacatcg acgagacgct gctgccaacc   540
cttaaggagt tcttcgacgc gtgcatgaat gagaacatca tccaccactt cgacgccagg   600
gtgtacgcct acacgaggga ttgcgtcatc ccagccctgg tggctggcct tgagatcaag   660
gaccacttct acatcgacgg ccgcgacaag gccaagaggt attacagcct gcaaggttac   720
gccgagcttc tgaagggctt cccgaagctc tggcagggcg ttgatccgga gatcctggct   780
aagctgtaca tcctggaggc ccagatggac cacaagaagc acaggccatg cgccgcttac   840
gcgttcatcg gcgaggattc ctacagcagg gtgcagtacc ttctgggcaa caactacacc   900
tccttcagcc cctacgccct cggcgttgat ctggatgacg tgacctgcgg cgatgacgct   960
gaggctgata cacagttccc caagaacaag gtgatccagt tcagccaggg caagaaggtg   1020
accaagctgt ccctgaccgt gagcaggggc aaggaggata ccaacaagta ctccttcgat   1080
gtgttcctgg ccgacaagta cagcaacggc tcctacaagc caagcccgta cttctctgac   1140
ctgtccgttt gggtgagcga gatcgtgcatg ctgatgagt tcacccgcaa gggcgagagg   1200
gtgcaggcta ttgtgaagga gccatccctc atttaccgca agggcgcctt ctacgtgagg   1260
cttaatatgg gcgtgattca ggacacctcc ccggagatca cgacctgta ctggtacttg   1320
tcctccggcg ccccaatgtc catgaccgat aggtccaagg cttccgagac cccgaagaac   1380
accgagaggc tggagtcaat taagggcaag agctaccgct tcctgggcat cgacctgggc   1440
cttaggtccc cattcgcctg ggctgttggc gaggcttca tctccggcgt catcaacaag   1500
ccgacgatca ttgccaccgg cgactacacc accgccaggg atactaggta cgacacgctc   1560
ttcttcgccc tcaagaatgc gggcaaggtg attggcgtga ccaagtccct cgccaacggc   1620
aaggacgctt ctttcaatgg cctgatgggc accatcaccg ccgctaggga gtaccttgcg   1680
cactactccg gcgtcgctac ccataaggtg gccgctatca aggccttctg ccaggatgac   1740
aacccgctgg agacccttaa gggcctgctc aagtcctaca caaccgcct cgtcaccctc   1800
aagaaggacc ctaggttcat cggcggcatc ctgctcaggt acgccaggct tctgaagggc   1860
gagcttgtga cctccaggaa gatgcacctg cgggagcact ccgtggagtc taagttcggc   1920
caggagtaca tgtggctgaa tattctggag agggagaaga gggtgtgcag gagcctgtcc   1980
tacctgggcc ttgcaacga cagggacagc gttatcatgg cgaacctgac cacgccgtac   2040
aaccactgca aggagaacct gcttaagcag ctggccgacg gattgtgtc actggctgtg   2100
gagaataagc gccacgttat cgtgatggag tccctgggcg ctccaacaa gtccatgaat   2160
accaggggcc agaacttcct cgaggccttc tggtccccac agaagatcaa ggacaccatc   2220
atcaacgccc ccgcctggca tggcatcatg gttgctgagg tgagcgagag ccagacctcc   2280
caggtttgct tcgagaccgg caccttcggc cacagggata gggcttctct gtacttcctg   2340
gacaagaacg cgcacctcca ggagacgcat gccgatatga cgccgccaa gaacctcgtg   2400
```

-continued

```
gagagggttca ccaccaggca caccaacctg aggcaggtga atatggactc cctccccaag    2460
gagggcccgg ataagacacc aaagaagtcc ccgtccaaga agaagatgga gaaggcgaag    2520
atggacaacc cagaggacca gtccaagagg ctcaagggct tcctgaccgt gaagttcggc    2580
aatgtgaagg ccgcccagga gtacttcgcc tctaggaagc cggagcagag ctacagcggc    2640
aagaaggacg aggccatcta ctggtacttg gacggcgacg agtggatcac caagaaggag    2700
aaggagtcca gggtcagcgt gattgagggc ctggtgggcc ttaaggaggt ggctgttggc    2760
agcggctcca agaggccagc tgctactaag aaggccggcc aggctaagaa gaagaagtga    2820
```

```
SEQ ID NO: 76            moltype = DNA  length = 2622
FEATURE                 Location/Qualifiers
source                  1..2622
                        mol_type = other DNA
                        organism = synthetic construct
SEQUENCE: 76
atgggcccaa agaagaagag gaaggtgatg gactacaagg accacgacgg cgactacaag    60
gatcacgaca tcgactacaa ggacgacgac gacaagatgg cgttccagag caagaggagg    120
attgtgggca acctggtgaa ggagcagtgc ctcaaggccg tggatggcaa ggtgatcctg    180
accgaccagg agaagaggga gctgatcaag aggtacgagc tgcacctgga gccgtacaag    240
tggctgctga ggctgttcct gtccggctac gagggcaggg atgacggctt ctacgaggag    300
ctgggcaaca cgaacctgga caaggagaag ttcttcgagg tcaccgcggg cctcagggat    360
gctcttctta ggcagtctgg ctcctccagg gcgcttaagt cctccatgct gggcaagtgc    420
ccgccatcag ctgctgttgg caaggctgct aagcacatcc aggctctgcg cgacgctgag    480
attcttccat tcaagacggg cctcacctcc ggcgaggatt acaacgtgct tcagcaggcc    540
gtccagcagc tgaggtcatg ggttgcttgc gatcacagga ccaggaggc gtacgctgag    600
cagcaggaga agacatccca ggccgaggag gctgctaaga aggctgtgaa cgaggtgaag    660
ccagaggacg ccaagagcct ggagaggcat gagagggctc tgacgaagct gaggaagcag    720
gagaggaggc tggagaggat gaggagccac gctcagttca gcctggacga gatggactgc    780
acgggctaca gcctgtgcat gggcgctaac tacctgaagg actactgcct ggagaaggag    840
ggcagggggc ttaggcttac cctgaagaat agcactatgg ccggcagcta ctacgtttcc    900
gtgggcgatg gccagcacgc tggcatgaag aacccaggta ctccggcggg cggctctcca    960
gagaagggca ggaggaggaa catcctgttc gacttcgcgg ttgagaagtg cggcgacaac    1020
tacctttttca ggtacgacga gaacggcaag cgcccgaggg ctggcgttgt taaggagcca    1080
aggttctgct ggaggcggaa gggcaactcc gtggagcttt acctggccat gccgatcaac    1140
atcgagaaca gcatgaggaa catcttcgtc ggcaagcaga gagcggcaa gcactccgat    1200
ttcacccggc agtggccaaa ggaggtggag ggccttgacg agctgaggga tgctgtggtg    1260
ctgggcgttg acatcggcat caacagggcg gcttctgcg cggctctgaa gacttcccgc    1320
ttcgagaacg gcctgccggc tgatgttcag gttatggata ccacctgcga tgctctgacc    1380
gagaagggcc aggagtacag gcagctgagg aaggacgcca cctgccttgc ttggctgatc    1440
aggacaacca ggaggttcaa ggccgaccca ggtaacaagc acaaccagat caaggagaag    1500
gacgtggaga ggttcgacag cgccgacggc gcttacagga ggtacatgga cgccatcgcg    1560
gagatgccgt ccgatccact tcaggtgtgg gaggctgcca ggatcaccgg ctacggcgag    1620
tgggctaagg agattttcgc caggttcaat cactacaagc acgagcatgc ctgctgcacc    1680
gtctcccttt ccctgtctga ccgcctggtg tggtgcaagc ttatcgatag gatcttgtct    1740
ctcaagaagt gccttcactt cggcggctac gagtccaagc acaggaaggg cttctgcaag    1800
tccctctaca ggcttaggca caatgccagg aacgacgtca ggaagaagct ggccaggttc    1860
gtggtggacg ccgctgttga tgcggcgct tctgttatcg cgatggaaaa gctcccgtcc    1920
tccggcggca agcagtctag ggatgacaac cggatctggg acctgatggc cccaaacacc    1980
ctggctacca ccgtgtgcct catggctaag gttgagggca tcggcttcgt gcaggtggac    2040
ccagagttca cctcccagtg ggtgttcgag cagagggtga ttggcgatag ggagggcagg    2100
attgtgtcct gcctggacgc tgagggcgtg aggaggggat acgacgctga cgagaacgcc    2160
gcgaagaaca tcgcctggct ggctcttact agggaggcgg agccattctg catggccttc    2220
gagaagcgga atggcgtggt ggagccgaag ggcttcaggt tcgacattcc ggaggagccg    2280
accagggagc aggatgagtc aaaccaggac ttcaagaaga ggctggagga gagggacaag    2340
ctgatcgaga ggctgcaggc gaagagcgat aggatgaggg cgatcgtgag gaggctcttc    2400
ggcgatagga ggccgtggga tgctttcgct gacaggattc ctggtaccga gtccaagagg    2460
ctgttccggc acaggggatgg cctggttctg aacaagccgt tcaagggcct gtgcggctcc    2520
gagaatagcg agcagaaggc ctccgccagg aactctaggg gctctggctc taagaggcct    2580
gccgctacta gaaggcgggg ccaggctaag aagaagaagt ga                       2622
```

```
SEQ ID NO: 77            moltype = DNA  length = 3021
FEATURE                 Location/Qualifiers
source                  1..3021
                        mol_type = other DNA
                        organism = synthetic construct
SEQUENCE: 77
atgggcccaa agaagaagag gaaggtgatg gactacaagg accacgacgg cgactacaag    60
gatcacgaca tcgactacaa ggacgacgac gacaagatgg acacgacac ggagctgagc    120
gacgaggttg agctgagcga tgaggtggag ctgagcgacg aggtggagct ttccgacgag    180
gtggagctga cggtgaagaa ggtgaagacg acgacggtga caatttcaag    240
aaggagctgt tcgagctgtt caatcacttc accagcgtgg cgagcggcat caaggacagg    300
ctttacgacc tgcagttcga tgagaacact gcctccatct tcaagggcta catcaaggag    360
gccaagaggg gccacggcgc tgctactact gtgttcacta agctgaaccc gaagaagatc    420
tactccggca agaagtcctt cccaagggat tacagggacc ggggcatctt cccgttctac    480
aacaaggagt ctggcaagta cgacctgtcc acctgcgaag ccactacag cgctaacgcc    540
gagattcaca cccagctcaa cagccacgac gagtgcaaca gcagtgcga gaaggagtac    600
gcggcgctgg agaaggagag gaacaagtac aagcatgagt tcacgaggca gttcaaggcc    660
gagaacgtga gaagttcag caacttcgtg agaaagctga cactgatggg ctggaggtac    720
gatgcgacct tcaggaactt cttcgagctg cacatgcacc aaagctcaa gacgtccgag    780
accacctaca gggccaccta caagctgccg tccggcaagt ctaagcggta ctccttctcc    840
```

```
agggacgata ttgccgacga gatcgccaag aacccccgagt tctggccaat gctggagtcc    900
tccaacgccg tttcctggat caactccaac aatctgctct ccaggaagaa ggagaaggcc    960
aattactcca gcaccagcct gatcaagtcc cagattaggc tgtacctggg cgacaacggc   1020
gtgccattca ccgctaggga gcacgatggc aggatctact tcagcttcag gctcccgtcc   1080
atcaacggcg agaagggcag gaacgtcgag atcccatgct cctacaagaa ggtcttcaat   1140
ggcaaggcca ggaagtcctg ctacctgggc ggccttacca tcgagaacac cggcggctca   1200
aagcacattt tcaagtactc cgtgaacaac aagaagccgc aggtggcgga gctgaacgag   1260
tgcttcctga ggctggtcgt gaggaatcat ggctacttca acaagatggt gaacggcaag   1320
ctcacggata aggacggcaa gctgcacgcc gactacttcg atttctgcat cgacctgccg   1380
cttaacgtga aggaggaccc gatccacgac ctgacctacc aggagattaa cggcgtgaag   1440
gccaacccgg agaagaacat cgagaagaag gtgggcctgc tgggcttcta ccagtccgct   1500
tacccagaga tcaagaacct cggctcccag atcgagaccg gcaagaacct gacctgcccg   1560
atcaccaaga cccacaacat catgggcatc gacctcggcc agcgcaaccc attcgcttac   1620
tgcatcaagg acaacaacgg caagttcatc gcgaagaacc acatggacgg ctccaagaac   1680
gagacataca agaagtacat caatttcggc aaggagagca cctcagtctc ccacctgatc   1740
aaggagacca ggtcctacct gcatggcgat ccggaggcta tctccaagga gctgtacaac   1800
gaggtcagcg gcctgtgcaa ctctccgctt agctacgagg agtaccttaa gtacctggac   1860
agcaagaagt tcctgatcaa caaggaggac ctgaacaaga acgccatgca cctgctgagg   1920
cagaaggacc acaactggat cggcagggac tggctgtggt acatcagcaa gcagtacaag   1980
aagcacaacg agaacaggat gcaggacgcc gactggaggc agactctgta ctggatcgac   2040
agcctgtaca ggtacatcga tgtgatgaag tccttccaca acttcggcag cttctacgac   2100
aagaacctga agaagaaggt gaacgcacc gccgtgaagt tctgcaagac tatctacgac   2160
cagatcaaca acaacaacaa ggacatgttc aagaagttca ccaatgagct gatcccgatc   2220
atccgcaagc acaaggtgtc cgtggtggcc cttgagaaga tggagtccat gctgggcgac   2280
aagtccagga acacattcga gaacaggaac cacaacctgt ggccagtcgg ccagctgaag   2340
accttcatcg agaacaagct ggatggcttc aacgtgatcg tggtggaggt ggacgagagg   2400
aacacgagcc agatgtgcga cggcaactgg tcctacaggg aggctgacga cctctactac   2460
gtcaaggacg gcgagctgag ggaggttcac gctgatgaga atgcggccaa caacatcgtc   2520
gacaggtgca tctccaggca taccaacatc ttcagcctgt acatgaccaa cccgatggac   2580
gactactacg tgccggcgtg catctgggac aggtcagaga atggcaagag gggcagggcc   2640
ttcctgacca agatgtacaa gaacagcgac gtggtgttca ccaagaagga cgacaagctg   2700
gtgaagtcca agatgtccgt gaaggagctg aagaagctgg tggacaagac caaggagaag   2760
aggggccagt actggtactt gttcgagggc aagagctgga tcaacgccgc cgatagggat   2820
accattatct ccaacgcgaa gaagctcttc agggagaggg atggcggcga gcagtcaact   2880
gataccggct ctcagaacgt gacggtgtcc gtgctggacg tgtgcgagac tgtggagaag   2940
aagaagctgg tcctggtggg ctccggctca aagaggccag ctgctactaa gaaggccggc   3000
caggctaaga agaagaagtg a                                              3021
```

```
SEQ ID NO: 78          moltype = DNA   length = 3162
FEATURE                Location/Qualifiers
source                 1..3162
                       mol_type = other DNA
                       organism = synthetic construct
SEQUENCE: 78
atgggcccaa agaagaagag gaaggtgatg gactacaagg accacgacgg cgactacaag     60
gatcacgaca tcgactacaa ggacgacgac gacaagatga gcacggaggt ggacgtgaag    120
acgatcaacc tgaagatcgc gaagaagggc ggcgtgtacc cgattctgga gcagtcaatt    180
aaggagaact gcaagagcaa cgacctgctg gagttcttca tggtgctgaa caggctgcag    240
acctactaca tcgagagcaa cgaggagatt ctggtggact tcccccaagaa gtacgacgag    300
ctgttcgaca tcgtgaagaa caacgactcc tccgtgacca gggaatactt cgactccctc    360
tgcgacaagt acatcacaga ggtgtgcgcc aatggcttcg tcaacaacgt gtacattgcc    420
cacaacaaga accaggagct gaactgggct gagacgagca acgaccgcaa gatcaagagc    480
aacaagacct tcatgttcgg caagatcaag ggcctgatcc gcgacaagtt cggcagggag    540
gagctgtcag acaaggacgc tacgaagcag ctgtgcgagg acatcttcaa cctcttcatc    600
ctgaacaacg ccaacatcga gctggacgag aagtacaaca tcatcaagga cgagctgatc    660
cagatctgga acgagaggaa caaggagttc atccacatca aggacatcac cctgctgttc    720
aggcagtggg gcatcctgcc tacctacgac aacatcaccc acaactgcga gctgaaggcc    780
atcatcgccg agccagtgag gaggttcaag tcctggctgg agtgcaactc tgaggcgaac    840
aagaactacg acaccgagag ggagaatgtgc accaagtaca tggacgtgat ggactccgac    900
ctgaccgtgg agttcagcaa gatggtgacg gagctgggca acccattcgg cgctaacgac    960
aagaacatct acaagtactt caaccagaag ttcctcctgt tcttcaagca ggttgtgcag   1020
cccaagttcg ttaacggcga gccgctggac gagtctaatg gctcttactc cggcgagatc   1080
aagatcaact ccgcgggcaa ggtggagaac tactccatcg ccgtgtccgt gattgacacc   1140
atcaagaagt acccgacgat ctggtccgac cgctccgtgg gcagtctgt tatctccacc   1200
gtggccaaga ttgatccgca gtacggcatc gacgacatca ccgacgatat gcaggtgtcc   1260
ccgttctacc tcttctacgg ctacttcacc gcctacaact acatccagca gcacaagagg   1320
aacgccaagt acacccgat ctccaaggac tccctgccat ccctgtacct cggcaacaac   1380
tacatccccat tcaagatcga ctgcgagaac gtcgacgacg accggttcta catcaccatc   1440
aagaacatga acaacctgaa gctgaacgtc ctctaccgca agcccaagct gaagttcgcc   1500
aagaccaagg agaagaccaa gaggaacaag tgctacttcg acaacctcaa gatcaccaac   1560
accaacaaca acttcaagtt cgagtacaac atcaacggcg acccaaacag gtccgtggtg   1620
gcttacctga aggagccagt gatccgctac aacaacagga ggactactt ctacctgagc   1680
gccacaatca gcaaggacgt ggagaccgac tccgagctga cctctgcttg ctggtcgaag   1740
atctccaacg acaccgcccg cagggtcaac gctgagcagt acttcaacga caacgcgcgtg   1800
aacatcgtgg gcattgacct gggcatgaac ccgatcatcg cctactctgt tctgcactac   1860
aagaacaacg agttcattga cctgaacatt accggcaaga tcgccgacaa ggataagcac   1920
cccaatctga actacaagag gatgtacgag aagaggtccg agatcaagaa gctcaagacc   1980
ctgatcaaga tgatcccgga ctacgtgaac agcgacagca acatcttcga gggcgacaat   2040
aacgtgttca gcagctgga caagaagagc aagggcaggt tcaggtcctc cgagtacatg   2100
```

```
ggctactacg acaagctgaa cgtggacggc aagttcatct ccgagctgga gatcgtgaag   2160
aaggtggtga acacaaagca ctacaagaat gacaccgaga agaacaacga tattatgagg   2220
gtgtacaagg gcaataagaa gaacatcatc aagaaggaga tcgacaccca caggcaccag   2280
atccactcca tcaaggacat gaacaggagg tccgacgaga gcaacctgtg ctacgtgtac   2340
gacatggtga gctacatcga cgacttcaag aagctggtga cctcctacaa caagatcggc   2400
gaggactaca acaacccgat caagccgctg agcgacccga tgctttctc caagtccaag   2460
ctgtacgagt acaggcagaa catcagggac aatttcctga aggacatctg ctaccagatg   2520
gtgaagatcg ccaagcagta caatgccgtg ctggtgcacg agcacttcga gcagaggaag   2580
ggcggcattg acagggtgaa caacatcctg atggccctgt tcacgccgaa cgacatcatc   2640
aagaagctga agtgcgtggc caagagggag ggcgttctgg ttttcaacac caacaagaac   2700
catacctccc agtacgtgta caacaagaac accgtcggct accgcgacag caacaacaag   2760
cacaacctgt actacatcga ggacgagacc accaggaagc tcggcgttgt ggactccgac   2820
atcaacgcct ccaagaacat cgccgcccgc ccattcaaca agccactcta cgccatcaag   2880
gtgaagaact acgatgacgg cctgttcctg tcagactaca acaataagta cgttctgtac   2940
aagaaggacg cgacaagta cgtggccatc ggcgatacat acaggatcga caagaagaag   3000
atcaagcagg gctccgtgac cctgtacctg cataacggct actacgtgga tggcgagtac   3060
aagaacaatt acatcgagaa tatcaagaag ctggtcctgg gcagcggcag caagaggcca   3120
gctgctacta agaaggccgg ccaggctaag aagaagaagt ga                       3162

SEQ ID NO: 79          moltype = DNA   length = 2622
FEATURE                Location/Qualifiers
source                 1..2622
                       mol_type = other DNA
                       organism = synthetic construct SEQUENCE: 79
atgggcccaa agaagaagag gaaggtgatg gactacaagg accacgacgg cgactacaag   60
gatcacgaca tcgactacaa ggacgacgac gacaagatgg cgttccagag caagaggagg   120
attgtgggca acttcgtgaa ggagcagtgc ctgaaggccg tggatggcaa ggtgatcctg   180
acggaccagg agaagaggga gctgattaag aggtacgagc tgcacctgga gccgcataag   240
tggctgctga ggctgttcct gtccggctac gagggcaggg atgacggctt ctacgaggag   300
ctgggcaaca cgaacctgga caaggagaag ttcttccgagg tcaccgcggg cctgagggat   360
gctcttctta ggcagtctgg cagcagcagg gcgcttaagt cctccatgct gggcaagtgc   420
ccgccatcag ctgctgttgg caaggctgct aagcacatcc agaccctgag ggacgccggc   480
attctcccat tcaagacggg cctgacctcc ggcgaggatt acaacgtgct gcagcaggcc   540
gtgcagcagc ttaggtcatg ggtggcttgc gaccacagga cgaggggagc ttacgctgag   600
cagcaggaga agacaagcca ggccgaggag gctgctaaga aggctgctaa cgaggtgaag   660
ccggaggatg cgaagtctct ggagaggcac gagagggtgc tgacgaagct gaggaagcag   720
gagaggaggc tggagaggat gaaagagcac gcgcagttca gcctggacga gatggactgc   780
acgggctact ccctgtgcat gggcgctaat tacctgaaga actactgcct ggagaaggag   840
ggcaggggcc ttaggcttac cctgaagaat agcacgatgg ctggcagcta ctacgtttcc   900
gtgggcgacg gccagcacgc tggcatgaag aatccgggca ccccagctgg cggctctcca   960
gagaagggca ggaggaggaa tatcctgttc gacttcaccg tggagaagtg cggcgacaat   1020
tacctgttca ggtacgacga gaacggcaag aggccgaggg ctggcgttgt taaggagcca   1080
aggttctgct ggaggcggaa gggcaacagc gtggagcttt acctggcgat gccgatcaac   1140
atcgagaaca gcatgaggaa catcttcgtg ggcaagcaga gtccggcaa gcactccgct   1200
ttcacccggc agtggccaaa ggaggtcgag ggccttgacg agcttaggga cgctgtggtg   1260
ctgggcgttg acatcggcat caacaggcg gctttctgcg ccgctctgaa gacttccagg   1320
ttcgagaatg gcctgccggc cgatgtgcag gttatggata ccacctgcga tgcgctgacc   1380
gagaagggcc aggagtacag gcagctgagg aaggacgcca cctgccttgc ttggctgatc   1440
aggacgacca ggaggttcaa ggctgaccca ggtaacaagc acaaccagat caaggagaag   1500
gacgtggaga ggttcgacag cgccgacggc gcttacagga ggtacatgga gccatcgcg   1560
gagatgccga gcgatccact tcaggtctgg gaggctgcca ggatcaccgg ctacggcgag   1620
tgggctaagg agattttcgc caggttcaac cactacaagc atgagcacgc ctgctgcgcc   1680
gtgtctcttt ctctttccga caggctggtg tggtgcaggc tcatcgacag gatcttgtct   1740
ctgaagaagt gcctccactt cggcgagctac gagtccaagc acaggaaggg cttctgcaag   1800
tccctgtaca ggctgaggca caacgccagg aacgacgtga ggaagaagct ggcaggttc   1860
atcgtggatg ccgccgttga cgcgggcgct tctgttattg cgatggagaa gctgccgtcc   1920
tctggcggca agcagtcaaa ggacgacaac aggatctggg acctgatggc cccgaacacc   1980
ctggctacta ctgtgtgcct gatggccaag gtggagggca tcggcttcgt ccaggtcgat   2040
ccagagttca cctcccagtg ggtgttcgag cagaggatga ttggcgatag ggagggcagg   2100
atcgtgagct gcctccgatgc tgagggcgtg aggaggggatt acgacgctga cgagaacgcc   2160
gcgaagaaca tcgcctggct ggctcttacc agggaggctg agccattctg catggcgttc   2220
gagaagagga acggcgtggt ggagccgaag ggccttaggt tcgacatccc ggaggagcct   2280
accagggagc aggatgagtc ggaccaggac ttcaagaaga gctgggagga gagggacaag   2340
ctgatcgaga ggctgcaggc gaaggcggat aggatgcagg ctatcgttca gaggctttc   2400
ggcgacagga ggccgtggga tgctttcgct gacaggattc ctgagggcaa gagcaagagg   2460
ctgttcaggc acagggacgg cctggttctg aacaagccgt tcaagggcct gtgcggctcc   2520
gagaatagcg gccagaaggc ttctgctagg aacgccgcg gctccggctc taagaggcca   2580
gctgctacta agaaggcggg ccaggctaag aagaagaagt ga                       2622

SEQ ID NO: 80          moltype = DNA   length = 35
FEATURE                Location/Qualifiers
source                 1..35
                       mol_type = other DNA
                       organism = synthetic construct SEQUENCE: 80
nnnnnnnngg tataacaact tcgacgagct ctaca                                35

SEQ ID NO: 81          moltype = RNA   length = 27
```

```
FEATURE              Location/Qualifiers
source               1..27
                     mol_type = other RNA
                     organism = synthetic construct
SEQUENCE: 81
ggtataacaa cttcgacgag ctctaca                                        27

SEQ ID NO: 82        moltype = RNA  length = 26
FEATURE              Location/Qualifiers
source               1..26
                     mol_type = other RNA
                     organism = synthetic construct
SEQUENCE: 82
gagccagaga ggatcctggg agggag                                         26

SEQ ID NO: 83        moltype = RNA  length = 24
FEATURE              Location/Qualifiers
source               1..24
                     mol_type = other RNA
                     organism = synthetic construct
SEQUENCE: 83
cttccatcag agaacctcac tgcg                                           24

SEQ ID NO: 84        moltype = DNA  length = 52
FEATURE              Location/Qualifiers
source               1..52
                     mol_type = other DNA
                     organism = synthetic construct
SEQUENCE: 84
tttgcttacg atggagccag agaggatcct gggagggaga gcttggcagg gg           52

SEQ ID NO: 85        moltype = DNA  length = 52
FEATURE              Location/Qualifiers
source               1..52
                     mol_type = other DNA
                     organism = synthetic construct
SEQUENCE: 85
aaacgaatgc tacctcggtc tctcctagga ccctccctct cgaaccgtcc cc           52

SEQ ID NO: 86        moltype = DNA  length = 35
FEATURE              Location/Qualifiers
source               1..35
                     mol_type = other DNA
                     organism = synthetic construct
SEQUENCE: 86
tttgcttacg atggagccag agagcttggc agggg                              35

SEQ ID NO: 87        moltype = DNA  length = 35
FEATURE              Location/Qualifiers
source               1..35
                     mol_type = other DNA
                     organism = synthetic construct
SEQUENCE: 87
tttgcttacg atggagccag agaggattgc agggg                              35

SEQ ID NO: 88        moltype = DNA  length = 44
FEATURE              Location/Qualifiers
source               1..44
                     mol_type = other DNA
                     organism = synthetic construct
SEQUENCE: 88
tttgcttacg atggagccag agaggatcca gagcttggca gggg                    44
```